US007985889B2

(12) United States Patent
He et al.

(10) Patent No.: US 7,985,889 B2
(45) Date of Patent: Jul. 26, 2011

(54) **ATMIN7 MEDIATED DISEASE RESISTANCE TO *PSEUDOMONAS SYRINGAE* IN *ARABIDOPSIS***

(75) Inventors: Sheng Yang He, Okemos, MI (US); Kinya Nomura, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 365 days.

(21) Appl. No.: 12/070,959

(22) Filed: Feb. 21, 2008

(65) Prior Publication Data

US 2009/0031456 A1 Jan. 29, 2009

Related U.S. Application Data

(60) Provisional application No. 60/902,576, filed on Feb. 21, 2007.

(51) Int. Cl.

| | |
|---|---|
| ***A01H 5/00*** | (2006.01) |
| ***A01H 5/10*** | (2006.01) |
| ***C12N 15/09*** | (2006.01) |
| ***C12N 15/82*** | (2006.01) |
| ***C12N 15/29*** | (2006.01) |

(52) U.S. Cl. ........ 800/279; 800/278; 800/298; 800/295; 800/320; 800/317; 536/23.6; 435/320.1; 435/468; 435/419

(58) Field of Classification Search ........................ None
See application file for complete search history.

(56) References Cited

U.S. PATENT DOCUMENTS

| | | | | |
|---|---|---|---|---|
| 2004/0123343 | A1 * | 6/2004 | La Rosa et al. | 800/278 |
| 2004/0237137 | A1 * | 11/2004 | Osumi et al. | 800/279 |

FOREIGN PATENT DOCUMENTS

WO WO 03000898 * 1/2003

OTHER PUBLICATIONS

Seffernick et al. Bacteriol. vol. 183, pp. 2405-2410 (2001).*
Broun et al. Science, vol. 282, pp. 1315-1317 (1998).*

* cited by examiner

*Primary Examiner* — Medina A Ibrahim
(74) *Attorney, Agent, or Firm* — Medlen & Carroll, LLP

(57) ABSTRACT

The present invention relates to compositions and methods for enhancing plant defenses against pathogens. More particularly, the invention relates to enhancing plant immunity against bacterial pathogens, wherein AtMIN7 mediated protection is enhanced and/or there is a decrease in activity of an AtMIN7 associated virulence protein such as a *Pseudomonas syringae* pv. tomato DC3000 HopM1. Reagents of the present invention provide a means of studying cellular trafficking while formulations of the present inventions provide increased pathogen resistance in plants.

22 Claims, 50 Drawing Sheets
(5 of 50 Drawing Sheet(s) Filed in Color)

SEQ ID NO: 1
AtMIN7, Arabidopsis thaliana guanyl-nucleotide exchange factor (AT3G43300)
ACCESSION NM_114198/ Q9LXK4_ARATH
MAAGGFLTRAFDTMLKESGGKKFPDLQKAIQAYQDGSKVVTQAAPSSIVESSQA
EGGGEKTGVEADEPQKVTSAEVAQQASQSKSETINVSLANAGHTLGGAEVELVL
KPLRLAFETKNLKIFDAALDCLHKLIAYDHLEGDPGLDGGKNSAPFTDILNMVCS
CVDNSSPDSTVLQVLKVLLTAVASGKFKVHGEPLLGVIRVCYNIALNSPINQATS
KAMLTQMISIVFRRMETDIVSASSTVSQEEHVSGDTSSPKNEEITAADENEKEMT
LGDALTQAKDTTLASVEELHTLVGGADIKGLEAALDKAVHLEDGKKIKRGIELE
SMSIGQRDALLVFRTLCKMGMKEDSDEVTTKTRILSLELLQGMLEGVSHSFTKN
FHFIDSVKAYLSYALLRASVSQSSVIFQYASGIFSVLLLRFRDSLKVSMDCYLSPY
FSDPKSHSQGEIGIFFPIIVLRSLDNSECPNDQKMGVLRMLEKVCKDPQMLVDVY
VNYDCDLEAPNLFERMVTTLSKIAQGSQSADPNPAMASQTASVKGSSLQCLVNV
LKSLVDWEKIRREAENSTRNANEDSASTGEPIETKSREDVPSNFEKAKAHKSTME
AAISEFNRNSVKGVEYLIANKLVERNPASVAQFLRSTSSLSKVMIGDYLGQHEEF
PLAVMHAYVDSMKFSEMKFHSAIREFLKGFRLPGEAQKIDRIMEKFAERYCADN
PGLFKNADTAYVLAYAVIMLNTDAHNPMVWPKMSKSDFTRMNATNDPEDCAP
TELLEEIYDSIVQEEIKLKDDDTMKKLSSQRPGGEERGGLVSILNLGLPKRISAAD
AKSETEDIVRKTQEIFRKHGVKRGVFHTVEQVDIIRPMVEAVGWPLLAAFSVTME
VGDNKPRILLCMEGFKAGIHIAYVLGMDTMRYAFLTSLVRFTFLHAPKEMRSKN
VEALRILLGLCDSEPDTLQDTWNAVLECVSRLEFIISTPGIAATVMHGSNQISRDG
VVQSLKELAGRPAEQVFVNSVKLPSESVVEFFTALCGVSAEELKQSPARVFSLQK
LVEISYYNIARIRMVWARIWSVLAEHFVSAGSHHDEKIAMYAIDSLRQLGMKYL
ERAELTNFTFQNDILKPFVIIMRNTQSQTIRSLIVDCIVQMIKSKVGSIKSGWRSVF
MIFTAAADDEVESIVEKSFENVEQVILEHFDQVIGDCFMDCVNCLIRFANNKASD
RISLKAIALLRICEDRLAEGLIPGGVLKPVDGNEDETFDVTEHYWFPMLAGLSDLT
SDYRPEVRNCALEVLFDLLNERGNKFSTPFWESIFHRILFPIFDHVSHAGKESLISS
GDVKFRETSIHSLQLLCNLFNTFYKEVCFMLPPLLSLLLDCAKKSDQTVVSISLGA
LVHLIEVGGHQFSEGDWDMLLKSIRDASYTTQPLELLNALSFDNPKKNLVLAGDI
EADASDSPRVDRNPDDIKDNGKVSAQASPRIGTHGTSLESGIPPKADGSEGRPSSS
GRAQKDVDDVNLQRSQTFGQRFMDNLFLRNLTSQPKSSVAEVTVPSSPYKHEDP
TEPDSREEESPALGAIRGKCITQLLLLGAINSIQQKYWSNLKTPQKIAIMDILFSFIE
FASSYNSYSNLRTRMNHIPTERPPLNLLRQELEGTTIYLDVLQKTTSGLADDASNS
EDRLEGAAEEKLVSFCEQVLKETSDLQSTLGETTNMDVHRVLELRSPVIVKVLEG
MCFMNNTIFRKHMREFYPLLTRLVCCEQMEIRGALANLFKAQLKPLLQQ SEQ ID NO: 2
AtMIN7, Arabidopsis thaliana guanyl-nucleotide exchange factor (AT3G43300) mRNA; complete cds. ACCESSION NM_114198/ Q9LXK4_ARATH
atggcggctggtggatttttgactcgagcatttgatacgatgcttaaggagtctggaggaaagaagtttcctgatctccagaaagct
attcaagcttatcaagatggttcaaaggttgttacgcaggctgcaccctcgagcatagtggagagttcacaagctgaaggtggag
gtgaaaaaactggggtagaagcagatgaaccgcaaaaagtcacgagtgctgaagtagcgcagcaggctagccagtcaaaaa FIG 11 SHEET 1 of 8 gtgagactataaacgtttccttagcaaatgctggacacacattagggggagcggaagtggagcttgtgctgaaacctctacgcct
tgcatttgagacaaagaacttaaaaatatttgatgctgctttggattgtcttcataaactcattgcctatgatcatttggaaggggatcc
ggggttggatggtggaaaaaattctgcacctttcaccgacattctgaacatggtttgcagctgtgttgataattcatcaccagacag
cactgtactccaagtactgaaggttcttcttacagctgttgcttcaggaaagttcaaagtgcatggggagccattgctgggagttatt
agagtttgctataacattgctctaaacagcccaattaaccaagcaacttctaaagcaatgctgactcagatgataagcattgtattca
ggagaatggagactgacattgtttccgcatcatccacagtgtctcaagaagaacatgtttcaggtgacacttcaagccctaaaaat
gaagaaataactgcagctgacgaaaatgagaaagaaatgaccttaggagatgcactcactcaggctaaagacacaactcttgca
tctgttgaagagctgcatacccttgtgggcggtgctgatattaagggtttagaagccgcccttgacaaagctgtgcatcttgaagat
ggcaagaagataaaacggggcatcgagctggagagcatgagtattggacagcgtgatgcattgcttgttttccgtaccctttgca
agatgggtatgaaagaagatagtgatgaagtcacaaccaagacccgtatattgtctcttgagcttcttcagggtatgttagaagga
gttagtcactcatttacaaagaactttcactttatagattcagtgaaagcctacctctcatatgcattgttgcgggcgtcggtttctcag
tcttctgtcatatttcagtatgcatctggtatcttctccgtgcttttgctgcggttcagagacagtttaaaagtaagcatggattgttacct
ttcaccatatttttctgatcctaaatctcactctcagggtgaaattggtatatttttccccatcatcgtcttaagatcattagataactccg
agtgtcccaatgaccaaaagatgggtgttcttaggatgcttgagaaagtctgcaaagatcctcagatgcttgttgatgtgtatgtaa
actatgattgtgatctagaggccccaaacttgtttgagcgcatggtaacaactttgtctaaaattgctcaagggtctcagagtgctga
tccaaatcctgccatggcttcgcagacagcttcggttaaaggttcatcccttcagtgcctggtcaacgttcttaaatcactagttgatt
gggagaaaataaggagagaggcagaaaatagtacaagaaatgcaaacgaggactctgcttctactggagagccaattgaaac
caaaagcagggaagatgtcccaagcaactttgagaaggctaaagctcataaatccacaatggaggctgccatctccgagttcaa
caggaattcagtgaagggtgtcgaatatctaattgcaaacaagttggttgaaaggaatcctgcttcagttgcacagtttctgagaag
tacttcgagtctgagcaaggttatgattggcgattacctgggccaacacgaggagtttcctcttgctgtcatgcatgcatatgttgatt
caatgaaattttcagaaatgaagtttcattcggctattcgtgaatttctcaaaggttttagacttcctggagaggcccaaaaaattgat
cgtattatggaaaagttcgcagaaagatattgcgcagacaatccgggtcttttcaagaatgcagatacagcctacgttctagcctat
gcagttatcatgttaaatacagatgcgcataatcctatggtttggcctaagatgtcaaaatcagatttcacacgtatgaatgccacta
atgatcctgaagattgtgctccaactgaacttctggaagagatctatgattctattgtacaagaagaaattaaactaaaagacgatg
acaccatgaagaagctcagtagtcaaaggccaggaggagaagaaagaggtggtcttgtcagcattcttaatctgggtttgccaa
agagaatatcagcagctgatgctaaatctgagactgaggacattgttaggaaaacacaggaaattttccgaaagcatggagtgaa
aagaggagtctttcacacggttgagcaagtggacattataaggcccatggtggaagctgttgggtggcctctgcttgctgctttctc
cgttacaatggaagtaggtgataacaaaccaaggattcttctctgcatggagggatttaaagctggaatacatattgcttatgttctt
ggaatggatacaatgcgatatgcatttctaacatcgcttgtcaggttcactttcttgcatgctccaaaagaaatgcggagcaaaaat
gttgaagcattgaggatattactggggttgtgtgactcagaacctgacacccttcaagatacttggaatgcagttttagaatgtgtttc
taggctggaattcattatttctactcccggaattgctgcaacagtaatgcatggatcaaaccagatctccagggatggggttgttca
atcattgaaggagttagccgggagacctgctgaacaagtttttgtaaacagtgtcaagctgcccagtgaatctgttgtggagtttttt
actgcgctatgtggtgtttcagctgaagaattgaagcagtctcctgcccgtgttttcagcttgcagaagctagttgagatcagttatta
caatatagcacgtatccgaatggtctgggcaagaatatggtctgtccttgccgaacatttcgtatctgctggtagccatcatgatga
aaagattgcaatgtatgccatagattctctgagacagctcgggatgaagtatttagaacgtgctgagctcaccaatttcactttccaa
aatgatattctcaaaccgttcgttattatcatgcggaatactcaaagtcagaccataaggagcctaattgttgactgcatcgttcagat
gataaaatctaaagttggaagtatcaaatcgggatggaggagtgtttttatgatatttacagcagctgcagatgacgaagttgaatc
gatagttgaaaaatcatttgagaatgttgagcaagttattctggaacactttgaccaggtgataggtgactgcttcatggattgtgtca
attgtctcatcaggtttgccaataacaaagcttcagaccggataagcctgaaagctattgcccttctcagaatatgtgaggatcggc
ttgcagagggacttatacccggtggtgttcttaagcccgttgatggcaatgaggatgaaacttttgatgtgacagagcattactggt
ttccgatgcttgccggtctatctgatctcacatctgattataggcccgaagttagaaactgtgctctggaggtgttgtttgatttgctaa
atgaaaggggaaacaagttctccacacctttctgggagagtatcttccatcgcatcttgtttccaattttgatcatgtgagtcatgct
ggaaaggaaagcttaatatcttccggggatgtaaaatttcgtgaaacaagcattcattcccttcagctcctctgcaatctcttcaata
cgttctacaaggaagtatgttttatgctgcctccacttttaagtttgctcctagactgtgcgaagaaatcagatcagacagttgtttcaa
tttcattaggagcattggttcacctcatcgaggttggaggccaccaatttagtgagggagactgggatatgctcttgaaaagcataa
gagatgcatcatacacaactcaaccgctggagctgttgaatgctttgagttttgacaatccgaaaaagaacctagttttggcagga FIG 11 SHEET 2 of 8 gacatagaggccgatgcctctgattctccacgagttgatcgtaatccggacgatattaaagataatgggaaagtgtccgcccagg
catctccaaggattggtactcatggtacttccctagaatctgggataccgcctaaggctgatggttcggaaggtcgtccatcgtcat
ctggaagggctcaaaaggatgtggatgatgtgaatctgcagcggagtcagacttttggccaaagattcatggacaatctcttcctc
cggaatctcacatctcaaccaaaaagctctgttgcagaagtgactgtaccctcctctccatataagcatgaagatcctacagagcc
tgacagcagagaagaagagagtccagcattgggagctattagaggaaaatgcatcacacaattactactacttggtgctatcaac
agcatccagcaaaaatactggagtaatttgaaaaccccacagaagattgcgattatggacatcttattctctttcatcgaatttgcttc
ttcctacaattcatattctaaccttagaacacgtatgaatcacattcccacagagaggccacctctaaaccttctccggcaagagct
ggaaggaaccaccatatatttggacgtcttgcaaaagacaacttctgggcttgcggatgatgcatctaactcggaagatagacta
gaaggtgcagcagaagaaaaattggtatcgttctgtgaacaggttctgaaagaaacatctgatctccagtccactttgggggaga
ctactaacatggatgttcatcgggtactggagctacgttctcccgtgattgtgaaggttttggaaggcatgtgcttcatgaacaaca
caatattcaggaagcacatgagagagttctaccctctgctcacgaggctcgtttgctgtgaacagatggagataagaggtgcact
agccaaccttttcaaagcacaattgaagccacttttgcaacagtaaatgatctatacgctatgatattgtggcaaagcaaaacactct
caatgtcatttacttccaacagttttttttttttttttctacattggattgatttttctcctgattaaagagcacatcccgattaaattgccag
tggtactcatacccgtatcagttgtttttttctttgcgattctttgctcccatcttattttggtttatttttagtatgatgttcgcaagtctgttgt
tcaggcatcgtttagtcacctaaaaagtattatttggtcacagagtactggttgtttcttagacattgttaacttgaatggtgttatcata
gtttcgatcaaac SEQ ID NO: 3
Q9LXK4_ARATH Guanine nucleotide-exchange-like protein [F7K15_150] [Arabidopsis thaliana (Mouse-ear cress)]
MAAGGFLTRAFDTMLKESGGKKFPDLQKAIQAYQDGSKVVTQAAPSSIVESSQA
EGGGEKTGVEADEPQKVTSAEVAQQASQSKSETINVSLANAGHTLGGAEVELVL
KPLRLAFETKNLKIFDAALDCLHKLIAYDHLEGDPGLDGGKNSAPFTDILNMVCS
CVDNSSPDSTVLQVLKVLLTAVASGKFKVHGEPLLGVIRVCYNIALNSPINQATS
KAMLTQMISIVFRRMETDIVSASSTVSQEEHVSGDTSSPKNEEITAADENEKEMT
LGDALTQAKDTTLASVEELHTLVGGADIKGLEAALDKAVHLEDGKKIKRGIELE
SMSIGQRDALLVFRTLCKMGMKEDSDEVTTKTRILSLELLQGMLEGVSHSFTKN
FHFIDSVKAYLSYALLRASVSQSSVIFQYASGIFSVLLLRFRDSLKGEIGIFFPIIVLR
SLDNSECPNDQKMGVLRYNIFLLVQMMLEKVCKDPQMLVDVYVNYDCDLEAP
NLFERMVTTLSKIAQGSQSADPNPAMASQTASVKGSSLQAENSTRNANEDSAST
GEPIETKSREDVPSNFEKAKAHKSTMEAAISEFNRNSVKGVEYLIANKLVERNP
ASVAQFLRSTSSLSKVMIGDYLGQHEEFPLAVMHAYVDSMKFSEMKFHSAIREF
LKDNPGLFKNADTAYVLAYAVIMLNTDAHNPMVWPKMSKSDFTRMNATNDPE
DCAPTELLEEIYDSIVQEEIKLKDDDTMKKLSSQRPGGEERGGLVSILNLGLPKRIS
AADAKSETEDIVRKTQEIFRKHGVKRGVFHTVEQVDIIRPMVEAVGWPLLAAFS
VTMEVGDNKPRILLCMEGFKAGIHIAYVLGMDTMRYAFLTSLVRFTFLHAPKEM
RSKNVEALRILLGLCDSEPDTLQDTWNAVLECVSRLEFIISTPGIAATVMHGSNQI
SRDGVVQSLKELAGRPAEQVFVNSVKLPSESVVEFFTALCGVSAEELKQSPARVF
SLQKLVEISYYNIARIRMVWARIWSVLAEHFVSAGSHHDEKIAMYAIDSLRQLG
MKYLERAELTNFTFQNDILKPFVIIMRNTQTAADDEVESIVEKSFENVEQVILEHF
DQVIGDCFMDCVNCLIRFANNKASDRISLKAIALLRICEDRLAEGLIPGGVLKPVD
GNEDETFDVTEHYWFPMLAGLSDLTSDYRPEVRNCALEVLFDLLNERGNKFSTP
FWESIFHRILFPIFDHVSHAGKESLISSGDVKFRETSIHSLQLLCNLFNTFYKEVCF
MLPPLLSLLLDCAKKSDQTVVSISLGALVHLIEVGGHQFSEGDWDMLLKSIRDAS
YTTQPLELLNALSFDNPKKNLVLAGDIEADASDSPRVDRNPDDIKDNGKVSAQA
SPRIGTHGTSLESGIPPKADGSEGRPSSSGRAQKDVDDVNLQRSQTFGQRFMDNL FIG 11 SHEET 3 of 8

FLRNLTSQPKSSVAEVTVPSSPYKHEDPTEPDSREEESPALGAIRGKCITQLLLLGA
INSIQQKYWSNLKTPQKIAIMDILFSFIEFASSYNSYSNLRTRMNHIPTERPPLNLLR
QELEGTTIYLDVLQKTTSGLADDASNSEDRLEGAAEEKLVSFCEQVLKETSDLQS
TLGETTNMDVHRVLELRSPVIVKVLEGMCFMNNTIFRKHMREFYPLLTRLVCCE
QMEIRGALANLFKAQLKPLLQQ

SEQ ID NO: 4
tr|Q9LXK4|Q9LXK4_ARATH Guanine nucleotide-exchange-like protein - Arabidopsis thaliana (Mouse-ear cress)
cttgataagcttgaatagctttctggagatcaggaaacttctttcctccagactccttaagcatcgtatcaaatgctcgagtcaaaaat
ccaccagccgccatctctccactatgctcgagggtgcagcctgcgtaacaacctttgaaccatatgaagacaatccaaagcagc
atcaaatatttttaagttctttgtctcaaatgcaaggcgtagaggtttcagcacaagctccacttccgctccccctaatgtgtgtccag
catttgctaaggaaacgtttatagtctcactttttgactggctagcctgctgcgctacttcagcactcgtgactttttgcggttcatctgc
ttctaccccagtttttcacctccaccttcagcttgtgaactgtctggtgatgaattatcaacacagctgcaaaccatgttcagaatgtc
ggtgaaaggtgcagaatttttccaccatccaaccccggatccccttccaaatgatcataggcaatgagtttctttgaactttcctga
agcaacagctgtaagaagaaccttcagtacttggagtacagtgctgtttagagcaatgttatagcaaactctaataactcccagca
atggctccccatgcaaatgtcagtctccattctcctgaatacaatgcttatcatctgagtcagcattgctttagaagttgcttggttaatt
gggcttaatatcagcaccgcccacaagggtatgcagctcttcaacagatgcaagagttgtgtctttagcctgagtgagtgcatctc
ctaaggtcatttctttctcatttcgtcagctgcagttatttcttcatttttagggcttgaagtgtcacctgaaacatgttcttcttgagaca
ctgtggatgatgcggaaaccgttttatcttcttgccatcttcaagatgcacagctttgtcaagggcggcttctaaacccttgcaaagg
gtacggaaaacaagcaatgcatcacgctgtccaatactcatgctctccagctcgatgcccctgaagaagctcaagagacaatata
cgggtcttggttgtgacttcatcactatcttctttcatacccatctgaaatatgacagaagactgagaaaccgacgcccgcaacaat
gcatatgagaggtaggctttcactgaatctataaagtgaaagttctttgtaaatgagtgactaactccttctaacatacctttttaaactg
tctctgaaccgcagcaaaagcacggagaagataccagatgcataatctggacgagcagaaaaatattgtacctaagaacaccc
atcttttggtcattgggacactcggagttatctaatgatcttaagacgatgatggggaaaaatataccaatttcacccatgcgctcaa
acaagtttggggcctctagatcacaatcatagtttacatacacatcaacaagcatctgaggatctttgcagactttctcaagcatcct
gaagggatgaacctttaaccgaagctgtctgcgaagccatggcaggatttggatcagcactctggacccttgagcaattttagac
aaagttgttacctcggagatggcagcctccattgtggatttatgagctttagccttctcaaagttgcttgggacatcttccctgcttttg
gtttcaattggctctccagtagaagcagagtcctcgtttgcatttcttgtactatttctgccttgctcagactcgaagtacttctcagaa
actgtgcaactgaagcaggattcctttcaaccaacttgtttgcaattagatattcgacacccttcactgaattcctgttgaactttgaga
aattcacgaatagccgaatgaaacttcatttctgaaaatttcattgaatcaacatatgcatgcatgacagcaagaggaaactcctcg
tgttggcccaggtaatcgccaatcataacctgacaagcgatgttagaaatgcatatcgcattgtatccattccaagaacataagca
atatgtattccagctttaaatccctccatgcagagaagaatccttggtttgttatcacctacttccattgtaacggagaaagcagcaa
gcagaggccacccaacagcttccaccatgggccttataatgtccacttgctcaaccgtgtgaaagactcctcttttcactccatgct
ttcggaaaatttcctgtgttttcctaacaatgtcctcagtctcagatttagcatcagctgctgatattctctttggcaaacccagattaag
aatgctgacaagaccacctctttcttctcctcctggcctttgactactgagcttcttcatggtgtcatcgtcttttagtttaatttcttcttgt
acaatagaatcatagatctcttccagaagttcagttggagcacaatcttcaggatcattagtggcattcatacgtgtgaaatctgattt
tgacatcttaggccaaaccataggattatgcgcatctgtatttaacatgataactgcataggctagaacgtaggctgtatctgcattc
ttgaaaagacccggattgtcattcggatacgtgctatattgtaataactgatctcaactagcttctgcaagctgaaaacacgggcag
gagactgcttcaattcttcagctgaaacaccacatagcgcagtaaaaaactccacaacagattcactgggcagcttgacactgttt
acaaaaacttgttcagcaggtctcccggctaactccttcaatgattgaacaaccccatccctggagatctggtttgatccatgcatta
ctgttgcagcaattccgggagtagaaataatgaattccagcctagaaacacattctaaaactgcattccaagtatcttgaagggtgt
caggttctgagtcacacaaccccagtaatatcctcaatgcttcaacatttttgctccgcatttcttttggagcatgcaagaaagtgaa
ctttgagtattccgcatgataataacgaacggtttgagaatatcattttggaaagtgaaattggtgagctcagcacgttctaaatactt
catcccgagctgtctcagagaatctatggcatacattgcaatcttttcatcatgatggctaccagcagatacgaaatgttcggcaag
gacagaccatattcttgcccagaccttgctcaacattctcaaatgatttttcaactatcgattcaacttcgtcatctgcagctgctctgc FIG 11 SHEET 4 of 8 aagccgatcctcacatattctgagaagggcaatagctttcaggcttatccggtctgaagctttgttattggcaaacctgatgagaca
attgacacaatccatgaagcagtcacctatcacctggtcaaagtgttccagaataacttgtagaacgtattgaagagattgcagag
gagctgaagggaatgaatgcttgtttcacgaaattttacatccccggaagatattaagctttcctttccagcatgactcacatgatca
aaaattggaaacaagatgcgatggaagatactctcccagaaaggtgtggagaacttgtttccccttttcatttagcaaatcaaacaa
cacctccagagcacagtttctaacttcgggcctataatcagatgtgagatcagatagaccggcaagcatcggaaaccagtaatgc
tctgtcacatcaaaagtttcatcctcattgccatcaacgggcttaagaacaccaccgggtataagtcccttatgcttttcaagagcat
atcccagtctccctcactaaattggtggcctccaacctcgatgaggtgaaccaatgctcctaatgaaattgaaacaactgtctgatc
tgatttcttcgcacagtctaggagcaaacttaaaagtggaggcagcataaaacatacttccttccgaaccatcagccttaggcggt
atcccagattctagggaagtaccatgagtaccaatccttggagatgcctgggcggacactttcccattatctttaatatcgtccggat
tacgatcaactcgtggagaatcagaggcatcggcctctatgtctcctgccaaaactaggttctttttcggattgtcaaaactcaaag
cattcaacagctccagcggttgagttgtgtatgatgcatctcttatatggagaggagggtacagtcacttctgcaacagagcttttg
gttgagatgtgagattccggaggaagagattgtccatgaatctttggccaaaagtctgactccgctgcagattcacatcatccacat
ccttttgagccccttccagatgacgatggacgacctggatgctgttgatagcaccaagtagtagtaattgtgtgatgcattttcctcta
atagctcccaatgctggactctcttcttctctgctgtcaggctctgtaggatcttcatgctctctgtgggaatgtgattcatacgtgttct
aaggttagaatatgaattgtaggaagaagcaaattcgatgaaagagaataagatgtccataatcgcaatcttctgtggggttttcaa
attactccagtatttttgcttcacaatcacgggagaacgtagctccagtacccgatgaacatccatgttagtagtctcccccaaagtg
gactggagatcagatgtttctttcagaacctgttcacagaacgataccaatttttcttctgctgcaccttctagtctatcttccgagttag
atgcatcatccgcaagcccagaagttgtcttttgcaagacgtccaaatatatggtggttccttccagctcttgccggagaaggttta
gaggtggcctgttcacagcaaacgagcctcgtgagcagagggtagaactctctcatgtgcttcctgaatattgtgttgttcatgaa
gcacatgccttccaaaacttactgttgcaaaagtggcttcaattgtgctttgaaaaggttggctagtgcacctcttatctccat SEQ ID NO: 5
oilseed_rape|CD824809 homologue to UP|Q9LXK4 (Q9LXK4) Guanine nucleotide-exchange-like protein, partial (13%) ACCESSION CD824809
LLVQMIKSKVGSIKSGWRSVFMIFTAAADDDVESIVEKSFENVEQVILEHFDQVIG
DCFMDCVNCLIRFANNKASDRISLKAIAFLRICEDRLAEGLIPGGVLKPVNTNEDE
TFDVTEHYWYPMLAGLSDLTSDFRPEVRNCALEVLFDLLNERGKKFSTPFWESIF
HRILFPIFDHVSHAGKEGLVSSGDVQFRETSIHSLQLLCNLFNTFYKEVCFMLPPL
LSLLLDCAKKSDQKV .

SEQ ID NO: 6
oilseed_rape|CD824809 homologue to UP|Q9LXK4 (Q9LXK4) Guanine nucleotide-exchange-like protein, partial (13%) ACCESSION CD824809
attgttgactgctcgttcagatgatcaaatctaaagttggaagtataaaatcgggttggaggagtgtttttatgatatttacagcagct
gcagatgacgatgttgaatccatagttgaaaaatcatttgagaatgtggagcaagttattctggaacactttgaccaggtgatcggt
gactgcttcatggattgcgtcaactgtctcatccgatttgccaataacaaagcttcagaccggataagcctgaaagctattgcctttc
tcagaatatgcgaggatcggcttgcagagggacttataccgggtggtgttctcaagcctgtcaataccaatgaggatgaaactttt
gatgtgacagagcattactggtatccgatgcttgctggtttatctgatctcacgtcagattttagacctgaagttagaaactgcgctct
ggaggtgctgtttgatttgctgaatgaaagaggcaaaaagttctccacgcctttctgggagagcatcttccatcgcatcttgtttcca
atttttgatcatgtgagtcatgctggaaaggaaggcttagtatcgtcgggggatgttcaatttcgtgaaacaagcattcattcccttca
gcttctctgtaatctctttaatacattctacaaggaagtttgttttatgctacctccacttttaagcttgctcctggactgtgcgaagaaat
cagatcagaaagttgt SEQ ID NO: 7
BTI Lycopersicon esculentum tomato|AW040716 EST283580 tomato mixed elicitor, cDNA clone cLET8M22, mRNA sequence.

VPEGLDRSQTIGQKIMGNMMDNRFIRSFTSKPKIQASDILPTSPSKLLADDAEPEA
KDEDESSMLATIRSKCITQLLLLSAIDSIQKKYWNKLKPTHKITIMDILFSVLEFAA
SYNSYSNLRLRMRQIPAERPPFNLLRQELAGTSIYLDILQKTTAGINSVRGRIN

SEQ ID NO: 8
BTI Lycopersicon esculentum tomato|AW040716 EST283580 tomato mixed elicitor, cDNA clone cLET8M22, mRNA sequence.
gttccagaaggtcttgaccgtagtcaaacaataggtcagaaaattatgggaaatatgatggacaaccgcttcatcagaagtttcac
ctctaaaccaaagattcaggcttctgatattttaccaacttcaccgtcaaagctattagctgatgatgcggagcctgaagcaaaaga
cgaggatgaaagttcaatgttggctactattaggagcaaatgcatcacacagttgttacttctcagtgcaattgatagcattcagaa
gaaatactggaacaagttaaaaccaacacacaagataactataatggacatcttgttctctgtgttagagtttgctgcatcatataatt
cgtattccaatctgagattgcggatgcgccaaatacctgctgaaaggccaccatttaatcttctccgccaggaattagcaggaactt
ccatctatcttgatatcttacagaagacgacagctgggatcaattctgtaaggggaagaatcaactgaaactacc SEQ ID NO: 9
Lycopersicon esculentum tomato|CD002362 cDNA clone LePU0380 similar to Acc# ref |NP_195533.1| ; guanine nucleotide-exchange protein -like; protein id: At4g38200.1 [Arabidopsis thaliana], mRNA sequence. ACCESSION CD002362
YSDGKDLPEDYLGALYDQIVRNEIKMKADSSVPQNKQGNSLNKLLGLDGILNLV
WKQREEKPLGANGVLVRHIQEQFKVKSGKSESVYYVIADPAILRFMVEVCWGP
MLAAFSVTLDQSDNKNATSQCLLGFRHAVHITAVMGMQTQRDAFVTSMAKFTN
LHC SEQ ID NO: 10
Lycopersicon esculentum tomato|CD002362 cDNA clone LePU0380 similar to Acc# ref |NP_195533.1| ; guanine nucleotide-exchange protein -like; protein id: At4g38200.1 [Arabidopsis thaliana], mRNA sequence. ACCESSION CD002362
Gtactccgacgggaaggatttacctgaagattatttgggtgctctttatgaccaaattgtgagaaacgagataaagatgaaagca
gattcttccgtgccacaaaacaagcaggggaatagtcttaataagctgttgggcttggatggtatactgaatctagtatggaagca
gagagaggaaaaaccactgggtgcaaacggagttctcgtgaggcatattcaagagcagtttaaagtaaaatctggaaaatctga
gtctgtctattatgttattgcagatccagctattttgagatttatggtagaagtctgctggggtcccatgcttgctgctttcagtgtcacc
ctagaccagagtgataataagaatgccacttctcaatgtttgctagggttcaggcatgctgtgcatattacagctgtgatgggtatg
cagacgcagagagatgcttttgtcacctctatggcaaagttcactaatcttcattgt SEQ ID NO: 11
trQ7XIK7 Q7XIK7_ORYSA Putative guanine nucleotide-exchange protein GEP2 [OJ1773_H01.101] [Oryza sativa (japonica cultivar-group)]
MAGAAGGFVTRAFEAMLKECTANRGKFAALQQSIQSYLDAIKGAAAAGQEEGG
DAAAAPITQVLASAGRVLEGTQAELVLQPLRLAFETKHVKLVEPALDCLHKLIA
YDHLEGDPGLEGGKNSPLFTDILNMVCGCVDNTSSDSTVLQVLKVLLNAVASNR
FRVHGEPLLGVIRVCYNIALNRRMESEQAKNFPHNFYWHYAKGDDLLKEREASP
ASVEELQSLAGGADIKGLEAVLDKAVELEDGKKVSGGIDLDTVNIIQRDALLLFR
TLCKMSMKEESDEVATKTRLLSLELLQGLLEGVSDSFTKNFHFIDSVKAYLSYAI
LRAAVSSSAVVFQYACGIFAVLLLRFRESLKGEIGVFFPLIVLRSLDSSDSPLSQRA
SVLRMLEKVCKDSQMLADMFVNYDCDLEGPNLFERMVSALSRIAQGSQNADTN
TAASSQTVSVKGSSLQSLVDWEQARRDSLKQGSVAEACENDSSARSITSDEIKSQ FIG 11 SHEET 6 of 8

EDGRNQFEIAKAHKSTMEAAISEFNRKPARGIEYLLLNKLIENNATSVAHFLKSNS
SLDKAMIGEYLGQHEEFPLAVMHAYVDSMKFSGLKFDAAIREFLKGFRLPGEAQ
KIDRIMEKFAERYCADNPGLFKNADTAYVLAYAVIMLNTDAHNPMVWPKMSKS
DFVRMNTASDAEECAPKELLEEIYDSIVQEEIKMKDDFPDSAKTNKPRRETEERG
VVNILNLALPRLKSASDTKAESEKIIKQTQALFKNQGQKRGVFHVAQQVELVRP
MLEAVGWPLLATFSVTMEEGDSKPRVVLCMEGFRAGIHLTRVLGMDTMRYAFL
TSLVRFTFLHAPKEMRSKNVEALRTLLGLADTDMDALQDTWNAVLECVSRLEYI
TSNPSIAATVMQGSNQISRESVVQSLKELSGKPAEQVFVNSVKLPSDSIVEFFTAL
CGVSAEELKQTPARVFSLQKLVEISYYNMARIRLVWARIWSVLSQHFIAAGSHHE
EKVAMYAIDSLRQLGMKYLERAELNKFTFQNDILKPFVILMRNSHSEKIRGLIVD
CIVQLIKSKVGSIKSGWRCVFMIFTAAADDENEHIVESAFENVEQVILEHFDQVVG
DCFMDCVNCLIGFANNKCTPRISLKAIALLRICEDRLAEGCIPGGAVKPVDDVPE
AHFDVTEHYWFPMLAGLSDLTLDPRPEVRHCALEVLFDLLNERGHKFSSPFWESI
FHRVLFPIFDHVRHAGRDGLSSGDDWLRDTSIHSLQLICNLFNTFYKVMYVVLPC

SEQ ID NO: 12
trQ7XIK7 Q7XIK7_ORYSA Putative guanine nucleotide-exchange protein GEP2
[OJ1773_H01.101] [Oryza sativa (japonica cultivar-group)]
cgaggtaggactggatggattgctgcagcgcggcgaacttgccgcggttggctgtgcactccttgagcatggcctcgaaggcc
cgcgtgacgaaccctcccgcggcgcccgccatatggaggcagtcgagcgcgggctcgacgagcttgacgtgcttggtctcga
aggcgaggcggagcggctgcagcaccagctcggcctgagtcccctccagcacgcgccccgccgacgccagcacctgcgtg
atgggcgccgccgccgcgtcgccgccctcctcctgtcccgccgccgccgccccccttgatggcatctgtcagaggaggtgttat
caacacaaccgcagaccatgttcaggatgtcagtaaatagaggggaatttttaccaccctctaaaccagggtcgccttctagatg
gtcataagcaataagtttctctaaatctatttgaagcaacagcattgagaagcactttcaagacttggagaacagtgctgttgagag
caatattatagcatactctaatcactccaagcaaaggttctccatgtactcgttccttcagtaaatcatctccctttgcataatgccaat
agaagttatggggaaaatttttgcctgctcagattccatccgccttaatatcagctcctcctgcaagactctgaagctcttcaacag
atgctggagatgcttcctgatactttctttccatcctcaagttcaacagccttgtcaagaacagcctccaaccccttgcagagagtcc
ggaagagcaatagtgcatcacgctgtattatgttcacagtgtccaggtctattccactgtaacagttcgagtgatagcagccttgtct
ttgtagcaacctcatcactctcttccttcatgctcatctgaaaaacaaccgcagatgaagacacagccgctcgcagaatagcatag
gaaagataggctttaactgaatcgatgaagtggaaatttttggtaaatgaatcactgactccttctagcaatcccttcagactctctcg
aaaacgaagcaatagaactgcaaatatcccacaagcgtactaaggacactggccctttggctgagtggactgtcagagctatcg
agagaccttaaaactatcagaggaaagaagacaccgatctcacccatgcgttcaaaaaggtttggcccctcaaggtcacaatcat
aatttacaaacatgtctgcaagcatttgtgaatccttgcagactttctccagcatcctgaagagatgagcctttcacagaaactgtttg
agaagatgcggcagtgtttgtatccgcattttgagatccttgtgcaatccttgagagtgcactgacctctgagattgcagcctccatt
gttgacttatgagctttagctatctcaaactgattgcgaccatcctcttggctctttatttcatcacttgttatgctccttgcagaagaatc
attttcacaagcttcggcaacactcccctgtttcaaggaatctcttcgagcttgctcccaatcaaccaatgacttatccaagctagaa
ttgctcttgagaaagtgagctacagatgttgcattattttcgatcaacttatttaataacaaatactcaatccccccttgctggtttgcgat
tgaacgctcagcaaacttttccattatgcgatcaatcttttgtgcctccccaggaaggcgaaaccctttcaagaactcacgaattgc
agcatcaaacttcaatcccgaaaatttcattgaatcaacataagcatgcatcacagcaagagggaactcctcatgttgtcccaaata
ttcaccaatcatagccgcactaaggatgtcaagaaagcatagcgcatggtgtccatcccaagaacacgagtaagatggatgcca
gccctaaacccttccatgcatagcacaaccctaggcttgctgtcaccttcctccatggtaacagaaaatgttgcaagcaaaggcc
atcctacagcttcaagcattggcctaacaagctcgacctgctgagcaacatgaaaaacacctctcttctgtccctgatttttgaaaa
gtgcttgagtctgcttaatgatttctcactttctgctttggtatcacttgctgacttcagtcttggaagagctaaattgaggatattgaca
acacccctttcttctgtttctcgtctgggtttattagtttttgctgaatcagggaaatcgtctttcatctttatctcttcctggacaatggaat
cataaatttcctccaagagctcctttggggcacattcctctgcatcactcgcagtgttcattcgtacgaaatctgattttgacattttag
gccacaccattgggttgtgggcgtcagtattcaacattataacagcataagcaagaacataagcagtatctgcatttttgaaaagtc

FIG 11 SHEET 7 of 8 caggg ttatcagcacagtaccaaacgtatccgagccatattatagtagcttatctcgacaagcttttgtaagctaaagacacgagc
aggtgtctgtttcagttcttctgcagaaacaccacaaagagcagtgaagaattcaacaatggaatcacttggtagttttacactgttt
acaaagacttgttcagcaggcttcccagacaactctttcagtgactggacaacagattctctcgatatttgatttgatccctgcata
acagttgcagcaattgaaggatttgaagtgatatattcaagcctggagacacattctaaaacagcattccaagtatcttgcaaagca
tccatatctgtgtcagctaagccaaggagggtccgtaaagcctcaacatttttactacgcatttccttaggagcatgcaaaaatgta
aacctgaacaatgcaatcaacaattagaccacggatttttcactgtgactatttctcattaaaataacaaaaggcttcaatatgtcatt
ctgaaatgtgaatttgttcaattctgcacgttccaagtacttcataccaagctgcctcaatgagtcaattgcatacatggcaactttctc
ctcgtggtggctcccagcggcaataaaatgctgtgacaagacagaccatattctcgcccacaccttgttctacattttcaaaagca
ctttcaacaatatgttcattctcatcatcagctgccgcggtgaatatcatgaacacacaacgccaacctgactttatgctgccaacttt
tgatttgatcaactctgccaaacggtcttcacatatgcgtaggagagcgatagcctttaaactaattcgaggtgtgcatttattatttg
cgaaaccaataagacagttgacgcagtccatgaagcaatcaccaacaacttgatcaaaatgctccaagataatcagcaggga
gaacaacatacattaccttgtagaaagtattgaaaaggttgcagattaactgcagagaatgaatgctggtatcacgaagccagtca
tccccagaagaaaggccatcccttccagcatgccttacatgatcaaatatgggaaataatacacgatgaaaaatgctctcccaaa
aaggtgaggagaatttatgacctctctcattcagaagatcaaacaacacttcaagtgcacagtgtctaacttctggtctggggtcta
aagttaaatctgataggccagctagcataggaaaccaataatgctcagtaacatcaaaatgggcctctggaacatcatcaacagg
tttaacagcaccaccaggaatgcaacc

SEQ ID NO: 13
AtMIN2 Atlg16190 NM_101486 Arabidopsis thaliana damaged DNA binding (AT1G16190) mRNA, complete cds.
MKLTVKTLKGSHFEIRVLPTDTIMAVKKNIEDSQSKDNYPCGQQLLIHNGKVLK
DETTLVENKVTEEGFLVVMLSKSKTASSAGPSSTQPTSTTTSTISSTTLAAPSTTQS
IAVPASNSTPVQEQPTAQSDTYGQAASTLVSGSSIEQMVQQIMEMGGGSWDKET
VTRALRAAYNNPERAVDYLYSGIPETVTIPATNLSGVGSGRELTAPPPSGGPNSSP
LDLFPQEAVSDAAGGDLGTLEFLRGNDQFQQLRSMVNSNPQILQPMLQELGKQN
PQLLRLIQENQAEFLQLLNEPYEGSDGDVDIFDQPDQEMPHSVNVTPEEQESIERL
EAMGFDRAIVIEAFLSCDRNEELAANYLLEHSADFED SEQ ID NO: 14
AtMIN2 Atlg16190 NM_101486 Arabidopsis thaliana damaged DNA binding (AT1G16190) mRNA, complete cds.
atgaagctcactgttaagactctcaagggtagccattttgagattagggttcttcccaccgacacgataatggcggtgaagaagaa
tattgaagattcacaaagcaaagacaactatccttgtgggcagcaattactgattcacaatggaaaggttttgaaagatgaaactac
cttggtggagaacaaggttaccgaggagggtttcttgtcgtgatgcttagcaagagcaaaactgcaagttcagctggtccctctt
ctactcagcctacttctaccacgacatctaccatatcttcaaccacgcttgcagctccgtcgacaacccagtctattgctgtgccgg
cttcaaattctactcccgttcaagaacaaccaacggcacaaagtgacacctatggtcaagctgcttcaactttagttagtggcagta
gtattgagcaaatggttcaacaaataatggaaatgggaggaggcagttgggacaaagaaacggttactcgtgcacttcgtgcag
catataacaaccctgagagagcagtggattatctatattctggaattcctgaaacagtaaccattccagcaactaatttatctggagt
aggatctggtagagaacttactgctcctcctccctctggaggccctaattcatctcctctggatttgtttccccaggaagcagtttctg
atgcagcaggtggagatcttggaacgcttgaattcctcagaggcaatgatcagttccaacaattacgctccatggtcaattccaac
ccccagattctgcagcctatgcttcaagagctcggaaagcagaacccccaacttctgaggctaattcaagagaaccaagccgaa
tttcttcagttactaaacgagccctacgaaggatctgacggggatgtggatatcttcgatcaacctgatcaagaaatgccccactca
gtcaacgttacccctgaagagcaagaatcaattgaacggcttgaggcaatggggtttgatagagcaatagtcatagaagccttcc
tttcctgtgaccgtaacgaggaattggctgcaaactatctactagagcactcagcagattttgaagactga SEQ ID NO: 15
AtMIN3 Atlgl8490 Arabidopsis thaliana unknown protein (AT1G18490) mRNA, complete cds. ACCESSION NM_101707
MLSRLFKAGEKVLSNLVSKKDIYMASRNQEKSPKVQELYDLCKETFTGKAPSPA
SMAIQKLCSVLDSVSPADVGLEEVSQDDDRGYGVSGVSRFNRVGRWAQPITFLD
IHECDTFTMCIFCFPTSSVIPLHDHPEMAVFSKILYGSLHVKAYDWVEPPCIITQDK
GVPGSLPARLAKLVSDKVITPQSEIPALYPKTGGNLHCFTALTPCAVLDILSPPYK
ESVGRSCSYYMDYPFSTFALENGMKKVDEGKEDEYAWLVQIDTPDDLHMRPGS
YTGPTIRV SEQ ID NO: 16
AtMIN3 Atlgl8490 Arabidopsis thaliana unknown protein (AT1G18490) mRNA, complete cds. ACCESSION NM_101707
attcgaacaattaccgacacacaaaaagtttgaagagaaaaacaaaaaatgttgtcgagattgttcaaggcaggtgaaaaggtttt
gtcgaatctcgttagcaagaaagacatttacatggcgtcgaggaatcaggagaaatctcccaaagtgcaagagctttacgacctc tgcaaagagactttcactggcaaagctccttctcctgcttccatggctatccaaaagctatgctctgtgttggactcagttagtcctg
cagatgttgggcttgaagaggtatctcaagacgatgatcgaggctatggagtttctggggttagccgtttcaatagagtaggacga
tgggcacaaccgataacattcttagacattcatgaatgtgatactttacaatgtgtattttctgcttcccaacgtcttcagtgatcccat
tgcatgatcatccagagatggctgtgtttagtaaaatcctctatggatcacttcatgttaaagcttacgattgggtcgaacctccatgt
attatcacacaagataaaggcgtccccggttctcttccagcaaggttggcgaaattggtgagtgacaaagttataacgcctcagtc
tgagataccggcgttgtacccaaagactggaggcaatctccattgcttcactgcgttgactccatgtgctgtgctcgacattctctc
acctccttacaaagaaagtgttggcaggagttgcagttactacatggactatccgttttccactttcgcattggagaacggaatgaa
gaaggtggatgaaggaaaggaagacgaatacgcatggcttgtacagattgacacgcccgatgatcttcacatgcgtcccggat
catatactggtccaactatcagagtctagatatttgtggtttgttttgtagcaaagtagagcaactcttgtaacattccaagataagttt
ctggagaagatatcaatacgatttcagattaaagatgaactctttgtttagtccatgtccacttctcagttctcacacgcattcaagca
aatgaaactgcggaaaactacaaatagatcggcaatgagaaatgttaagatttcatttc SEQ ID NO: 17
AtMIN4 At2g14910 Arabidopsis thaliana unknown protein (AT2G14910) mRNA, complete cds ACCESSION NM_201735
MATTTLSSFSLSLPQLLHKPTKPLPFLFLLPRFNRRFRSLTITSSSTTSSNNFSSNCG
DDGFSLDDFTLHSDSRSPKKCVLSDLIQEIEPLDVSLIQKDVPVTTLDAMKRTISG
MLGLLPSDRFQVHIESLWEPLSKLLVSSMMTGYTLRNAEYRLFLEKNLDMSGGG
LDSHASENTEYDMEGTFPDEDHVSSKRDSRTQNLSETIDEEGLGRVSSEAQEYIL
RLQSQLSSVKKELQEMRRKNAALQMQQFVGEEKNDLLDYLRSLQPEKVAELSE
PAAPEVKETIHSVVHGLLATLSPKMHSKFPASEVPPTETVKAKSDEDCAELVENT
SLQFQPLISLTRDYLARLLFWLEELPSSTSLSLAC SEQ ID NO: 18
AtMIN4 At2g14910 Arabidopsis thaliana unknown protein (AT2G14910) mRNA, complete cds ACCESSION NM_201735
gttccggattgttttgtggctgacgataaaacagagcacaaaagaagaaaaatctagggtttgtttgagactaagaggaagagaa
agaagaagaagagaaaattcgtacaattccgccattaaagcttcaacctttaatggcgacaacgactctttcttccttctctctttctct
tcctcaacttctccataaacccacaaagcctcttcctttcctcttccttcttcctcgattcaatcggagatttcgaagtctcactatcactt
cttcttctacaacttcttcaaacaatttcagtagtaattgtggcgatgatggcttctctcttgacgatttcactctccattctgattctcgat
cacctaaaaaatgtgtcctttctgatcttatacaagagattgagccattagatgtgagtttgattcagaaggatgttccagttactactt
tggatgcaatgaaaagaacaatctcaggcatgttgggtcttcttccatctgataggtttcaggttcatattgagtcactttgggaacct
ttgtctaagcttttggtatcttcaatgatgactgggtatacattgaggaatgctgaatatcggctttttcttgaaaaaaaccttgatatga
gtggtggaggcttggacagccacgcttcggaaaacactgaatatgatatggaagggacgtttcctgatgaagatcatgtttcatcc
aaaagggatagcagaactcagaacctttctgaaacgattgatgaagaaggtttgggcagagtatcctctgaagctcaagaatata
tcttacgtttgcagtcacaattgtcttctgtgaaaaaggaattacaagaaatgagacgaaagaacgctgccctacaaatgcaacaa
tttgttggcgaagagaagaatgatttgttggactatttacgatctttgcaacctgagaaggtagctgagttgtcagaacctgcggctc
ctgaggtgaaagagactattcattctgttgttcacggtcttttggcaactctatcaccgaagatgcactctaagtttccagcatcaga
agttccacctactgaaacggtgaaagcaaaaagtgatgaagattgtgctgaacttgtagagaacacttcgttgcagtttcagcctct
tatctcactgactcgagactaccttgctcgtcttctcttctggttagaagaactgcctagctctacctctctttctcttgcttgctaggatt
tagatggatatcgtatatttacgtataaactacaaacacaaatagatcctctcaaaagaaactttagtgtttctttggttgtattaccaaa
gacatcttataccacagtgtctgctttctattgctaggtgcatgctattgggacattatctcagaggtttggaatatcgaatggaactg
atggaggtcctgtctttgacatgcgatgccaatgggtctgagaacgtcgcttgaagctatctttatacatctcaacattgtcttacatg
cgtatcagcggccttgacactcttaaaccaacaaagtgggcaagtgactaggagacaggccagcctttgagctttagctcttgca
catatatgcagctttgtgctggcctgaaaattcatgggcgaggtaaagtgtaacataagaaatcacttctactaaaattatttttcgttg
cattatcgtgtgatggatctgcaaagcaataaagctaagtgtaattgtattcaggaatatactcgtttggtcattaagtatagtttgtcct FIG 12 SHEET 2 of 9 acaattattggctcagaaatagcaatctcgagcgggttcgtttggcctggcccgtcccttttaggcttggctcaagagtttaccttag
tcaagccttagttttatttttcgccagtttacgcttgttggataccgtaaacaaaatccaacacttccgttattcgataaacaagcaattt
t SEQ ID NO: 19
AtMIN6 At2g47710 Arabidopsis thaliana unknown protein (AT2G47710) mRNA, complete cds.ACCESSION NM_130339
MATGDGKSVMVVGVDDSEQSTYALEWTLDRFFAPYAPNYPFKLFIVHAKPNAV
SAVGLAGPGTAEVVPYVDADLKHTAAKVVEKAKAICQSRSVHGAVIEVFEGDA
RNILCEVVDKHHASILVVGSHGYGAIKRAVLGSTSDYCAHHAHCSVMIVKKPKI
KV SEQ ID NO: 20
AtMIN6 At2g47710 Arabidopsis thaliana unknown protein (AT2G47710) mRNA, complete cds.ACCESSION NM_130339
accaaaactctctttttctgtgcaaacactttggaggattcttctaggcttctttctaccacaaacacaagagcgcgttttcttcacgcc
ggcgaacaacgtcagagtcatggccaccggagatgggaaatcggtgatggtcgtcggagttgacgacagcgagcagagcac
ttacgccttggagtggacgctcgatcgtttcttcgctccttacgctcccaattatccttttaagctcttcatcgtccacgccaaacctaa
cgccgtctccgccgttggtctcgctggtcccggaactgcggaggttgtaccttatgttgatgctgatctgaagcataccgctgcta
aggttgtcgagaaagccaaagcaatttgtcagagcagatcggttcatggcgcggtgatcgaagttttcgaaggtgatgcaagga
atatcctatgtgaagttgtagataagcatcatgcttctattcttgttgtgggaagccatggatatggagctatcaagagggcggttct
cgggagtacgagtgactactgcgctcatcatgctcattgctcggtgatgatcgtgaagaagcctaagatcaaggtctgaaaccta
agggaaggctactcggtcaaagcaaagtctctgcatagtcttctaattcagaagaataaagtgaaataatattagcttgatgtgaaa
caacgattcaagacaatatacatttgcatctatatgtgtaattgtttactacatacaatgttttggtatccttagacaatcaatattcgtgt
gttataatatgctaatctttctcata SEQ ID NO: 21
AtMIN9 At5g64180 NM_125814 648 bp Arabidopsis thaliana unknown protein (AT5G64180) mRNA, complete cds.
MEEQFGGSDERWKGSLENITEMASNLDSLQKLLLKKAVFVEEDTFSRASLVSEQ
ARTIKVLEQRVQTLERELDAAITAAAHARSEKRQAESSQKAAESRAQDVTKELE
NTTKVFKLHMEELRGMQEQISKRDNEIKLLEAIIQTLGGKERLGKSDVNG SEQ ID NO: 22
AtMIN9 At5g64180 NM_125814 648 bp Arabidopsis thaliana unknown protein (AT5G64180) mRNA, complete cds.
Tttagttgtttttccgatcgatctgcgagtcgagtagttttttatttgccggcgccgggagagatcctttgatctttttccgatggagg
agcaattcggcgggagcgatgagagatggaaaggatcattggagaatataacggagatggcatcgaatctcgattcgcttcaga
aacttctcctcaagaaagcagtcttcgttgaagaagacactttctctagagcttctctcgtctccgagcaagcccgaacaatcaag
gttcttgagcaaagagtacaaacactagaaagagaactagatgctgccattacagctgctgctcatgctcggtctgagaaacgcc
aagctgagtcctctcaaaaggctgctgaatcacgtgcccaagatgtcacaaaagagcttgaaaacaccacaaaggttttcaagct
gcatatggaagagcttcgaggaatgcaagaacagatatccaaacgcgataacgagatcaaactcttagaagctataatccaaac
gctcggcggcaaagagcggttgggaaaaagcgacgtgaatggatgatgatgatgcgtttttcacttgtaaaggtttgtactcctg
agtttgtggagatgtatcacttcgaagataaatgtatttttgtctgtc

SEQ ID NO: 23

AtMIN10 Arabidopsis thaliana putative 14-3-3 protein GF14kappa grf8 (At5g65430) mRNA, complete cds.
MATTLSRDQYVYMAKLAEQAERYEEMVQFMEQLVSGATPAGELTVEERNLLSV
AYKNVIGSLRAAWRIVSSIEQKEESRKNEEHVSLVKDYRSKVETELSSICSGILRL
LDSHLIPSATASESKVFYLKMKGDYHRYLAEFKSGDERKTAAEDTMIAYKAAQD
VAVADLAPTHPIRLGLALNFSVFYYEILNSSEKACSMAKQAFEEAIAELDTLGEES
YKDSTLIMQLLRDNLTLWTSDMQEQMDEA SEQ ID NO: 24
AtMIN10 Arabidopsis thaliana putative 14-3-3 protein GF14kappa grf8 (At5g65430) mRNA, complete cds.
cagaaatttcctccgatttcaaaattttccggtgaaatcgaaaaaaaaagcgagatcttcttctctaatggcgacgaccttaagcag
agatcaatatgtctacatggcgaagctcgccgagcaagccgagcgttacgaagagatggttcaattcatggaacagctcgtaag
tggagctacaccggccggtgagctgaccgtagaagagaggaatcttctctcggtcgcgtataagaacgtgattggatctcttcgt
gcggcatggagaatcgtgtcttcgattgagcaaaaggaagagagcaggaagaacgaagaacacgtgtcgcttgttaaggatta
cagatctaaagttgagactgagctttcttcgatctgttctgggattctcaggttacttgattcgcatctaattccttcagctactgccagt
gagtctaaggtttttacctgaagatgaaaggagattatcatcgttatttggctgagtttaaatctggtgatgagaggaaaactgctg
ctgaagatactatgatcgcttacaaagctgctcaggacgttgcagttgctgatctagcacctacacatccgatcaggcttggtttgg
ctcttaacttctcagtgttttactacgagattctcaactcttcagagaaagcttgtagcatggcgaaacaggcttttgaagaagccatt
gctgagctggacacattgggagaggagtcatacaaggacagtactctcatcatgcagttgctaagggacaatctaaccctttgga
cctccgatatgcaggagcagatggatgaggcctgaaggtctaatggaagaaaagacggttatgtaatgtacctgcaaccgtaac
cgaaaatctgagttcaacctcctttgctgtaaaacttgtcgaaaagaaaagtttgttttttatgacagattatgtgcacagctttggtgt
tatctgctgctctgtatcaactctgtttttgtttggtaatttatcctcatctttgctccaaaaaaaaaaaaaaa SEQ ID NO: 25
AtMIN11 At5g64180 NM_125814 648 bp Arabidopsis thaliana unknown protein (At5g66420) mRNA, complete cds.
GIPIIGGGAGTGISAKFEEAGGIDLIVIYNSGRFRMAGRGSLAGLLPFADANAVVL
EMANEVLPVVKAVPVLAGVCATDPFRRMDYFLKQLESIGFVGVQNFPTVGLFD
GNFRQNLEETGMGYGLEVKMISEAHKMGLLTTPYAFNPKEGEEMAKAGADIIV
AHMGLTTSGNIGAKTAVSVEESVVRVQAIADAARRFNPDIIVLCHGGPISGPEEA
EFVLKRTQGCVHGFYGASSMERLPVEQAITNTVQKYKSISIK SEQ ID NO: 26
AtMIN11 At5g64180 NM_125814 648 bp Arabidopsis thaliana unknown protein (At5g66420) mRNA, complete cds.
ggaataccaataattgggggaggtgctggtactggaatatctgcaaagtttgaggaagctggtgggattgatttgatagtgatata
caactctggacgttttcgtatggctggaagaggatccttagcaggcttacttccatttgctgatgccaatgcagtcgtgcttgaaatg
gcaaatgaagttttacctgtagtgaaggcggtgcctgttctggctggggtgtgcgcaacagatccatttcgtcgtatggactatttc
ctgaagcagttggagtccattgggttcgttggtgtccagaactttccaactgttggtctctttgatggtaattttagacaaaatcttgag
gagacaggaatgggatatggtcttgaagttaaaatgatctcagaagcgcacaaaatggggctgttgaccactccatatgctttcaa
cccaaaagaaggagaagaaatggcaaaagcgggagctgatatcatagtagcccacatgggtctaacgacatccggaaatattg
gggcgaaaaccgcagtttcagtggaagaaagcgttgttcgtgtacaagctattgcagatgctgctcgtagattcaacccagacatt
atcgtcctctgccacggaggtccgatatcgggtccagaagaggcagagtttgtgttgaagagaacacagggttgtgtccatggct
tctacggagcatcaagcatggaaaggctacctgtagaacaagcaataacaaacactgttcaaaaatacaagtccatatcgatcaa
gtgaagtcaaaataataagttcacttagaaacctttatctttggtgtttctagtatatttgcatgtgttgtggcctatgggtgtggatgttt ccttttgttgcatggtttttttttctggtcatctttgattgcctctgcaggatcttatatgatctctagttctgtattacacgtttttgtattttaa
taaagttcatagtgctcaactcttatcaaataaaaaa SEQ ID NO: 27
At1g01960 Arabidopsis thaliana guanyl-nucleotide exchange factor (AT1G01960) mRNA, complete cds. ACCESSION NM_100076
MASTEVDSRLGRVVIPALDKVIKNASWRKHSKLAHECKSVIERLRSPENSSPVAD
SESGSSIPGPLHDGGAAEYSLAESEIILSPLINASSTGVLKIVDPAVDCIQKLIAHGY
VRGEADPTGGPEALLLSKLIETICKCHELDDEGLELLVLKTLLTAVTSISLRIHGDS
LLQIVRTCYGIYLGSRNVVNQATAKASLVQMSVIVFRRMEADSSTVPIQPIVVAE
LMEPMDKSESDPSTTQSVQGFITKIMQDIDGVFNSANAKGTFGGHDGAFETSLPG
TANPTDLLDSTDKDMLDAKYWEISMYKSALEGRKGELADGEVEKDDDSEVQIG
NKLRRDAFLVFRALCKLSMKTPPKEDPELMRGKIVALELLKILLENAGAVFRTSD
RFLGAIKQYLCLSLLKNSASNLMIIFQLSCSILLSLVSRFRAGLKAEIGVFFPMIVLR
VLENVAQPDFQQKMIVLRFLDKLCVDSQILVDIFINYDCDVNSSNIFERMVNGLL
KTAQGVPIVDRNLEEGSHPVENGKGDGGHGGFERSDSQSELSSGNSDALAIEQRR
AYKLELQEGISIFNQKPKKGIEFLIKANKVGDSPEEIAAFLKDASGLNKTLIGDYL
GEREDLSLKVMHAYVDSFEFQGMEFDEAIRAFLRGFRLPGEAQKIDRIMEKFAER
FCKCNPKDFSSADTAYVLAYSVILLNTDAHNPMVKSKMTADGFIRNNRGIDDGK
DLPEEYLRALYERISRNEIKMKDDGLGPQQKQPTNSSRLLGLDTILNIVVPRRGDD
MNMETSDDLIRHMQERFKEKARKSESVYYAASDVIILRFMVEVCWAPMLAAFS
VPLDQSDDAVITTLCLEGFHHAIHVTSVMSLKTHRDAFVTSLAKFTSLHSPADIK
QKNIEAIKAIVKLAEEEGNYLQDAWEHILTCVSRFEHLHLLGEGAPPDATFFAFPQ
TESGNSPLAKPNSVPAIKERAPGKLQYAASAMIRGSYDGSGVAGKASNTVTSEQ
MNNLISNLNLLEQVGDMSRIFTRSQRLNSEAIIDFVKALCKVSMDELRSPSDPRVF
SLTKIVEIAHYNMNRIRLVWSSIWHVLSDFFVTIGCSDNLSIAIFAMDSLRQLSMK
FLEREELANYNFQNEFMKPFVVVMRKSGAVEIRELIIRCVSQMVLSRVDNVKSG
WKSMFMIFTTAAHDAHKNIVFLSFEMVEKIIRDYFPHITETETTTFTDCVNCLVAF
TNCKFEKDISLQAIAFLQYCARKLAEGYVGSSLRRNPPLSPQGGKIGKQDSGKFL
ESDEHLYSWFPLLAGLSELSFDPRAEIRKVALKVLFDTLRNHGDHFSLALWERVF
ESVLFRIFDYVRQDVDPSEDDSTDQRGYNGEVDQESWLYETCSLALQLVVDLFV
NFYKTVNPLLKKVLMLFVSLIKRPHQSLAGAGIAALVRLMRDVGHQFSNEQWLE
VVSCIKEAADATSPDFSYVTSEDLMEDVSNEDETNDNSNDALRRRNRQLHAVVT
DAKSKASIQIFVIQAVTDIYDMYRMSLTANHMLMLFDAMHGIGSNAHKINADLL
LRSKLQELGSSLESQEAPLLRLENESFQTCMTFLDNLISDQPVGYNEAEIESHLISL
CREVLEFYINISCSKEQSSRWAVPSGSGKKKELTARAPLVVAAIQTLGNMGESLF
KKNLPELFPLIATLISCEHGSGEVQVALSDMLQTSMGPVLLRSCC SEQ ID NO: 28
At3g60860 Arabidopsis thaliana mRNA for guanine nucleotide exchange factor - like protein, partial cds, clone: RAFL07-72-J20.
PLGDESIELPVLKTLLSAINSISLRIHGKCLLLVVRTCYDIYLGSKNVVNQTTAKAS
LIQILVIVFRRMEADSSTVPIQPIVVAELMEPLEKSDADGTMTQFVQGFITKIMQDI
DGVLNPTMSGSGSGSGSGGQDGAYGTTTVETTNPTDLLDSTDKDMLDAKYWEI
SMYKSALEGRKGELTDGDAERDDDLEVQIENKLRRDACLVFRALCKLSMKAPP
KESSADPQSMRGKILALELLKILLENAGAVFRTSEKFSADIKQFLCLSLLKNSAST FIG 12 SHEET 5 of 9

LMIIFQLSCSIFISLVARFRAGLKAEIGVFFPMIVLRVVENVAQPNFQQKMIVLRFL
DKLCLDSQILVDIFLNYDCDVNSSNIFERMVNGLLKTAQGVPPGTATTLMPPQEA
AMKLEAMKCLVAILKSMGDWLNKQLRLPVSNSLNKSDVIEIDLGPGSPQLANGN
ADESADGSDTYSESSGGTSDALAIEQRRAYKLELQEGISLFNRKPTKGIEFLINAG
KVGESPEEIAGFLKDASVMTPTY

SEQ ID NO: 29
At4g38200 Arabidopsis thaliana mRNA for guanine nucleotide-exchange protein-like, partial cds, clone: RAFL09-95-N13. ACCESSION AK227209
CLSRIEHLQLLGEGAPSDASYFASTETEEKKALGFPNLKKKGALQNPVMMAVVR
GGSYDSSTIGPNMPGLVKQDQINNFIANLNLLDQIGSFQLNNVYAHSQRLKTEAI
VAFVKALCKVSMSELQSPTDPRVFSLTKLVEIAHYNMNRIRLVWSRIWSILSDFF
VSVGLSENLSVAIFVMDSLRQLSMKFLEREELANYNFQNEFLRPFVIVMQKSSSA
EIRELIVRCISQMVLSRVSNVKSGWKSVFKVFTTAAADERKNIVLLAFETMEKIV
REYFSYITETEATTFTDCVRCLITFTNSTFTSDVSLNAIAFLRFCALKLADGGLVW
NEKGRSSSPSTPVTDDHSPSTQNFMDADENISYWVPLLTGLSKLTSDSRSAIRKSS
LEVLFNILKDHGHIFSRTFWIGVFSSVIYPIFNSVWGENDLLSKDEHSSFPSTFSSHP
SEVSWDAETSAMAAQYLVDLFVSFFTVIRSQLSSVVSLLAGLIRSPAQGPTVAGV
GALLRLADELGDRFSENEWKEIFLAVNEAASLTLSSFMKTLRTMDDIPDEDTLSD
QDFSNEDDIDEDSLQTMSYVVARTKSHITVQLQVVQVVTDLYRIHQQSLLASHV
TVILEILSSISSHAHQLNSDLILQKKVRRACSILELSEPPMLHFENDTFQNYLDILQA
IVTNNPGVSLELNVESQLMTVCMQILKMYLKCTLFQGDELEETRQPKNWILPMG
AASKEEAAARSPLVVAVLKALRELKRDSFKRYAPNFFPLLVELVRSEHSSSQVPQ
VLSTVFHTCMGAMMDE SEQ ID NO: 30
At4g35380 Arabidopsis thaliana guanyl-nucleotide exchange factor (AT4G35380) mRNA, complete cds. ACCESSION NM_119704
MSTSQTLGGATRCGRIIGPSLDKIIKNAAWRKHTYLVSSCKSVLDKLESLPDDFH
DPSSVVSGLAASDADSVLQPFLLSLETAYSKVVEPSLDCAFKLFSLSILRGEIQSSK
QDSILFKLVNAVSKVGAIAEEPIQLAVLRVLLAAVRSPCILIRGDCLLHVVKTCYN
IYLGGLSGTTQICAKSVLAQMMLVIFTRSEEDSLDVSVKTIYVNELLTFTDKSVNE
GSSVYFCQGFVNEVMAAGQGSPLPPPDVIQILLQNPETETVMTPDSPSFRGYVAN
GEGDSETGDMSKVRQDAFLLFKNLCKLSMRFSSKENNDDQIMVRGKTLSLELLK
VIIDNGGSVWRTNESFINAVKQYLCLSLLKNSAVSIMSIFQLQCAIFMSLLSKLRS
VLKAEIGIFFPMIVLRVLENVLQPSYLQKMTVLNLLDKMSQDPQLMVDIFVNYD
CDVESSNILERIVNGLLKTALGPPTGSSTTLSPAQDSTFRNDSVKCLVNLAKAMG
NWMDQQLKVNETVWPKGSQVYASMDSNASQISELEGTISDCDSQPDTSNPEAY
DASMLEQRRAYKIELQKGISLFNRKPSKGVEFLISTKKIGSSPEEVASFLMKTAGL
NGTVIGDYLGERDELPLKVMHAYVDSFNFEKKDFVEAIRFFLRGFRLPGEAQKID
RIMEKFAEHYWKCNPGSFTSADTAYVLAYSVIMLNTDAHNNMVKDKMTKADF
VRNNRGIDDGKDLPEEYLGSLYDRVVKEEIRMNSDTLAPQNKQVNGLNKLLGL
DGILNLVSWMQPDEKPHGANGRLIRDIQEQFQAKPEKSESVYHTVTDISILRFILE
VSWGPMLAAFSVTIDQSDDRLATSLCLQGFRYAVHVTAVMGMQTQRDAFVTS
MAKFTNLHCAADMKQKNVDAVKAIITIAIEDGNHLHGSWEHILTCLSRIEHLQLL
GEVSPSEKRYVPTKKAEVDDKKALGFPNLKKRGSFQNPSVMAVVRGGSYDSTSL FIG 12 SHEET 6 of 9

VKSVPKLVTPEQIKSFIANLNLLDQIGNFELNHVYANSQRLNSEAIVSFVKALCKV
SMSELQSPTDPRVFSLTKLVETAHYNMNRIRLVWSRIWNVLSDFFVSVGLSENLS
VAIFVMDSLRQLSMKFLEREELANYHFQHEFLRPFVVVMQKSSSAEIRELIVRCV
SQMVLSRVSNVKSGWKNVFTVFTTAALDERKNIVLLAFETIEKIVRDHFHCIIETE
ITVYADCIRCLITFTNSKFEGDIGFNTIEFLRFCALKLEEGGLVLNEKLKNNTISAL
KEDFSDTQSFTDLDEQVSYWIPLLTGLCKQVSDPRPAIRKRSIEVLFHILMDHGHL
FTRPFWTGIFSSIILPVFNNIRSKTDMLFEESVDSPSSASLDTEETTWDVETSTLAL
QLLVDLLVKFFRSVRSQLPSVVSIIVGFIKSPFQGSTGSGISVLLHLADGLARSASE
DEWREIFLALKEAASLTFAGFMKVLRTMDDIEDVETLSGQSVNIGDLDDDSLHIM
SYVVSRTKKHIDVLSQIVEVVSDLYRRNQFSLSASHVDILADIFSCIASHAQQLNT
DTVLRRKFKRACSVQNLTEPQLLNFENEAYKSYMMFLQDMVTCNPNVSKELDL
ESRLVTECAKIVKIYLKCTDPQQQEQQQRKPVLWVLPMESDRVEEATARTSLLV
SSLEALCSLEAESLKKHVSSFFPLLVDLVRTEHCSPQVPYVLSNVLKSCIGPILA

SEQ ID NO: 31
At1g13980 Arabidopsis thaliana GN (GNOM) (GN) mRNA, complete cds.
ACCESSION NM_101264

MGRLKLHSGIKAIEEEPEDFECTDSSNTTTLACMIDTEIAAVLAVMRRNVRWGGR
YMSGDDQLEHSLIQSLKALRKQVFSWNQPWHTISPMLYLQPFLDVIRSDETGAPI
TSIALSSVYKILNLNVIDQNTANIEDAMHLVVDSVTSCRFEVTDPASEEVVLMKIL
QVLLACMKNKASVMLSNQHVCTVVNTCFRVVHQAGMKGELLQRVARHTMHE
LVRCIFSHLPDVERTETTLVNRAGSIKQEKAGVDSDYAIVSKPVEDGNANSEYDV
ENSMATFATGAQSLMDDGPVGPGSRKPASPYDLHIMTEPYGVPSMVEIFHFLCSL
LNVVEHVGMGSRSNTIAFDEDVPLFALNLINSAIELGGSSIRHHPRLLSLIQDELFR
NLMQFGLSMSPLILSMVCSIVLNLYQHLRTELKLQLEAFFSCVILRLAQGKYGPS
YQQQEVAMEALVNFCRQKSFMVEMYANLDCDITCSNVFEELSNLLSKSTFPVNC
PLSAMHILALDGLIAVIQGMAERISNGLTGLDLGPVHLDEYTPFWMVKCDNYSD
PNHWVSFVRRRKYIKRRLMIGADHFNRDPKKGLEFLQGTHLLPDKLDPQSVACF
FRYTAGLDKNLVGDFLGNHDEFCVQVLNEFAGTFDFQYMNLDTALRLFLETFRL
PGESQKIQRVLEAFSERYYMQSPEILANKDAALVLSYSIIMLNTDQHNVQVKKK
MTEEDFIRNNRHINGGNDLPREFLSELFHSICNNEIRTTPEQGAGFPEMTPSRWIDL
MHKSKKTAPYILADSRAYLDHDMFAIMSGPTIAAISVVFDHAEHEDVYQTCIDGF
LAIAKISACHHLEDVLDDLVVSLCKFTTLLNPSSVDEPVLAFGDDAKARMATITIF
TIANKYGDYIRTGWRNILDCILRLHKLGLLPARVASDAADESEHSSEQGQGKPLA
NSLSSAHLQSMGTPRRSSGLMGRFSQLLSLDTEEPRSQPTEQQLAAHQRTLQTIQ
KCHIDSIFTESKFLQAESLLQLARALIWAAGRPQKGTSSPEDEDTAVFCLELLIAIT
LNNRDRIVLLWQGVYEHIATIAQSTVMPCNLVDKAIFGLLRICQRLLPYKESLAD
ELLRSLQLVLKLDARVADAYCEQIAIEVSRLVKANANHIRSQAGWRTITSLLSITA
RHPEASESGFDAVSFVMSEGTHLYPANYVLCVDAARQFAESRVGQSERSIRALD
LMGDSLEFLAKWALSAKENMGEEDFGKMSQDIGEMWLRLVQGLRKVCLDQRE
DVRNHALQSLQKCLGGVDGINLAHSMWSQCFDKVIFTVLDDLLEIAAGSQKDYR
NMEGTLLLAIKLLSKVFLQQLQELSQLSTFCKLWLGVLTRMEKYMKVKVRGKK
SDKLQESVPELLKNILLVMKTKGVLLQRSALGGDSLWELTWLHVNNIAPSMRLE
LFPDQESSQLGDDETVSNGLSSPENTTGS

SEQ ID NO: 32
At5g39500 Arabidopsis thaliana unknown protein (AT5G39500) mRNA, complete cds.
ACCESSION NM_123312
MGYQNHPSGSNSFHGEFKRCHSKPSKGAVASMINSEIGAVLAVMRRNVRWGVR
YIADDDQLEHSLIHSLKELRKQIFSWQSNWQYVDPRLYIQPFLDVILSDETGAPIT
GVALSSVYKILTLEVFTLETVNVGEAMHIIVDAVKSCRFEVTDPASEEVVLMKIL
QVLLACVKSKASNGLSNQDICTIVNTCLRVVHQSSSKSELLQRIARHTMHELIRCI
FSQLPFISPLANECELHVDNKVGTVDWDPNSGEKRVENGNIASISDTLGTDKDDP
SSEMVIPETDLRNDEKKTEVSDDLNAAANGENAMMAPYGIPCMVEIFHFLCTLL
NVGENGEVNSRSNPIAFDEDVPLFALGLINSAIELGGPSFREHPKLLTLIQDDLFCN
LMQFGMSMSPLILSTVCSIVLNLYLNLRTELKVQLEAFFSYVLLRIAQSKHGSSYQ
QQEVAMEALVDLCRQHTFIAEVFANFDCDITCSNVFEDVSNLLSKNAFPVNGPLS
AMHILALDGLISMVQGMAERVGEELPASDVPTHEERYEEFWTVRCENYGDPNF
WVPFVRKVKHIKKKLMLGADRFNRDPNKGLQYLQGVHLLPEKLDPKSVACFFR
YTCGLDKNVMGDFLGNHDQFCIQVLHEFAKTFDFQNMNLATALRLFVGTFKLS
GEAQKIHRVLEAFSERYYEQSPHILIDKDAAFVLAYSIILLNTDQHNAQVKTRMT
EEDFIRNNRTINGGADLPREYLSEIYHSIRHSEIQMDEDKGTGFQLMTASRWISVI
YKSKETSPYIQCDAASHLDRDMFYIVSGPTIAATSVVFEQAEQEDVLRRCIDGLL
AIAKLSAYYHLNSVLDDLVVSLCKFTPFFAPLSADEAVLVLGEDARARMATEAV
FLIANKYGDYISAGWKNILECVLSLNKLHILPDHIASDAADDPELSTSNLEQEKPS
ANPVPVVSQSQPSAMPRKSSSFIGRFLLSFDSEETKPLPSEEELAAYKHARGIVKD
CHIDSIFSDSKFLQAESLQQLVNSLIRASGKDEASSVFCLELLIAVTLNNRDRILLI
WPTVYEHILGIVQLTLTPCTLVEKAVFGVLKICQRLLPYKENLTDELLKSLQLVL
KLKAKVADAYCERIAQEVVRLVKANASHVRSRTGWRTIISLLSITARHPEASEAG
FEALRFIMSEGAHLLPSNYELCLDAASHFAESRVGEVDRSISAIDLMSNSVFCLAR
WSQEAKNSIGETDAMMKLSEDIGKMWLKLVKNLKKVCLDQRDEVRNHAISML
QRAIAGADGIMLPQPLWFQCFDSAVFILLDDVLTFSIENSRKTLKKTVEETLVLAT
KLMSKAFLQSLQDISQQPSFCRLWVGVLNRLETYMSTEFRGKRSEKVNELIPELL
KNTLLVMKATGVLLPGDDIGSDSFWQLTWLHVNKISPSLQSEVFPQEELDQFQR
RNAKPEDPPVPGNEV SEQ ID NO: 33
At5g19610 Arabidopsis thaliana unknown protein (AT5G19610) mRNA, complete cds.
ACCESSION NM_121966
MDRIAVRAKRKELGISCMLNTEVGAVLAVIRRPLSESYLSPQETDHCDSSVQQSL
KSLRALIFNPQQDWRTIDPSVYLSPFLEVIQSDEIPASATAVALSSILKILKIEIFDEK
TPGAKDAMNSIVSGITSCRLEKTDLVSEDAVMMRILQVLTGIMKHPSSELLEDQA
VCTIVNTCFQVVQQSTGRGDLLQRNGRYTMHELIQIIFSRLPDFEVRGDEGGEDS
ESDTDEIDMSGGYGIRCCIDIFHFLCSLLNVVEVVENLEGTNVHTADEDVQIFALV
LINSAIELSGDAIGQHPKLLRMVQDDLFHHLIHYGASSSPLVLSMICSCILNIYHFL
RKFMRLQLEAFFSFVLLRVTAFTGFLPLQEVALEGLINFCRQPAFIVEAYVNYDC
DPMCRNIFEETGKVLCRHTFPTSGPLTSIQIQAFEGLVILIHNIADNMDREEDEGNE
EDDNNSNVIKPSPVEIHEYIPFWIDKPKEDFETWVDHIRVRKAQKRKLAIAANHF
NRDEKKGLEYLKYNYLVSDPLDPMALASFFRFTPGLDKTMIGDYLGDPDELHLS
VLRSFTHTFEFTGMNLDTALRTFLESFRLPGESQKIERMIEAFSERFYDQQSSDIFA
SKDTVHILCYSLIMLNTDQHNPQVRRKMTEDEFIRNNRAINAGNDLPKEYLSELF FIG 12 SHEET 8 of 9

QSIATNAFALSTHSGPVEMNPNRWIELMNRTKTTQPFSLCQFDRRIGRDMFATIA
GPSIAAVSAFFEHSDDDEVLHECVDAMISIARVAQYGLEDILDELIASFCKFTTLL
NPYTTPEETLFAFSHDMKPRMATLAVFTLANTFGDSIRGGWRNIVDCLLKLRKL
QLLPQSVIEFEINEENGGSESDMNNVSSQDTKFNRRQGSSLMGRFSHFLALDNVE
ESVALGMSEFEQNLKVIKQCRIGQIFSKSSVLPDVAVLNLGRSLIYAAAGKGQKF
STAIEEEETVKFCWDLIITIALSNVHRFNMFWPSYHEYLLNVANFPLFSPIPFVEKG
LPGLFRVCIKILASNLQDHLPEELIFRSLTIMWKIDKEIIETCYDTITEFVSKIIIDYSA
NLHTNIGWKSVLQLLSLCGRHPETKEQAVDALIGLMSFNASHLSQSSYAYCIDCA
FSFVALRNSSVEKNLKILDLMADSVTMLVKWYKTASTDTANSYSPASNTSSSSS
MEENNLRGVNFVHHLFLKLSEAFRKTTLARREEIRNRAVTSLEKSFTMGHEDLG
FTPSGCIYCIDHVIFPTIDDLHEKLLDYSRRENAEREMRSMEGTLKIAMKVLMNV
FLVYLEQIVESAEFRTFWLGVLRRMDTCMKADLGEYGDNKLQEVVPELLTTMIG
TMKEKEILVQKEDDDLWEITYIQIQWIAPALKDELFPDEEI

SEQ ID NO: 34
Q887D0_PSESM Pseudomonas syringae pv. tomato str. DC3000 type III effector
HopM1 AAO54897; AE016853.1
MISSRIGGAGGVELSRVNQQHDTVPAQTAHPNAVTAGMNPPLTPDQSGSHATES
SSAGAARLNVAARHTQLLQAFKAEHGTAPVSGAPMISSRAALLIGSLLQAEPLPF
EVMAEKLSPERYQLKQFQGSDLQQRLEKFAQPGQIPDKAEVGQLIKGFAQSVAD
QLEHFQLMHDASPATVGQHAKADKATLAVSQTALGEYAGRASKAIGEGLSNSIA
SLDEHISALDLTLQDAEQGNKESLHADRQALVDAKTTLVGLHADFVKSPEAKRL
ASVAAHTQLDNVVSDLVTARNTVGGWKGAGPIVAAAVPQFLSSMTHLGYVRLS
TSDKLRDTIPETSSDANMLKASIIGMVAGIAHETVNSVVKPMFQAALQKTGLNER
LNMVPMKAVDTNTVIPDPFELKSEHGELVKKTPEEVAQDKAFVKSERALLNQKK
VQGSSTHPVGELMAYSAFGGSQAVRQMLNDVHQINGQTLSARALASGFGGAVS
ASSQTLLQLKSNYVDPQGRKIPVFTPDRAESDLKKDLLKGMDLREPSVRTTFYSK
ALSGIQSSALTSALPPVTAQAEGASGTLSAGAILRNMALAATGSVSYLSTLYTNQ
SVTAEAKALKAAGMGGATPMLDRTETALNNIRHPNRESLPHTFQKSTLSGIPRV
AENAYHMGRGALQLPTQMAVDTVRVVDEGVLNAVASAREALKQPTKDDDALR
ALEEGLLDPR SEQ ID NO: 35
Q887D0_PSESM Pseudomonas syringae pv. tomato str. DC3000 type III effector
HopM1 AAO54897; AE016853.1
atgatcagttcgcggatcggcggggccggtggcgtcgaactcagccgggtaaaccagcagcacgatactgttcccgcccagacagctcacccaaatgca
gtcactgcaggcatgaatccgccgctgactcccgatcagtcagggtcacacgcgacagaaagctcgtctgccggcgcggcgcggctgaatgtcgcggct
cgacacacacagcttttgcaggccttcaaggctgagcatgggacggctccggtcagcggcgcgccgatgatcagttcgcgtgctgcgttgttgatcggtag
tctgctgcaggccgagcctttgccttttgaagtcatggccgagaaattgtctcctgagcgctatcaactgaagcagtttcagggctcggacttgcagcagcgg
ctggaaaaattcgcccagccgggtcagataccggataaagccgaggtcgggcaactgatcaagggttttgctcagtcggtcgctgatcaactggagcactt
tcaactgatgcatgacgcttcgcccgcaacggtaggccagcatgcaaaagcggacaaggcgacgcttgccgtcagtcagactgcccttggcgaatacgc
cggtcgtgcaagcaaggcaatcggcgaaggcctgagcaacagcatcgcgtcgctggatgagcacatcagtgcgctggatctcactctgcaagatgccga
acagggcaacaaggagtctctgcacgctgacaggcaggcgctggtcgacgccaaaaccaccctggtaggtttgcacgccgatttcgtcaagtcgccgga
ggccaagcgccttgcttcggtcgccgcacatacgcaactggacaacgtcgtcagcgatctcgtcactgcccgtaacacggtgggtggctggaaaggtgca
gggccgattgtcgcggctgcggttccgcagttcttgtcttcaatgacacacttgggttatgtgcgtttgtccaccagcgacaagctgcgagacacgattcccg
agaccagcagcgacgccaacatgctcaaggcttcgataatcgggatggtggcgggcattgctcacgagacggtcaacagcgtggtcaagccgatgtttca
ggccgccttgcagaagactggcctcaacgaacgcctgaacatggtgccaatgaaggctgtggataccaatacggttattcctgaccccttcgagctgaaaa
gcgaacacggtgagctggtcaaaaaaacgcccgaggaagtcgctcaggacaaggcgttcgtgaaaagtgaacgcgcgctgctgaaccagaagaaggtt
cagggttcgtccacccatccggtaggtgagctgatggcttacagtgccttcggtggttctcaggctgtgcgccagatgctcaacgatgttcaccagatcaatg
ggcagacgctgagtgcaagagctctggcatccggttttggcggggcggtgtctgccagttcgcaaacgctgctgcaattgaagtcgaattatgtcgacccg
caagggcgcaaaattccggtatttaccccggaccgcgccgagagcgatctgaaaaaggacctgctcaaaggtatggacctgcgcgagccgtcggtacgc
accacgttctacagcaaggctctttcgggtattcagagttctgcactgacctcggcactgccgcctgtgaccgctcaggctgaaggcgcaagtggcacgctc
agtgcgggggctattttgcgcaacatggccctggcagcgacgggttcggtgtcctatctgtccacgttgtacaccaaccagtcggttaccgcagaagccaa
ggcgttgaaagcggcaggcatgggcggtgcaacacctatgctggaccgtaccgagacggctttgaataacatccgtcatccgaacagggagtctctgcca
catacgttccagaagagcacgttgagcggtatcccacgagtcgcggaaaacgcctatcacatgggacgaggcgcattgcagttgcctacccagatggccg
tggatacggttcgggtcgtggatgaaggtgtgttgaacgcagtcgcgtcagcacgcgaggcgcttaagcagccgacaaaagacgatgacgcattgaggg
cacttgaagagggcttgcttgacccgcgttaa SEQ ID NO: 36
Pseudomonas syringae pv. syringae B728a type III effector HopM1
tr|Q4ZX82|Q4ZX82_PSEU2 Q4ZX82_PSEU2 AAY36240

MIGTRVGGSGSTEIVQANQPQPSAAVAQAHPHAVSPSSNPPLTASQSAAQAPESS
AAGAARLPVAPRHLPTLEKFRAEQPTVQGTSTPTISANAALLIGSLLQSEKLPFEV
MAARLSPERYALQQFHGSDLQQMLGRFAEPGHLPGKAETEQLIKGFARSLADQL
EHFQLMHDATAEAFGPGGLRDRNTLAVSQAALGEYAGRASKSIEAGLNHSLAVL
DERIAALDSQLEGATEDSRPVLLMDRQALETARAMLSDLHVDFCKSPEAKRLSA
VAAHTQMDALIDKLNVDRSSVGGWKGIGPIVAAAVPQFMVSMLHLGYIRTATS
DAMKDAVPEKSADASMKRALAVGLTAGVAHEGVTNLLKPMVQAGFQKAGLN
ERLNMVPLKGIDTDSVIPDPFELKNDNGALVRKTPEEAAEDKAFVASERAVLNQ
KKVQVSSTHPLGEMIPYGAFGGGQAVRQMLNDFNLLNGQTLSARAVTSGIAGAI
SATTQTIAQLNSTYVDPRGRKIPVFTPDRANADLGKDLAKGLDLREPAVRTAFYS
KAVSGVQSAALNGALPSVAVQPQGASGTLSAGNIMRNMALAATGSVSYLSTLY
ANQSVTAEAKALKEAGMGGATPMVARTETALSNIRHPDRASLPHTFQPDTLGG
VPRAVENAYHMARGALQLPTQVVVDTVRVVEDGVASGVSSLRDAHKPAETSSP
TADDAAAVELTAMEEGRRR

SEQ ID NO: 37
Pseudomonas syringae pv. syringae B728a type III effector HopM1 Q4ZX82_PSEU2
AAY36240
atgattggcacacgagtcggcggatcaggcagtaccgaaatcgttcaggcgaaccagccgcagccgtctgccgctgtcgcccaggctcatccacacgcg
gtaagcccgagcagcaacccgccgctgaccgccagccagtcggccgcgcaagcgccggaaagctcggcggccggtgccgctcgcctgccagtcgcg
ccgcgacatctgccgacattggagaagtttcgtgccgaacagcccaccgtacaaggcacttccacgccgactatcagcgctaacgcggccctgctgatcg
gcagtctgttgcagtctgaaaaactgcccttcgaggtcatggccgcccgtttgtcgcctgagcgttatgcgttgcagcagtttcacggctccgatttacagcaa
atgctcggacgattcgctgagccagggcatctgccaggcaaggccgagaccgaacaactgatcaagggctttgcccggtcgctcgcagaccagctgga
gcacttccagctcatgcatgacgcgacggctgaggcattcggccccggagggctgcgcgaccgcaacacactggcggtcagtcaagcggcgcttggcg
aatacgccggtcgggcgagtaaatccatcgaagcggggctgaaccacagtctcgcggtgctggacgagcgcatcgccgcgctggacagccagttggag
ggcgccactgaggacagcagaccggttttgctgatggacaggcaggcgctggaaacggccagggcgatgctgagcgacctgcacgtcgacttctgcaa
atcgcctgaagccaagcggttgagtgccgttgccgctcacacgcaaatggatgctctgatcgacaagctgaacgttgatcgcagctcggtcggcggctgg
aaggggatcggtccgatcgtcgcggcagcggtgccgcagtttatggtgtccatgctccacctggggtatatccgcacggccaccagtgacgcgatgaaag
atgccgttcccgaaaaaagcgccgacgccagcatgaagagggccctggccgtaggactgactgccggggtggctcacgagggcgttaccaacctcttg
aagccgatggtgcaggccgggtttcagaaagccggcctcaacgagcggctgaatatggtgccgctcaagggtattgataccgactcggtgattcccgacc
ctttcgagttgaagaacgacaacggcgcactggtcagaaaaacgcctgaggaagccgctgaggacaaagccttcgtcgcaagcgagcgagcggttttga
atcagaaaaaggttcaggtttcgtctacccatccactgggtgagatgatcccctacggcgcctttggtggcgggcaggcggtacgccagatgctcaatgatt
tcaatctgctcaatggccagaccctgtcggccagagcggtgacctccgggatcgccggggccatatcagccaccacccagaccattgcacagctgaactc
gacctatgtcgatccgcgcgggcgcaagatcccggtcttcaccccggaccgcgccaatgccgacctgggcaaggacctggccaaaggcctggaccttc
gcgaaccggcggtacgcaccgcgttctacagcaaggctgtttcaggtgtgcagagcgcagcgctgaacggcgcgctaccatcggttgccgtccagcccc
aaggtgcatccggcacgctcagcgcggggaatatcatgcgcaacatggcgctggcggcaaccggttcggtgtcttacctgtcgaccctgtatgccaacca
gtcggtcacggccgaggccaaggccctgaaagaggcgggcatgggcggcgcaacgccaatggtagctcgcactgaaaccgccctgagcaacatccg
ccatccggacagagcttcactgccgcatacgttccagccggataccctgggtggcgtccccagggccgtggaaaacgcctatcacatggcccggggcgc
gctgcaattaccgacccaggtggtggtcgatacggtgcgtgtcgtggaagacggcgtagcaagcggggtgtcctcgttgcgcgatgcacataaaccagc
ggaaacatcatcgccaacagctgatgacgccgctgctgtcgaactgacggcgatggaggagggccgccgacgctga SEQ ID NO: 38
HopPtoM-like protein [Pseudomonas viridiflava] ACCESSION AAT96166; AY597277
LP23.1a pathogenicity island PAI-Region-1
MINSRVGGSGDIQMVAVRTEEGNPSITSAHPNAVTPSNNPPLLPRQMGQHLEPSL
ESHAANLGIALRHTELLATFQAEQASTRSTDAPQVSAHAALLIGGMLEEANGHA
SETGKVGFEVMAERLCGPHLALESFQSSDVKLLLEKLTNKDEIPDKAEVGQLLK
GHAGAIADQLEHFQLMHNASSVHQGECSAPDRKTFEVSQAALGEYAGRASKAIS
SVLSEKTADLDKRLADVDKQLEGMAEGGEKSRLLTQKETLGEAKTMLADIQND
FSKSPQAKHLKSVAAHARFDAQLKELNADRAGMGFLQGSGRVIAAAIPQFLSSM FIG 13 SHEET 2 of 3

THLGFIRSATNDEFRAAVPGSSSDASMLEATVIGLVAGIAHEGVTNLVKPMVQSG
LQASGLDKRLGMAPLKGVDTESVIPDPLEFKSQDGVMVKKSDEELTAEKAQVK
AQRAVFEQKKVQVSSTHPLGELIPYMSFGGGQAIRQLLHDFNQINGQTVTARAL
ASGMAGAVSASAQALYQMKATYTDPQGRQIPVFTTDKATSELGKELAKGLDPR
DATVRTSFYSKAVSGIQSAALTAELPAIAAAGVNSGLSAGRIAGNMALAALGSVS
YLSSLYANQSVTAEGKALKAAGEGGATPILERTEVAFTNVRRPNRESLPHTFSSD
QLVGLPRMAENTYHRARGVLQAPSQIAVDVLRAVDDGVRSSFSSLQDKLTSQFQ
RQTTATPPPHEAAVDNPVVTESVVSPEPEPGPKMMNVQQPRNGAIDDDALRMLE
EGILPQTTSQPQRTPQQQRTPQPPRTAQPQRAPQPRAQQSAPVAPPYDPPLEAME
AGFLKPAPSNDPSR

SEQ ID NO: 39
HopPtoM-like protein [Pseudomonas viridiflava] ACCESSION AAT96166; AY597277
LP23.1a pathogenicity island PAI-Region-1 atgattaattcacgcgtagggggatcaggcgacatacaaatggttgcggtgagaacggaggagggtaatccgtccattacctctgctcacccgaatgcggt
cactcccagcaacaatcccccgttactcccaaggcaaatgggtcaacaccttgagccctctctggagtcgcatgcggcgaacctgggtatagcgttgcgcc
acactgagttgctggcgacgtttcaggctgagcaggcgagcacacgctcaaccgatgcaccacaggtcagtgcgcatgcggcgctattgattggaggcat
gctcgaagaggccaacggtcacgcttccgaaaccggcaaggtgggctttgaggtcatggcagagcgcttgtgcgggccgcaccttgcgctggagagttt
ccagtccagtgacgtcaaactcctgctcgagaagctcactaataaggacgagataccggacaaggcagaggtcgggcaactgctcaaaggccatgccgg
tgcgatcgccgatcaacttgagcattttcagctgatgcacaacgcttccagcgtgcaccaaggtgaatgctcggctcccgaccgaaagacctttgaagtcag
ccaggctgcgttgggcgaatacgctggacgtgcgagcaaagcgatttccagcgtactgagcgagaaaactgcagatctggacaagcgccttgcggacgt
ggacaaacagctcgagggtatggctgaaggcggggaaaaatccagacttttgacccagaaagagacgcttggcgaagccaaaaccatgctggccgaca
ttcagaacgatttttcgaaatcgcctcaggcaaagcatctgaaatccgttgctgctcatgcgcgattcgacgcgcagctcaaagagctgaacgcggatcgtg
ccggaatgggatttctgcaaggctcgggacgggtcatagccgctgcgattccccagtttctttcatcaatgacgcacttgggctttatccgctctgccaccaac
gatgagttcagagcggcggtgccaggctcaagcagcgacgccagtatgctggaagccactgtgatagggctggtcgcagggatcgctcatgaaggcgtc
accaacctggtgaagccgatggtgcaatccggcttgcaggcgtcaggccttgataagcgcctgggcatggcgccgctcaaaggcgtcgataccgaatcg
gtgattcctgatccgcttgaattcaagtcgcaagacggtgtgatggtcaaaaagtccgacgaggaactgacggccgagaaagcgcaggtcaaagcgcag
cgcgcggtgtttgaacagaagaaggttcaagtgtcttctacgcatccgctcggcgaactgatcccctatatgagttttggcggcggtcaggcaatacgccaa
ctgttgcatgatttcaatcagatcaacggtcagacggtcactgccagggcgttggcttcagggatggccggtgcagtgtcggcctcggctcaggcgctttat
cagatgaaggccacctacaccgatccgcaagggcgacagattccggtattcaccaccgacaaagccaccagtgaactgggcaaggaactggccaaggg
attggacccgcgcgatgccaccgttcggacttcgttctacagcaaggctgtttcgggtatccagagtgctgcgttgactgcagagctgccagcaatagcggc
ggctggcgtcaatagtgggctgagtgcaggcaggatcgcgggcaatatggctctggccgcgctgggttcggtatcttatttgtcctcgctgtacgccaatca
gtcggttacggctgaaggaaaggcgttgaaggccgctggcgagggcggagcgaccccgattctggagcgtaccgaagtcgcgtttaccaacgttcgtcg
tccgaacagagagtcactcccgcatacgttctcttctgatcagttggtaggcttgcctcgtatggcagagaacacctaccaccgtgccagggcgtgttgca
agcacccagtcaaattgctgtcgacgtgctgcgcgctgttgacgatggcgtgcgcagcagcttctcgtcgctgcaggataaactcacgagccagtttcaac
gccagacgacggcgacgccacctccccacgaagcggctgtcgacaacccggtcgtcacagagtccgttgtatcgcctgaacctgagccagggccaaaa
atgatgaacgttcagcagccgagaaacggtgcgatcgacgacgacgctttacgaatgctcgaagaggggatcctgccgcagacaacgtcgcagccaca
gcgcacgccacagcaacaacgaacgccacagccgccacgaacggcgcagccacagcgtgcgcctcagcccagggcgcaacaatctgctccagtcgc
acctccctatgacccgccgctggaggccatggaagcgggctttttaaagccagccccaagcaatgatccttcacgttga FIG 13 SHEET 3 of 3

| SEQ ID NO:XX | Name | Primer Direction | 5' – 3' | Cut site |
|---|---|---|---|---|
| SEQ ID NO: **40** | $HopM1_{1-100}$ | Sense primer | GGCTCGAGACCATGGGGCATCATCATCATCAT CATATCAGTTCGCGGATCGGC | *Xho*I site underlined |
| SEQ ID NO: **41** | $HopM1_{1-100}$ | Antisense primer | GGACTAGTTTAGGCCATGACTTCAAAAGGCAA AGG | *Spe*I site underlined |
| SEQ ID NO: **42** | $HopM1_{1-200}$ | Sense primer | GGCTCGAGACCATGGGGCATCATCATCATCAT CATATCAGTTCGCGGATCGGC | *Xho*I site underlined |
| SEQ ID NO: **43** | $HopM1_{1-200}$ | Antisense primer | GGACTAGTTTAGCTCAGGCCTTCGCCGATTGCC | *Spe*I site underlined |
| SEQ ID NO: **44** | $HopM1_{1-300}$ | Sense primer | GGCTCGAGACCATGGGGCATCATCATCATCAT CATATCAGTTCGCGGATCGGC | *Xho*I site underlined |
| SEQ ID NO: **45** | $HopM1_{1-300}$ | Antisense primer | GGACTAGTTTAAGACAAGAACTGCGGAACCGC | *Spe*I site underlined |
| SEQ ID NO: **46** | $HopM1_{1-400}$ | Sense primer | GGCTCGAGACCATGGGGCATCATCATCATCAT CATATCAGTTCGCGGATCGGC | *Xho*I site underlined |
| SEQ ID NO: **47** | $HopM1_{1-400}$ | Antisense primer | GGACTAGTTTACTCGGGCGTTTTTTGACCAGC TC | *Spe*I site underlined |
| SEQ ID NO: **48** | $HopM1_{1-500}$ | Sense primer | GGCTCGAGACCATGGGGCATCATCATCATCAT CATATCAGTTCGCGGATCGGC | *Xho*I site underlined |
| SEQ ID NO: **49** | $HopM1_{1-500}$ | Antisense primer | GGACTAGTTTAGTCCGGGGTAAATACCGG | *Spe*I site underlined |
| SEQ ID NO: **50** | $HopM1_{1-600}$ | Sense primer | GGCTCGAGACCATGGGGCATCATCATCATCAT CATATCAGTTCGCGGATCGGC | *Xho*I site underlined |
| SEQ ID NO: **51** | $HopM1_{1-600}$ | Antisense primer | GGACTAGTTTATGCACCGCCCATGCCTGCCGC | *Spe*I site underlined |
| SEQ ID NO: **52** | $HopM1_{1-712}$ | Sense primer | GGCTCGAGACCATGGGGCATCATCATCATCAT CATATCAGTTCGCGGATCGGC | *Xho*I site underlined |
| SEQ ID NO: **53** | $HopM1_{1-712}$ | Antisense primer | GGACTAGTTTAACGCGGGTCAAGCAGCCCTC | *Spe*I site underlined |

Fig. 14 A

| | | | | |
|---|---|---|---|---|
| SEQ ID NO: **54** | HopM1$_{101-712}$ | Sense primer | GGCTCGAGACCATGGGGCATCATCATCATCAT CATCTGCTGCAGGCCGAGCCTTTGCC | *Xho*I site underlined |
| SEQ ID NO: 55 | HopM1$_{101-712}$ | Antisense primer | GCACTAGTTTAACGCGGGTCAAGCAAGCCCTC | *Spe*I site underlined |
| SEQ ID NO: **56** | HopM1$_{201-712}$ | Sense primer | GGCTCGAGACCATGGGGCATCATCATCATCAT CATGCCGGTCGTGCAAGCAAGGC | *Xho*I site underlined |
| SEQ ID NO: 57 | HopM1$_{201-712}$ | Antisense primer | GCACTAGTTTAACGCGGGTCAAGCAAGCCCTC | *Spe*I site underlined |
| SEQ ID NO: **58** | HopM1$_{301-712}$ | Sense primer | GGCTCGAGACCATGGGGCATCATCATCATCAT CATGGGCCGATTGTCGCGGCTGCG | *Xho*I site underlined |
| SEQ ID NO: **59** | HopM1$_{301-712}$ | Antisense primer | GCACTAGTTTAACGCGGGTCAAGCAAGCCCTC | *Spe*I site underlined |
| SEQ ID NO: **60** | HopM1$_{401-712}$ | Sense primer | GGCTCGAGACCATGGGGCATCATCATCATCAT CATAAAAGCGAACACGGTGAGCTGG | *Xho*I site underlined |
| SEQ ID NO: **61** | HopM1$_{401-712}$ | Antisense primer | GCACTAGTTT AACGCGGGTCAAGCAAGCCCTC | *Spe*I site underlined |
| SEQ ID NO: **62** | HopM1$_{501-712}$ | Sense primer | GGCTCGAGACCATGGGGCATCATCATCATCAT CATGACCCGCAAGGGCGCAAAATTCCG | *Xho*I site underlined |
| SEQ ID NO: **63** | HopM1$_{501-712}$ | Antisense primer | GCACTAGTTTAACGCGGGTCAAGCAAGCCCTC | *Spe*I site underlined |
| SEQ ID NO: **64** | HopM1$_{601-712}$ | Sense primer | GGCTCGAGACCATGGGGCATCATCATCA TCATCATGAAGCCAAGGCGTTGAAAGCGGC | *Xho*I site underlined |
| SEQ ID NO: **65** | HopM1$_{601-712}$ | Antisense primer | GCACTAGTTTAACGCGGGTCAAGCAAGCCCTC | *Spe*I site underlined |
| SEQ ID NO: **66** | AtMIN2 | Sense primer | AATTCTCGAGATGAAGCTCACTGTTAAGACTC | *Xho*I site underlined |
| SEQ ID NO: **67** | AtMIN2 | Antisense primer | ATACTAGTCTAGGCATAATCTGGCACATCATA AGGGTAGTCTTCAAAATCTGCTGAGTGC | *Spe*I site underlined |
| SEQ ID NO: **68** | AtMIN7 | Sense primer | AATTGTCGACATGGCGGCTGGTGGATTTTTGA C | *Sal*I site underlined |

Fig. 14 B

| | | | | |
|---|---|---|---|---|
| SEQ ID NO: 69 | AtMIN7 | Antisense primer | TAGGTACCCTAGGCATAATCTGGCACATCATAAGGGTACTGTTGCAAAAGTGGCTTCAATTG | *Kpn*I site underlined |
| SEQ ID NO: 70 | AtMIN10 | Sense primer | TTCCCTCGAGTTCAAAATTTTCCGGTGAAATC | *Xho*I site underlined |
| SEQ ID NO: 71 | AtMIN10 | Antisense primer | TTACTAGTCTAGGCATAATCTGGCACATCATAAGGGTAGGCCTCATCCATCTGCATATCG | *Spe*I site underlined |
| SEQ ID NO: 72 | AtMIN12 | Sense primer | AATTCTCGAGTCGAAGCACACTTCTCTGTTTC | *Xho*I site underlined |
| SEQ ID NO: 73 | AtMIN12 | Antisense primer | AAACTAGTCTAGGCATAATCTGGCACATCATAAGGGTACTTTAATCCATCAAGGCCTGGT | *Spe*I site underlined |
| SEQ ID NO: 74 | Full-length HopM1 | Sense primer | GGAATTCATGATCAGTTCGCGGATCGGC | *Eco*RI site underlined |
| SEQ ID NO: 75 | Full-length HopM1 | Antisense primer | CCTGCTCGAGTGACGGATGTTATTCAAAG | *Xho*I site underlined |
| SEQ ID NO: 76 | $HopM1_{1-300}$ | Sense primer | GGAATTCATGATCAGTTCGCGGATCGGC | *Eco*RI site underlined |
| SEQ ID NO: 77 | $HopM1_{1-300}$ | Antisense primer | GGCCCTCGAGCTTACCAGCCACCCACCG | *Xho*I site underlined |
| SEQ ID NO: 78 | AtMIN7 | Sense primer | CGCCCAGCATATGCCAAGGATTGGTACTC | *Nde*I site underlined |
| SEQ ID NO: 79 | AtMIN7 | Antisense primer | TGAATTCTTACTGTTGCAAAAGTGGCTTC | *Eco*RI site underlined |

Fig. 14 C

SEQ ID NO: 80
$HopM1_{1-100}$
MISSRIGGAGGVELSRVNQQHDTVPAQTAHPNAVTAGMNPPLTPDQSGSHATESSSAGA
ARLNVAARHTQLLQAFKAEHGTAPVSGAPMISSRAALLIGS

SEQ ID NO: 81
$HopM1_{1-200}$
MISSRIGGAGGVELSRVNQQHDTVPAQTAHPNAVTAGMNPPLTPDQSGSHATESSSAGA
ARLNVAARHTQLLQAFKAEHGTAPVSGAPMISSRAALLIGSLLQAEPLPFEVMAEKLSPE
RYQLKQFQGSDLQQRLEKFAQPGQIPDKAEVGQLIKGFAQSVADQLEHFQLMHDASPA
TVGQHAKADKATLAVSQTALGEY

SEQ ID NO: 82
$HopM1_{1-300}$
MISSRIGGAGGVELSRVNQQHDTVPAQTAHPNAVTAGMNPPLTPDQSGSHATESSSAGA
ARLNVAARHTQLLQAFKAEHGTAPVSGAPMISSRAALLIGSLLQAEPLPFEVMAEKLSPE
RYQLKQFQGSDLQQRLEKFAQPGQIPDKAEVGQLIKGFAQSVADQLEHFQLMHDASPA
TVGQHAKADKATLAVSQTALGEYAGRASKAIGEGLSNSIASLDEHISALDLTLQDAEQG
NKESLHADRQALVDAKTTLVGLHADFVKSPEAKRLASVAAHTQLDNVVSDLVTARNT
VGGWKGA

SEQ ID NO: 83
$HopM1_{1-400}$
MISSRIGGAGGVELSRVNQQHDTVPAQTAHPNAVTAGMNPPLTPDQSGSHATESSSAGA
ARLNVAARHTQLLQAFKAEHGTAPVSGAPMISSRAALLIGSLLQAEPLPFEVMAEKLSPE
RYQLKQFQGSDLQQRLEKFAQPGQIPDKAEVGQLIKGFAQSVADQLEHFQLMHDASPA
TVGQHAKADKATLAVSQTALGEYAGRASKAIGEGLSNSIASLDEHISALDLTLQDAEQG
NKESLHADRQALVDAKTTLVGLHADFVKSPEAKRLASVAAHTQLDNVVSDLVTARNT
VGGWKGAGPIVAAAVPQFLSSMTHLGYVRLSTSDKLRDTIPETSSDANMLKASIIGMVA
GIAHETVNSVVKPMFQAALQKTGLNERLNMVPMKAVDTNTVIPDPFEL

Fig. 14 D

SEQ ID NO: 84
HopM1$_{1-500}$
MISSRIGGAGGVELSRVNQQHDTVPAQTAHPNAVTAGMNPPLTPDQSGSHATESSSAGA
ARLNVAARHTQLLQAFKAEHGTAPVSGAPMISSRAALLIGSLLQAEPLPFEVMAEKLSPE
RYQLKQFQGSDLQQRLEKFAQPGQIPDKAEVGQLIKGFAQSVADQLEHFQLMHDASPA
TVGQHAKADKATLAVSQTALGEYAGRASKAIGEGLSNSIASLDEHISALDLTLQDAEQG
NKESLHADRQALVDAKTTLVGLHADFVKSPEAKRLASVAAHTQLDNVVSDLVTARNT
VGGWKGAGPIVAAAVPQFLSSMTHLGYVRLSTSDKLRDTIPETSSDANMLKASIIGMVA
GIAHETVNSVVKPMFQAALQKTGLNERLNMVPMKAVDTNTVIPDPFELKSEHGELVKK
TPEEVAQDKAFVKSERALLNQKKVQGSSTHPVGELMAYSAFGGSQAVRQMLNDVHQI
NGQTLSARALASGFGGAVSASSQTLLQLKSNYV

SEQ ID NO: 85
HopM1$_{1-600}$
MISSRIGGAGGVELSRVNQQHDTVPAQTAHPNAVTAGMNPPLTPDQSGSHATESSSAGA
ARLNVAARHTQLLQAFKAEHGTAPVSGAPMISSRAALLIGSLLQAEPLPFEVMAEKLSPE
RYQLKQFQGSDLQQRLEKFAQPGQIPDKAEVGQLIKGFAQSVADQLEHFQLMHDASPA
TVGQHAKADKATLAVSQTALGEYAGRASKAIGEGLSNSIASLDEHISALDLTLQDAEQG
NKESLHADRQALVDAKTTLVGLHADFVKSPEAKRLASVAAHTQLDNVVSDLVTARNT
VGGWKGAGPIVAAAVPQFLSSMTHLGYVRLSTSDKLRDTIPETSSDANMLKASIIGMVA
GIAHETVNSVVKPMFQAALQKTGLNERLNMVPMKAVDTNTVIPDPFELKSEHGELVKK
TPEEVAQDKAFVKSERALLNQKKVQGSSTHPVGELMAYSAFGGSQAVRQMLNDVHQI
NGQTLSARALASGFGGAVSASSQTLLQLKSNYVDPQGRKIPVFTPDRAESDLKKDLLKG
MDLREPSVRTTFYSKALSGIQSSALTSALPPVTAQAEGASGTLSAGAILRNMALAATGSV
SYLSTLYTNQSVTA

SEQ ID NO: 86
HopM1$_{101-712}$

Fig. 14 E

LLQAEPLPFEVMAEKLSPERYQLKQFQGSDLQQRLEKFAQPGQIPDKAEVGQLIKGFAQ
SVADQLEHFQLMHDASPATVGQHAKADKATLAVSQTALGEYAGRASKAIGEGLSNSIA
SLDEHISALDLTLQDAEQGNKESLHADRQALVDAKTTLVGLHADFVKSPEAKRLASVA
AHTQLDNVVSDLVTARNTVGGWKGAGPIVAAAVPQFLSSMTHLGYVRLSTSDKLRDTI
PETSSDANMLKASIIGMVAGIAHETVNSVVKPMFQAALQKTGLNERLNMVPMKAVDTN
TVIPDPFELKSEHGELVKKTPEEVAQDKAFVKSERALLNQKKVQGSSTHPVGELMAYSA
FGGSQAVRQMLNDVHQINGQTLSARALASGFGGAVSASSQTLLQLKSNYVDPQGRKIP
VFTPDRAESDLKKDLLKGMDLREPSVRTTFYSKALSGIQSSALTSALPPVTAQAEGASGT
LSAGAILRNMALAATGSVSYLSTLYTNQSVTAEAKALKAAGMGGATPMLDRTETALNN
IRHPNRESLPHTFQKSTLSGIPRVAENAYHMGRGALQLPTQMAVDTVRVVDEGVLNAV
ASAREALKQPTKDDDALRALEEGLLDPR

SEQ ID NO: 87
HopM1 $_{201-712}$
AGRASKAIGEGLSNSIASLDEHISALDLTLQDAEQGNKESLHADRQALVDAKTTLVGLH
ADFVKSPEAKRLASVAAHTQLDNVVSDLVTARNTVGGWKGAGPIVAAAVPQFLSSMT
HLGYVRLSTSDKLRDTIPETSSDANMLKASIIGMVAGIAHETVNSVVKPMFQAALQKTG
LNERLNMVPMKAVDTNTVIPDPFELKSEHGELVKKTPEEVAQDKAFVKSERALLNQKK
VQGSSTHPVGELMAYSAFGGSQAVRQMLNDVHQINGQTLSARALASGFGGAVSASSQT
LLQLKSNYVDPQGRKIPVFTPDRAESDLKKDLLKGMDLREPSVRTTFYSKALSGIQSSAL
TSALPPVTAQAEGASGTLSAGAILRNMALAATGSVSYLSTLYTNQSVTAEAKALKAAG
MGGATPMLDRTETALNNIRHPNRESLPHTFQKSTLSGIPRVAENAYHMGRGALQLPTQ
MAVDTVRVVDEGVLNAVASAREALKQPTKDDDALRALEEGLLDPR

SEQ ID NO: 88
HopM1 $_{301-712}$
GPIVAAAVPQFLSSMTHLGYVRLSTSDKLRDTIPETSSDANMLKASIIGMVAGIAHETVN
SVVKPMFQAALQKTGLNERLNMVPMKAVDTNTVIPDPFELKSEHGELVKKTPEEVAQD
KAFVKSERALLNQKKVQGSSTHPVGELMAYSAFGGSQAVRQMLNDVHQINGQTLSAR
ALASGFGGAVSASSQTLLQLKSNYVDPQGRKIPVFTPDRAESDLKKDLLKGMDLREPSV
RTTFYSKALSGIQSSALTSALPPVTAQAEGASGTLSAGAILRNMALAATGSVSYLSTLYT

Fig. 14 F

NQSVTAEAKALKAAGMGGATPMLDRTETALNNIRHPNRESLPHTFQKSTLSGIPRVAEN
AYHMGRGALQLPTQMAVDTVRVVDEGVLNAVASAREALKQPTKDDDALRALEEGLL
DPR

SEQ ID NO: 89
HopM1$_{401-712}$
KSEHGELVKKTPEEVAQDKAFVKSERALLNQKKVQGSSTHPVGELMAYSAFGGSQAVR
QMLNDVHQINGQTLSARALASGFGGAVSASSQTLLQLKSNYVDPQGRKIPVFTPDRAES
DLKKDLLKGMDLREPSVRTTFYSKALSGIQSSALTSALPPVTAQAEGASGTLSAGAILRN
MALAATGSVSYLSTLYTNQSVTAEAKALKAAGMGGATPMLDRTETALNNIRHPNRESL
PHTFQKSTLSGIPRVAENAYHMGRGALQLPTQMAVDTVRVVDEGVLNAVASAREALK
QPTKDDDALRALEEGLLDPR

SEQ ID NO: 90
HopM1$_{501-712}$
DPQGRKIPVFTPDRAESDLKKDLLKGMDLREPSVRTTFYSKALSGIQSSALTSALPPVTA
QAEGASGTLSAGAILRNMALAATGSVSYLSTLYTNQSVTAEAKALKAAGMGGATPML
DRTETALNNIRHPNRESLPHTFQKSTLSGIPRVAENAYHMGRGALQLPTQMAVDTVRVV
DEGVLNAVASAREALKQPTKDDDALRALEEGLLDPR

SEQ ID NO: 91
HopM1$_{601-712}$
QAEGASGTLSAGAILRNMALAATGSVSYLSTLYTNQSVTAEAKALKAAGMGGATPML
DRTETALNNIRHPNRESLPHTFQKSTLSGIPRVAENAYHMGRGALQLPTQMAVDTVRVV
DEGVLNAVASAREALKQPTKDDDALRALEEGLLDPR

SEQ ID NO: 92
HopM1$_{1-100}$
Atgatcagttcgcggatcggcggggccggtggcgtcgaactcagccgggtaaaccagcagcacgatactgttcccgcccagacagctc
acccaaatgcagtcactgcaggcatgaatccgccgctgactcccgatcagtcagggtcacacgcgacagaaagctcgtctgccggcgcg

Fig. 14 G gcgcggctgaatgtcgcggctcgacacacacagcttttgcaggccttcaaggctgagcatgggacggctccggtcagcggcgcgccgat
gatcagttcgcgtgctgcgttgttgatcggtagt SEQ ID NO: 93
$HopM1_{1-200}$
atgatcagttcgcggatcggcggggccggtggcgtcgaactcagccgggtaaaccagcagcacgatactgttcccgcccagacagctca
cccaaatgcagtcactgcaggcatgaatccgccgctgactcccgatcagtcagggtcacacgcgacagaaagctcgtctgccggcgcgg
cgcggctgaatgtcgcggctcgacacacacagcttttgcaggccttcaaggctgagcatgggacggctccggtcagcggcgcgccgatg
atcagttcgcgtgctgcgttgttgatcggtagtctgctgcaggccgagcctttgccttttgaagtcatggccgagaaattgtctcctgagcgcta
tcaactgaagcagtttcagggctcggacttgcagcagcggctggaaaaattcgcccagccgggtcagataccggataaagccgaggtcg
ggcaactgatcaagggttttgctcagtcggtcgctgatcaactggagcactttcaactgatgcatgacgcttcgcccgcaacggtaggccag
catgcaaaagcggacaaggcgacgcttgccgtcagtcagactgcccttggcgaatac SEQ ID NO: 94
$HopM1_{1-300}$
atgatcagttcgcggatcggcggggccggtggcgtcgaactcagccgggtaaaccagcagcacgatactgttcccgcccagacagctca
cccaaatgcagtcactgcaggcatgaatccgccgctgactcccgatcagtcagggtcacacgcgacagaaagctcgtctgccggcgcgg
cgcggctgaatgtcgcggctcgacacacacagcttttgcaggccttcaaggctgagcatgggacggctccggtcagcggcgcgccgatg
atcagttcgcgtgctgcgttgttgatcggtagtctgctgcaggccgagcctttgccttttgaagtcatggccgagaaattgtctcctgagcgcta
tcaactgaagcagtttcagggctcggacttgcagcagcggctggaaaaattcgcccagccgggtcagataccggataaagccgaggtcg
ggcaactgatcaagggttttgctcagtcggtcgctgatcaactggagcactttcaactgatgcatgacgcttcgcccgcaacggtaggccag
catgcaaaagcggacaaggcgacgcttgccgtcagtcagactgcccttggcgaatacgccggtcgtgcaagcaaggcaatcggcgaag
gcctgagcaacagcatcgcgtcgctggatgagcacatcagtgcgctggatctcactctgcaagatgccgaacagggcaacaaggagtctc
tgcacgctgacaggcaggcgctggtcgacgccaaaaccaccctggtaggtttgcacgccgatttcgtcaagtcgccggaggccaagcgc
cttgcttcggtcgccgcacatacgcaactggacaacgtcgtcagcgatctcgtcactgcccgtaacacggtgggtggctggaaaggtgca SEQ ID NO: 95
$HopM1_{1-400}$
atgatcagttcgcggatcggcggggccggtggcgtcgaactcagccgggtaaaccagcagcacgatactgttcccgcccagacagctca
cccaaatgcagtcactgcaggcatgaatccgccgctgactcccgatcagtcagggtcacacgcgacagaaagctcgtctgccggcgcgg
cgcggctgaatgtcgcggctcgacacacacagcttttgcaggccttcaaggctgagcatgggacggctccggtcagcggcgcgccgatg

Fig. 14 H atcagttcgcgtgctgcgttgttgatcggtagtctgctgcaggccgagcctttgccttttgaagtcatggccgagaaattgtctcctgagcgcta
tcaactgaagcagtttcagggctcggacttgcagcagcggctggaaaaattcgcccagccgggtcagataccggataaagccgaggtcg
ggcaactgatcaagggttttgctcagtcggtcgctgatcaactggagcactttcaactgatgcatgacgcttcgcccgcaacggtaggccag
catgcaaaagcggacaaggcgacgcttgccgtcagtcagactgcccttggcgaatacgccggtcgtgcaagcaaggcaatcggcgaag
gcctgagcaacagcatcgcgtcgctggatgagcacatcagtgcgctggatctcactctgcaagatgccgaacagggcaacaaggagtctc
tgcacgctgacaggcaggcgctggtcgacgccaaaaccaccctggtaggtttgcacgccgatttcgtcaagtcgccggaggccaagcgc
cttgcttcggtcgccgcacatacgcaactggacaacgtcgtcagcgatctcgtcactgcccgtaacacggtgggtggctggaaaggtgcag
ggccgattgtcgcggctgcggttccgcagttcttgtcttcaatgacacacttgggttatgtgcgtttgtccaccagcgacaagctgcgagaca
cgattcccgagaccagcagcgacgccaacatgctcaaggcttcgataatcgggatggtggcgggcattgctcacgagacggtcaacagc
gtggtcaagccgatgtttcaggccgccttgcagaagactggcctcaacgaacgcctgaacatggtgccaatgaaggctgtggataccaata
cggttattcctgaccccttcgagctg SEQ ID NO: 96
HopM1$_{1-500}$
atgatcagttcgcggatcggcggggccggtggcgtcgaactcagccgggtaaaccagcagcacgatactgttcccgcccagacagctca
cccaaatgcagtcactgcaggcatgaatccgccgctgactcccgatcagtcagggtcacacgcgacagaaagctcgtctgccggcgcgg
cgcggctgaatgtcgcggctcgacacacacagcttttgcaggccttcaaggctgagcatgggacggctccggtcagcggcgcgccgatg
atcagttcgcgtgctgcgttgttgatcggtagtctgctgcaggccgagcctttgccttttgaagtcatggccgagaaattgtctcctgagcgcta
tcaactgaagcagtttcagggctcggacttgcagcagcggctggaaaaattcgcccagccgggtcagataccggataaagccgaggtcg
ggcaactgatcaagggttttgctcagtcggtcgctgatcaactggagcactttcaactgatgcatgacgcttcgcccgcaacggtaggccag
catgcaaaagcggacaaggcgacgcttgccgtcagtcagactgcccttggcgaatacgccggtcgtgcaagcaaggcaatcggcgaag
gcctgagcaacagcatcgcgtcgctggatgagcacatcagtgcgctggatctcactctgcaagatgccgaacagggcaacaaggagtctc
tgcacgctgacaggcaggcgctggtcgacgccaaaaccaccctggtaggtttgcacgccgatttcgtcaagtcgccggaggccaagcgc
cttgcttcggtcgccgcacatacgcaactggacaacgtcgtcagcgatctcgtcactgcccgtaacacggtgggtggctggaaaggtgcag
ggccgattgtcgcggctgcggttccgcagttcttgtcttcaatgacacacttgggttatgtgcgtttgtccaccagcgacaagctgcgagaca
cgattcccgagaccagcagcgacgccaacatgctcaaggcttcgataatcgggatggtggcgggcattgctcacgagacggtcaacagc
gtggtcaagccgatgtttcaggccgccttgcagaagactggcctcaacgaacgcctgaacatggtgccaatgaaggctgtggataccaata
cggttattcctgaccccttcgagctgaaaagcgaacacggtgagctggtcaaaaaaacgcccgaggaagtcgctcaggacaaggcgttcg
tgaaaagtgaacgcgcgctgctgaaccagaagaaggttcagggttcgtccacccatccggtaggtgagctgatggcttacagtgccttcgg
tggttctcaggctgtgcgccagatgctcaacgatgttcaccagatcaatgggcagacgctgagtgcaagagctctggcatccggttttggcg
gggcggtgtctgccagttcgcaaacgctgctgcaattgaagtcgaattatgtc

Fig. 14 I

SEQ ID NO: 97

$HopM1_{1-600}$ atgatcagttcgcggatcggcggggccggtggcgtcgaactcagccgggtaaaccagcagcacgatactgttcccgcccagacagctca
cccaaatgcagtcactgcaggcatgaatccgccgctgactcccgatcagtcagggtcacacgcgacagaaagctcgtctgccggcgcgg
cgcggctgaatgtcgcggctcgacacacacagcttttgcaggccttcaaggctgagcatgggacggctccggtcagcggcgcgccgatg
atcagttcgcgtgctgcgttgttgatcggtagtctgctgcaggccgagcctttgccttttgaagtcatggccgagaaattgtctcctgagcgcta
tcaactgaagcagtttcagggctcggacttgcagcagcggctggaaaaattcgcccagccgggtcagataccggataaagccgaggtcg
ggcaactgatcaagggttttgctcagtcggtcgctgatcaactggagcactttcaactgatgcatgacgcttcgcccgcaacggtaggccag
catgcaaaagcggacaaggcgacgcttgccgtcagtcagactgcccttggcgaatacgccggtcgtgcaagcaaggcaatcggcgaag
gcctgagcaacagcatcgcgtcgctggatgagcacatcagtgcgctggatctcactctgcaagatgccgaacagggcaacaaggagtctc
tgcacgctgacaggcaggcgctggtcgacgccaaaaccaccctggtaggtttgcacgccgatttcgtcaagtcgccggaggccaagcgc
cttgcttcggtcgccgcacatacgcaactggacaacgtcgtcagcgatctcgtcactgcccgtaacacggtgggtggctggaaaggtgcag
ggccgattgtcgcggctgcggttccgcagttcttgtcttcaatgacacacttgggttatgtgcgtttgtccaccagcgacaagctgcgagaca
cgattcccgagaccagcagcgacgccaacatgctcaaggcttcgataatcgggatggtggcgggcattgctcacgagacggtcaacagc
gtggtcaagccgatgtttcaggccgccttgcagaagactggcctcaacgaacgcctgaacatggtgccaatgaaggctgtggataccaata
cggttattcctgaccccttcgagctgaaaagcgaacacggtgagctggtcaaaaaaacgcccgaggaagtcgctcaggacaaggcgttcg
tgaaaagtgaacgcgcgctgctgaaccagaagaaggttcagggttcgtccacccatccggtaggtgagctgatggcttacagtgccttcgg
tggttctcaggctgtgcgccagatgctcaacgatgttcaccagatcaatgggcagacgctgagtgcaagagctctggcatccggttttggcg
gggcggtgtctgccagttcgcaaacgctgctgcaattgaagtcgaattatgtcgacccgcaagggcgcaaaattccggtatttaccccggac
cgcgccgagagcgatctgaaaaaggacctgctcaaaggtatggacctgcgcgagccgtcggtacgcaccacgttctacagcaaggctctt
tcgggtattcagagttctgcactgacctcggcactgccgcctgtgaccgctcaggctgaaggcgcaagtggcacgctcagtgcgggggct
attttgcgcaacatggccctggcagcgacgggttcggtgtcctatctgtccacgttgtacaccaaccagtcggttaccgca

SEQ ID NO: 98

$HopM1_{101-712}$ cttttgcaggccttcaaggctgagcatgggacggctccggtcagcggcgcgccgatgatcagttcgcgtgctgcgttgttgatcggtagtct
gctgcaggccgagcctttgccttttgaagtcatggccgagaaattgtctcctgagcgctatcaactgaagcagtttcagggctcggacttgca
gcagcggctggaaaaattcgcccagccgggtcagataccggataaagccgaggtcgggcaactgatcaagggttttgctcagtcggtcgc
tgatcaactggagcactttcaactgatgcatgacgcttcgcccgcaacggtaggccagcatgcaaaagcggacaaggcgacgcttgccgt
cagtcagactgcccttggcgaatacgccggtcgtgcaagcaaggcaatcggcgaaggcctgagcaacagcatcgcgtcgctggatgagc

Fig. 14 J acatcagtgcgctggatctcactctgcaagatgccgaacagggcaacaaggagtctctgcacgctgacaggcaggcgctggtcgacgcc
aaaaccaccctggtaggtttgcacgccgatttcgtcaagtcgccggaggccaagcgccttgcttcggtcgccgcacatacgcaactggaca
acgtcgtcagcgatctcgtcactgcccgtaacacggtgggtggctggaaaggtgcagggccgattgtcgcggctgcggttccgcagttctt
gtcttcaatgacacacttgggttatgtgcgtttgtccaccagcgacaagctgcgagacacgattcccgagaccagcagcgacgccaacatg
ctcaaggcttcgataatcgggatggtggcgggcattgctcacgagacggtcaacagcgtggtcaagccgatgtttcaggccgccttgcaga
agactggcctcaacgaacgcctgaacatggtgccaatgaaggctgtggataccaatacggttattcctgaccccttcgagctgaaaagcga
acacggtgagctggtcaaaaaaacgcccgaggaagtcgctcaggacaaggcgttcgtgaaaagtgaacgcgcgctgctgaaccagaag
aaggttcagggttcgtccacccatccggtaggtgagctgatggcttacagtgccttcggtggttctcaggctgtgcgccagatgctcaacgat
gttcaccagatcaatgggcagacgctgagtgcaagagctctggcatccggttttggcggggcggtgtctgccagttcgcaaacgctgctgc
aattgaagtcgaattatgtcgacccgcaagggcgcaaaattccggtatttaccccggaccgcgccgagagcgatctgaaaaaggacctgct
caaaggtatggacctgcgcgagccgtcggtacgcaccacgttctacagcaaggctctttcgggtattcagagttctgcactgacctcggcac
tgccgcctgtgaccgctcaggctgaaggcgcaagtggcacgctcagtgcgggggctattttgcgcaacatggccctggcagcgacgggtt
cggtgtcctatctgtccacgttgtacaccaaccagtcggttaccgcagaagccaaggcgttgaaagcggcaggcatgggcggtgcaacac
ctatgctggaccgtaccgagacggctttgaataacatccgtcatccgaacagggagtctctgccacatacgttccagaagagcacgttgagc
ggtatcccacgagtcgcggaaaacgcctatcacatgggacgaggcgcattgcagttgcctacccagatggccgtggatacggttcgggtc
gtggatgaaggtgtgttgaacgcagtcgcgtcagcacgcgaggcgcttaagcagccgacaaaagacgatgacgcattgagggcacttga
agagggcttgcttgacccgcgt

SEQ ID NO: 99

$HopM1_{201-712}$ gccggtcgtgcaagcaaggcaatcggcgaaggcctgagcaacagcatcgcgtcgctggatgagcacatcagtgcgctggatctcactct
gcaagatgccgaacagggcaacaaggagtctctgcacgctgacaggcaggcgctggtcgacgccaaaaccaccctggtaggtttgcac
gccgatttcgtcaagtcgccggaggccaagcgccttgcttcggtcgccgcacatacgcaactggacaacgtcgtcagcgatctcgtcactg
cccgtaacacggtgggtggctggaaaggtgcagggccgattgtcgcggctgcggttccgcagttcttgtcttcaatgacacacttgggttat
gtgcgtttgtccaccagcgacaagctgcgagacacgattcccgagaccagcagcgacgccaacatgctcaaggcttcgataatcgggatg
gtggcgggcattgctcacgagacggtcaacagcgtggtcaagccgatgtttcaggccgccttgcagaagactggcctcaacgaacgcctg
aacatggtgccaatgaaggctgtggataccaatacggttattcctgaccccttcgagctgaaaagcgaacacggtgagctggtcaaaaaaa
cgcccgaggaagtcgctcaggacaaggcgttcgtgaaaagtgaacgcgcgctgctgaaccagaagaaggttcagggttcgtccacccat
ccggtaggtgagctgatggcttacagtgccttcggtggttctcaggctgtgcgccagatgctcaacgatgttcaccagatcaatgggcagac
gctgagtgcaagagctctggcatccggttttggcggggcggtgtctgccagttcgcaaacgctgctgcaattgaagtcgaattatgtcgacc
cgcaagggcgcaaaattccggtatttaccccggaccgcgccgagagcgatctgaaaaaggacctgctcaaaggtatggacctgcgcgag

Fig. 14 K ccgtcggtacgcaccacgttctacagcaaggctctttcgggtattcagagttctgcactgacctcggcactgccgcctgtgaccgctcaggct
gaaggcgcaagtggcacgctcagtgcgggggctattttgcgcaacatggccctggcagcgacgggttcggtgtcctatctgtccacgttgt
acaccaaccagtcggttaccgcagaagccaaggcgttgaaagcggcaggcatgggcggtgcaacacctatgctggaccgtaccgagac
ggctttgaataacatccgtcatccgaacagggagtctctgccacatacgttccagaagagcacgttgagcggtatcccacgagtcgcggaa
aacgcctatcacatgggacgaggcgcattgcagttgcctacccagatggccgtggatacggttcgggtcgtggatgaaggtgtgttgaacg
cagtcgcgtcagcacgcgaggcgcttaagcagccgacaaaagacgatgacgcattgagggcacttgaagagggcttgcttgacccgcgt SEQ ID NO: 100
HopM1$_{301-712}$
gggccgattgtcgcggctgcggttccgcagttcttgtcttcaatgacacacttgggttatgtgcgtttgtccaccagcgacaagctgcgagac
acgattcccgagaccagcagcgacgccaacatgctcaaggcttcgataatcgggatggtggcgggcattgctcacgagacggtcaacag
cgtggtcaagccgatgtttcaggccgccttgcagaagactggcctcaacgaacgcctgaacatggtgccaatgaaggctgtggataccaat
acggttattcctgacccccttcgagctgaaaagcgaacacggtgagctggtcaaaaaaacgcccgaggaagtcgctcaggacaaggcgttc
gtgaaaagtgaacgcgcgctgctgaaccagaagaaggttcagggttcgtccacccatccggtaggtgagctgatggcttacagtgccttcg
gtggttctcaggctgtgcgccagatgctcaacgatgttcaccagatcaatgggcagacgctgagtgcaagagctctggcatccggttttggc
ggggcggtgtctgccagttcgcaaacgctgctgcaattgaagtcgaattatgtcgacccgcaagggcgcaaaattccggtatttaccccgg
accgcgccgagagcgatctgaaaaaggacctgctcaaaggtatggacctgcgcgagccgtcggtacgcaccacgttctacagcaaggct
ctttcgggtattcagagttctgcactgacctcggcactgccgcctgtgaccgctcaggctgaaggcgcaagtggcacgctcagtgcggggg
ctattttgcgcaacatggccctggcagcgacgggttcggtgtcctatctgtccacgttgtacaccaaccagtcggttaccgcagaagccaag
gcgttgaaagcggcaggcatgggcggtgcaacacctatgctggaccgtaccgagacggctttgaataacatccgtcatccgaacaggga
gtctctgccacatacgttccagaagagcacgttgagcggtatcccacgagtcgcggaaaacgcctatcacatgggacgaggcgcattgca
gttgcctacccagatggccgtggatacggttcgggtcgtggatgaaggtgtgttgaacgcagtcgcgtcagcacgcgaggcgcttaagca
gccgacaaaagacgatgacgcattgagggcacttgaagagggcttgcttgacccgcgt SEQ ID NO: 101
HopM1$_{401-712}$
Aaaagcgaacacggtgagctggtcaaaaaaacgcccgaggaagtcgctcaggacaaggcgttcgtgaaaagtgaacgcgcgctgctg
aaccagaagaaggttcagggttcgtccacccatccggtaggtgagctgatggcttacagtgccttcggtggttctcaggctgtgcgccagat
gctcaacgatgttcaccagatcaatgggcagacgctgagtgcaagagctctggcatccggttttggcggggcggtgtctgccagttcgcaa
acgctgctgcaattgaagtcgaattatgtcgacccgcaagggcgcaaaattccggtatttaccccggaccgcgccgagagcgatctgaaaa
aggacctgctcaaaggtatggacctgcgcgagccgtcggtacgcaccacgttctacagcaaggctctttcgggtattcagagttctgcactg

Fig. 14 L acctcggcactgccgcctgtgaccgctcaggctgaaggcgcaagtggcacgctcagtgcgggggctattttgcgcaacatggccctggca
gcgacgggttcggtgtcctatctgtccacgttgtacaccaaccagtcggttaccgcagaagccaaggcgttgaaagcggcaggcatgggc
ggtgcaacacctatgctggaccgtaccgagacggctttgaataacatccgtcatccgaacagggagtctctgccacatacgttccagaaga
gcacgttgagcggtatcccacgagtcgcggaaaacgcctatcacatgggacgaggcgcattgcagttgcctacccagatggccgtggata
cggttcgggtcgtggatgaaggtgtgttgaacgcagtcgcgtcagcacgcgaggcgcttaagcagccgacaaaagacgatgacgcattg
agggcacttgaagagggcttgcttgacccgcgt SEQ ID NO: 102
$HopM1_{501-712}$
gacccgcaagggcgcaaaattccggtatttaccccggaccgcgccgagagcgatctgaaaaaggacctgctcaaaggtatggacctgcg
cgagccgtcggtacgcaccacgttctacagcaaggctctttcgggtattcagagttctgcactgacctcggcactgccgcctgtgaccgctc
aggctgaaggcgcaagtggcacgctcagtgcgggggctattttgcgcaacatggccctggcagcgacgggttcggtgtcctatctgtcca
cgttgtacaccaaccagtcggttaccgcagaagccaaggcgttgaaagcggcaggcatgggcggtgcaacacctatgctggaccgtacc
gagacggctttgaataacatccgtcatccgaacagggagtctctgccacatacgttccagaagagcacgttgagcggtatcccacgagtcg
cggaaaacgcctatcacatgggacgaggcgcattgcagttgcctacccagatggccgtggatacggttcgggtcgtggatgaaggtgtgtt
gaacgcagtcgcgtcagcacgcgaggcgcttaagcagccgacaaaagacgatgacgcattgagggcacttgaagagggcttgcttgacc
cgcgt SEQ ID NO: 103
$HopM1_{601-712}$
Caggctgaaggcgcaagtggcacgctcagtgcgggggctattttgcgcaacatggccctggcagcgacgggttcggtgtcctatctgtcc
acgttgtacaccaaccagtcggttaccgcagaagccaaggcgttgaaagcggcaggcatgggcggtgcaacacctatgctggaccgtac
cgagacggctttgaataacatccgtcatccgaacagggagtctctgccacatacgttccagaagagcacgttgagcggtatcccacgagtc
gcggaaaacgcctatcacatgggacgaggcgcattgcagttgcctacccagatggccgtggatacggttcgggtcgtggatgaaggtgtg
ttgaacgcagtcgcgtcagcacgcgaggcgcttaagcagccgacaaaagacgatgacgcattgagggcacttgaagagggcttgcttga
cccgcgt SEQ ID NO: 104
Xyloglucan 6-xylosyltransferase (AtXT1) At3g62720 <u>XT1_ARATH</u> Q9LZJ3
aaaatttaaatcttcattgaatgctttttctgaagctttatctaataaatctcttcgttgatccttcctttccattaacgaggtagaaattccaaaacgc
gtaataatcttgtcgtcattacaaattacaataaaaagaagacatttttatttagatttccctctgatcctctcttttagatttcgaatcgagaccagat

Fig. 14 M ctgcgtgaagatgatagagaagtgtataggagcgcatcggtttcggagattacagagattcatgcgtcaagggaaagtgacgattctttgtct
cgttctcaccgtcatcgtcttacgtggcacaatcggagccggtaagtttggtacgccggagaaagatatcgaggagatccgtgagcatttctt
ctacacgcgtaaacgcggcgagcctcaccgtgtcctcgtcgaggtctcttccaaaacgacgtcgtccgaagacggaggaaatggtggtaa
cagctacgagaccttcgatatcaacaagctattcgttgatgaaggagacgaagagaaatctcgagaccggactaataaaccttattctcttgg
tcccaagatctctgattgggatgagcagagacgtgattggctcaaacaaaaccctagcttccctaatttcgtggcgccaaacaagcctagg
gttcttcttgtcacaggttcagctcctaaaccgtgtgagaatcctgtaggagaccattacctcttgaaatcgattaagaacaaaatcgattactgt
agaatacacggaatcgagatcttctacaacatggcgttgctcgatgctgagatggctggattctgggctaagcttccgttgattaggaagttac
tcttgtcacatcctgagattgagtttctatggtggatggatagtgatgccatgttcacggacatggtgttcgagcttccatgggagaggtacaaa
gattacaacttggtgatgcatggttggaacgagatggtttatgaccagaagaattggattggtctcaacacgggaagtttcttgctcaggaact
cacagtggtcgcttgatcttcttgacgcttgggctcctatgggcccaaaagggaagatccgagaagaagcgggtaaagtcttgacccggga
acttaaagaccgacccgctttcgaagctgacgatcaatcggcgatggtttatctgctggcgacggagagagagaaatggggaggcaaagt
ttatctagagagtggttattacttgcacggttattgggggattttggtagaccggtacgaggagatgattgagaatcataaaccgggttttggag
accatcggtggccattggttacgcatttcgtcgggtgtaaaccgtgcgggaaatttggagattatccggtggaacggtgtctacggcagatg
gatagagcgtttaatttcggagacaatcagatccttcaaatgtatggtttcacgcataaatcgcttgggagccggcgcgtgaaacccacgcgc
aatcagacggataggccgctcgatgccaaggacgagtttgggctgcttcatccgccgttcaaagcggccaagcttagtacgacgacgacg
tgagtgagtgagaggatatattgttttgtatcttttaattttgcgtttaggggacacacgtttatttgttttattcaattttatttgtttgtagtttacttaatt
gttttgatctcccattcatggtggagtcgtgtatggagtatttaatgatttattgtagacgttatttc SEQ ID NO: 105
HopPtoM-like protein$_{1\text{-}300}$
MINSRVGGSGDIQMVAVRTEEGNPSITSAHPNAVTPSNNPPLLPRQMGQHLEPSLESHAA
NLGIALRHTELLATFQAEQASTRSTDAPQVSAHAALLIGGMLEEANGHASETGKVGFEV
MAERLCGPHLALESFQSSDVKLLLEKLTNKDEIPDKAEVGQLLKGHAGAIADQLEHFQL
MHNASSVHQGECSAPDRKTFEVSQAALGEYAGRASKAISSVLSEKTADLDKRLADVDK
QLEGMAEGGEKSRLLTQKETLGEAKTMLADIQNDFSKSPQAKHLKSVAAHARFDAQLK
ELNADR SEQ ID NO: 106
Pseudomonas syringae pv. syringae B728a type III effector HopM1$_{1\text{-}300}$ ACCESSION
AAY36240

Fig. 14 N

MIGTRVGGSGSTEIVQANQPQPSAAVAQAHPHAVSPSSNPPLTASQSAAQAPESSAAGA
ARLPVAPRHLPTLEKFRAEQPTVQGTSTPTISANAALLIGSLLQSEKLPFEVMAARLSPER
YALQQFHGSDLQQMLGRFAEPGHLPGKAETEQLIKGFARSLADQLEHFQLMHDATAEA
FGPGGLRDRNTLAVSQAALGEYAGRASKSIEAGLNHSLAVLDERIAALDSQLEGATEDS
RPVLLMDRQALETARAMLSDLHVDFCKSPEAKRLSAVAAHTQMDALIDKLNVDRSSV
GGWKGI

SEQ ID NO: 107
Pseudomonas syringae pv. syringae B728a type III effector HopM1$_{1\text{-}300}$ ACCESSION
AAY36240
Atgattggcacacgagtcggcggatcaggcagtaccgaaatcgttcaggcgaaccagccgcagccgtctgccgctgtcgcccaggctca
tccacacgcggtaagcccgagcagcaacccgccgctgaccgccagccagtcggccgcgcaagcgccggaaagctcggcggccggtg
ccgctcgcctgccagtcgcgccgcgacatctgccgacattggagaagtttcgtgccgaacagcccaccgtacaaggcacttccacgccga
ctatcagcgctaacgcggccctgctgatcggcagtctgttgcagtctgaaaaactgcccttcgaggtcatggccgcccgtttgtcgcctgag
cgttatgcgttgcagcagtttcacggctccgatttacagcaaatgctcggacgattcgctgagccagggcatctgccaggcaaggccgaga
ccgaacaactgatcaagggctttgcccggtcgctcgcagaccagctggagcacttccagctcatgcatgacgcgacggctgaggcattcg
gccccggagggctgcgcgaccgcaacacactggcggtcagtcaagcggcgcttggcgaatacgccggtcgggcgagtaaatccatcga
agcggggctgaaccacagtctcgcggtgctggacgagcgcatcgccgcgctggacagccagttggagggcgccactgaggacagcag
accggttttgctgatggacaggcaggcgctggaaacggccagggcgatgctgagcgacctgcacgtcgacttctgcaaatcgcctgaagc
caagcggttgagtgccgttgccgctcacacgcaaatggatgctctgatcgacaagctgaacgttgatcgcagctcggtcggcggctggaa
ggggatc SEQ ID NO:108
Pseudomonas syringae pv. phaseolicola 1448A coding for 1-300
MNTPRIGGSGAIELSRINQQPDAIPAQTAHPNAVTPGMNPPLTPNQAGPHAAESSATGAA
RLNVAARHTQLLQAFKAEQATAPVSGAPMISSRAALLIGSLLQAEKLPFEVMAERLSPE
RYQLKQFHGSDLQQLLDKFTQPGQVPDKAEVGQLIKGFAQSVADQLEHFQLMHDATPT
KTGPHANEDRATLAVSQTALGEYAGRASKAIGEGLSKGIVSLDDHIAALDVSLQSAEEG
AKDALHSNRQALVDAKTTLVGLHADFVKSPEAKRLASVAAHTQLDTVVSDLVTARNS
VGGWKGA

Fig. 14 O

SEQ ID NO:109
Pseudomonas syringae pv. phaseolicola 1448A coding for 1-300 na 1475020-1475874
Atgaacactccgcgaatcggtggatcgggcgccatcgagctctcccggataaaccagcagcccgatgctattcccgcccagaccgctca
cccgaatgcagtgacgccaggcatgaatccgccgctgactcccaatcaggcagggccgcacgcagcagaaagctcggctaccggtgcc
gcgcggctgaatgttgcggcgcgacacacgcagcttttgcaggccttcaaggctgagcaggcgacagctccggtcagcggcgcgccgat
gatcagctcgcgtgccgcgttattgattggcagcttgctgcaggctgaaaagctgccttttgaagtcatggccgagcgtctctcccctgagcg
ctatcaactgaagcagtttcatggttcggacttgcaacaactgctggacaagtttacccagccgggtcaggtacccgacaaagccgaagtcg
gtcaactgatcaagggcttcgcgcaatcggtcgccgatcaactggagcactttcagttgatgcatgacgctacgcccaccaagacaggccc
gcatgccaacgaggatcgggcgacgcttgccgtcagtcagacagcccttggcgagtacgccggtcgtgcgagcaaggcaatcggcgaa
gggctgagcaaaggcatcgtgtcgctggatgatcacatcgctgcactggatgtgagcctgcaaagtgccgaagagggcgccaaggacgc
tttgcactctaacagacaggcgctggttgatgcgaaaaccactctggtcggcctgcacgccgatttcgtcaaatcgccagaggctaaacgcc
ttgcttcggtcgccgcacatacacaactggacaccgtcgtcagtgatcttgtcactgcccgcaactcggttggcggctggaaaggtgcc SEQ ID NO:110
HopPtoM-like protein [Pseudomonas viridiflava] ACCESSION AAT96166; AY597277
LP23.1a pathogenicity island PAI-Region-1 coding for 1-300 na
Atgattaattcacgcgtaggggggatcaggcgacatacaaatggttgcggtgagaacggaggagggtaatccgtccattacctctgctcacc
cgaatgcggtcactcccagcaacaatcccccgttactcccaaggcaaatgggtcaacaccttgagccctctctggagtcgcatgcggcgaa
cctgggtatagcgttgcgccacactgagttgctggcgacgtttcaggctgagcaggcgagcacacgctcaaccgatgcaccacaggtcag
tgcgcatgcggcgctattgattggaggcatgctcgaagaggccaacggtcacgcttccgaaaccggcaaggtgggctttgaggtcatggc
agagcgcttgtgcgggccgcaccttgcgctggagagtttccagtccagtgacgtcaaactcctgctcgagaagctcactaataaggacgag
ataccggacaaggcagaggtcgggcaactgctcaaaggccatgccggtgcgatcgccgatcaacttgagcattttcagctgatgcacaac
gcttccagcgtgcaccaaggtgaatgctcggctcccgaccgaaagacctttgaagtcagccaggctgcgttgggcgaatacgctggacgt
gcgagcaaagcgatttccagcgtactgagcgagaaaactgcagatctggacaagcgccttgcggacgtggacaaacagctcgagggtat
ggctgaaggcggggaaaaatccagacttttgacccagaaagagacgcttggcgaagccaaaaccatgctggccgacattcagaacgattt
ttcgaaatcgcctcaggcaaagcatctgaaatccgttgctgctcatgcgcgattcgacgcgcagctcaaagagctgaacgcggatcgt SEQ ID NO:111
Pseudomonas syringae pv. phaseolicola 1448A HopM1 CP000058 REGION:
1474976..1477211
MNTPRIGGSGAIELSRINQQPDAIPAQTAHPNAVTPGMNPPLTPNQAGPHAAESSATGAA

Fig. 14 P

RLNVAARHTQLLQAFKAEQATAPVSGAPMISSRAALLIGSLLQAEKLPFEVMAERLSPE
RYQLKQFHGSDLQQLLDKFTQPGQVPDKAEVGQLIKGFAQSVADQLEHFQLMHDATPT
KTGPHANEDRATLAVSQTALGEYAGRASKAIGEGLSKGIVSLDDHIAALDVSLQSAEEG
AKDALHSNRQALVDAKTTLVGLHADFVKSPEAKRLASVAAHTQLDTVVSDLVTARNS
VGGWKGAGPIVAAAVPQFLSSMTHLGYVRLSTSDKLREEVPETSSDASMLKAAITGMV
TGIAHETVNSVVKPVFQATFQKTGLNERLNMVPLKAIDTNSVIPDPFELKSEHGELIRKTP
EEIAQDKAFVKGERAVLNQKKVQGSSTHPLGEMIGYSAFGGSHAVRQMLNDLHQINGQ
TLSARALASGFGGAVSVSSQTLLQLKSTYVDPAGRKIPVFTPDRAETELKKDLAKGMDL
REASVRTTFYSKAISGYSELGADLGTAACDSPAGRRARYAQCGEYPAQYGSGRNGLDF
LSVHALRQPVCHRRSQGVEGCGDGGRNADAGSYRNSLEQHPPSEQGIAATYLPAEHVE
RYSKGYGKRLSHGTRRVAAANPDGRGHGSSVGRRCAERRVVSTRCAYASKTA

SEQ ID NO:112
Pseudomonas syringae pv. phaseolicola 1448A HopM1 CP000058 REGION:
1474976..1477211
atgaacactccgcgaatcggtggatcgggcgccatcgagctctcccggataaaccagcagcccgatgctattcccgcccagaccgctcac
ccgaatgcagtgacgccaggcatgaatccgccgctgactcccaatcaggcagggccgcacgcagcagaaagctcggctaccggtgccg
cgcggctgaatgttgcggcgcgacacacgcagcttttgcaggccttcaaggctgagcaggcgacagctccggtcagcggcgcgccgatg
atcagctcgcgtgccgcgttattgattggcagcttgctgcaggctgaaaagctgccttttgaagtcatggccgagcgtctctcccctgagcgc
tatcaactgaagcagtttcatggttcggacttgcaacaactgctggacaagtttacccagccgggtcaggtacccgacaaagccgaagtcg
gtcaactgatcaagggcttcgcgcaatcggtcgccgatcaactggagcactttcagttgatgcatgacgctacgcccaccaagacaggccc
gcatgccaacgaggatcgggcgacgcttgccgtcagtcagacagcccttggcgagtacgccggtcgtgcgagcaaggcaatcggcgaa
gggctgagcaaaggcatcgtgtcgctggatgatcacatcgctgcactggatgtgagcctgcaaagtgccgaagagggcgccaaggacgc
tttgcactctaacagacaggcgctggttgatgcgaaaaccactctggtcggcctgcacgccgatttcgtcaaatcgccagaggctaaacgcc
ttgcttcggtcgccgcacatacacaactggacaccgtcgtcagtgatcttgtcactgcccgcaactcggttggcggctggaaaggtgccgg
gccgattgtcgcagctgcggttccacagttcctgtcgtcaatgacgcacctgggttatgtgcgtttgtccaccagtgacaagctgcgagagg
aggtgcctgagaccagcagcgacgccagtatgctcaaggcggcgataaccggaatggtcacgggcattgcccacgagacagtcaacag
cgtagtgaaaccggtgtttcaggctacttttcagaaaactggcctgaacgaacggctgaacatggtgccactcaaggctatcgataccaattc
ggtgattcctgaccccttcgaactgaaaagcgagcacggtgagctgatcagaaaaacgcccgaggaaatcgctcaggacaaggcattcgt
caagggcgaacgcgcggtgctgaatcagaagaaggtccagggttcgtccacccacccgttgggtgaaatgataggttacagtgcctttggt
ggttcacatgccgtgcgccagatgctcaacgatttacaccagatcaatggtcagacgctgagtgcaagagccttggcatccggctttggcg

Fig. 14 Q gggcggtgtctgtcagttcgcaaacgcttttgcagttgaagtcgacgtatgtcgatcccgcagggcgcaaaattccggtattcacgccagac
cgagccgagacagagctgaaaaaggatctggccaaaggtatggacctgcgcgaagcctcggtacgtaccacgttctacagcaaggcaat
atccgggtattcagagctcggcgctgacctcggcactgccgcctgtgacagcccagctggaaggcgcgcgcggtacgctcagtgcggg
gaatatcctgcgcaatatggctctggtcgcaacgggctcgatttcctatctgtccacgctttacgccaaccagtctgtcaccgccgaagccaa
ggcgttgaaggatgcggggatggggggcgcaacgccgatgctggatcgtaccgaaacagccttgaacaacatccgccatccgaacagg
gcatcgctgccacataccttccagccgagcacgttgagcggtattccaagggctatggaaagcgcttatcacatgggacgaggcgcgttgc
agctgccaacccagatggccgtggacacggttcgagtgttggcagacggtgcgctgaacggcgtgtcgtcagcacgcgctgcgcttacg
ccagcaaaaccgcctgaagctcgcgtgtccgtcgacgagctccggaacacggccccaacgccgccatccagccccacagtgcagcgg
ccggcaccctccgttccgcttgacgacgagcagttgcgggcgctcgaagaaagcttgctcgctccgcgttga SEQ ID NO:113
Q9LZJ3|XT1_ARATH Xyloglucan 6-xylosyltransferase - Arabidopsis thaliana (Mouse-ear cress)
MIEKCIGAHRFRRLQRFMRQGKVTILCLVLTVIVLRGTIGAGKFGTPEKDIEEIREHFFYT
RKRGEPHRVLVEVSSKTTSSEDGGNGGNSYETFDINKLFVDEGDEEKSRDRTNKPYSLG
PKISDWDEQRRDWLKQNPSFPNFVAPNKPRVLLVTGSAPKPCENPVGDHYLLKSIKNKI
DYCRIHGIEIFYNMALLDAEMAGFWAKLPLIRKLLLSHPEIEFLWWMDSDAMFTDMVFE
LPWERYKDYNLVMHGWNEMVYDQKNWIGLNTGSFLLRNSQWSLDLLDAWAPMGPK
GKIREEAGKVLTRELKDRPAFEADDQSAMVYLLATEREKWGGKVYLESGYYLHGYWG
ILVDRYEEMIENHKPGFGDHRWPLVTHFVGCKPCGKFGDYPVERCLRQMDRAFNFGDN
QILQMYGFTHKSLGSRRVKPTRNQTDRPLDAKDEFGLLHPPFKAAKLSTTTT

Fig. 14 R

ATMIN7 MEDIATED DISEASE RESISTANCE TO *PSEUDOMONAS SYRINGAE* IN *ARABIDOPSIS*

GOVERNMENT SUPPORT

The invention was made in part with Government support from the Department of Energy and National Institutes of Health, National Institute Of Allergy And Infectious Diseases, grants 1R01AI060761-01A2 and 1R21AI060761-01. As such, the Government has certain rights in the invention.

SEQUENCE LISTING

A Sequence Listing has been submitted on a compact disc, the entire content of which is herein incorporated by reference. The compact disc and its duplicate are labeled Copy 1 and Copy 2, respectively. Each disk contains a file named "13600seq.txt" created on Jul. 7, 2008 that is 294,912 bytes, and each disk is identical to the other.

FIELD OF THE INVENTION

The present invention relates to compositions and methods for enhancing plant defenses against pathogens. More particularly, the invention relates to enhancing plant immunity against bacterial pathogens, wherein AtMIN mediated protection is enhanced and/or there is a decrease in activity of an AtMIN7 associated virulence protein such as a *Pseudomonas syringae* pv. tomato DC3000 HopM1. Reagents of the present invention provide a means of studying cellular trafficking while formulations of the present inventions provide increased pathogen resistance in plants.

BACKGROUND OF THE INVENTION

Plants have a powerful immune system to defend against colonization by most microbial organisms. However, virulent plant pathogens, such as *Pseudomonas syringae*, have developed countermeasures and inject virulence proteins into the host cell of a susceptible plant to overcome plant immunity and cause disease. Host plants include tomato plants and collard plants, such as cabbage and kale. In particular, *Pseudomonas syringae* pv. tomato causes an economically devastating disease called bacterial speck of tomato plants.

Bacteria control strategies are based on a combination of practices such as use of pathogen-free seed and transplants, elimination of volunteer tomato plants, resistant cultivars, and frequent application of a copper and mancozeb mixture (Jones, et al. 1986, Phytopathology 76:430-434; Jones, et al. 1991, Phytopathology 81:714-719; Sherf, et al. 1986, In: Vegetable Diseases and Their Control. John Wiley and Sons, New York; all of which are herein incorporated by reference). Chemical control has been used extensively for controlling bacterial spot. In the 1950s, streptomycin was used, but resistant bacterial strains developed and rendered antibiotics ineffective (Stall, R. E., and Thayer, P. L. 1962, Plant Dis. Rep. 46:389-392; herein incorporated by reference). However, these strategies are of limited use, especially in the tropics and subtropics where weather conditions favor infection (Kucharek, T. 1994, Plant pathology fact sheet, PP-3, University of Florida, Gainesville; herein incorporated by reference).

One method of treatment is a biopesticide product containing as active ingredients bacteriophages of *Xanthomonas campestris* pv. *vesicatoria* and *Pseudomonas syringae* pv. tomato "AgriPhage" EPA Registration #67986-1.

However, *Pseudomonas* quickly develops resistance to these treatment methods. Further, despite intensive research efforts, the molecular targets of bacterial virulence proteins important for plant disease development have remained obscure.

Therefore, there is a need for effective and economical bacterial pathogen treatments, and further, for enhancing plant immunity to virulent plant pathogens.

SUMMARY OF THE INVENTION

The present invention relates to compositions and methods for enhancing plant defenses against pathogens. More particularly, the invention relates to enhancing plant immunity against bacterial pathogens, wherein AtMIN7 mediated protection is enhanced and/or there is a decrease in activity of an AtMIN7 associated virulence protein such as a *Pseudomonas syringae* pv. tomato DC3000 HopM1. Reagents of the present invention provide a means of studying cellular trafficking while formulations of the present inventions provide increased pathogen resistance in plants.

In one embodiment, the invention provides an expression vector construct comprising a nucleic acid molecule at least 57% identical to SEQ ID NO:02. Accordingly, in other embodiments, the present invention provides an expression vector construct comprising a nucleic acid molecule at least 57%, 60%, 65%, 70%, 75%, 80%, 85%, 90%, 95%, 98%, 99% (or more) identical to any of SEQ ID NO:02. In one embodiment, the nucleic acid molecule encodes a polypeptide that alters pathogen resistance in a plant. The present invention is not limited to any particular source of said nucleic acid molecule. Indeed, a variety of sources are contemplated, including but not limited to Brassicaceae, Solanaceae, and Poaceae. In some embodiments, the nucleic acid molecule encodes a polypeptide that is at least 38% identical to SEQ ID NO:01, wherein said polypeptide alters pathogen resistance in a plant. Accordingly, in other embodiments, the present invention provides an expression vector construct comprising a polypeptide at least 38%, 40%, 45%, 50%, 55%, 60%, 65%, 70%, 75%, 80%, 85%, 90%, 95%, 98%, 99% (or more) identical to any of SEQ ID NO:01. In one embodiment, the polypeptide alters pathogen resistance in a plant. The present invention is not limited to any particular type of polypeptide for altering pathogen resistance in a plant. In a preferred embodiment, the polypeptide increases pathogen resistance in a plant. In some embodiments, the nucleic acid is operably linked to an exogenous promoter. The present invention is not limited to any particular type of promoter. Indeed, the use of a variety of promoters is contemplated. In some embodiments, the promoter is a eukaryotic promoter. In some embodiments, the eukaryotic promoter is active in cell. In some embodiments, the eukaryotic promoter is active in a yeast cell. In some embodiments, the eukaryotic promoter is active in a plant cell. The present invention is not limited to any particular type of vector construct. Indeed, the use of a variety of vectors is contemplated. In some embodiments, the vector is an expression vector. In some embodiments, the expression vector is a eukaryotic expression vector. In other embodiments, said eukaryotic expression vector is a plant expression vector. In other embodiments, said plant expression vector comprises a T-DNA vector. In other embodiments, said expression vector is a prokaryotic expression vector.

In one embodiment, the invention provides a plant comprising a heterologous nucleic acid molecule encoding a polypeptide that is at least 38% identical to SEQ ID NO:01, wherein said polypeptide provides pathogen resistance.

Accordingly, in other embodiments, the present invention provides an expression vector construct comprising a polypeptide at least 38%, 40%, 45%, 50%, 55%, 60%, 65%, 70%, 75%, 80%, 85%, 90%, 95%, 98%, 99% (or more) identical to any of SEQ ID NO:01, wherein said polypeptide provides pathogen resistance. The present invention is not limited to any particular source of said nucleic acid molecule. Indeed, a variety of sources are contemplated, including but not limited to Brassicaceae, Solanaceae, and Poaceae. In a preferred embodiment, the plant is a transgenic plant. In some embodiments, the pathogen resistance is increased pathogen resistance. In some embodiments, the increased pathogen resistance is increasing the resistance of a plant to a pathogen-induced symptom. The present invention is not limited to any particular type of pathogen-induced symptom. Indeed, a variety of symptoms are contemplated, including but not limited to a canker, a leaf canker, a stem canker, flower blast, dieback, brown spot, a necrotic leaf spot, a blister, and the like. The present invention is not limited to any particular type of pathogen. In some embodiments, the pathogen is a microbial pathogen. Indeed, a variety of microbial pathogens are contemplated, including but not limited to a bacterium, a virus and a fungus. The present invention is not limited to any particular type of bacterium. Indeed, a variety of bacteria are contemplated, including but not limited to a *Pseudomonas* species. The present invention is not limited to any particular type of fungi. Indeed, a variety of fungi are contemplated, including but not limited to a *Cytospora* species and *Nectria* species. The present invention is not limited to any particular type of plant. Indeed a variety of plants are contemplated, including but not limited to a fruit plant, a vegetable plant, a grass plant, a crop plant, a woody plant, and an ornamental plant. In some embodiments, the plant is an *Arabidopsis* plant. In some embodiments, the plant is a tomato plant. In some embodiments, the plant is a rice plant. In some embodiments, the plant is an oil seed rape plant. In some embodiments, the plant is a soybean plant. In some embodiments, the plant is a plant part. The present invention is not limited to any particular type of plant part. Indeed, a variety of plant parts are contemplated, including but not limited to a tiller, a seed, a leaf, and the like.

In one embodiment, the invention provides a method for providing pathogen resistance in a plant, comprising, a) providing, i) a plant, and ii) a nucleic acid molecule, wherein said nucleic acid molecule encodes a polypeptide that is at least 38% identical to SEQ ID NO:01, and b) introducing said nucleic acid molecule into said plant under conditions such that said nucleic acid is expressed and provides pathogen resistance in the plant. In some embodiments, the expressed nucleic acid is overexpressed. In some embodiments, the providing pathogen resistance in the plant is increasing expression of the nucleic acid molecule. In some embodiments, the plant is a transgenic plant. The present invention is not limited to any particular type of pathogen. In some embodiments, the pathogen is a microbial pathogen. Indeed, a variety of microbial pathogens are contemplated, including but not limited to a bacterium, a virus and a fungus. The present invention is not limited to any particular type of bacterium. Indeed, a variety of bacteria are contemplated, including but not limited to a *Pseudomonas* species. The present invention is not limited to any particular type of fungi. Indeed, a variety of fungi are contemplated, including but not limited to a *Cytospora* species and *Nectria* species. The present invention is not limited to any particular type of introducing. In some embodiments, the introducing said nucleic acid molecule into said plant is by transfection. In some embodiments, the introducing said nucleic acid molecule into said plant is by introgression of the nucleic acid molecule into a plant. In some embodiments, the plant is a transgenic plant. In some embodiments, the introducing said nucleic acid molecule into said plant is by transfection or by traditional breeding methods. In some embodiments, the providing pathogen resistance in the plant is by overexpression of the nucleic acid molecule.

In one embodiment, the invention provides an expression vector, comprising a nucleic acid sequence encoding a double stranded RNA sequence, one strand of which is complementary to a sequence at least 75% identical to SEQ ID NO:35. Accordingly, in other embodiments, the present invention provides a sequence at least 75%, 80%, 85%, 90%, 95%, 98%, 99% (or more) identical to any of SEQ ID NOs:35. Accordingly, in some embodiments, the nucleic acid at least 75% identical to SEQ ID NO:35 comprises a full-length nucleic acid or a nucleic acid encoding a C-terminal fragment. The present invention is not limited to any particular C-terminal fragment. Indeed, a variety of C-terminal fragments are provided, including but not limited to nucleic acids comprising 333-2136 nucleic acids of the C-terminus. Accordingly, in other embodiments, the present invention provides a nucleic acid comprising at least 333, 433, 533, 633, 733, 833, 933, 1033, 1133, 1233, (or more) contiguous C-terminal nucleic acids. In some embodiments, the nucleic acid at least 75% identical to SEQ ID NO:35 ranges in size from 10-2136 contiguous C-terminal nucleic acids. In some embodiments, the double stranded RNA sequence mediates RNA interference. The present invention is not limited to any particular type of interference. In some embodiments, the nucleic acid product that interferes is an antisense sequence. In some embodiments, the interference is decreased translation of the polypeptide encoded by SEQ ID NO:35. Accordingly, in some embodiments, the polypeptide is at least 51% identical to SEQ ID NO:34. Accordingly, in other embodiments, the present invention provides a polypeptide at least 51%, 55%, 60%, 65%, 70%, 75%, 80%, 85%, 90%, 95%, 98%, 99% (or more) identical to any of SEQ ID NO:34. Accordingly, in some embodiments, the polypeptide at least 51% identical to SEQ ID NO:34 comprises a full-length polypeptide or a C-terminal fragment. The present invention is not limited to any particular C-terminal fragment. Indeed, a variety of C-terminal fragments are provided, including but not limited to polypeptides comprising 111-611 amino acids of the C-terminus. Accordingly, in other embodiments, the present invention provides a polypeptide comprising at least 100, 200, 300, 400, 500, 600 (or more) contiguous C-terminal amino acids. In some embodiments, the polypeptide at least 51% identical to SEQ ID NO:34 ranges in size from 4-712 contiguous C-terminal amino acids. In some embodiments, the interference is an inhibition of the polypeptide expression.

The inventions further provide a kit for identifying expression of an ATMIN nucleotide or protein. In some embodiments, the kit comprises an expression vector construct comprising an ATMIN polynucleotide. In some embodiments, the kit comprises an ATMIN polypeptide. In some embodiments, the kit comprises an expression vector of the present invention comprising an ATMIN nucleotide.

DESCRIPTION OF THE FIGURES

The patent or application file contains at least one drawing executed in color. Copies of this patent or patent application publication with color drawing(s) will be provided by the Office upon request and payment of the necessary fee.

FIG. 11 shows exemplary sequences for AtMIN7, *Arabidopsis thaliana* guanyl-nucleotide exchange factor (AT3G43300) and homologs in oilseed rape, tomato, and rice (SEQ ID NOs:01-12).

FIG. 12 shows exemplary nucleic acid and amino acid sequences for AtMIN2, AtMIN3, AtMIN4, AtMIN6, AtMIN9, AtMIN10, and AtMIN11, (SEQ ID NOs: 13-26) and exemplary amino acid sequences for ADP-ribosylation factor (ARF) guanine nucleotide exchange factor (GEF) proteins i.e., At1g01960, At3g60860, At4g38200, At4g35380, At1g13980 (GNOM), At5g39500, and At5g19610 (SEQ ID NOs: 27-33, respectively), see, exemplary phylogenetic tree constructions shown in FIG. 9.

FIG. 13 shows exemplary sequences for type III effector HopM1 virulence factor from *Pseudomonas syringae* pv. tomato str. DC3000 and *Pseudomonas syringae* pv. *syringae* B728a (SEQ ID NOs: 34-39).

FIG. 14 shows exemplary primer sequences for amplifying HOPM1 gene segments and AtMIN genes (SEQ ID NOs:40-79); exemplary amino acid sequences and nucleic acid sequences, respectively, encoding exemplary HopM1 fragments of the present inventions (SEQ ID NOs:80-103); an exemplary sequence used as a negative control for plasma membrane localization Xyloglucan 6-xylosyltransferase (AtXT1; At3g62720) (SEQ ID NOs:104 and 113); and exemplary related/homologous sequences for HopM1: *Pseudomonas viridiflava* HopPtoM-like protein$_{1-300}$ (SEQ ID NOs:105 and 110); and *Pseudomonas syringae* pv. *syringae* B728a type III effector HopM1$_{1-300}$ (SEQ ID NOs:106 and 107), *Pseudomonas syringae* pv. *phaseolicola* 1448A HopM1$_{1-300}$ (SEQ ID NOs:108 and 109), and *Pseudomonas syringae* pv. *phaseolicola* 1448A HopM1 (SEQ ID NOs:111 and 112).

DEFINITIONS

Figure 1A:
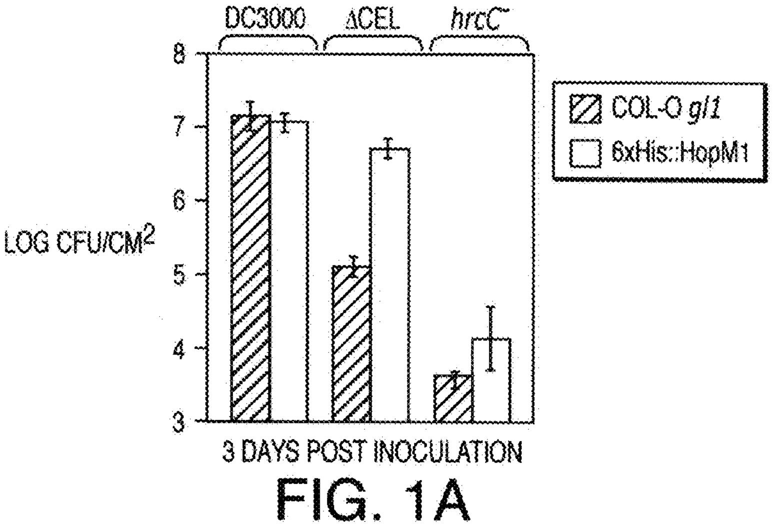
FIG. 1 shows an exemplary analysis of HopM1 transgenic *Arabidopsis* plants. Bacterial multiplication in leaves of wild-type (WT) *Arabidopsis* plants (Col-0 gl1) and transgenic plants expressing full-length HopM1 (A), and in WT leaves of Col-0 gl1 and transgenic plants expressing deletion derivatives of HopM1 (C). Plants were sprayed with dexamethasone (DEX; see, Examples) 24 h before bacterial inoculation ($1\times10^6$ cfu/ml). Bacterial populations were determined at day 3 after inoculation. (B) Immunoblot analysis of HopM1, H+ATPase, and Golgi-localized *Arabidopsis thaliana* xyloglucan xylosyltransferase (AtXTI, SEQ ID NO: 113) of HopM1 transgenic *Arabidopsis* leaf proteins separated into the indicated subcellular fractions. TM: Total membrane; S: Soluble fraction; PM: Plasma-membrane; and EM: Endomembranes.

To facilitate an understanding of the present invention, a number of terms and phrases as used herein are defined below:

The use of the article "a" or "an" is intended to include one or more. As used herein, terms defined in the singular are intended to include those terms defined in the plural and vice versa.

The "effective amount" or "biologically effective amount" refers to the amount of a compound such as a protein that causes a desired biological effect, such as inhibiting pathogen growth on or in a plant. For instance, the effective amount of a peptide can be an amount necessary to inhibit bacterial proliferation, measurably decrease the progression of a bacterial infection, reduce the number of bacteria present or reduce the symptoms of bacterial infection in a plant.

The term "sample" is used in its broadest sense. In one sense it can refer to a plant cell or tissue. In another sense, it is meant to include a specimen, such as a bacterium or spore, or a culture obtained from any source, such as tissue culture or a bacterial culture, as well as biological samples, such as a protein sample, a nucleotide sample, a microbial sample, and the like, and environmental samples, such as microbial sampling. Biological samples may be obtained from plants, a leaf from infected plants, or microorganisms (including bacteria) and encompass fluids, solids, tissues, and gases. Environmental samples include environmental material such as surface matter, soil, water, industrial, and agricultural samples. These examples are not to be construed as limiting the sample types applicable to the present invention.

The term "host cell" refers to any cell capable of replicating and/or transcribing and/or translating a heterologous gene. Thus, a "host cell" refers to any eukaryotic or prokaryotic cell (e.g., plant cells, such as *Arabidopsis*, tomato etc., bacterial cells such as *E. coli*, yeast cells, insect cells, etc.), whether located in vitro or in vivo. For example, host cells may be located in a transgenic plant.

The terms "eukaryotic" and "eukaryote" are used in it broadest sense. It includes, but is not limited to, any organisms containing membrane bound nuclei and membrane bound organelles. Examples of eukaryotes include but are not limited to plants, fungi, alga, diatoms, protists, and animals.

The terms "prokaryote" and "prokaryotic" are used in it broadest sense. It includes, but is not limited to, any organisms without a distinct nucleus. Examples of prokaryotes include but are not limited to bacteria, blue-green algae, archaebacteria, actinomycetes and mycoplasma. In some embodiments, a host cell is any microorganism.

As used herein the term "microorganism" refers to microscopic organisms and taxonomically related macroscopic organisms within the categories of algae, bacteria, fungi, protozoa, viruses, and subviral agents.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Actinomyces, Streptomyces*, and *Sporumosa* and further including cocci, bacilli, spirochetes, spheroplasts, protoplasts, etc. Also included within bacteria are prokaryotic organisms that are gram negative or gram positive.

As used herein, the terms "Gram negative" and "Gram positive" refer to staining patterns with the Gram-staining process that is well known in the art. (See, e.g., Finegold and Martin, Diagnostic Microbiology, 6th Ed., C V Mosby St. Louis, pp. 13-15 [1982]). "Gram positive bacteria" are bacteria that retain the primary dye used in the Gram stain, causing the stained cells to appear dark blue to purple under the microscope. "Gram negative bacteria" do not retain the primary dye used in the Gram stain, but are stained by the counterstain and appear red. In some embodiments, the bacteria are those capable of causing disease (i.e. pathogens) and those that cause product degradation or spoilage. Examples of gram-negative bacteria aerobic rods and cocci relevant to the present inventions include but are not limited to Pseudomonadaceae, such as *Frateuria, Pseudomonas, Xanthomonas, Zooglea*; Azotobacteriaceae, such as *Azomonas, Azotobacter*; Rhizobiaceae, such as *Agrobacterium, Bradyrhizobium, Phyllobacterium, Rhizobium*; Neisseriaceae, such as *Acinetobacter Kingella, Moraxella* and *Neisseria*.

As used herein the terms "*Pseudomonas* species" or "*P.* spp." refer to a Gram negative, aerobic, and motile bacterium. For example, virulent forms of *Pseudomonas syringae* are economically important plant pathogens causing diseases in tomato plants, bean plants and other susceptible plant species. For example, virulent forms of *P. syringae* pv. *syringae* cause disease such as brown spot on bean and snap bean plants and speck on tomatoes.

The term "pathovar" or "pv" refers to a strain or set of strains with the same or similar characteristics, differentiated on the basis of distinctive but not exclusive pathogenicity to one or more plant hosts. For example, *Pseudomonas syringae* pv. tomato, (Okabe, (1933) Bacterial diseases of plants occurring in Formosa. II. Bacterial leaf spot of tomato. Journal of the Society of Tropical Agriculture, Taiwan 5:26-36; Young, et al. Genus *Pseudomonas Migula* 1894. In: Young, et al. (1978) A proposed nomenclature and classification for plant pathogenic bacteria. New Zealand Journal of Agricultural Research 21:153-177; all of which are herein incorporated by reference), is a pathogen of tomato plants, causing disease such as bacterial speck, that also infects *Arabidopsis* plants and *Nicotiana benthamiana* plants, while *P. syringae* pv. *glycinea* infects soybean and may also infect *Arabidopsis* plants, see, Young et al. 1991, Rev. Pl. Pathol. 70:211-221 for a review of bacteria nomenclature; herein incorporated by reference.

The term "biovar" refers to a variety of a species; may be a name or number designation, for example, "biovar 2."

The term "strain" or "Bacterium Strain" or "Bacterium Strain designation" refers to a designation, such as DC3000, listed after a species or pathovar designation, for example, *Pseudomonas syringae* pv. tomato DC3000, where *Pseudomonas syringae* pv. tomato may also refer to type strains such as CFBP 2212; ICMP 2844; LMG 5093; or NCPPB 1106; *P. syringae* pv. *syringae* B728a refers to strain B728a; *P. syringae* pv. *phaseolicola* 1448A is an isolate designated 1448 that may cause halo blight on bean.

The term "Race" in reference to a bacterium refers to naming a subdivision of a species, for example, *P. syringae* pv. *phaseolicola* 1448A, Race 6.

The terms "fungi" and plural "fungus" refer to organisms that form a large group of plant-like living organisms that do not contain chlorophyll, including yeasts, molds, and mushrooms The term "mildew" refers to fungi that form a superficial, usually whitish growth on plants and various organic materials and also refers to a plant disease caused by such fungi.

The term "protist" refers to a heterogeneous group of organisms having relatively simple organization (unicellular, or multicellular), without highly specialized tissues, including unicellular algae, protozoa, slime molds, and water molds, animal-like protozoa, plant-like algae, and fungi-like mold, such as water mold, slime molds, diatoms, golden algae, brown algae, et cetera.

The term "water mold" or "Oomycota" refers to a fungus-like protist, for e.g., *Phytopthana infestans* that destroyed potato crops causing the Irish potato blight or Great Potato Famine, also referred to as "downy mildews" and "white rusts."

The term "downy mildew" refers to a disease characterized by yellowish to brownish areas of irregular size and shape (oval to cylindrical) on infected leaves or seed stalks of susceptible plants, such as vine plants and vegetables that grow on vine-like plants, e.g. cucumbers, etc., caused by certain fungi and protists, such as several types of water mold, such as *Plasmopara viticol* that infects grape plants and *Peronospora parasitica* that infects Brassicae plants such as broccoli, Brussels sprouts, cabbage, and cauliflower plants.

The term "powdery mildew" refers to a disease characterized by spots or patches of white to grayish of superficial powdery growth on leaves and shoots caused by fungi that grow on the surface of a plant.

The term "avirulent" refers to mutants of a bacterium or virus that lost the capacity to infect a host productively, that is, to make more bacterium or virus.

As used herein, "Avr" or "Avirulence protein" refers to a protein found through the avirulence phenotype.

The term "virulence" refers to a degree of pathogenicity of a given pathogen.

The term "virulent" refers to a capability for causing a severe disease; e.g. strongly pathogenic.

The term "virulence factor" or "virulence protein" refers to molecules that are produced by pathogens and further allow pathogens to invade host organisms, cause disease, or evade immune responses, such factors include but are not limited to adhesion molecules that are involved in the adhesion of bacteria to host cells, e.g. host cell receptors for bacteria at the surface of host cells; colonization factors; invasion factors; immune response blockers, and toxins.

As used herein the term "pathogen" and grammatical equivalents refers to an organism, including microorganisms, that cause disease in another organism (e.g., plants) by directly infecting the other organism, or by producing agents that cause or enhance disease in another organism (e.g., bacteria that produce virulence proteins and/or pathogenic toxins and the like).

The term "pathogenicity" refers to a capability of a pathogen to cause disease.

The term "susceptible" refers to lacking an inherent ability to resist disease or attack by a given pathogen; e.g. nonimmune. When used in reference to a plant, such as a "susceptible plant" refers to a plant that is not able to resist infection of a pathogen and exhibits disease symptoms. A plant may be susceptible to one pathogen, but resistant to another.

The term "susceptibility" refers to an inability of a plant to resist the effect of a pathogen or other damaging factor, such as a virulence factor.

The term "resistance" refers to an ability of an organism to exclude or overcome, completely or in some degree, the effect of a pathogen or other damaging factor, e.g. immune. When used in reference to a plant gene, as in "resistance genes" or "r genes" resistance refers to a plant gene associated with recognition of pathogen avirulence factors, for example, putative receptors of avirulence factors such as leucine-rich repeat proteins and/or kinases.

The term "resistant" refers to possessing qualities that hinder the development of a given pathogen, e.g., a plant that is exposed to a pathogenic organism that does not become infected or shows few disease symptoms. When used in reference to a plant, as in a "resistant plant" refers to a plant that is able to resist pathogen infection and exhibits no or few disease symptoms. A plant may be resistant to one pathogen, but susceptible to another.

The term "symptom" in reference to an infection or disease refers to an external and internal reaction or alteration of a plant as a result of a disease, for example, formation of papilla, water-soaking, chlorosis, necrosis, et cetera.

The term "papilla" in reference to a plant papilla refers to a structure that may be induced and observed at the pathogen infection site between the primary cell wall and the plasma membrane of a host plant cell, where a papilla contains cell wall materials, such as callose and lignin.

The term "water-soaking" in reference to a plant refers to a disease symptom during a bacterial infection that may be caused by infected plant release of water into the apoplast.

As used herein the term "disease" refers to any malfunctioning of host cells and tissues that results from continuous irritation by a pathogenic agent or environmental factor and leads to development of symptoms (e.g., blight, leaf spot, seed spot, fruit spot and fruit scab, papilla, gall, crown gall, witches'-broom, canker, rot, leaf curl, mosaic, and yellows, wilt, stunting, mold, mildew, abnormal leaf color, abnormal vein patterns of leaves, mottling in leaves, spotting patterns in leaves, abnormal leaf shape, such as pronounced upward rolling and twisting of leaflets, stunted plant growth, abnormalities of flower color, abnormalities of fruit size, abnormalities of fruit shape, abnormalities of fruit color, etc). A disease may be caused or result from contact by microorganisms and/or pathogens, for example, fungi cause diseases such as Dutch elm disease, chestnut blight, rust, smut, certain mildews, and ergot.

The term "necrosis" refers to living tissues in plants that are undergoing nonapoptotic cell death. Necrosis may cause discoloring of stems or leaves or kill a plant entirely. A necrotic area refers to dead plant tissue or dead plant parts.

The term "chlorosis" refers to a yellowing of normally green tissues.

The term "Genomic Islands" or "GI" refer to mobile genetic elements that are transferred through horizontal gene transfer, such as by plasmid, phage, or a conjugative transposon, and have been integrated into an organism's genome, such as elements relating to the pathogenicity of an organism. A Genomic Island may confer upon an organism fitness to occupy a particular ecological niche (Hentschel et al. (2001) Microbes Infect. 3(7):545-8; herein incorporated by reference).

The term "genomic pathogenicity island" or "pathogenicity islands" or "PAIs" refers to a distinct class of genomic islands which are acquired by horizontal transfer. A pathogenicity island is incorporated in the genome of the majority of pathogenic microorganisms but are typically absent from or nonfunctional in those of non-pathogenic organisms of the same or closely related species. Pathogenicity islands usually occupy relatively large genomic regions ranging from 10-200 kb and encode genes which contribute to the virulence of the respective pathogen, for example, genes encoding adherence factors, toxins, iron uptake systems, invasion factors and secretion systems such as type III secretion-associated hrp/hrc genes, an exchangeable effector locus" or "EEL" encoding diverse putative effector proteins and a conserved effector locus" or "CEL" are located in pathogenicity islands.

The terms "horizontal gene transfer" or "HGT," also "lateral gene transfer" or "LGT" refer to a process in which an organism transfers genetic material (i.e. DNA) to another cell that is not its offspring.

The term "gall" refers to a spherical-like overgrowth or swelling of plant cells that may be the result of an attack by certain insects, bacteria, fungi, or nematodes.

The term "host" or "subject," as used herein, refers to a target of a pathogen or heterologous gene, or a susceptible organisms to be treated by the compositions of the present invention, such as organisms that are exposed to, or suspected of being exposed to, one or more pathogens or the subject of prophylactic treatment. Host organisms include, but are not limited to plants (e.g., crop plants), algae, yeast, and animals.

The term "host cell" refers to any cell capable of replicating and/or transcribing and/or translating a heterologous gene of a plant pathogen or a plant.

As used herein, the terms "contacted" and "exposed" refer to bringing one or more of the compositions of the present invention into contact with a pathogen or a sample to be protected against pathogens such that the compositions of the present invention may inactivate the microorganism or pathogenic agents, if present. The present invention contemplates that the disclosed compositions are contacted to the pathogens or microbial agents in sufficient volumes and/or concentrations to inactivate the pathogens or microbial agents.

The term "pathovar" or "pv" refers to a strain or set of strains with the same or similar characteristics, differentiated at an infrasubspecific level from other strains of the same species or subspecies on the basis of distinctive but not exclusive pathogenicity to one or more plant hosts. For example, *Pseudomonas syringae* pv. tomato DC3000 that is an economically destructive pathogen of tomato plant that also infects *Arabidopsis* plants. *Pseudomonas syringae* pv. tomato strains DC300, either containing or lacking the avirulence gene avrRPM.

As used herein, the terms "agronomic trait" and "economical trait" refers to any selected trait that is desirable in a plant, such that a desirable trait increases the commercial value of a plant or plant part, for example, a preferred oil content, protein content, seed protein content, seed fatty acid content, seed size, seed color, hilium color, seed coat thickness, seed sugar content, seed free amino acid content, seed germination rate, seed texture, seed fiber content, seed Vitamin E content, seed isoflavone content, seed phytate content, seed phytosterol content, seed isoflavone content, lecithin content, food-grade quality, hilium color, seed yield, plant type, plant height, lodging, shatter, herbicide resistance, disease resistance, insect resistance, nematode resistance, drought tolerance, drought resistance, water tolerance, water resistance, temperature tolerance, such as cold weather resistance, hot weather resistance, and the like, growth habit, maturity group, field tolerance, and growth in a hardiness zone.

As used herein, the terms "formulation" in reference to an "agronomic formulation" refers to a composition comprising a peptide or nucleic acid of the present invention for use on or around plants.

As used herein, "AtMIN" or "*Arabidopsis thaliana* HopM interactors" refers to at least 21 *Arabidopsis thaliana* AtMIN proteins, such as AtMIN2, AtMIN7, etc., and further may refer to a homolog, ortholog or paralog in *Arabidopsis* or other plants.

As used herein, "AtMIN7" refers to an *Arabidopsis thaliana* GEF.

As used herein, "GEF" or "guanyl-nucleotide exchange factor activity" or "guanyl-nucleotide release factor activity" or "guanyl-nucleotide releasing factor" or "GNRP" refers to a gene encoding for or a protein that stimulates (catalyse) an exchange of guanyl nucleotides by a GTPase, i.e. the exchange of GTP for GDP bound to the protein.

As used herein, "ADP-ribosylation factor" or "Arf" or "ARF" refers to a family of nucleotides and protein that encode a low molecular mass Ras-related GTPase.

As used herein, "exchange factors for ARF GTPases" or "ARF-GEFs" refers to a gene or protein of an ADP-ribosylation factor G.

As used herein, "GNOM" refers to a guanine nucleotide exchange factor (GEF) that acts on ADP ribosylation factor (ARF) type G proteins (ARF-GEF) (see, Busch et al. 1996; Shevell et al. 1994 and Steinmann et al. 1999; herein incorporated by reference).

As used herein, "Hop" or "hopPtoM" or "Hrp outer protein" refers generically to proteins translocated and/or secreted by a Hrp system of *P. syringae* and other plant pathogens with similar Hrp systems (e.g., *Erwinia* and *Pantoea* spp), see, "*P. syringae* Hop Identification and Nomenclature Home Page" at pseudomonas-syringae.org/pst_func_gen2.htm.

As used herein, "Hrp" or "hypersensitive response and pathogenicity" refers to mutations in the TTSS machinery that abolish the ability of *P. syringae* to elicit the "HR" in nonhosts or to be pathogenic in hosts.

As used herein, "hrc or "hrp conserved" refer to conserved genes associated with the pathogenicity of a pathogen, such as those found in *P. syringae* pv. *syringae* (causing brown spot of bean and other plants), *Erwinia amylovora* (causing fire blight of apple and pear), *Ralstonia* (*Pseudomonas*) *solanacearum* (causing bacterial wilt of tomato), and *Xanthomonas campestris* pv. *vesicatoria* (causing bacterial spot of pepper and tomato and also found in nonpathogenic bacteria such as *Escherichia coli* and *Pseudomonas fluorescens* (see, for reference, Bogdanove, et al., (1996) Mol. Microbiol. 20(3): 681-3; herein incorporated by reference).

As used herein, "effector" refers to a virulence protein injected into host cells by a TTSS, which is broadly applicable to various plant and animal pathogens. As used herein, "TTSS" or "T3SS" type III secretion system" or "Type III secretion pathway" such as in "Hrp pathway in *P. syringae* pathovars" refers to secretion or translocation through this pathway is considered the defining characteristic for *P. syringae* effector proteins. Type III effector proteins are essential for the virulence of *Pseudomonas syringae, Xanthomonas* spp., *Ralstonia solanacearum* and *Erwinia* species. For the purposes of the present inventions, Gram-negative bacteria may deliver effector proteins into the cells of their eukaryotic hosts using the type III secretion system.

The terms "exchangeable effector locus" or "EEL" refer to a group of genes that flank a TTSS region, for example, three putative effector proteins encoded by the *P. syringae* pv. *syringae* B728a EEL include HopPsyC, HopPsyE, and HopPsyV.

As used herein, "helper protein" or "translocator" refers to a term of convenience referring to extracellular accessory proteins (such as HrpA) plus other TTSS substrates (such as harpins) whose primary function is likely to be the translocation of true effectors through host barriers.

As used herein, "harpin" refers to a presumed helper proteins that are secreted by the TTSS in more abundance than true effectors, appear to interact with plant cell walls and membranes, are glycine-rich and devoid of cysteine, and possess a heat-stable ability to elicit the hypersensitive response when infiltrated into the intercellular (apoplastic) spaces of plant leaves.

The term "plant" is used in it broadest sense. A type of plant includes, but is not limited to, any species of woody plant, ornamental plant or decorative plant, crop or cereal plant, fruit plant or vegetable plant, and algae.

The term "crop" or "crop plant" is used in its broadest sense. The term includes, but is not limited to, any species of plant or algae edible by humans or used as a feed for animals or used or consumed by humans, or any plant or algae used in industry or commerce. A crop plant includes a family of plants, for example Brassicaceae, that includes but is not limited to cabbage, kale, radish, mustard plants and thale plants, or a genus of plants, such as *Arabidopsis* (rockcress) plants that includes but is not limited to Thale and Mouse Cress (*Arabidopsis thaliana*), *Solanaceae* including but is not limited to these examples, *Nicotiana* plants, such as Tobacco (*Nicotiana* spp., L.) plants, that refer to a genus of broad-leafed plants of the nightshade family, including but not limited to a *Nicotiana benthamiana* plant, and *Lycopersicon* spp., including but is not limited to *Lycopersicon esculentum* (tomato) plants and Poaceae (grass family), *Oryza* spp., including *Oryza sativa* and *Oryza glaberrima* rice plants.

The term "variety" refers to a biological classification for an intraspecific group or population, that can be distinguished from the rest of the species by any characteristic (for example morphological, physiological, cytological, etc.). A variety may originate in the wild but can also be produced through selected breeding (for example, see, cultivar).

The terms "cultivar," "cultivated variety," and "cv" refer to a group of cultivated plants distinguished by any characteristic (for example morphological, physiological, cytological, etc.) that when reproduced sexually or asexually, retain their distinguishing features to produce a cultivated variety.

A plant also refers to an intact living structure or a partial living structure, such as a plurality of plant cells that form a structure that is present at any stage of a plant's development, such as a plant part. Such structures include, but are not limited to, a leaf, shoot, stem, a fruit, flower, petal, et cetera.

The term "plant part" as used herein refers to a plant structure or a plant tissue. A plant part may comprise one or more of a leaf, stem, tiller, plug, rhizome, sprig, stolen, meristem, crown, and the like.

The term "seed" refers to a ripened ovule, consisting of the embryo and a casing.

The term "stem" refers to a main ascending axis of a plant.

The term "tiller" refers to a portion of a plant growing from the base of the stem of a plant, also referred to as a "shoot." A tiller may also be described as a lateral stem (or shoot), usually erect, that develops from the central crown, and may also refer to the branch or shoot that originates at a basal node. A tiller is often used for propagation, such as vegetative propagation, of a plant.

The term "propagation" refers to the process of producing new plants, either by vegetative means involving the rooting or grafting of pieces of a plant, or by sowing seeds. The terms "vegetative propagation" and "asexual reproduction" refer to the ability of plants to reproduce without sexual reproduction, by producing new plants from existing vegetative structures that are clones, i.e., plants that are identical in all attributes to the mother plant and to one another. For example, the division of a clump, rooting of proliferations, or cutting of mature crowns can produce a new plant.

As used herein, the term "hybrid" in reference to a seed or plant is produced as the result of controlled cross-pollination as opposed to a "non-hybrid" seed produced as the result of natural pollination, as in a "hybrid seed" produced by breeding methods of the present invention.

As used herein, the terms "introgress" and "introgressing" refer to incorporating a genetic substance, such as germplasm, loci, allele, gene, DNA, and the like for introducing a trait into an organism, such as a plant, a plant cell, a yeast cell, and the like, for example, incorporating pathogen resistant transgenic material and/or transgenes into a previously pathogen susceptible plant variety. Introgression may refer to one of several types of breeding methods for a incorporating a genetic trait, such as pathogen resistance provided by expression of a transgene, including compositions and methods for identifying the expression of a heterolous transgene, such as by a Northern blot or immunoblotting or PCR analysis.

The terms "leaf" and "leaves" refer to a structure attached to a stem or branch of a plant where photosynthesis and transpiration take place.

The term "epidermis" refers to an outer most layer of cells of the leaf and of young stems and roots.

The term "cell wall" refers to a rigid layer of extracellular matrix material that completely surrounds a plant cell or fungal cell or a bacterium.

The terms "tissue culture" and "micropropagation" refer to a form of asexual propagation undertaken in specialized laboratories, in which clones of plants are produced from small cell clusters from very small plant parts (e.g. buds, nodes, leaf segments, root segments, etc.), grown aseptically (free from any microorganism) in a container where the environment and nutrition can be controlled.

The term "plant tissue" includes differentiated and undifferentiated tissues of plants including those present in roots, shoots, leaves, pollen, seeds and tumors, as well as cells in culture (e.g., single cells, protoplasts, embryos, callus, etc.).

The term plant cell "compartments or organelles" is used in its broadest sense. The term includes but is not limited to vacuoles, the endoplasmic reticulum, Golgi apparatus, trans Golgi network, plastids, sarcoplasmic reticulum, glyoxysomes, mitochondrial, chloroplast, nuclear membranes, and the like.

For the purposes of the present invention, a "protoplast" refers to a cell, such as a plant, fungal or bacterium, that does not have a cell wall where a cell wall would have been present in its natural state.

The terms "allele" and "alleles" refer to each version of a gene for a same locus that has more than one sequence. For example, there are multiple alleles for eye color at the same locus.

The terms "recessive," "recessive gene," and "recessive phenotype" refer to an allele that has a phenotype when two alleles for a certain locus are the same as in "homozygous" or as in "homozygote" and then partially or fully loses that phenotype when paired with a more dominant allele as when two alleles for a certain locus are different as in "heterozygous" or in "heterozygote."

The terms "dominant," "dominant allele," and "dominant phenotype" refer to an allele that has an effect to suppress the expression of the other allele in a heterozygous (having one dominant allele and one recessive allele) condition.

The terms "transgenic" when used in reference to a plant or leaf or fruit or seed or plant part for example a "transgenic plant," "transgenic leaf," "transgenic fruit," "transgenic seed," and a "transgenic host cell" refer to a plant or leaf or fruit or seed or part or cell that contains at least one heterologous or foreign gene in one or more of its cells.

The term "transgenic plant material" refers broadly to a plant, a plant structure, a plant tissue, a plant seed or a plant cell that contains at least one heterologous gene in one or more of its cells.

The term "heterologous" when used in reference to a gene or nucleic acid refers to a gene that has been manipulated in some way. For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.).

Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The term "accession" when used herein associated with sequences of genes and proteins refers to a gene or group of similar genes or proteins from these genes or proteins received from a single source at a single time. The term "accession number" when used herein refers to a unique identifier for protein and gene sequences and is assigned when an accession is entered into a database (for example GenBank at NCBI, European Molecular Biology Laboratory (EMBL), SWISS-PROT, and the like.

The term "gene" encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region termed "exon" or "expressed regions" or "expressed sequences" interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitution refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on). Thus, nucleotide sequences of the present invention can be engineered in order to introduce or alter an AtMIN or HOPM1 coding sequence for a variety of reasons, including but not limited to initiating the production of tolerance to pathogens; alterations that modify the cloning, processing and/or expression of the gene product (such alterations include inserting new restriction sites and changing codon preference), as well as varying the protein function activity (such changes include but are not limited to differing binding kinetics to nucleic acid and/or protein or protein complexes or nucleic acid/protein complexes, differing binding inhibitor affinities or effectiveness, differing reaction kinetics, varying subcellular localization, and varying protein processing and/or stability) for enhancing pathogen resistance in a plant.

The term "fusion" when used in reference to a polypeptide refers to a chimeric protein containing a protein of interest joined to an exogenous protein fragment (the fusion partner). The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences include those obtained from the same or from different species of organisms. The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The terms "nucleic acid," "nucleic acid sequence," "nucleotide sequence of interest," and "nucleic acid sequence of interest" refer to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

The term "structural" when used in reference to a gene or to a nucleotide or nucleic acid sequence refers to a gene or a nucleotide or nucleic acid sequence whose ultimate expression product is a protein (such as an enzyme or a structural protein), an rRNA, an sRNA, a tRNA, and the like.

The term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The term "polynucleotide" refers to a molecule comprised of several deoxyribonucleotides or ribonucleotides, and is used interchangeably with oligonucleotide. Typically, oligonucleotide refers to shorter lengths, and polynucleotide refers to longer lengths, of nucleic acid sequences.

The term "an oligonucleotide (or polypeptide) having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc., may be placed in close proximity to the coding region of the gene if needed to permit proper initiation of transcription and/or correct processing of the primary RNA transcript. Alternatively, the coding region utilized in the expression vectors of the present invention may contain endogenous enhancers, exogenous promoters, splice junctions, intervening sequences, polyadenylation signals, etc., or a combination of both endogenous and exogenous control elements.

The "fragment" or "portion" in reference to a nucleotide sequence refers to a sequence that may range in size from an exemplary 100, 200, 300, or 399 contiguous nucleotide residues to the entire nucleic acid sequence coding region minus one nucleic acid residue. Thus, a nucleic acid sequence comprising "at least a portion of" a nucleotide sequence comprises from ten (10) contiguous nucleotide residues of the nucleotide sequence to the entire nucleotide sequence length of coding region minus one.

The terms "protein," "polypeptide," "peptide," "encoded product," "amino acid sequence" are used interchangeably to refer to compounds comprising amino acids joined via peptide bonds and a "protein" encoded by a gene is not limited to the amino acid sequence encoded by the gene, but includes post-translational modifications of the protein. Where the term "amino acid sequence" is recited herein to refer to an amino acid sequence of a protein molecule, the term "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein. The deduced amino acid sequence from a coding nucleic acid sequence includes sequences which are derived from the deduced amino acid sequence and modified by post-translational processing, where modifications include but not limited to glycosylation, hydroxylations, phosphorylations, and amino acid deletions, substitutions, and additions. Thus, an amino acid sequence comprising a deduced amino acid sequence is understood to include post-translational modifications of the encoded and deduced amino acid sequence. The term "X" may represent any amino acid.

The term "portion" or "fragment" when used in reference to a protein (as in "a fragment of a given protein") refers to a sequence that may range in size from four amino acid residues to the entire amino sequence minus one amino acid.

The term "fragment" when in reference to a specific protein (such as "HopM1 proteins" etc.) refers to an exemplary 100, 200, 300, or 399 amino acid sequence. Accordingly, a fragment of a that protein may range in size from four (4) contiguous amino acid residues to the entire amino acid sequence minus one amino acid residue. Thus, a polypeptide sequence comprising "at least a portion of an amino acid sequence" comprises from four (4) contiguous amino acid residues of the amino acid sequence to the entire amino acid sequence.

The terms "homolog," "homologue," "homologous," and "homology" when used in reference to amino acid sequence or nucleic acid sequence or a protein or a polypeptide refers to a degree of sequence identity to a given sequence, or to a degree of similarity between conserved regions, or to a degree of similarity between three-dimensional structures or to a degree of similarity between the active site, or to a degree of similarity between the mechanism of action, or to a degree of similarity between functions. In some embodiments, a homolog has a greater than 20% sequence identity to a given sequence. In some embodiments, a homolog has a greater than 30% sequence identity to a given sequence. In some embodiments, a homolog has a greater than 50% sequence identity to a given sequence. In some embodiments, a homolog has a greater than 70% sequence identity to a given sequence. In some embodiments, a homolog has a greater than 90% sequence identity to a given sequence. In some embodiments, a homolog has a greater than 95% sequence identity to a given sequence. In some embodiments, homology is determined by comparing internal conserved sequences to a given sequence. In some embodiments, homology is determined by comparing designated conserved functional regions. In some embodiments, homology is determined by comparing designated conserved "motif" regions.

The term "homology" when used in relation to nucleic acids or proteins refers to a degree of identity. There may be partial homology or complete homology. The following terms are used to describe the sequence relationships between two or more polynucleotides and between two or more polypeptides: "identity," "percentage identity," "identical," "reference sequence," "sequence identity," "percentage of sequence identity," and "substantial identity." "Sequence identity" refers to a measure of relatedness between two or more nucleic acids or proteins, and is described as a given as a percentage "of homology" with reference to the total comparison length. A "reference sequence" is a defined sequence used as a basis for a sequence comparison; a reference sequence may be a subset of a larger sequence, for example, the sequence that forms an active site of a protein or a segment of a full-length cDNA sequence or may comprise a complete gene sequence. Since two polynucleotides or polypeptides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as used herein, refers to a conceptual segment of in internal region of a polypeptide. In one embodiment, a comparison window is at least 77 amino acids long. In another embodiment, a comparison window is at least 84 amino acids long. In another embodiment, conserved regions of proteins are comparison windows. In a further embodiment, an amino acid sequence for a conserved transmembrane domain is 24 amino acids. Calculations of identity—may be performed by algorithms contained within computer programs such as the ClustalX algorithm (Thompson, et al. Nucleic Acids Res. 24, 4876-4882 (1997)); herein incorporated by reference); MEGA2 (version 2.1) (Kumar, et al. Bioinformatics 17, 1244-1245 (2001)); "GAP" (Genetics Computer Group, Madison, Wis.), "ALIGN" (DNAStar, Madison, Wis.), BLAST (National Center for Biotechnology Information; NCBI as described at http://www.ncbi.nlm-.nih.g-ov/BLAST/blast_help.shtml) and MultAlin (Multiple sequence alignment) program (Corpet, Nucl. Acids Res., 16 (22), 10881-10890 (1988) at //prodes.toulouse.inra.fr/multalin/multalin.html), all of which are herein incorporated by reference).

For comparisons of nucleic acids, 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math. 2:482 (1981)) by the homology alignment algorithm of Needleman and Wunsch (Needleman and Wunsch, J. Mol. Biol. 48:443 (1970); herein incorporated by reference), by the search for similarity method of Pearson and Lipman (Pearson and Lipman, Proc. Natl. Acad. Sci. (U.S.A.) 85:2444 (1988); herein incorporated by reference), by computerized implementations of these algorithms (GAP, BESTFIT, FASTA, and TFASTA in the Wisconsin Genetics Software Package Release 7.0, Genetics Computer Group, 575 Science Dr., Madison, Wis.; herein incorporated by reference), or by inspection, and the best alignment (i.e., resulting in the highest percentage of homology over the comparison window) generated by the various methods is selected. The term "sequence identity" means that two polynucleotide or two polypeptide sequences are identical (i.e., on a nucleotide-by-nucleotide basis or amino acid basis) over the window of comparison. The term "percentage of sequence identity" is calculated by comparing two optimally aligned sequences over the window of comparison, determining the number of positions at which the identical nucleic acid base (e.g., A, T, C, G, U, or I) or amino acid, in which often conserved amino acids are taken into account, occurs in both sequences to yield the number of matched positions, dividing the number of matched positions by the total number of positions in the window of comparison (i.e., the window size), and multiplying the result by 100 to yield the percentage of sequence identity.

The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

The term "ortholog" refers to a gene in different species that evolved from a common ancestral gene by speciation. In some embodiments, orthologs retain the same function.

The term "paralog" refers to genes related by duplication within a genome. In some embodiments, paralogs evolve new functions. In further embodiments, a new function of a paralog is related to the original function.

The term "partially homologous nucleic acid sequence" refers to a sequence that at least partially inhibits (or competes with) a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence that is completely complementary to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial-degree of identity (e.g., less than about 30% identity); in the absence of non-specific binding the probe will not hybridize to the second non-identical target.

The term "substantially homologous" when used in reference to a double-stranded nucleic acid sequence such as a cDNA or genomic clone refers to any probe that can hybridize to either or both strands of the double-stranded nucleic acid sequence under conditions of low to high stringency as described above.

The term "substantially homologous" when used in reference to a single-stranded nucleic acid sequence refers to any probe that can hybridize (i.e., it is the complement of) the single-stranded nucleic acid sequence under conditions of low to high stringency as described above.

The term "hybridization" in reference to a nucleic acid refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. Melting temperature $T_m$ is the midpoint of the temperature range over which nucleic acids are denatured (e.g. DNA:DNA, DNA:RNA and RNA:RNA, etc.). Methods for calculating the $T_m$ of nucleic acids are well known in the art (Sambrook, et al., Molecular Cloning: A Laboratory Manual, 2$^{nd}$ ed., Cold Spring Harbor Laboratory Press, New York (1989) pp. 9.50-51, 11.48-49 and 11.2-11.3; herein incorporated by reference).

The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent (50×Denhardt's contains per 500 ml:0.05 g Ficoll (Type 400, Pharmacia):0.05 g BSA (Fraction V; Sigma)) and 100 μg/ml denatured salmon sperm DNA followed by washing in a solution comprising 5×SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 1.0×SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.). "Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "expression" when used in reference to a nucleic acid sequence, such as a gene, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (as when a gene encodes a protein), through "translation" of mRNA. Gene expression can be regulated at many stages in the process.

"Up-regulation" or "activation" or "enhanced" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination," "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The terms "RNA interference" or "RNAi" and "interference" in reference to RNA refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector and/or an expression vector that is not integrated into the genome. The expression of the gene is either completely or partially inhibited. RNAi may also be considered to inhibit the function of a target RNA; the function of the target RNA may be complete or partial. In both plants and animals, RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger, although the protein components of this activity are unknown. However, the 22-nucleotide RNA sequences are homologous to the target gene that is being suppressed. Thus, the 22-nucleotide sequences appear to serve as guide sequences to instruct a multicomponent nuclease, RISC, to destroy the specific mRNAs. Carthew has reported (Curr. Opin. (2001) Cell Biol. 13(2):244-248) that eukaryotes silence gene expression in the presence of dsRNA homologous to the silenced gene. Biochemical reactions that recapitulate this phenomenon generate RNA fragments of 21 to 23 nucleotides from the double-stranded RNA. These stably associate with an RNA endonuclease, and probably serve as a discriminator to select mRNAs. Once selected, mRNAs are cleaved at sites 21 to 23 nucleotides apart.

The term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, and the like.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237 (1987); herein incorporated by reference). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Maniatis, et al., supra (1987); herein incorporated by reference).

The terms "promoter element," "promoter," or "promoter sequence" refer to a DNA sequence that is located at the 5' end (i.e., precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length. Promoters may be tissue specific or cell specific. The term "tissue specific" as it applies to a promoter refers to a promoter that is capable of directing selective expression of a nucleotide sequence of interest to a specific type of tissue (e.g., seeds) in the relative absence of expression of the same nucleotide sequence of interest in a different type of tissue (e.g., leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected.

The term "cell type specific" as applied to a promoter refers to a promoter that is capable of directing selective expression of a nucleotide sequence of interest in a specific type of cell in the relative absence of expression of the same nucleotide sequence of interest in a different type of cell within the same tissue.

The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody that is specific for the polypeptide product encoded by the nucleotide sequence of interest whose expression is controlled by the promoter. A labeled (e.g., peroxidase conjugated) secondary antibody that is specific for the primary antibody is allowed to bind to the sectioned tissue and specific binding detected (e.g., with avidin/biotin) by microscopy. Promoters may be "constitutive" or "inducible."

The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098; herein incorporated by reference), and ubi3 promoters (see e.g., Garbarino and Belknap, Plant Mol. Biol. 24:119-127 (1994); herein incorporated by reference). Such promoters have been used successfully to direct the expression of heterologous nucleic acid sequences in transformed plant tissue.

In contrast, an "inducible" promoter is one that is capable of directing a level of transcription of an operably linked nucleic acid sequence in the presence of a stimulus (e.g., heat shock, chemicals, light, etc.) that is different from the level of transcription of the operably linked nucleic acid sequence in the absence of the stimulus.

The term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, and the like.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species).

The term "naturally linked" or "naturally located" when used in reference to the relative positions of nucleic acid sequences means that the nucleic acid sequences exist in nature in the relative positions.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., Molecular Cloning: A Laboratory Manual, 2nd ed., Cold Spring Harbor Laboratory Press, New York (1989) pp. 16.7-16.8; herein incorporated by reference). A commonly used splice donor and acceptor site is the splice junction from the 16S RNA of SV40. Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly (A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6-16.7; herein incorporated by reference).

The term "vector" refers to nucleic acid molecules that transfer DNA segment(s). Transfer can be into a cell, cell to cell, et cetera. The term "vehicle" is sometimes used interchangeably with "vector."

The terms "expression vector" and "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome-binding site, often along with other sequences. Eukaryotic cells are known to utilize promoters, enhancers, and termination and polyadenylation signals.

The term "expression vector" in reference to a construct, such as "expression vector construct" refers to an artificial vector engineered for expressing a nucleic acid in a particular organism, such as a plant, and can be more specifically engineered for expression within a particular type or species of plant or plant tissue.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The terms "stable transfection" and "stably transfected" refer to the introduction and integration of foreign DNA into the genome of the transfected cell. The term "stable transfectant" refers to a cell that has stably integrated foreign DNA into the genomic DNA.

The terms "transient transfection" and "transiently transfected" refer to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The terms "infecting" and "infection" when used with a bacterium refer to co-incubation of a target biological sample, (e.g., cell, tissue, etc.) with the bacterium under conditions such that nucleic acid sequences contained within the bacterium are introduced into one or more cells of the target biological sample.

The term "*Agrobacterium*" refers to a soil-borne, Gram-negative, rod-shaped phytopathogenic bacterium that causes crown gall. *Agrobacterium* is a representative genus of a soil-borne, Gram-negative, rod-shaped phytopathogenic bacterium family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. *Agrobacterium tumefaciens* causes crown gall disease by transferring some of its DNA to the plant host. The transferred DNA (T-DNA) is stably integrated into the plant genome, where its expression leads to the synthesis of plant hormones and thus to the tumorous growth of the cells. A putative macromolecular complex forms in the process of T-DNA transfer out of the bacterial cell into the plant cell.

The term "*Agrobacterium*" includes, but is not limited to, the strains *Agrobacterium tumefaciens* (which typically causes crown gall in infected plants), and *Agrobacterium* rhizogens (which causes hairy root disease in infected host plants). Infection of a plant cell with *Agrobacterium* generally results in the production of opines (e.g., nopaline, agropine, octopine, etc.) by the infected cell. Thus, *Agrobacterium* strains which cause production of nopaline (e.g., strain GV3101, LBA4301, C58, A208, etc.) are referred to as "nopaline-type" *Agrobacteria; Agrobacterium* strains which cause production of octopine (e.g., strain LBA4404, Ach5, B6, etc.) are referred to as "octopine-type" *Agrobacteria*; and *Agrobacterium* strains which cause production of agropine (e.g., strain EHA105, EHA101, A281, etc.) are referred to as "agropine-type" *Agrobacteria.*

The terms "bombarding, "bombardment, and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807; herein incorporated by reference), and are commercially available (e.g. the helium gas-driven microprojectile accelerator, such as a PDS-1000/He, BioRad).

The term "microwounding" when made in reference to plant tissue refers to the introduction of microscopic wounds in that tissue. Microwounding may be achieved by, for example, particle bombardment as described herein.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (in Virol., 52:456 (1973); herein incorporated by reference), is well-known to have been modified by several groups to optimize conditions for particular types of cells.

The term "transgene" refers to a foreign gene that is placed into an organism by the process of transfection.

The term "foreign gene" refers to any nucleic acid (e.g., gene sequence) that is introduced into the genome of an organism by experimental manipulations and may include gene sequences found in that organism so long as the introduced gene does not reside in the same location, as does the naturally occurring gene.

The terms "transformants" and "transformed cells" include the primary transformed cell and cultures derived from that cell without regard to the number of transfers. Resulting progeny may not be precisely identical in DNA content, due to deliberate or inadvertent mutations. Mutant progeny that have the same functionality as screened for in the originally transformed cell are included in the definition of transformants.

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotransferase (NPTII) gene that confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See, e.g., deWet et al., Mol. Cell. Biol. 7:725 (1987) and U.S. Pat. Nos. 6,074,859; 5,976,796; 5,674,713; and 5,618,682; all of which are herein incorporated by reference), green fluorescent protein (e.g., GenBank Accession Number U43284; GFP variants commercially available from CLONTECH Laboratories, Palo Alto, Calif.; herein incorporated by reference), chloramphenicol acetyltransferase, β-galactosidase (lacZ gene), alkaline phosphatase, and horse radish peroxidase.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex that is transcribed by a cell in its natural state into a "sense mRNA." Thus, an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand". The strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The terms "hpRNA" and "hairpin RNA" refer to self-complementary RNA that forms hairpin loops and functions to silence genes (e.g. Wesley et al. (2001) The Plant Journal 27(6): 581-590; herein incorporated by reference). The term "ihpRNA" refers to intron-spliced hpRNA that functions to silence genes.

The term "target RNA molecule" refers to an RNA molecule to which at least one strand of the short double-stranded region of a siRNA is homologous or complementary. Typically, when such homology or complementary is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA genomes.

The terms "posttranscriptional gene silencing" and "PTGS" refer to silencing of gene expression in plants after transcription, and appears to involve the specific degradation of mRNAs synthesized from gene repeats.

The term "cosuppression" refers to silencing of endogenous genes by heterologous genes that share sequence identity with endogenous genes.

The term "overexpression" generally refers to the production of a gene product in transgenic organisms that exceeds levels of production in normal or non-transformed organisms.

The term "cosuppression" refers to the expression of a foreign gene that has substantial homology to an endogenous gene resulting in the suppression of expression of both the foreign and the endogenous gene.

As used herein, the term "altered levels" refers to the production of gene product(s) in transgenic organisms in amounts or proportions that differ from that of normal or non-transformed organisms.

The terms "overexpression" and "overexpressing" and grammatical equivalents, are specifically used in reference to levels of mRNA to indicate a level of expression approximately 2-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots).

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook, et al., Molecular Cloning: A Laboratory Manual, 2nd ed., Cold Spring Harbor Laboratory Press, New York (1989) pp. 9.31-9.58; herein incorporated by reference).

The term "Northern blot analysis," "Northern blot," and "Northern" refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, et al. supra, pp 7.39-7.52, (1989); herein incorporated by reference).

The terms "RACE" and "Rapid Amplification of cDNA Ends" refer to a PCR technique used to obtain the 3' end of a cDNA as in 3' RACE and to obtain the 5' end of a cDNA as in 5' RACE.

The terms "blot analysis," "Western blot," and "Western" refer to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

The term "isolated" when used in relation to a nucleic acid or polypeptide, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules, either nucleic or amino acid sequences that are removed from their natural environment isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

As used herein, the terms "purified" and "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "reagent" in reference to a method and a kit, refers to a substance or molecule, such as a polynucleotide, an antisense nucleotide, peptide, an antibody, a chemical a buffer, an expression vector, and the like, necessary for various test methods and kits of the present invention, including those compounds used for measuring the expression level of the indicator gene, or protein, such as HOPM1, ATMIN7, and the like, are useful as reagents. These test reagents can be made into a kit for testing for altered trafficking, for pathogen infection, for a plant's response to a pathogen, the capability of a plant's response to a pathogen, for example, labeling a protein or nucleotide, with a substrate compound used for detection of the label, a buffer for diluting the sample, or a positive or negative standard sample. Furthermore, an instruction sheet and such indicating the method of using the kit can be packaged in the kit for the testing of this invention.

The peptide, polynucleotide, antibody, cell line, or model animal and plant, including animal and plant cells, which are necessary for the various methods of screening of this invention, can be combined in advance to produce a kit. More specifically, such a kit may comprise, for example, a cell that expresses the indicator gene, and a reagent for measuring the expression level of the gene or location of a protein. As a reagent for measuring the expression level of the indicator gene, for example, an oligonucleotide that has at least 15 nucleotides complementary to the polynucleotide comprising the nucleotide sequence of at least one indicator gene or to the complementary strand thereof may be used. Alternatively, an antibody that recognizes a peptide comprising amino acid sequence of at least one indicator protein may be used as a reagent.

In these kits may be packaged a substrate compound used for the detection of the indicator, medium and a vessel for cell culturing, positive and negative standard samples, and furthermore, a manual describing how to use the kit. A kit of this invention, for detecting the effect of a candidate compound on the expression level of the indicator gene or peptide of this invention, can be used for screening for a compound that modifies the expression level of the indicator gene of this invention. Test candidate compounds used in these methods include, in addition to compound preparations synthesized by known chemical methods, steroid derivatives and compound preparations synthesized by combinatorial chemistry, and mixtures of multiple compounds such as extracts from animal or plant tissues, or microbial cultures and their purified preparations.

GENERAL DESCRIPTION OF THE INVENTION

The present invention relates to compositions and methods for enhancing plant defenses against pathogens. More particularly, the invention relates to enhancing plant immunity against bacterial pathogens, wherein AtMIN7 mediated protection is enhanced and/or there is a decrease in activity of an AtMIN7 associated virulence protein such as a *Pseudomonas syringae* pv. tomato DC3000 HopM1. Reagents of the present invention provide a means of studying cellular trafficking while formulations of the present inventions provide increased pathogen resistance in plants.

*Pseudomonas syringae* infects a wide range of economically important crop plant species, including but not limited to tomatoes, beans, cabbage and *Brassica* species. In the past two decades, *P. syringae* strains were used as an important model for the discovery of many fundamental mechanisms in host-pathogen interactions. *Pseudomonas syringae* is divided into pathovars differing in host specificity, for example, *P. syringae* pv. *syringae* (Psy) and *P. syringae* pv. tomato (Pto) represent particularly divergent pathovars that primarily infect beans and tomato plants, respectively, however both can cause pathogenic symptoms in *Arabidopsis* plants.

To render plant tissue suitable for microbial growth pathogens alter the physiology of the host. Such modifications include inhibiting anti-microbial defenses, releasing of water and/or nutrients into the apoplast, and inducing certain disease symptoms. Previous studies by others have revealed that *P. syringae* utilizes at least two different mechanisms to deliver virulence factors that promote these events: i) secretion of toxins into the apoplast and/or ii) direct injection of bacterial proteins into the host cell through a specialized delivery apparatus known as the Type III secretion system (TTSS).

In *Arabidopsis*, Pto DC3000 multiplies aggressively in leaves, in particular within spaces in between plant cells, a region referred to as "apoplast," for about 2 days before the onset of disease symptoms. Symptoms include water soaking in the apoplast, followed by tissue necrosis and chlorosis (Whalen (1991) Plant Cell 3:49-59; Katagiri, et al. (2002) in The *Arabidopsis Book*, eds. Somerville and Meyerowitz, (Am. Soc. Plant Biologists, Rockville, Md.); all of which are incorporated by reference). The ability of DC3000 to infect *Arabidopsis* depends on TTSS as demonstrated by hrp mutants [e.g., hrpS and hrcC (formerly hrph) mutants] of DC3000 that do not multiply or cause disease in *Arabidopsis* plants (Yuan and He (1996) *J. Bacteriol.* 178:6399-6402, Roine, et al. (1997) *Proc. Natl. Acad. Sci. USA* 94:3459-3464; all of which are incorporated by reference). A TTSS of DC3000 is believed to secrete and/or translocate at least 30 effector proteins into the host cell (Boch, et al. (2002) Mol. Microbiol. 44:73-88; Fouts, et al. (2002) Proc. Natl. Acad. Sci. USA 99:2275-2280; Guttman, et al. (2002) Science 295: 1722-1726; Petnicki-Ocwieja, et al. (2002) Proc. Natl. Acad. Sci. USA 99:7652-7657; Salanoubat, et al. (2002) Nature 415:497-502; Zwiesler-Vollick, et al. (2002) Mol. Microbiol. 45:1207-1218; all of which are herein incorporated by reference). Cumulatively, these effectors alter host cellular processes and promote disease development through unknown mechanisms.

Although the primary function of type III effectors is to promote plant susceptibility, some effectors may be recognized by the corresponding plant disease resistance proteins in resistant plants and trigger defense responses, including the hypersensitive response (HR) (Goodman and Novacky (1994) Am. Phytopathol. Soc., St. Paul); Greenberg (1997) Annu. Rev. Plant Physiol. Plant Mol. Biol. 48:525-545; all of which are herein incorporated by reference). Further, many type III effector genes in *P. syringae* were discovered based on their ability to trigger a HR in resistant plants and have been named avr (for avirulence) genes (Ronald et al. (1992) *J. Bacteriol.* 174:1604-1611; herein incorporated by reference). For example, the type III effector, AvrPto, was identified based on its avirulence activity in plants (Ronald, et al. (1992) J. Bacteriol. 174:1604-1611; Scofield, et al. (1996) Science, 274:2063-2065; Tang, et al. (1999) Plant Cell 11:15-30; all of which are herein incorporated by reference). Although the ability of type III effectors to trigger defense responses in resistant plants is well understood, the mechanism by which type III effectors, as a group, enable plant pathogenic bacteria to proliferate in the intercellular space of a susceptible plant remains enigmatic. In addition to type III effectors, DC3000 also produces the phytotoxin coronatine (COR), which is required for full virulence in *Arabidopsis* (Ma, et al. (1991) Mol. Plant-Microbe Interact. 4:69-74; Mittal and Davis, (1995) Mol. Plant-Microbe Interact. 8:165-171; Bender, et al. (1999) Microbiol. Mol. Biol. Rev. 63:266-292; all of which are herein incorporated by reference).

The *P. syringae* strains examined during the course of studies for developing the present invention contain a common genomic pathogenicity island, which is composed of type III secretion-associated hrp/hrc genes, an exchangeable effector locus (EEL), and a conserved effector locus (CEL) (Alfano et al. (2000) Proc. Natl. Acad. Sci. U.S.A. 97:4856; herein incorporated by reference). Deletion of the CEL in Pst DC3000 resulted in dramatic reduction of the bacterial population and complete elimination of disease symptoms (necrosis and chlorosis) in infected tomato and *Arabidopsis* plants, suggesting a particularly important role of CEL-encoded effectors in *P. syringae* interactions with different host plants (Alfano et al. (2000) Proc. Natl. Acad. Sci. U.S.A. 97:4856; DebRoy et al. (2004) Proc. Natl. Acad. Sci. U.S.A. 101:9927; all of which are herein incorporated by reference). Hop (Hrp-dependent outer protein), such as HopPsyA, is one example of a protein encoded by pathogenicity island of *Pseudomonas syringae* that contributes to pathgenicity (For further examples, see, U.S. Pat. No. 6,852,835; herein incorporated by reference).

A virulence defect in ΔCEL mutant bacteria is caused by the deletion of the functionally redundant effector genes hopM1 (formerly hopPtoM) and avrE (DebRoy et al. (2004) Proc. Natl. Acad. Sci. U.S.A. 101:9927; herein incorporated by reference). pORF43 is a plasmid expressing HopM1 that with its cognate chaperone ShcM, is sufficient to fully complement the virulence defect of the ΔCEL mutant in *Arabidopsis* (DebRoy et al. (2004) Proc. Natl. Acad. Sci. U.S.A. 101:9927; herein incorporated by reference).

Pst DC3000 HopM1 is a novel 712-aa protein that lacks cysteine residues. Previous studies by the inventors showed that HopM1 is translocated into the host cell (Badel et al. Mol. Microbial. 49:1239 (2003); herein incorporated by reference). During the course of developing the present inventions, HopM1 expression was found to restore the virulence of the Pst DC3000 ΔCEL mutant in a host plant cell.

Figure 9A:
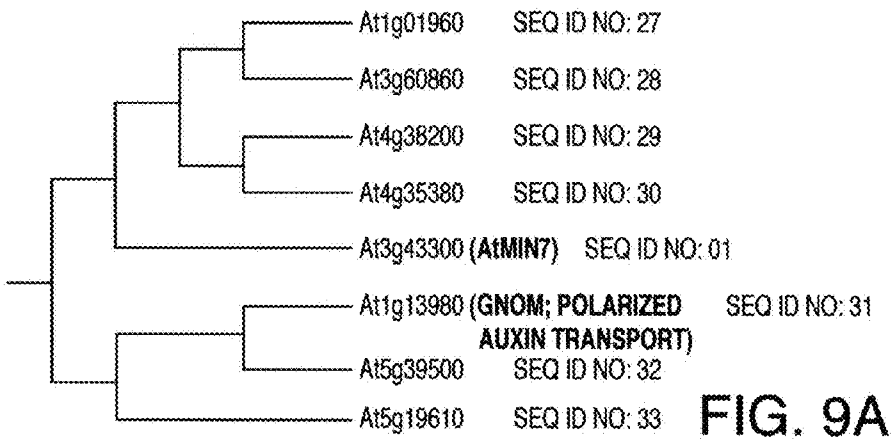
FIG. 9 shows (A) an exemplary phylogenetic tree indicating the relationship among *Arabidopsis* ADP-ribosylation factor (ARF) guanine nucleotide exchange factor (GEF) proteins, The *Arabidopsis* Book Article: pp. 1-35. Protein sequences (SEQ ID NOs:01, and 27-33, were aligned using the ClustalW program (http://align.genome.jp) to construct the tree. (B) Yeast two-hybrid interaction assay of the physical interaction between HopM11-300 expressed from pGILDA (Clontech) and selected Arf GEF proteins expressed from pB42AD (Clontech). Yeast colonies were grown on complete minimal medium containing galactose and X-gal. A blue color indicates interaction, whereas a white color indicates no interaction. (C) Immunoblot analysis of Arf GEF proteins in yeast when co-expressed with full-length HopM1 or HopM11-300. Arf GEF fusion proteins expressed from pB42AD were visualized by the HA epitope antibody. HopM1 fusion proteins expressed from pGilda were visualized by the LexA antibody. Coomassie Brilliant Blue-stained gels were used as loading controls. AtMIN7 was destabilized by full-length HopM1.
Figure 9B:
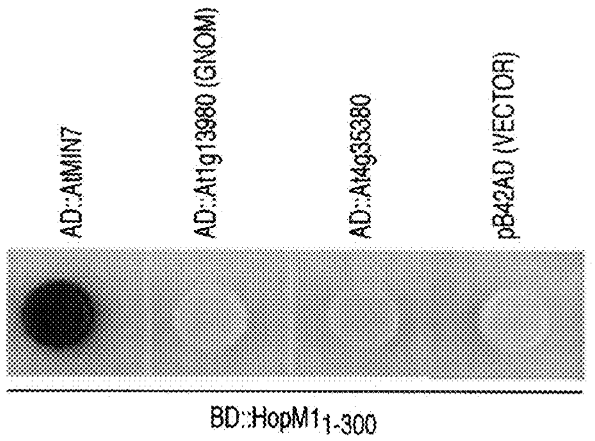
Figure 9C:
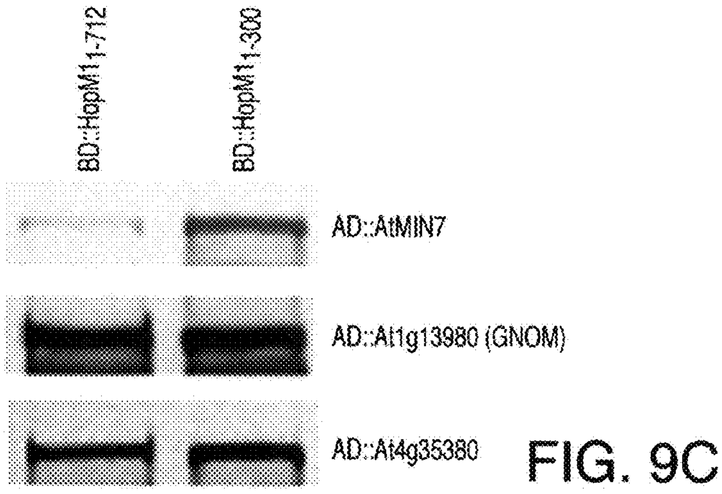

AtMIN7 encodes one of the eight members of the *Arabidopsis* Arf GEF protein family (Sanderfoot and Raikhel, in The *Arabidopsis* Book, Somerville, Meyerowitz, Eds., American Society of Plant Biologists, Rockville, Md., 2002; herein incorporated by reference), FIG. 9 and SEQ ID NOs:1 and 2. Adenosine dinucleotide (ADP) ribosylating factor (ARF) GEFs are key components of the vesicle trafficking system in eukaryotic cells and are the primary molecular targets of BrefeldinA (BFA), an inhibitor of vesicle trafficking well known in the art (Mossessova et al. (2003) Mol. Cell. 12:1403; Steinmann et al. (1999) Science 286:316; all of which are herein incorporated by reference).

DETAILED DESCRIPTION OF THE INVENTION

The present invention relates to compositions and methods for enhancing plant defenses against pathogens. More particularly, the invention relates to enhancing plant immunity against bacterial pathogens, wherein AtMIN7 mediated protection is enhanced and/or there is a decrease in activity of an AtMIN7 associated virulence protein such as a *Pseudomonas syringae* pv. tomato DC3000 HopM1. Reagents of the present invention provide a means of studying cellular trafficking while formulations of the present inventions provide increased pathogen resistance in plants.

TABLE 1

AtMIN proteins that are destabilized by HopMl. Further, these proteins and not predicted to be targeted to organelles.

| Name | SEQ ID NOs: XX | At locus | SALK lines used | Homology (number of putative gene family members) | Putative function |
|---|---|---|---|---|---|
| AtMIN2 | 13 & 14 | At1g16190[1] | SALK_064980.56.00.x SALK_066603.56.00.x | RAD23/hHR23A (3 members) | Binding to ubiquitin and proteasome, p53 degradation, DNA repair |
| AtMIN3 | 15 & 16 | At1g18490 | SALK_103109.23.60.x SALK_103215.33.55.x | Expressed protein (1 member) | Not available |
| AtMIN4 | 17 & 18 | At2g14910 | SALK_000496.38.95.x SALK_009273.19.95.x | Expressed protein (1 member) | Not available |
| AtMIN6 | 19 & 20 | At2g47710 | SALK_OI5279.54.75.X SALK_099811.44.65.x | Universal stress protein (USP) family protein, similar to ER6 protein (1 member) | Response to stress |
| AtMIN7 | 1 & 2 | At3g43300 | SALK_OI2013.54.75.x SALK_013761.46.95.x | Guanine nucleotide exchange factor (GEF) protein (8 members) | Guanyl-nucleotide exchange factor activity |
| AtMIN9 | 21 & 22 | At5g64180 | SALK_OI6899.19.70.x SALK_092105.52.05.x | Expressed protein (1 member) | ATPbinding |
| AtMIN10 | 23 & 24 | At5g65430 | SALK_036856.29.30.x SALK_092382.15.65.x | 14-3-3 protein (14 members) | Signal transduction protein, binding to phosphoproteins |
| AtMIN11 | 25 & 26 | At5g66420 | SALK_077054.31.05.x SALK_082859.26.60.x | Expressed protein (1 member) | Hydrolase activity, hydrolyzing O-glycosyl compounds, carbohydrate metabolism, defense response |

[1]At1g16190: 'At' indicates *Arabidopsis thaliana*; '1g' indicates that this gene is on chromosome 1.

The present invention relates to compositions and methods for increasing plant defenses against pathogens. More particularly, the invention relates to increasing plant immunity against bacterial pathogens, wherein ATMIN mediated protection is enhanced and/or there is a decrease in activity of an ATMIN associated virulence protein such as a *Pseudomonas syringae* pv. tomato DC3000 HopM1 virulence protein. Formulations of the present invention comprising a protective HopM1 fragment, such as $HopM1_{1-200}$ and $HopM1_{1-300}$, find use for providing plants with protection against pathogens and/or increasing pathogen resistance in plants. The present invention further relates to compositions and methods for enhancing plant defenses against pathogens, wherein ATMIN7 mediated protection is enhanced and/or there is a decrease in activity of an ATMIN7 associated virulence protein such as a *Pseudomonas syringae* pv. tomato DC3000 HopM1 (see, Nomura, et al., Science. 2006 Jul. 14; 313 (5784):220-3, herein incorporated by reference in it's entirety).

The present invention relates to compositions and methods for increasing plant defenses against pathogens and protecting plants against pathogens, wherein HopM1 fragments mediate protection by decreasing activity of full-length HopM1, such as by providing $HopM1_{1-200}$ or a $HopM1_{1-300}$ protective fragments to a plant.

Reagents of the present invention comprising ATMIN and/or HopM1 and/or HopM1 fragments further provide methods for studying cellular trafficking.

I. ATMIN, HopM1, and Like Genes, Coding Sequences and Polypeptides.

The present invention is not limited to the use of any particular homolog or variant or mutant of an ATMIN or ATMIN-like gene or an ATMIN or ATMIN-like protein. Indeed, in some embodiments a variety of ATMIN or ATMIN-like genes or ATMIN or ATMIN-like proteins, homologs, variants and mutants may be used so long as they retain at least a portion of the activity of the corresponding wild-type protein. In particular, retaining activity that would increase resistance to a pathogen in a plant. In some embodiments, ATMIN or ATMIN-like genes and proteins encoded by the nucleic acids and amino acids of SEQ ID NOs:01-02, 03-12, and 13-36, find use in the present inventions.

In some embodiments, ATMIN7 or ATMIN7-like genes and proteins encoded by the nucleic acids and amino acids of SEQ ID NOs:01 and 02 find use in the present inventions. Accordingly, in other embodiments, nucleic acids that comprise sequences at least 57%, 60%, 65%, 70%, 75%, 80%, 85%, 90%, 95%, 98%, 99% (or more) identical to any of SEQ ID NO:02 find use in the present inventions. In other embodiments, nucleic acids encoding proteins that comprise polypeptides at least 38%, 40%, 45%, 50%, 55%, 60%, 65%, 70%, 75%, 80%, 85%, 90%, 95%, 98%, 99% (or more) identical to any of SEQ ID NO:01 find use in the present inventions. In other embodiments, the present invention provides polypeptides at least 38%, 40%, 45%, 50%, 55%, 60%, 65%, 70%, 75%, 80%, 85%, 90%, 95%, 98%, 99% (or more) identical to any of SEQ ID NO:01 find use in the present inventions. (See, Table 2).

The present invention is not limited to the use of HopM1 genes, proteins, and specific HopM1 fragments. Indeed, in some embodiments a variety of HopM1 proteins or HopM1 genes, homologs, variants and mutants may be used so long as they retain at least a portion of the activity of the corresponding wild-type HopM1 protein. Specifically, HopM1 is contemplated for use in identifying additional ATMIN or ATMIN-like genes and proteins that provide a plant with protection against pathogens. Further, HopM1 genes, homologs, variants and mutants may be used for identify control points in cellular trafficking, in particular the trafficking associated with increasing or decreasing virulence of pathogens. Accordingly, in some embodiments, HopM1 genes and proteins encoded by the nucleic acids and amino acids of SEQ ID NO:35 and 34 find use in the present inventions. In some embodiments, the present invention provides a nucleic acid at least 75%, 78%, 80%, 85%, 90%, 95%, 98%, 99% (or more) identical to any of SEQ ID NO:35. In other embodiments, nucleic acids encoding proteins that comprise polypeptides at least 510%, 55%, 60%, 65%, 70%, 75%, 80%, 85%, 90%, 95%, 98%, 99% (or more) identical to any of SEQ ID NO:34 find use in the present inventions. In other embodiments, the present invention provides polypeptides at least 51%, 55%, 60%, 65%, 70%, 75%, 80%, 85%, 90%, 95%, 98%, 99% (or more) identical to any of SEQ ID NO:34 find use in the present inventions. (See, Table 3).

The present invention also provides HopM1 protective fragments for protecting plants against pathogens. Furthermore, the present invention is not limited to a homolog or variant or mutant of a HopM1 protective fragment, such as a $HopM1_{1-300}$ and $HopM1_{1-200}$ protective fragments provided by SEQ ID NO:94 and polypeptide sequences comprising SEQ ID NO:82. In other embodiments, nucleic acids comprising sequences at least 74%, 79%, 80%, 85%, 90%, 95%, 98%, 99% (or more) identical to any of SEQ ID NO:94 find use in the present inventions. In other embodiments, polypeptides at least 46%, 50%, 55%, 60%, 65%, 70%, 75%, 80%, 85%, 90%, 95%, 98%, 99% (or more) identical to any of SEQ ID NO:82 find use in the present inventions. In other embodiments, the present invention provides a nucleic acid at least 46%, 50%, 55%, 60%, 65%, 70%, 75%, 80%, 85%, 90%, 95%, 98%, 99% (or more) identical to any of SEQ ID NO:82 find use in the present inventions. Further, the present inventions provide homologs of $HopM1_{1-300}$ (See, Table 4). Functional variants can be screened by expressing the variant in an appropriate vector (described in more detail below) in a host cell, such as a yeast cell, plant cell, bacterium, and then analyzing the host cell's response to a pathogen or a virulence protein of a pathogen (e.g. *Pseudomonas* spp., full-length HopM1, etc.).

Further, the nucleic acid sequences and polypeptides of the present inventions provide compositions and methods for altering vesicular trafficking in a cell. In particular, the methods are used for identifying proteins and are contemplated for use in identifying protein binding domains that alter trafficking in a cell, such as proteins that alter trafficking of proteins produced by pathogens, for example, virulence proteins.

A. Nucleic Acid Sequences and Polypeptides:

1. ATMIN and HopM1 Genes:

The present invention provides plant ATMIN or ATMIN-like genes and proteins, including their homologs, orthologs, paralogs, variants and mutants. In some embodiments of the present invention, isolated nucleic acid sequences comprising ATMIN or ATMIN-like genes are provided. Mutations in these genes are contemplated that would alter the encoded ATMIN or ATMIN like proteins to provide increased resistance to pathogen infections. In some embodiments, isolated nucleic acid sequences comprising ATMIN7 or ATMIN7-like are provided. These sequences include sequences comprising ATMIN7 or ATMIN7-like and cDNA/genomic sequences, for example, SEQ ID NOs:2, 4, 6, 8, 10, and 12. In some embodiments of the present invention provide nucleic acid sequences that encode polypeptides that are homologous to at least one of SEQ ID NOs:1, 3, 5, 7, 9, and 11.

The present invention provides HopM1 or HopM1-like genes and polypeptides and fragments thereof, including their homologs, orthologs, paralogs, variants and mutants. In some embodiments of the present invention, isolated nucleic acid sequences comprising HopM1 or HopM1-like genes are provided. Mutations in these genes are contemplated that would alter the encoded HopM1 or HopM1-like proteins to provide increased resistance to pathogen infections. These sequences include sequences comprising HopM1 or HopM1-like and cDNA sequences, for example, SEQ ID NOs:35, 37, and 39. In some embodiments of the present invention provide nucleic acid sequences that encode polypeptides that are homologous to at least one of SEQ ID NOs:34, 36, and 38.

2. Additional ATMIN and ATMIN-Like Genes:

The present invention provides nucleic acid sequences comprising additional ATMIN, HopM1 and -like genes. For example, some embodiments of the present invention provide nucleic acid sequences that encode polypeptides that are homologous to at least one of SEQ ID NOs:01. In some embodiments, the polypeptides are at least 38%, 40%, 45%, 50%, 55%, 60%, 65%, 70%, 75%, 80%, 85%, 90%, 95%, 98%, 99% (or more) identical to SEQ ID NO:01. For example, some embodiments of the present invention provide nucleic acid sequences that encode polypeptides set forth in any one of SEQ ID NOs: 3, 5, 7, 9, 11 and 13, 15, 17, 19, 21, 23, 25, 27, and 28-33. For example, some embodiments of the present invention provide nucleic acid sequences that encode polypeptides that are homologous to at least one of SEQ ID NOs: 3, 5, 7, 9, 11 and 13, 15, 17, 19, 21, 23, 25, 27, and 28-33.

In other embodiments, the present invention provides nucleic acid sequences that hybridize under conditions ranging from low to high stringency to at least one of SEQ ID NO: 02, as long as the polynucleotide sequence capable of hybridizing to at least one of SEQ ID NOs: 02, 4, 6, 8, 10, 12, and 14, 16, 18, 20, 22, 24, and 26 encodes a protein that retains a desired biological activity of a protective pathogen response protein. In some preferred embodiments, the hybridization conditions are high stringency. In preferred embodiments, hybridization conditions are based on the melting temperature ($T_m$) of the nucleic acid binding complex and confer a defined "stringency" as explained above (See e.g., Wahl et al., (1987) Meth. Enzymol., 152:399-407; incorporated herein by reference). In other embodiments of the present invention, alleles of pathogen resistance genes, and in particular of an exogenous ATMIN or ATMIN-like gene, such as ATMIN7 or ATMIN7-like, or a protective fragment of a virulence protein, such as a protective HopM1 fragment (for example, $HopM1_{1-300}$), homologs or mutants or variants thereof, are provided. In preferred embodiments, alleles result from a mutation, (i.e., a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions, or insertions, or substitutions of nucleic acids. Each of these types of changes may occur alone, or in combination with the others, and at the rate of one or more times in a given sequence. Mutational changes in alleles also include rearrangements, insertions, deletions, additions, or substitutions in upstream regulatory regions.

In other embodiments of the present invention, the polynucleotide sequence encoding an exogenous ATMIN or ATMIN-like gene, such as ATMIN7 or ATMIN7-like, homologs or mutants or variants thereof, is extended utilizing the nucleotide sequences (e.g., SEQ ID NO:02) in various methods known in the art to detect upstream sequences such as promoters and regulatory elements. For example, it is contemplated that for an exogenous ATMIN or ATMIN-like gene, such as ATMIN7 or ATMIN7-like, homologs or mutants or variants thereof, including related ATMIN OR ATMIN-like genes, the sequences upstream of the start site or downstream from the poly A tail can be identified using information in databases containing plant genomic information such as The Institute for Genomic Research (TIGR), Plant Functional Genomics Projects, Plant Gene Indices for rice, tomato, rape, wheat, barley, rye, maize, sorghum, soybean, potato, cotton, etc. (http://www.tigr.org/tdb/tgi/plant-.shtml); GrainGenes for wheat, barley, rye, triticale, and oats (http://wheat.pw.usda.gov/QueryDB.shtml); Gramene: A Comparative Mapping Resource for Grains (http://www.gramene.org); rice (http://rgp.dna.affrc.gojp/), maize (MaizeGDB http://www.maizegdb.org/); barley (http://hordeum.oscs.montana.-edu/), soybean (http://stadler.agron.iastate.edulblast/blast.html); *Arabidopsis* (http://www.arabidopsis.org/) databases; and United Kingdom Crop Plant Bioinformatics Network (UK CropNet) at ukcrop.net/db.html; all of which are herein incorporated by reference.

An example of such a method for extending coding region information using a RACE PCR method is described herein for the identification of ATMIN or ATMIN-like segments upstream and downstream of the originally cloned segment. For ATMIN or ATMIN-like specific information, such as ATMIN7 or ATMIN7-like, (SEQ ID NO:4, 6, 8, 10, 12, and the like, or mutants or variants thereof, for which public genomic or expressed information is not available, or not complete, it is contemplated that polymerase chain reaction (PCR) methods in addition to RACE finds use in the present invention. In another embodiment, inverse PCR is used to amplify or extend sequences using divergent primers based on a known region (Triglia et al., (1988) Nucleic Acids Res., 16:8186, herein incorporated by reference). In yet another embodiment of the present invention, capture PCR (Lagerstrom et al., PCR Methods Applic., 1:111-19 (1991), herein incorporated by reference) is contemplated for use in obtaining additional sequences. In still other embodiments, walking PCR is contemplated for use in obtaining additional sequences. Walking PCR is a method for targeted gene walking that permits retrieval of unknown sequence (Parker et al., Nucleic Acids Res., 19:3055-60 (1991), herein incorporated by reference). The PROMOTERFINDER kit (Clontech) uses PCR, nested primers and special libraries to “walk in” genomic DNA. This process avoids the need to screen libraries and is useful in finding intron/exon junctions. In yet other embodiments of the present invention, add TAIL PCR is used as a preferred method for obtaining flanking genomic regions, including regulatory regions (Liu and Whittier, Genomics, 25(3):674-81 (1995); Liu et al., Plant J., 8(3):457-63 (1995); all of which are herein incorporated by reference). Preferred libraries for screening for full-length cDNAs include libraries that have been size-selected to include larger cDNAs. Also, random primed libraries are preferred, in that they contain more sequences that contain the 5' and upstream gene regions. A randomly primed library may be particularly useful in cases where an oligo d(T) library does not yield full-length cDNA. Genomic Libraries are useful for obtaining introns and extending 5' sequence.

3. Variant ATMIN or ATMIN-Like Genes:

In some embodiments, the present invention provides isolated variants of the disclosed nucleic acid sequences encoding an ATMIN or ATMIN-like gene, such as ATMIN or ATMIN-like, or a protective fragment of a virulence protein, such as a protective HopM1 fragment (for example, $HopM1_{1-300}$), homologs or mutants or variants thereof. These variants include mutants, fragments, fusion proteins or functional equivalents of genes and gene protein products.

a. Mutants:

Some embodiments of the present invention contemplate compositions comprising and/or using nucleic acid sequences encoding mutant forms of ATMIN or ATMIN-like gene, such as ATMIN or ATMIN-like, or a protective fragment of a virulence protein, such as a protective HopM1 fragment (for example, $HopM1_{1-300}$), homologs or mutants or variants thereof, (i.e., mutants), and the polypeptides encoded thereby. In preferred embodiments, mutants result from mutation of the coding sequence (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

Mutants of an ATMIN or ATMIN-like gene, such as ATMIN7 or ATMIN7-like, or a protective fragment of a virulence protein, such as a protective HopM1 fragment (for example, $HopM1_{1-300}$), homologs or mutants or variants thereof, can be generated by any suitable method well known in the art, including but not limited to EMS induced mutagenesis, site-directed mutagenesis, randomized “point” mutagenesis, and domain-swap mutagenesis. An example of domain-swap mutagenesis is contemplated in which portions of the ATMIN or ATMIN-like cDNA are “swapped” with the analogous portion of other ATMIN or ATMIN-like-encoding cDNAs such as used for identifying functional regions for pathogen resistance. Another example of domain-swap mutagenesis is contemplated in which portions of the mutants of a HopM1 or HopM1 fragment cDNA are “swapped” with the analogous portion of other HopM1 or HopM1 fragment-encoding cDNAs such as used for identifying functional regions for pathogen virulence or resistance. It is contemplated that is possible to modify the structure of a peptide having a protective activity (e.g., such as a $HopM1_{1-300}$ activity), for such purposes as increasing synthetic activity or altering the affinity of the ATMIN or ATMIN-like protein or protective peptide, $HopM1_{1-300}$, for a binding partner or a kinetic activity. Such modified peptides are considered functional equivalents of peptides having an activity of an ATMIN or ATMIN-like activity or $HopM1_{1-300}$ activity as defined herein. A modified peptide can be produced in which the nucleotide sequence encoding the polypeptide has been altered, such as by substitution, deletion, or addition. In some preferred embodiments of the present invention, the alteration increases or decreases the effectiveness of the ATMIN or ATMIN-like or HopM1 fragment gene product to exhibit a phenotype caused by altered responses of pathogen resistance genes and/or pathogen virulence genes and encoded proteins. In other words, construct “X” can be evaluated in order to determine whether it is a member of the genus of modified or variant ATMIN or ATMIN-like gene or HopM1 protective fragments of the present invention as defined functionally, rather than structurally. Accordingly, in some embodiments the present invention provides nucleic acids encoding a polypeptide comprising ATMIN or ATMIN-like binding domain sequence or a $HopM1_{1-300}$ binding domain sequence that can complement the polypeptides encoded by any one of SEQ ID NOs:01, and 82, as well as the polypeptides encoded by such nucleic acids.

Moreover, as described above, mutant forms of ATMIN or ATMIN-like proteins are also contemplated as being equivalent to those peptides that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. On the other hand, mutant forms of ATMIN or ATMIN-like proteins are contemplated as providing superior resistance to pathogens by affecting the biological activity of the resulting molecule, such that the altered biological activity increases pathogen resistance of a plant. It is contemplated that inhibiting the degradation rate of an ATMIN or ATMIN-like protein will increase pathogen resistance to the pathogen expressing a virulence protein that targets the wild-type ATMIN or ATMIN-like protein.

Accordingly, some embodiments of the present invention provide nucleic acids comprising sequences encoding variants of ATMIN or ATMIN-like gene products containing conservative replacements, as well as the amino acids of the proteins encoded by such nucleic acids. Such replacements are described herein. Whether a change in the amino acid sequence of a peptide results in a functional homolog can be readily determined by assessing the ability of the variant peptide to function in a fashion similar to the wild-type protein. Peptides having more than one replacement can readily be tested in the same manner.

b. Homologs:

In some embodiments, the present invention provides isolated variants of the disclosed nucleic acid sequence encoding a ATMIN or ATMIN-like gene, such as ATMIN7 or ATMIN7-like, or a protective fragment of a virulence protein, such as a protective HopM1 fragment (for example, $HopM1_{1-300}$), homologs or mutants or variants thereof, and the polypeptides encoded thereby; these variants include mutants, fragments, fusion proteins or functional equivalents genes and protein products.

Some homologs of encoded ATMIN or ATMIN-like gene, such as ATMIN or ATMIN-like, or a protective fragment of a virulence protein, such as a protective HopM1 fragment (for example, $HopM1_{1-300}$), homologs or mutants or variants thereof, have intracellular half-lives dramatically different than the corresponding wild-type protein. For example, the altered protein is rendered either more stable or less stable to proteolytic degradation or other cellular process that result in destruction of, or otherwise inactivate the encoded ATMIN or ATMIN-like or HopM1 product. Such homologs, and the genes that encode them, can be utilized to alter the activity of the encoded ATMIN or ATMIN-like or HopM1 products by modulating the half-life of the protein. For instance, a longer half-life may give rise to enhanced ATMIN or ATMIN-like biological effects. Other homologs have characteristics which are either similar to wild-type ATMIN or ATMIN-like or HopM1, or which differ in one or more respects from wild-type ATMIN or ATMIN-like or HopM1.

In some embodiments the combinatorial mutagenesis approach are contemplated for the present invention, the amino acid sequences for a population of ATMIN or ATMIN-like or HopM1 gene product homologs are aligned, preferably to promote the highest homology possible. Such a population of variants can include, for example, ATMIN or ATMIN-like or HopM1 gene homologs from one or more species or ATMIN or ATMIN-like or HopM1 gene homologs from the same species but which differ due to mutation. Amino acids that appear at each position of the aligned sequences are selected to create a degenerate set of combinatorial sequences.

In a preferred embodiment of the present invention, the combinatorial ATMIN or ATMIN-like or HopM1 gene library is produced by way of a degenerate library of genes encoding a library of polypeptides that each include at least a portion of candidate encoded ATMIN or ATMIN-like or HopM1 protein sequence. For example, a mixture of synthetic oligonucleotides is enzymatically ligated into gene sequences such that the degenerate set of candidate ATMIN or ATMIN-like or HopM1 sequences are expressible as individual polypeptides, or alternatively, as a set of larger fusion proteins (e.g., for phage display) containing the set of ATMIN or ATMIN-like or HopM1 sequences therein.

There are many ways by which the library of potential ATMIN or ATMIN-like or HopM1 homologs can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential ATMIN or ATMIN-like or HopM1 sequences or any combination of ATMIN or ATMIN-like sequences and ATMIN or ATMIN-like or HopM1 sequences. The synthesis of degenerate oligonucleotides is well known in the art (see e.g., Narang, Tetrahedron Lett., 39:3 9 (1983); Itakura et al., Recombinant DNA, in Walton (ed.), Proceedings of the 3rd Cleveland Symposium on Macromolecules, Elsevier, Amsterdam, pp 273-289 (1981); Itakura et al., Annu. Rev. Biochem., 53:323 (1984); Itakura et al., Science 198: 1056 (1984); Ike et al., Nucl. Acid Res., 11:477 (1983); all of which are herein incorporated by reference). Such techniques have been employed in the directed evolution of other proteins (see e.g., Scott et al., Science, 249:386-390 (1980); Roberts et al., Proc. Natl. Acad. Sci. USA, 89:2429-2433 (1992); Devlin et al., Science, 249: 404-406 (1990); Cwirla et al., Proc. Natl. Acad. Sci. USA, 87: 6378-6382 (1990); as well as U.S. Pat. Nos. 5,223,409; 5,198,346; and 5,096,815; all of which are herein incorporated by reference).

c. Directed Evolution:

Variants of ATMIN or ATMIN-like or HopM1 genes or coding sequences may be produced by methods such as directed evolution or other techniques for producing combinatorial libraries of variants. Thus, the present invention further contemplates a method of generating sets of nucleic acids that encode combinatorial mutants of the ATMIN or ATMIN-like or HopM1 proteins, as well as truncation mutants, and is especially useful for identifying potential variant sequences (i.e., homologs) that possess the biological activity of the encoded ATMIN or ATMIN-like or HopM1 proteins. In addition, screening such combinatorial libraries is used to generate, for example, novel encoded ATMIN or ATMIN-like gene product homologs that possess novel binding or other kinetic specificities or other biological activities. The invention further provides sets of nucleic acids generated as described above, where a set of nucleic acids encodes combinatorial mutants of the ATMIN or ATMIN-like or HopM1 proteins, or truncation mutants, as well as sets of the encoded proteins. The invention further provides any subset of such nucleic acids or proteins, where the subsets comprise at least two nucleic acids or at least two proteins.

It is contemplated that ATMIN or ATMIN-like gene, such as ATMIN7 or ATMIN7-like, or a protective fragment of a virulence protein, such as a protective HopM1 fragment (for example, $HopM1_{1-300}$), homologs or mutants or variants thereof, can be utilized as starting nucleic acids for directed evolution. These techniques can be utilized to develop encoded ATMIN or ATMIN-like or HopM1 product variants having desirable properties such as increased kinetic activity or altered binding affinity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458-67 (1996); Leung et al., Technique, 1:11-15 (1989); Eckert and Kunkel, PCR Methods Appln., 1:17-24 (1991); Caldwell and Joyce, PCR Methods Appln., 2:28-33 (1992); and Zhao and Arnold, Nuc. Acids. Res., 25:1307-08 (1997), all of which are herein incorporated by reference).

After mutagenesis, the resulting clones are selected for desirable activity (e.g., screened for abolishing or restoring hydroxylase activity in a constitutive mutant, in a wild type background where hydroxylase activity is required, as described above and below). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or special PCR procedures (e.g., Smith, Nature, 370:324-25 (1994); U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full-length molecules. Examples of various gene shuffling procedures include, but are not limited to, assembly following DNase treatment, the staggered extension process (STEP), and random priming in vitro recombination.

d. Screening Gene Products:

A wide range of techniques are known in the art for screening gene products of combinatorial libraries made by point mutations, and for screening cDNA libraries for gene products having a certain property. Such techniques are generally adaptable for rapid screening of the gene libraries generated by the combinatorial mutagenesis of ATMIN or ATMIN-like or HopM1 and/or ATMIN or ATMIN-like homologs, paralogs, and orthologs, and further for pathogen virulence proteins, such as HopM1 and/or HopM1 homologs, paralogs, and orthologs. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

Each of the illustrative assays described below are amenable to high throughput analysis as necessary to screen large numbers of degenerate sequences created by combinatorial mutagenesis techniques. Accordingly, in some embodiments of the present invention, the gene library is cloned into the gene for a surface membrane protein of a bacterial cell, (wherein the bacterial cell does not produce an endogenous virulence protein) and the resulting fusion protein detected by panning (WO 88/06630; Fuchs et al., (1991) BioTechnol., 9:1370-1371; and Goward et al., (1992) TIBS 18:136-140; all of which are herein incorporated by reference). In other embodiments of the present invention, fluorescently labeled molecules that bind encoded ATMIN or ATMIN-like or HopM1 products can be used to score for potentially functional ATMIN or ATMIN-like or HopM1 or $HopM1_{1-300}$ homologs, paralogs, and orthologs. Cells are visually inspected and separated under a fluorescence microscope, or, where the morphology of the cell permits, separated by a fluorescence-activated cell sorter.

In an alternate embodiment of the present invention, the gene library is expressed as a fusion protein on the surface of a viral particle. For example, foreign peptide sequences are expressed on the surface of infectious phage in the filamentous phage system, thereby conferring two significant benefits. First, since these phages can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and fl are most often used in phage display libraries, as either of the phage gIII or gVIII coat proteins can be used to generate fusion proteins without disrupting the ultimate packaging of the viral particle (See e.g., WO 90/02909; WO 92/09690; Marks et al., (1992) J. Biol. Chem., 267:16007-16010; Griffths et al., (1993) EMBO J., 12:725-734; Clackson et al., (1991) Nature 352:624-628; and Barbas et al., (1992) Proc. Natl. Acad. Sci., 89:4457-4461; all of which are herein incorporated by reference).

In another embodiment of the present invention, the recombinant phage antibody system (e.g., RPAS, Pharmacia Catalog number 27-9400-01) is modified for use in expressing and screening of encoded ATMIN or ATMIN-like and/or HopM1, and/or HopM1 protective fragment, homolog, paralog, and ortholog product combinatorial libraries. The pCANTAB 5 phagemid of the RPAS kit contains the gene that encodes the phage gIII coat protein. In some embodiments of the present invention, the ATMIN or ATMIN-like and/or HopM1, and/or HopM1 protective fragment, combinatorial gene library is cloned into the phagemid adjacent to the gIII signal sequence such that it is expressed as a gIII fusion protein. In other embodiments of the present invention, the phagemid is used to transform competent *E. coli* TG1 cells after ligation. In still other embodiments of the present invention, transformed cells are subsequently infected with M13KO7 helper phage to rescue the phagemid and its candidate ATMIN or ATMIN-like gene insert. The resulting recombinant phage containing phagemid DNA encoding a specific candidate ATMIN or ATMIN-like protein and display one or more copies of the corresponding fusion coat protein. In some embodiments of the present invention, the phage-displayed candidate proteins that display any property characteristic of an ATMIN or ATMIN-like or HopM1 or $HopM1_{1-300}$ protein are selected or enriched by panning. The bound phage is then isolated, and if the recombinant phages express at least one copy of the wild type gIII coat protein, they will retain their ability to infect *E. coli*. Thus, successive rounds of reinfection of *E. coli* and panning will greatly enrich ATMIN or ATMIN-like or HopM1 or $HopM1_{1-300}$ homologs, paralogs, and orthologs.

In light of the present disclosure, other forms of mutagenesis generally applicable will be apparent to those skilled in the art in addition to the aforementioned rational mutagenesis based on conserved versus non-conserved residues. For example, ATMIN or ATMIN-like or HopM1 or $HopM1_{1-300}$ homologs can be generated and screened using, for example, using alanine scanning mutagenesis and the like (Ruf et al., (1994) Biochem, 33:1565-1572; Wang et al., (1994) J. Biol Chem, 269:3095-3099; Balint (1993) Gene 137:109-118; Grodberg et al., (1993) Eur. J. Biochem., 218:597-601; Nagashima et al., (1993) J. Biol. Chem., 268:2888-2892;

Lowman et al., (1991) Biochem, 30:10832-10838; and Cunningham et al., (1989) Science, 244:1081-1085; all of which are herein incorporated by reference), by linker scanning mutagenesis (Gustin et al., (1993) Virol., 193:653-660; Brown et al., (1992) Mol. Cell. Biol., 12:2644-2652; McKnight and Kingsbury (1982) Science, 217(4557):316-24; all of which are herein incorporated by reference), or by saturation mutagenesis (Myers et al., (1986) Science, 232(4750): 613-618; herein incorporated by reference).

In some preferred embodiments, the ability of the ATMIN or ATMIN-like or HopM1 or HopM$1_{1-300}$ sequence to bind to its response element is tested in vitro. In some preferred embodiments, the ability of the ATMIN or ATMIN-like or HopM1 or HopM$1_{1-300}$ sequence to bind to its response element is tested in vivo. A response element of an ATMIN or ATMIN-like sequence may be a pathogen protein binding domain and/or an endogenous cellular protein domain. A response element of a HopM1 and/or HopM1 fragment sequence may be an endogenous cellular protein domain.

e. Truncation Mutants of HopM1 Proteins and/or ATMIN or ATMIN-Like Proteins:

In addition, the present invention provides isolated nucleic acid sequences encoding truncated fragments of encoded HopM1 polypeptides and contemplated truncated fragments of ATMIN or ATMIN-like genes (i.e., truncation mutants) and the polypeptides encoded by such truncated nucleic acid sequences. In preferred embodiments, the HopM1 and/or ATMIN or ATMIN-like fragment is biologically active.

In some embodiments of the present invention, when expression of a portion of a HopM1 and/or ATMIN or -like protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., J. Bacteriol., 169:751-757 (1987), herein incorporated by reference) and *Salmonella typhimurium* and its in vitro activity has been demonstrated on recombinant proteins (Miller et al., (1990) Proc. Natl. Acad. Sci. USA, 84:2718-1722, herein incorporated by reference). Therefore, removal of an N-terminal methionine, if desired, can be achieved either in vivo by expressing such recombinant polypeptides in a host that produces MAP (e.g., *E. coli* or CM89 or *S. cerevisiae*), or in vitro by use of purified MAP.

f. Fusion Proteins Containing HopM1 Proteins and/or ATMIN or ATMIN-Like Proteins:

The present invention also provides nucleic acid sequences encoding fusion proteins incorporating all or part of ATMIN or ATMIN-like and/or HopM1 or HopM$1_{1-300}$, and the polypeptides encoded by such nucleic acid sequences. In some embodiments of the present invention, chimeric constructs code for fusion proteins containing a portion of an ATMIN or ATMIN-like and/or HopM1 or HopM$1_{1-300}$ protein and a portion of another gene. In some embodiments, the fusion proteins have biological activity similar to the wild type ATMIN or ATMIN-like and/or HopM1 or HopM$1_{1-300}$ (e.g., have at least one desired biological activity of the protein). In other embodiments, the fusion protein has altered biological activity. In addition to utilizing fusion proteins to alter biological activity, it is widely appreciated that fusion proteins can also facilitate the expression and/or purification of proteins, such as the ATMIN or ATMIN-like and/or HopM1 or HopM$1_{1-300}$ protein of the present invention. Accordingly, in some embodiments of the present invention, it is contemplated that an ATMIN or ATMIN-like and/or HopM1 or HopM$1_{1-300}$ protein is generated as a glutathione-S-transferase (i.e., GST fusion protein). It is also contemplated that such a GST fusion proteins would enable easy purification of the ATMIN or ATMIN-like and/or HopM1 or HopM$1_{1-300}$ protein, such as by the use of glutathione-derivatized matrices (See e.g., Ausabel et al. (eds.), Current Protocols in Molecular Biology, John Wiley & Sons, NY (1991), herein incorporated by reference).

In some embodiments, the fusion proteins have an ATMIN or ATMIN-like and/or HopM1 or HopM$1_{1-300}$ functional domain with a fusion partner. Accordingly, in some embodiments of the present invention, the coding sequences for the polypeptide (e.g., an ATMIN or ATMIN-like functional domain) are incorporated as a part of a fusion gene including a nucleotide sequence encoding a different polypeptide. It is contemplated that such a single fusion product polypeptide is able to provide a transgenic plant with an increased resistance to pathogen infections.

In another embodiment of the present invention, a fusion gene coding for a purification leader sequence, such as a poly-(His)/enterokinase cleavage site sequence at the N-terminus of the desired portion of an ATMIN or ATMIN-like and/or HopM1 or HopM$1_{1-300}$ protein allows purification of the expressed ATMIN or ATMIN-like and/or HopM1 or HopM$1_{1-300}$ fusion protein by affinity chromatography using a $Ni_2$+ metal resin. In still another embodiment of the present invention, the purification leader sequence is then subsequently removed by treatment with enterokinase (See e.g., Hochuli et al., (1987) J. Chromatogr., 411:177; and Janknecht et al., (1991) Proc. Natl. Acad. Sci. USA, 88:8972; all of which are herein incorporated by reference). In yet other embodiments of the present invention, a fusion gene coding for a purification sequence appended to either the N or the C terminus allows for affinity purification; one example is addition of a hexahistidine tag to the carboxy terminus of an ATMIN or ATMIN-like and/or HopM1 or HopM$1_{1-300}$ protein that is optimal for affinity purification, see EXAMPLES for a description and use of a 6× Histidine tagged protein.

Techniques for making fusion genes are well known. Essentially, the joining of various nucleic acid fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments is carried out using anchor primers that give rise to complementary overhangs between two consecutive gene fragments that can subsequently be annealed to generate a chimeric gene sequence (See, e.g., Current Protocols in Molecular Biology, supra, herein incorporated by reference).

B. Encoded ATMIN or ATMIN-Like and/or HopM1 or HopM$1_{1-300}$ Gene Polypeptides:

The present invention provides isolated ATMIN or ATMIN-like and/or HopM1 or HopM$1_{1-300}$ polypeptides, as well as variants, homologs, mutants or fusion proteins thereof, as described above. In some embodiments of the present invention, the polypeptide is a naturally purified product, while in other embodiments it is a product of chemical synthetic procedures, and in still other embodiments it is produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention is glycosylated or non-glycosylated. In other embodiments, the polypeptides of the invention also include an initial methionine amino acid residue.

1. Purification of ATMIN, Hop M1 and $HopM1_{1-300}$ Polypeptides:

The present invention provides or contemplates purified ATMIN, Hop M1 and $HopM1_{1-300}$, and/or homologs thereof, polypeptides as well as variants, homologs, mutants or fusion proteins thereof, as described above. In some embodiments of the present invention, $HopM1_{1-300}$ and/or $HopM1_{1-300}$-like polypeptides purified from recombinant organisms are provided. In other embodiments, $HopM1_{1-300}$ and/or $HopM1_{1-300}$-like polypeptides purified from recombinant bacterial extracts transformed with *Pseudomonas* HopM1 and/or $HopM1_{1-300}$-like cDNA, and in particular any one or more of $HopM1_{1-300}$, and/or $HopM1_{1-300}$-like and or related $HopM1_{1-300}$, are provided.

The present invention also contemplates methods for recovering and purifying ATMIN, Hop M1 and $HopM1_{1-300}$, and/or homologs thereof, from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography.

The present invention further provides nucleic acid sequences having the coding sequence (or a portion of the coding sequence) for a ATMIN or ATMIN-like and/or HopM1 protein (including a fragment) and/or $HopM1_{1-300}$-like protein fused in frame to a marker sequence that allows for expression alone or for both expression and purification of the polypeptide of the present invention. A non-limiting example of a marker sequence is a hexahistidine (6×HIS) tag that is supplied by a vector, for example, a pQE-30 vector which adds a hexahistidine nucleotide tag to the N terminal of an ATMIN or ATMIN-like gene and/or HopM1 or HopM1 fragment gene which results in expression of the polypeptide with a 6×HIS tag, or, for another example, the marker sequence is a hemagglutinin (HA) tag. A HA tag corresponds to an epitope derived from the influenza hemagglutinin protein (Wilson et al., Cell, 37:767 (1984), herein incorporated by reference). See, Examples, for 6×HIS and HA tags.

2. Chemical Synthesis of $HopM1_{1-300}$ and/or $HopM1_{1-300}$-Like Nucleotide Sequences and Polypeptides:

In an alternate embodiment of the invention, a coding sequence of protective fragments, such as $HopM1_{1-300}$ and $HopM1_{1-200}$, genes and/or $HopM1_{1-300}$-like genes (see, examples in Table 4), are synthesized, in whole or in part, using chemical methods well known in the art (See, e.g., Caruthers et al., (1980) Nucleic Acids Symp Ser., 7:215-223; Crea and Horn, (1980) Nucl. Acids Res., 8(10):2331-2348; Matteucci and Caruthers, (1980) Tetrahedron Lett., 21:719; and Chow et al., (1981) Nucl. Acids Res., 10(21):6695-714, all of which are herein incorporated by reference). In other embodiments of the present invention, the protein itself is produced using chemical methods to synthesize an entire $HopM1_{1-300}$ or $HopM1_{1-200}$ and/or $HopM1_{1-300}$-like amino acid sequence (for examples, SEQ ID NOs:82, 105, 106, and 108) or a variant thereof. For example, peptides are synthesized by solid phase techniques, cleaved from the resin, and purified by preparative high performance liquid chromatography (See e.g., Creighton, Proteins Structures And Molecular Principles, W.H. Freeman and Co, New York N.Y. (1983), herein incorporated by reference). In other embodiments of the present invention, the composition of the synthetic peptides is confirmed by amino acid analysis or sequencing (See e.g., Creighton, supra, herein incorporated by reference).

Direct peptide synthesis can be performed using various solid-phase techniques (Roberge et al., (1995) Science, 269: 202-204, herein incorporated by reference) and automated synthesis may be achieved, for example, using ABI 431A Peptide Synthesizer (Perkin Elmer) in accordance with the instructions provided by the manufacturer. Additionally, the amino acid sequence of $HopM1_{1-300}$ and/or $HopM1_{1-300}$-like, or any part thereof, may be altered during direct synthesis and/or combined using chemical methods with other sequences to produce a variant polypeptide.

3. Generation of ATMIN or ATMIN-Like and/or HopM1 and/or HopM1 Fragment Antibodies:

In some embodiments of the present invention, antibodies are generated to allow for the detection and characterization of an ATMIN or ATMIN-like and/or HopM1 and/or HopM1 fragment proteins. The antibodies may be prepared using various immunogens. In one embodiment, the immunogen is an *Arabidopsis* ATMIN or ATMIN-like peptide (e.g., an amino acid sequence as depicted in SEQ ID NOs:01, or HopM1 or a fragment thereof, such as $HopM1_{1-300}$ SEQ ID NOs:82, to generate antibodies that recognize an ATMIN or ATMIN-like and/or a HopM1 protein. Such antibodies include, but are not limited to polyclonal, monoclonal, chimeric, single chain, Fab fragments, and Fab expression libraries.

Various procedures known in the art may be used for the production of polyclonal antibodies directed against an ATMIN or ATMIN-like or HopM1 protein. For the production of antibody, various host animals can be immunized by injection with the peptide corresponding to the ATMIN or ATMIN-like or HopM1 protein epitope including but not limited to rabbits, mice, rats, sheep, goats, et cetera. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface-active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward an ATMIN or ATMIN-like protein and/or HopM1 or HopM1-like protein, it is contemplated that any technique that provides for the production of antibody molecules by continuous cell lines in culture finds use with the present invention (See e.g., Harlow and Lane, Antibodies: A Laboratory Manual, Cold Spring Harbor Laboratory Press, Cold Spring Harbor, N.Y., herein incorporated by reference). These include but are not limited to the hybridoma technique originally developed by Kohler and Milstein (Kohler and Milstein, (1975) Nature, 256:495-497, herein incorporated by reference), as well as the trioma technique, the human B-cell hybridoma technique (See e.g., Kozbor et al., (1983) Immunol Today, 4:72, herein incorporated by reference), and the EBV-hybridoma technique to produce human monoclonal antibodies (Cole et al., (1985) in Monoclonal Antibodies and Cancer Therapy, Alan R. Liss, Inc., pp: 77-96, herein incorporated by reference).

In an additional embodiment of the invention, monoclonal antibodies are produced in germ-free animals utilizing technology such as that described in PCT/US90/02545). Furthermore, it is contemplated that plant tissue antibodies may be generated (e.g. Canas and Malmberg, (1992) Plant Sci 83:195-203, herein incorporated by reference) or by producing plant protein specific monoclonal antibodies by using mouse hybridomas (Lund et al., (1998) Plant Physiol 116: 1097-1110, herein incorporated by reference). In addition, it is contemplated that techniques described for the production of single chain antibodies (U.S. Pat. No. 4,946,778, herein incorporated by reference) find use in producing an ATMIN or ATMIN-like and/or HopM1 or HopM1-like protein-specific single chain antibodies. An additional embodiment of the invention utilizes the techniques described for the construction of Fab expression libraries (Huse et al., (1989) Science, 246:1275-1281, herein incorporated by reference) to allow rapid and easy identification of monoclonal Fab fragments with the desired specificity for an ATMIN or ATMIN-like and/or HopM1 or HopM1-like protein.

It is contemplated that any technique suitable for producing antibody fragments finds use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody is accomplished by techniques known in the art (e.g., radioimmunoassay), ELISA (enzyme-linked immunosorbant assay), "sandwich" immunoassays, immunoradiometric assays, gel diffusion precipitin reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, et cetera.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay. In some embodiments of the present invention, the foregoing antibodies are used in methods known in the art relating to the expression of an ATMIN or ATMIN-like protein (e.g., for Western blotting), measuring levels thereof in appropriate biological samples, etc. The antibodies can be used to detect an ATMIN or ATMIN-like and/or HopM1 or HopM1-like protein in a biological sample from a plant. The biological sample can be an extract of a tissue, or a sample fixed for microscopic examination.

The biological samples are then tested directly for the presence of an ATMIN or ATMIN-like or HopM1 protein or HopM1 fragment using an appropriate strategy (e.g., ELISA or radioimmunoassay) and format (e.g., microwells, dipstick (e.g., as described in WO 93/03367 herein incorporated by reference)), etc. Alternatively, proteins in the sample can be size separated (e.g., by polyacrylamide gel electrophoresis (PAGE), in the presence or not of sodium dodecyl sulfate (SDS), and the presence of an ATMIN or ATMIN-like or HopM1 polypeptide detected by immunoblotting (Western blotting). Immunoblotting techniques are generally more effective with antibodies generated against a peptide corresponding to an epitope of a protein, and hence, are particularly suited to the present invention.

C. Expression of Cloned ATMIN or ATMIN-Like or HopM1:

In some embodiments, genes described above may be used to generate recombinant DNA molecules that direct the expression of the encoded protein product in appropriate host cells. As will be understood by those of skill in the art, it may be advantageous to produce ATMIN or ATMIN-like or HopM1-encoding nucleotide sequences possessing non-naturally occurring codons. Therefore, in some preferred embodiments, codons preferred by a particular prokaryotic or eukaryotic host (Murray et al., (1989) Nucl. Acids Res., 17(2):477-498, herein incorporated by reference) can be selected, for example, to increase the rate of ATMIN or ATMIN-like or HopM1 expression or to produce recombinant RNA transcripts having desirable properties, such as a longer half-life, than transcripts produced from naturally occurring sequence.

1. Vectors for Production of ATMIN or ATMIN-Like or HopM1:

The nucleic acid sequences of the present invention may be employed for producing polypeptides by recombinant techniques. Thus, for example, the nucleic acid sequence may be included in any one of a variety of expression vectors for expressing a polypeptide.

In some embodiments of the present invention, vectors include, but are not limited to, chromosomal, nonchromosomal and synthetic DNA sequences (e.g., derivatives of plant tumor sequences, T-DNA sequences, derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the nucleic sequences as broadly described above. In some embodiments of the present invention, the constructs comprise a vector, such as a plasmid or eukaryotic vector, or viral vector, into which a nucleic acid sequence of the invention has been inserted, in a forward or reverse orientation. In preferred embodiments of the present invention, the appropriate nucleic acid sequence is inserted into the vector using any of a variety of procedures. In general, the nucleic acid sequence is inserted into an appropriate restriction endonuclease site(s) by procedures known in the art.

Large numbers of suitable vectors are known to those of skill in the art, and are commercially available. Such vectors for incorporation into host cells include, but are not limited to, the following vectors and their derivatives: 1) Prokaryotic and other host cells—pBI221, pBI121 (Clonetech), pYeDP60, pQE70, pQE60, pQE-9 (Qiagen), pBS, pD10, phagescript, psiX174, pbluescript SK, pBSKS, pNH8A, pNH16a, pNH18A, pNH45A (Stratagene); ptrc99a, pKK223-3, pKK233-3, pDR540, pRIT5 (Pharmacia); pBI2113Not, pBI2113, pBI101, pBI121, pGA482, pGAH, PBIG, and 2) Eukaryotic and other host cells—pHISi-1, pMLBART, *Agrobacterium tumefaciens* strain GV3101, pSV2CAT, pOG44, PXT1, pSG (Stratagene); pSVK3, pBPV, pMSG, and pSVL (Pharmacia); pLGV23Neo, pNCAT, and pMON200. Any other plasmid or vector may be used as long as they are replicable and viable in the host.

In some preferred embodiments of the present invention, plant expression vectors comprise an origin of replication, a suitable promoter and enhancer, and also any necessary ribosome binding sites, polyadenylation sites, splice donor and acceptor sites, transcriptional termination sequences, and 5' flanking nontranscribed sequences for expression in plants. In other embodiments, DNA sequences derived from the SV40 splice, and polyadenylation sites may be used to provide the required nontranscribed genetic elements.

In certain embodiments of the present invention, the nucleic acid sequence in the expression vector is operatively linked to an appropriate expression control sequence(s) (promoter) to direct mRNA synthesis. Promoters useful in the present invention include, but are not limited to, the LTR of SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, DNA encoding the polypeptides of the present invention is expressed with plant promoters. Plant promoters can by constitutive, leaky and transient. In some embodiments, a promoter is a transient promoter (e.g. transient rd29A promoter as in U.S. Pat. No. 6,495,742B1; U.S. Pat. No. 6,670,528; herein incorporated by reference). Examples of constitutive promoters contemplated for the present invention include a "cauliflower mosaic virus 35S promoter" and "CaMV35S promoter." In some embodiments, promoters of the present invention are stress response promoters and comprise one or more of a rd29A gene promoter (Yamaguchi-Shinozaki, et al., (1994) The Plant Cell 6:251-264); rd29B gene promoter (Yamaguchi-Shinozaki, et al., (1994) The Plant Cell 6:251-264); rd17 gene promoter (Iwasaki, et al., (1997) Plant Physiol., 115:1287); rd22 gene promoter (Iwasaki, et al., (1995) Mol. Gen. Genet., 247:391-398); DREB1A gene promoter (Shinwari, et al., (1988) Biochem. Biophys. Res. Com. 250:161-170); cor6.6 gene promoter (Wang, et al., (1995) Plant Mol. Biol. 28:619-634); cor15a gene promoter (Baker, et al., (1994) Plant Mol. Biol. 24:701-713); erd1 gene promoter (Nakashima et al., (1997) Plant J. 12:851-861); kin1 gene promoter (Wang, et al., (1995) Plant Mol. Biol. 28:605-617); all of which are herein incorporated by reference.

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

2. Host Cells for Production of ATMIN or ATMIN-Like or HopM1:

In a further embodiment, the present invention provides host cells containing the above-described constructs. In some embodiments of the present invention, the host cell is a higher eukaryotic cell (e.g., a plant cell). An example of a transgenic plant cell and methods thereof are provided in U.S. Patent Application Pub. No. 20030144192A1, herein incorporated by reference. In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerevisiae, Schizosaccharomyces pombe, Drosophila* S2 cells, Spodoptera Sf9 cells, Chinese hamster ovary (CHO) cells, COS-7 lines of monkey kidney fibroblasts, (Gluzman, (1981) Cell 23:175, herein incorporated by reference), 293T, C127, 3T3, HeLa and BHK cell lines, NT-1 (tobacco cell culture line), root cell and cultured roots in rhizosecretion (Gleba et al., (1999) Proc Natl Acad Sci USA 96: 5973-5977, herein incorporated by reference).

The constructs in host cells can be used in a conventional manner to produce the gene product encoded by the recombinant sequence. In some embodiments, introduction of the construct into the host cell can be accomplished by calcium phosphate transfection; DEAE-Dextran mediated transfection, or electroporation (See e.g., In Davis et al., (1986) Basic Methods in Molecular Biology, Elsevier, N.Y., herein incorporated by reference). Alternatively, in some embodiments of the present invention, the polypeptides of the invention can be synthetically produced by conventional peptide synthesizers.

Proteins can be expressed in eukaryotic cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, 2nd ed., Cold Spring Harbor Laboratory Press, New York (1989), herein incorporated by reference.

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonification, mechanical disruption, or use of cell lysing agents.

II. Methods of Modifying a Pathogen Resistance Phenotype by Manipulating ATMIN or ATMIN-Like and/or HopM1 Protective Fragment Gene Expression.

The present invention also provides methods of using ATMIN or ATMIN-like and/or HopM1 and/or HopM1 protective fragments, homologs, orthologs, and variants thereof, of genes and proteins. In some embodiments, the sequences are used for research purposes. For example, nucleic acid sequences comprising coding sequences of an ATMIN or ATMIN-like and/or HopM1 or HopM1 protective fragments orthologs, for example any one or more of ATMIN or ATMIN-like and/or HopM1, and/or HopM1 protective fragments or related pathogenic virulence polypeptide may be used to discover other genes that affect pathogen resistance.

In other embodiments, ATMIN or ATMIN-like gene sequences are utilized to alter pathogen resistance. In some embodiments, ATMIN or ATMIN-like sequences increase resistance to a pathogen. Thus, it is contemplated that nucleic acids encoding an ATMIN or ATMIN-like polypeptide of the present invention may be utilized to either increase or decrease the level of ATMIN or ATMIN-like mRNA and/or protein in transfected cells as compared to the levels in wild-type cells.

In yet other embodiments, the present invention provides methods to alter pathogen resistance in plants in which ATMIN or ATMIN-like or HopM1 or $HopM1_{1-300}$ proteins are not usually found and/or add a novel pathogen resistance protein, such as a HopM1 protective fragment, in which pathogen resistance to a particular pathogen is not otherwise found, by expression of at least one heterologous ATMIN or ATMIN-like gene or protective fragment, such as $HopM1_{1-300}$. Thus, in some embodiments, nucleic acids comprising coding sequences of at least one ATMIN or ATMIN-like gene or HopM1 or HopM1 fragment, for example any one or more of ATMIN or ATMIN-like, are used to transform plants without a pathway for producing a pathogen resistance to a particular pathogen. It is contemplated that some particular plant species or cultivars do not express any ATMIN or ATMIN-like genes or protective pathogen derived fragments. For these plants, it is necessary to transform a plant with the necessary ATMIN or ATMIN-like genes or HopM1 protective gene fragments required to confer the preferred pathogen resistance phenotype. It is contemplated that other particular plant species or cultivars may possess at least one ATMIN or ATMIN-like gene; thus, for these plants, it is necessary to transform a plant with those ATMIN or ATMIN-like genes that can interact with endogenous ATMIN or ATMIN-like genes or HopM1 protective gene fragments in order to confer a preferred pathogen resistance phenotype.

The presence of ATMIN or ATMIN-like and/or HopM1 genes, including HopM1 gene fragments, in a species or cultivar can be tested by a number of ways, including but not limited to using probes from genomic and cDNA from ATMIN or ATMIN-like and/or HopM1 and downstream ATMIN or ATMIN-like and/or HopM1 activated genes, or by using PCR analysis or by using Northern blotting, or antibodies specific to ATMIN or ATMIN-like and/or HopM1 polypeptides. The additional ATMIN or ATMIN-like and/or HopM1 genes needed to confer the desired phenotype can then be transformed into a plant to confer the phenotype. In these embodiments, plants are transformed with ATMIN or ATMIN-like and/or HopM1 and/or HopM1 truncated and fragment genes as described herein.

As described above, in some embodiments, it is contemplated that the nucleic acids encoding an ATMIN or ATMIN-like and/or HopM1 polypeptide of the present invention may be utilized to increase the level of ATMIN or ATMIN-like mRNA and/or protein in transfected cells as compared to the levels in wild-type cells.

A. Transgenic Plants, Seeds, and Plant Parts:

The present invention also provides a transgenic plant, a transgenic plant part, a transgenic plant cell, or a transgenic plant seed, comprising any of the nucleic acid sequences of the present invention described above, wherein the nucleic acid sequence is heterologous to the transgenic plant, a transgenic plant part, a transgenic plant cell, or a transgenic plant seed. In some embodiments, the nucleic acid sequence is operably linked to any of the promoters described above. In other embodiments, the nucleic acid is present in any of the vectors described above.

The present invention also provides a method for producing ATMIN and HopM1 genes and gene fragments and their encoded polypeptides, comprising culturing a transgenic host cell comprising a heterologous nucleic acid sequence, wherein the heterologous nucleic acid sequence is any of the nucleic acid sequences of the present invention described herein which encode an ATMIN or ATMIN-like and/or a HopM1 polypeptide or variant thereof, including fragments, under conditions sufficient for expression of an encoded ATMIN or ATMIN-like and/or a HopM1 polypeptide, and producing ATMIN or ATMIN-like and/or a HopM1 polypeptide in the transgenic host cell.

The present invention also provides a method for altering the phenotype of a plant, comprising providing an expression vector comprising any of the nucleic acid sequences of the present invention described above, and plant tissue, and transfecting plant tissue with the vector under conditions such that a plant is obtained from the transfected tissue and the nucleic acid sequence is expressed in the plant and the phenotype of the plant is altered. In some embodiments, the nucleic acid sequence encodes ATMIN or ATMIN-like and/or a HopM1 polypeptide or variant thereof. The present invention also provides a method for altering the phenotype of a plant, comprising growing a transgenic plant comprising an expression vector comprising any of the nucleic acid sequences of the present invention described above under conditions such that the nucleic acid sequence is expressed and the phenotype of the plant is altered. In some embodiments, the nucleic acid sequence is an ATMIN or ATMIN-like and/or a HopM1 polypeptide or variant thereof. In other embodiments, the nucleic sequence encodes a nucleic acid product which interferes with the expression of a nucleic acid sequence encoding full-length HopM1 polypeptide or variant thereof, wherein the interference is based upon the coding sequence of full-length HopM1 polypeptide or variant thereof.

Accordingly, in some embodiments, the present invention provides plants transformed with at least one heterologous gene encoding an ATMIN or ATMIN-like and/or a HopM1 gene, or encoding a sequence designed to increase ATMIN or ATMIN-like ATMIN or ATMIN-like and/or a HopM1 protective fragment gene expression. It is contemplated that these heterologous genes are utilized to increase the level of the polypeptide encoded by heterologous genes, or to decrease the level of the protein encoded by endogenous genes.

1. Plants and Seeds:

The present invention is not limited to any particular plant comprising a heterologous nucleic acid (e.g., plants comprising a heterologous nucleic acid encoding a polypeptide comprising SEQ ID NOs:01 or 82, or nucleic acids corresponding to SEQ ID NOs:02 and 94). Indeed, a variety of plants are contemplated, including but not limited to *Brassica* sp., such as *Arabidopsis*, oil seed rape, and the like, rice and tomato. The present invention is not meant to limit the varieties of plants and include natural, cultivated, selectively bred, engineered (transgenic), natural mutants, cultivated mutants, engineered mutants and the like.

The present invention is not limited to any particular use of the transgenic plant. Indeed, a variety of purposes are contemplated. In some embodiments, the transgenic plant is for food production. For example, oilseed rape, rice and tomatoes. In further embodiments, the transgenic plant is for use in breeding programs to increase pathogen resistance for a particular pathogen and for use in any plant used by humans and animals.

2. Vectors:

The methods of the present invention contemplate the use of at least one heterologous gene encoding ATMIN or ATMIN-like gene and/or HopM1 gene and/or HopM1 gene fragments thereof, or encoding a sequence designed to increase, ATMIN or ATMIN-like gene expression. Heterologous genes include but are not limited to naturally occurring coding sequences, as well variants encoding mutants, variants, truncated proteins, and fusion proteins, as described above.

Heterologous genes intended for expression in plants are first assembled in expression cassettes comprising a promoter. Methods, which are well known to or developed by those skilled in the art, may be used to construct expression vectors containing a heterologous gene and appropriate transcriptional and translational control elements. These methods include in vitro recombinant DNA techniques, synthetic techniques, and in vivo genetic recombination. Exemplary techniques are widely described in the art (see e.g., Sambrook, et al., Molecular Cloning: A Laboratory Manual, 2nd ed., Cold Spring Harbor Laboratory Press, New York (1989) and Ausubel, et al. (1989) Current Protocols in Molecular Biology, John Wiley & Sons, New York, N.Y., herein incorporated by reference).

In general, these vectors comprise a nucleic acid sequence encoding an ATMIN or ATMIN-like gene and/or HopM1 gene and/or gene fragments thereof, or encoding a sequence designed to increase ATMIN or ATMIN-like or HopM1 or protective HopM1 fragment gene expression, (such as $HopM1_{1-300}$) operably linked to a promoter and other regulatory sequences (e.g., enhancers, polyadenylation signals, etc.) required for expression in a plant.

Promoters include but are not limited to constitutive promoters, tissue-, organ-, and developmental-specific promoters, and inducible promoters. Examples of promoters include but are not limited to: constitutive promoter 35S of cauliflower mosaic virus; a wound-inducible promoter from tomato, leucine amino peptidase ("LAP," Chao et al., Plant Physiol 120: 979-992 (1999), herein incorporated by reference); a chemically-inducible promoter from tobacco, Pathogenesis-Related 1 (PR1) (induced by salicylic acid and BTH (benzothiadiazole-7-carbothioic acid S-methyl ester)); a tomato proteinase inhibitor II promoter (PIN2) or LAP promoter (both inducible with methyl jasmonate); a heat shock promoter (e.g. U.S. Pat. No. 5,187,267, herein incorporated by reference); a tetracycline-inducible promoter (e.g. U.S. Pat. No. 5,057,422, herein incorporated by reference); and seed-specific promoters, such as those for seed storage proteins (e.g., phaseolin, napin, oleosin, and a promoter for soybean beta conglycin (Beachy et al., (1985) EMBO J. 4: 3047-3053, herein incorporated by reference).

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters of the present invention. Transcriptional terminators are responsible for the termination of transcription beyond the transcript and its correct polyadenylation. Appropriate transcriptional terminators and those which are known to function in plants include, but are not limited to, the CaMV 35S terminator, the tm1 terminator, the pea rbcS E9 terminator, and the nopaline and octopine synthase terminator (see e.g., Odell et al., (1985) Nature 313:810; Rosenberg et al., (1987) Gene 56:125; Guerineau et al., (1991) Mol. Gen. Genet. 262:141; Proudfoot, (1991) Cell 64:671; Sanfacon et al., (1991) Genes Dev. 5:141; Mogen et al., (1990) Plant Cell 2:1261; Munroe et al., (1990) Gene, 91:151; Ballas et al., Nucleic Acids Res. (1989) 17:7891; Joshi et al., (1987) Nucleic Acid Res., 15:9627; all of which are incorporated herein by reference).

In addition, in some embodiments, constructs for expression of the gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells (Callis et al., (1987) Genes Develop. 1:1183; herein incorporated by reference). Intron sequences have been routinely incorporated into plant transformation vectors, typically within the non-translated leader.

In some embodiments of the present invention, the construct for expression of the nucleic acid sequence of interest also includes a regulator such as a nuclear localization signal (Kalderon et al., (1984) Cell 39:499; Lassner et al., (1991) Plant Molecular Biology 17:229; all of which are herein incorporated by reference), a plant translational consensus sequence (Joshi, (1987) Nucleic Acids Research 15:6643; herein incorporated by reference), an intron (Luehrsen and Walbot, (1991) MolGen Genet. 225:81; herein incorporated by reference), and the like, operably linked to the nucleic acid sequence encoding an ATMIN or ATMIN-like gene.

In preparing the construct comprising the nucleic acid sequence encoding an ATMIN or ATMIN-like gene, or encoding a sequence designed to decrease ATMIN or ATMIN-like gene expression, various DNA fragments can be manipulated, so as to provide for the DNA sequences in the desired orientation (e.g., sense or antisense) orientation and, as appropriate, in the desired reading frame. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (e.g., transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra, (1982) Gene 19: 259; Bevan et al., (1983) Nature 304:184, all of which are incorporated herein by reference), the bar gene which confers resistance to the herbicide phosphinothricin (White et al., (1990) Nucl Acids Res. 18:1062; Spencer et al., (1990) Theor. Appl. Genet. 79: 625, all of which are incorporated herein by reference), the hph gene which confers resistance to the antibiotic hygromycin (Blochlinger and Diggelmann, (1984) Mol. Cell. Biol. 4:2929; herein incorporated by reference), and the dhfr gene, which confers resistance to methotrexate (Bourouis et al., (1983) EMBO J., 2:1099, herein incorporated by reference).

In some preferred embodiments, the (Ti (T-DNA) plasmid) vector is adapted for use in an *Agrobacterium* mediated transfection process (see e.g., U.S. Pat. Nos. 5,981,839; 6,051,757; 5,981,840; 5,824,877; and 4,940,838; all of which are herein incorporated by reference). In some embodiments, strains of

*Agrobacterium tumefaciens* are C58, LBA4404, EHA101, C58C1Rif[R], EHA105, and the like. Examples of *Agrobacterium* mediated transfection in grasses are provided in International Patents WO 00/04133; WO 00/11138; and U.S. Patent Application Nos. 20030106108A1; 20040010816A1; and U.S. Pat. No. 6,646,185; all of which are herein incorporated by reference.

Construction of recombinant Ti and Ri plasmids in general follows methods typically used with the more common vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The use of T-DNA as a flanking region in a construct for integration into a Ti- or Ri-plasmid has been described in EPO No. 116,718 and International Appln. Nos. WO 84/02913, 02919 and 02920 all of which are herein incorporated by reference). See also Herrera-Estrella, Nature 303:209-213 (1983); Fraley et al., Proc. Natl. Acad. Sci, USA 80:4803-4807 (1983); Horsch et al., Science 223:496-498 (1984); and DeBlock et al., EMBO J. 3:1681-1689 (1984), all of which are herein incorporated by reference).

A second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available. In other embodiments of the invention, the nucleic acid sequence of interest is targeted to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (e.g. U.S. Pat. No. 5,501,967, herein incorporated by reference). Homologous recombination may be achieved using targeting vectors that contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

In yet other embodiments, the nucleic acids of the present invention are utilized to construct vectors derived from plant (+) RNA viruses (e.g., brome mosaic virus, tobacco mosaic virus, alfalfa mosaic virus, cucumber mosaic virus, tomato mosaic virus, and combinations and hybrids thereof). Generally, the inserted ATMIN or ATMIN-like polynucleotide can be expressed from these vectors as a fusion protein (e.g., coat protein fusion protein) or from its own subgenomic promoter or other promoter. Methods for the construction and use of such viruses are described in U.S. Pat. Nos. 5,846,795; 5,500,360; 5,173,410; 5,965,794; 5,977,438; and 5,866,785; all of which are incorporated herein by reference.

In some embodiments of the present invention the nucleic acid sequence of interest is introduced directly into a plant. One vector useful for direct gene transfer techniques in combination with selection by the herbicide Basta (or phosphinothricin) is a modified version of the plasmid pCIB246, with a CaMV 35S promoter in operational fusion to the *E. coli* GUS gene and the CaMV 35S transcriptional terminator (e.g. WO 93/07278; herein incorporated by reference).

3. Transformation Techniques:

Once a nucleic acid sequence encoding an ATMIN or ATMIN-like gene and/or HopM1 gene and/or gene fragments thereof, is operatively linked to an appropriate promoter and inserted into a suitable vector for the particular transformation technique utilized (e.g., one of the vectors described above), the recombinant DNA described above can be introduced into the plant cell in a number of art-recognized ways. Those skilled in the art will appreciate that the choice of method might depend on the type of plant targeted for transformation. In some embodiments, the vector is maintained episomally. In other embodiments, the vector is integrated into the genome.

In some embodiments, direct transformation in the plastid genome is used to introduce the vector into the plant cell (See e.g., U.S. Pat. Nos. 5,451,513; 5,545,817; 5,545,818; and International Patent WO 95/16783; all of which are incorporated herein by reference). The basic technique for chloroplast transformation involves introducing regions of cloned plastid DNA flanking a selectable marker together with the nucleic acid encoding the RNA sequences of interest into a suitable target tissue (e.g., using biolistic or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al., PNAS, 87: 8526-8530 (1990); Staub and Maliga, Plant Cell, 4: 39-45 (1992), all of which are incorporated herein by reference). The presence of cloning sites between these markers allowed creation of a plastid targeting vector introduction of foreign DNA molecules (Staub and Maliga, (1993) EMBO J., 12:601; herein incorporated by reference). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga, (1993) PNAS, 90: 913-917; herein incorporated by reference). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of the RNAs encoded by the DNA molecule.

In other embodiments, vectors useful in the practice of the present invention are microinjected directly into plant cells by use of micropipettes to mechanically transfer the recombinant DNA (e.g. Crossway, (1985) Mol. Gen. Genet, 202:179). In still other embodiments, the vector is transferred into the plant cell by using polyethylene glycol (e.g. Krens et al., (1982) Nature, 296:72; Crossway et al., (1986) BioTechniques, 4:320; all of which are herein incorporated by reference)); fusion of protoplasts with other entities, either mini-cells, cells, lysosomes or other fusible lipid-surfaced bodies (e.g. Fraley et al., Biochemistry, (1980) 19(26):6021-6029; herein incorporated by reference); protoplast transformation (EP 0 292 435); direct gene transfer (e.g. Paszkowski et al., (1992) Biotechnology 24:387-392; Potrykus et al., Mol Gen Genet. (1985) 199(2):169-177; all of which are herein incorporated by reference) including direct gene transfer into protoplasts (e.g. in *Arabidopsis thaliana*, Damm et al., (1989) Mol Gen Genet. 217(1):6-12; in rice, Meijer et al., (1991) Plant Mol Biol 16(5):807-820); all of which are herein incorporated by reference).

In still further embodiments, the vector may also be introduced into the plant cells by electroporation (e.g. Fromm, et al., (1985) Proc. Natl. Acad. Sci. USA, 82(17):5824-5828 and (1986) Nature 319(6056):791-793); Riggs and Bates, (1986) Proc. Natl. Acad. Sci. USA 83(15):5602-5606; all of which are herein incorporated by reference). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In yet other embodiments, the vector is introduced through ballistic particle acceleration using devices (e.g., available from Agracetus, Inc., Madison, Wis. and Dupont, Inc., Wilmington, Del.) (see, e.g., U.S. Pat. No. 4,945,050; and McCabe et al., (1988) Biotechnology 6:923; Weissinger et al., (1988) Annual Rev. Genet. 22:421; Sanford et al., (1987) Particulate Science and Technology, 5:27 (onion); Svab et al., (1990) Proc. Natl. Acad. Sci. USA, 87:8526 (tobacco chloroplast); Christou et al., (1988) Plant Physiol., 87:671 (soybean); McCabe et al., (1988) Bio/Technology 6:923 (soybean); Klein et al., (1988) Proc. Natl. Acad. Sci. USA, 85:4305 (maize); Klein et al., (1988) Bio/Technology, 6:559 (maize); Klein et al., (1988) Plant Physiol., 91:4404 (maize); Fromm et al., (1990) Bio/Technology, 8:833; and Gordon-Kamm et al., (1990) Plant Cell, 2:603 (maize); Koziel et al., (1993) Biotechnology, 11:194 (maize); Hill et al., (1995) Euphytica, 85:119; Koziel et al., Annals of the New York Academy of Sciences 792:164 (1996); Shimamoto et al., (1989) Nature 338: 274 (rice); Christou et al., (1991) Biotechnology, 9:957 (rice); Datta et al., (1990) Bio/Technology 8:736 (rice); European Appln. EP 0 332 581 (orchardgrass and other Pooideae); Vasil et al., (1993) Biotechnology, 11: 1553 (wheat); Weeks et al., (1993) Plant Physiol., 102:1077 (wheat); Wan et al., (1994) Plant Physiol., 104:37 (barley); Jahne et al., (1994) Theor. Appl. Genet. 89:525 (barley); Knudsen and Muller, (1991) Planta, 185:330 (barley); Umbeck et al., (1987) Bio/Technology 5:263 (cotton); Casas et al., (1993) Proc. Natl. Acad. Sci. USA, 90:11212 (sorghum); Somers et al., (1992) BioTechnology 10:1589 (oat); Torbert et al., (1995) Plant Cell Reports, 14:635 (oat); Weeks et al., (1993) Plant Physiol., 102:1077 (wheat); Chang et al., WO 94/13822 (wheat) and Nehra et al., (1994) The Plant Journal, 5:285 (wheat); all of which are herein incorporated by reference).

In addition to direct transformation, in some embodiments, vectors comprising a nucleic acid sequence encoding an ATMIN or ATMIN-like gene or are transferred using *Agrobacterium*-mediated transformation (Hinchee et al., Biotechnology, 6:915 (1988); Ishida et al., Nature Biotechnology 14(6):745-50 (1996); all of which are herein incorporated by reference). Heterologous genetic sequences (e.g., nucleic acid sequences operatively linked to a promoter of the present invention) can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome (Schell, Science, 237: 1176 (1987); herein incorporated by reference). Species, which are susceptible infection by *Agrobacterium*, may be transformed in vitro. The transformed cells are then cultured as suspension cells or regenerated as transgenic plants.

4. Regeneration:

After selecting for transformed plant material that can express a heterologous gene encoding an ATMIN or ATMIN-like gene, such as ATMIN7 or ATMIN7-like, or a protective fragment of a virulence protein, such as a protective HopM1 fragment (for example, $HopM1_{1-300}$) or variant thereof, including but not limited to methods described herein, whole plants are regenerated. Plant regeneration from cultured protoplasts was described in Evans et al., Handbook of Plant Cell Cultures, Vol. 1: (MacMillan Publishing Co., New York, 1983); and Vasil I. R. (ed.), Cell Culture and Somatic Cell Genetics of Plants, Acad. Press, Orlando, Vol. I, 1984, and Vol. III, 1986, herein incorporated by reference. It is known that many plants can be regenerated from cultured cells or tissues or parts, including but not limited to major species of grasses, such as rice, fodder plants; vegetables, such as tomato; and crop plants, such as Canola™ (Canadian Oil Low Acid) plants, a cultivar of a rapeseed variants from which rapeseed oil is obtained, also known as "LEAR" oil (for Low Erucic Acid Rapeseed). Means for regeneration vary from species to species of plants, but generally a suspension of transformed protoplasts containing copies of the heterologous gene is provided first, then callus tissue is formed for inducing shoots and leaves for subsequent rooting and plant formation.

Alternatively, embryo formation can be induced from the protoplast suspension. These embryos germinate and form mature plants, such as oilseed rape plant regeneration. The culture media will generally contain various amino acids and hormones, such as auxin and cytokinins. Shoots and roots normally develop simultaneously. Efficient regeneration will depend on the medium, on the genotype, and on the history of the culture. The reproducibility of regeneration depends on the control of these variables.

5. Generation and Evaluation of Transgenic Plant Lines/Cultivars:

a. Generation of Pathogen Resistance and Agronomic Traits:

Transgenic plants for developing plant lines with agronomic value for commercial use are established from transgenic plants by tissue culture propagation. Further, the presence of nucleic acid sequences encoding an exogenous ATMIN or ATMIN-like gene, such as ATMIN7 or ATMIN7-like), or a protective fragment of a virulence protein, such as a protective HopM1 fragment (for example, $HopM1_{1-300}$), homologs or mutants or variants thereof, may be transferred to related varieties by traditional plant breeding techniques. Examples of transgenic plant lines are described herein. These transgenic lines are then utilized for evaluation of pathogen resistance and other agronomic traits.

b. Evaluation of Pathogen Resistance and Agronomic Traits:

The transgenic plants, lines, and hybrid plants thereof, will be tested for the effects of the transgene on pathogen resistance and phenotype. The parameters evaluated for pathogen resistance are compared to those in control untransformed plants and lines. Parameters evaluated include evaluating numbers of multiplying bacteria in plant parts following inoculation protocols such as those described in the EXAMPLEs, in addition to selected general agronomic traits such as effects of heat, cold, drought, salt, light; effects on growth rates, and specific traits such as yield, seed color, and the like, depending upon the plant. Ranges of pathogen resistance can be expressed as a CFU per area, or callose deposits, or plant phenotype, in a particular tissue or at a developmental state; for example, pathogen resistance can be measured in young plants and in mature plants. The tests described herein were conducted in the greenhouse and are contemplated for field-testing.

III. Biocontrol Formulations of the Present Inventions:

The protective polypeptides of the present inventions may be provided in a biocontrol formulation for agronomic use. It is contemplated that the biocontrol formulation is a composition comprising the protective polypeptide as the active ingredient. The composition may be formulated for agronomic use in a variety of ways to provide an effective amount of the polypeptide to a plant. Polypeptides may be used in formulations as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include but are not limited to spreader-sticker adjuvants, stabilizing agents, other pesticidal additives, or surfactants. Liquid formulations may be aqueous-based or non-aqueous and employed as foams, suspensions, emulsifiable concentrates, or the like. The ingredients may include rheological agents, surfactants, emulsifiers, dispersant, or polymers.

Alternatively, the polypeptides of the present inventions may be prepared by recombinant bacterial expression systems in vitro and isolated for subsequent field application. Such polypeptides may be either in crude cell lysates, suspensions, colloids, etc., or alternatively may be purified, refined, buffered, and/or further processed, before formulating in an active biocontrol formulation. Likewise, under certain circumstances, it may be desirable to isolate peptide clumps and/or spores from bacterial cultures expressing the protective polypeptides and apply solutions, suspensions, or colloidal preparations of such peptides and/or spores as the active ingredient(s) of a biocontrol formulation.

The compositions of the biocontrol formulations may be made by formulating either the recombinant bacterial cell, peptide, and/or spore suspension, or an isolated polypeptide component with the desired agriculturally acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term “agriculturally-acceptable carrier” covers all adjuvants, e.g., inert components, dispersants, surfactants, tackifiers, binders, etc. that are ordinarily used in biocontrol formulation technology; these are well known to those skilled in biocontrol formulation. The formulations may be mixed with one or more solid or liquid adjuvants and prepared by various means, e.g., by homogeneously mixing, blending and/or grinding the biocontrol composition with suitable adjuvants using conventional formulation techniques.

It is contemplated that the biocontrol formulations of the present inventions will be applied to the environment of the target pathogen, typically onto the foliage of the plant or crop to be protected, by conventional methods, preferably by spraying. The strength and duration of biocontrol application will be set with regard to conditions specific to the particular pest(s), crop(s) to be treated and particular environmental conditions. The proportional ratio of active ingredient to carrier will naturally depend on the chemical nature, solubility, and stability of the active ingredient, as well as the particular formulation contemplated for use.

Other application techniques, e.g., dusting, sprinkling, soaking, soil injection, seed coating, seedling coating, spraying, aerating, misting, atomizing, and the like, are also feasible and may be required under certain circumstances such as when targeting pathogens that cause root or stalk infestation, or for applications to delicate vegetation or for applying to ornamental plants. These application procedures are well-known to those of skill in the art.

Regardless of the method of application, the amount of the active ingredient(s) are applied in an effective amount, which will vary depending on such factors as, for example, the specific pathogen to be controlled, the specific plant or crop to be treated, the environmental conditions, and the method, rate, and quantity of application of the active composition. The biocontrol formulation may be administered to a particular plant or target area in one or more applications as needed. An effective amount may be administered in a single dose, or in several doses, for example daily, during a course of treatment. However, the effective amount may depend on the composition applied or administered, the plant being treated, the severity and type of the infection, and the manner of administration.

The biocontrol formulations of the invention may be employed in the method of the invention singly or in combination with other compounds, including and not limited to other biocides. The method of the invention may also be used in conjunction with other treatments such as surfactants, detergents, polymers or time-release formulations. The biocontrol formulations of the present invention may be formulated for either systemic or topical use.

The concentration of biocontrol formulations which is used for environmental, systemic or foliar application will vary widely depending upon the nature of the particular formulation, means of application, environmental conditions, and degree of bio activity. Typically, the active ingredients will be present in the applied formulation at a concentration of at least about 0.5% by weight and may be up to and including about 99% by weight. Dry formulations of the compositions may be from about 0.5% to about 99% or more by weight of the composition, while liquid formulations may generally comprise from about 0.5% to about 99% or more of the active ingredient by weight.

EXPERIMENTAL

The following examples serve to illustrate certain embodiments and aspects of the present invention and are not to be construed as limiting the scope thereof.

In the experimental disclosures which follow, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); pg (picograms); L and l (liters); ml (milliliters); μl (microliters); cm (centimeters); mm (millimeters); μm (micrometers); nm (nanometers); U (units); min (minute); s and sec (second); k (kilometer); deg (degree); ° C. (degrees Centigrade/Celsius), colony-forming units (cfu), optical density (OD), polymerase chain reaction (PCR), (4-(2-hydroxyethyl)-1-piperazineethanesulfonic acid) (HEPES), potassium hydroxide (KOH), phenylmethylsulfonyl fluoride (PMSF).

Example I

This example describes the exemplary types of *Pseudomonas* bacteria used with materials and methods used for growing bacteria, inoculating plants and determining the magnitude of bacterial growth in infected plants of the present invention (Katagiri et al., in The *Arabidopsis* Book, Somerville, Meyerowitz, Eds. (American Society of Plant Biologists, Rockville, Md., 2002), website at dx.doi.org/10.1199/tab.0039; all of which are herein incorporated by reference in their entirety).

Bacterial Strains:

*Pseudomonas syringae* strains used for these examples and for exemplary inventions described herein were wild-type (WT) Pst DC3000 (Ma et al., Mol. Plant-Microbe Interact. 4:69 (1991); herein incorporated by reference), a Pst DC3000 ΔCEL mutant strain described in Alfano et al. (2000) Proc. Natl. Acad. Sci. USA. 97:4856; herein incorporated by reference, a Pst DC3000 ΔCEL mutant carrying pORF43, thus further expressed hopPtoM-shcM in a pUCP19, as described in Badel, et al. (2003) Molecular Microbiology 49(5):1239-1251 and used in DebRoy et al. (2004) Proc. Natl. Acad. Sci. U.S.A. 101:9927; all of which are herein incorporated by reference, and a Pst DC3000 hrcC mutant (formerly a hrpH mutant; Yuan et al. (1996) J. Bacteriol. 178:6399; herein incorporated by reference).

*Pseudomonas* Inoculum Preparation:

Each inoculum was prepared by calculating the proper dilution necessary for a desired bacterial concentration and then diluting that volume of bacteria in sterile water. In brief: 1) Bacteria were streaked out from a −80° C. glycerol stock onto a plate of low salt Luria Berating (LB) medium (10 g/L Tryptone, 5 g/L Yeast Extract and 5 g/L NaCl pH=7.0), with antibiotics (used as indicated at the following concentrations: ampicillin, 200 μg/ml; chloramphenicol, 34 μg/ml; rifampicin, 100 μg/ml; spectinomycin, 50 μg/ml) or without antibiotics depending upon the experimental design, and grown for 1 or 2 days at 30° C.; 2) Bacteria from the fresh streak were transferred to a liquid culture with appropriate antibiotics and grown with shaking at 30° for 8 to 12 hours then harvested when bacterial culture reached mid to late log phase growth ($OD_{600}$=0.6 to 1.0), (for growth on solid medium, bacteria were plated and grown on solid medium where confluent bacteria were then scraped off the plate for use in preparation of the inoculum); 3) A bacterial culture was centrifuged at 2500×g for 10 minutes in a swinging bucket rotor to pellet the bacteria; 4) The culture supernatant was poured off, the bacteria were resuspended in sterile water or 10 mM $MgCl_2$; 5) Under certain conditions, cells were washed 1 or 2 times in water (in volumes equal to that used to grow the bacteria) by repeating steps 3 and 4; and 6) Optical density of the bacterial cell suspension was quantified using a spectrophotometer set at 600 nm. For Pst DC3000 an $OD_{600}$=0.2 was approximately $1\times10^8$ CFU)/mLiter.

Methods of Spray or Dipping Inoculation (Infection):

Natural infection routes for *Pseudomonas syringae* and other foliar bacterial pathogens are through wounds or natural openings such as stomata. Dipping or spraying bacterial suspensions on *Arabidopsis* leaves mimics this natural method of entry into the apoplastic space.

Spray Inoculation:

Plants were grown with a bacterial suspension prepared as previously described. Plants in pots or entire flats were sprayed with a bacterial suspension containing 2 to $5\times10^8$ CFU/mL in water with 0.02 to 0.05% Silwet L-77 (Union Carbide) using a spray bottle with a fine mist setting to spray the bacterial suspension onto leaves until there was imminent runoff. Leaf surfaces were coated with the bacterial suspension and appeared evenly wet.

Dipping Inoculation:

Plants grown in pots with a mesh covering the pot were dipped upside down into a bacterial suspension similar to that used for spray inoculation. The inverted pot of plants were fully submerged in the bacterial suspension for 2 to 3 seconds and then removed. Leaf surfaces were evenly coated with the bacterial suspension. Following inoculation, plants were immediately placed under a plastic dome to maintain high humidity for 2 to 3 days. The high humidity (80 to 90% but not 100%) supported bacterial induced disease symptom development without saturating leaf intracellular spaces that mimicked abnormal disease symptom development.

Vacuum Infiltration:

The following is a brief outline of infiltration procedures: 1) inoculum was prepared as described above with the addition of a surfactant Silwet L-77 at a level of 0.004% (40 μl/L); 2) vacuum infiltration apparatus was assembled; the refrigerated condensation trap was turned on; 3) inoculum was poured into a container (such as a 1-L glass beaker), which also supported the inverted pot so that the whole pot was not submerged while the plants was entirely immersed in the inoculum; 4) the beaker with the immersed plants was placed in the vacuum chamber, sealed with the valve stopcock, and the vacuum pump was turned on; 5) when vacuum pressure reached a level of approximately 20 inches of mercury, it was maintained for 1 minute while the pump continued to pull a vacuum. After 1 minute, the vacuum pressure gauge read 22 to 25 inches mercury with bubbles that appeared on the surface of the leaves as well as on the top of the inoculum; 6) after 1 minute, the vacuum pressure was rapidly released by removing the valve stopcock. When the vacuum pressure returned to zero, the plants were removed from the chamber. During the rapid return to atmospheric pressure leaves became infiltrated with the bacterial suspension; 7) successful inoculation resulted in almost all the leaves being fully infiltrated with the inoculum. Effectiveness of the vacuum treatment was easily assessed by examining the plant leaves; infiltrated leaves look darker green (water-soaked) due to the presence of the bacterial suspension within the leaf intercellular spaces; 8) soil-contaminated bacterial suspension was discarded and replaced with fresh inoculum and steps 4 through 7 were repeated for inoculating additional plants; and 9) after inoculation, the plants were completely dried (for 1 to 3 hours), until the leaves did not appear to be water-soaked. The inoculated plants were then covered with a plastic dome for 2 to 3 days to maintain high humidity. As one example, Col-0 plants inoculated with Pst DC3000 at a dose of $OD_{600}$=0.002 Pst DC3000 ($10^6$ cfu/mL) showed a water-soaked disease symptom within 2 to 3 days followed by chlorosis and necrosis of the inoculated tissue that occurred 3 to 4 days post-inoculation.

Syringe Injection:

Plants were grown by standard techniques and the inoculum was prepared as described above. Individual leaves were infiltrated with bacteria using a syringe. Briefly: 1) A leaf was selected and marked for identification using a blunt-ended permanent marker; 2) The leaf was carefully inverted, exposing the abaxial (under) side. A 1-mL needleless syringe that contained a bacterial suspension was used to pressure-infiltrate the leaf intracellular spaces at the same time avoiding the vascular system of the leaf where damage of the midrib would have obvious detrimental effects on the viability of the leaf tissue; 3) as a small amount of inoculum (approximately 10 μL) infiltrated the leaf a water-soaking-like discoloration of the leaf was apparent; and 4) intercellular spaces of the infiltrated leaves were dried and the plants were covered with a plastic dome to maintain humidity for 2 to 3 days.

Bacterial Pathogen Enumeration Procedure:

A standard enumeration procedure involves pathogen inoculation, using any one of described methods, supra, followed by assaying bacterial populations present within host tissues at regular intervals. The population present within the tissue was calculated based on the dilution factor divided by the amount of tissue present in each sample. Plotting log (culturable bacterial number/$cm^2$ leaf tissue) against time (usually in days) after pathogen inoculation produced an unfitted curve, i.e. growth curve. For a review of methods, see, Katagiri et al., in The *Arabidopsis* Book, Somerville, Meyerowitz, Eds. (American Society of Plant Biologists, Rockville, Md., 2002), website://dx.doi.org/10.1199/tab.0039; herein incorporated by reference.

Following inoculation, infected plants were monitored daily over a 3- to 4-day period for symptom development and bacterial multiplication. For experiments described in FIGS. 1 and 5, plants were sprayed with 30 μM dexamethasone (DEX) 24 h before bacterial inoculation ($1\times10^6$ cfu/ml). Spraying transgenic plants expressing full-length HopM1 with 30 μM DEX induced rapid leaf necrosis within 10 h, which prevented bacterial multiplication. Therefore, in further experiments 0.003 μM MDEX was used for spraying plants, an amount that did not induce leaf necrosis, but induced complementation of the Pst DC3000 ΔCEL mutant (FIG. 1A).

Detailed Bacterial Counting Procedure:

Leaves were harvested and surface sterilized as follows: 1) whole leaves were removed from a host plant and gently mixed in a 70% ethanol solution for 1 minute. Leaves were blotted briefly on paper towels then rinsed in sterile distilled water for 1 minute, then blotted dry on paper towels. Leaf disks were excised from leaves with a 0.5 $cm^2$ or smaller cork borer, depending on the size of the sample leaves; 2) leaf disks from the leaves of 2 or more independent replicate plants were pooled for a single tissue sample and placed in a 1.5-mL microfuge tube with 100 μL sterile distilled water, the amount of leaf tissue per tube was recorded as leaf surface area. Three or more samples were harvested for each time point. Steps 1 and 2 were repeated for each sample; 3) Tissue samples were ground with a microfuge tube plastic pestle, by hand or by using a small hand-held electric drill. The samples were thoroughly macerated until pieces of intact leaf tissue were no longer visible; 4) the pestle was rinsed with 900 μL of water, with the rinse being collected in the original sample tube such that the sample was in a volume of approximately 1 mL; 5) steps 3 and 4 were repeated for harvesting additional samples; 6) following grinding of the tissue, samples were vortexed to evenly distribute the bacteria within the water/tissue sample. A 100-μl sample was removed and diluted in 900 μl sterile distilled water. A serial 1:10 dilution series was created for each sample by repeating this process. The number of serial dilutions necessary to get countable colonies were determined for each sample, however dilutions to $10^{-7}$ were usually sufficient for any bacterial strain; 7) The samples were plated on the appropriate medium (e.g., Low salt Luria Bertani) supplemented with the necessary antibiotics to select for the specific inoculated bacterial strain. Plating was done in the traditional way (100 μL of a single sample was spread on a single plate) or several 10 μL aliquots of the 1:10 serial dilutions were spotted on to a single plate and allowed to dry onto the surface; and 8) Plates were placed at 30° C. for approximately 2 days with a cfu value determined for each dilution of each sample. For the 10-μL spotting technique, a single spot was used for estimating the bacterial population when it had >10 and <70 colonies present in the spotted sample dilution.

Figure 15:
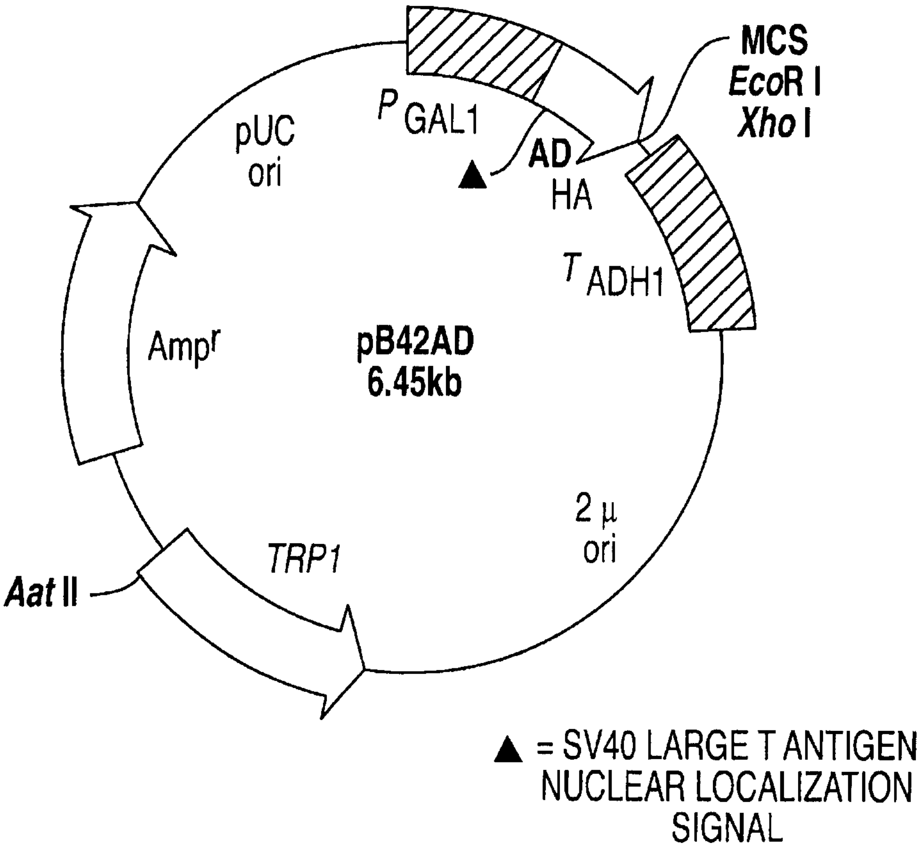
FIG. 15 shows pGILDA and pB42AD vector constructs for the yeast 2-Hybrid system, part of the MATCHMAKER LexA Two-Hybrid System (#K1609-1) (CLONTECHniques, OCTOBER 1999 p. 26-27, Clontech Laboratories Inc.; herein incorporated by reference in its entirety) used for providing expressed AtMIN proteins in yeast.

Yeast Plasmids and Systems:

pGILDA and pB42AD vector constructs for the yeast 2-Hybrid system are shown in FIG. 15.

AtMIN DNA fragments were amplified by PCR using the primers listed below, standard PCR procedures were used, then fragments were isolated and cloned into a pB42AD vector.

Yeast colonies were grown on complete minimal medium containing galactose and Xgal according to manufacture's instructions. A blue (dark) color indicated a protein-protein interaction, whereas a white (light) color indicates no such interaction. Further, a "+" symbol indicates positive control strain containing pLexA-p53 and pB42AD-T (AD/SV40 large T-antigen fusion) based on the known interaction of murine p53 and SV40 large T-antigen (CLONTECHniques, JULY 1996; Clonetech Labs; herein incorporated by reference in its entirety) (see, FIG. 2A).

Figure 6A:
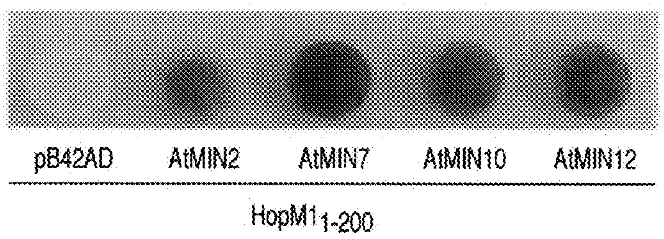
FIG. 6 (A) Yeast two-hybrid (Y2H) assay of physical interaction between HopM11-200 expressed from pGILDA (Clontech) and AtMIN proteins expressed from pB42AD (Clontech; shown for AtMIN2, 7, 10, 12). Yeast colonies were grown on complete minimal medium containing galactose and X-gal. A blue color indicates interaction, whereas a white color indicates no interaction. (B) AtMIN proteins were destabilized in yeast when co-expressed with full-length HopM1, but not with HopM11-300. AtMIN fusion proteins expressed from pB42AD were visualized by the HA epitope antibody. HopM1 fusion proteins expressed from pGilda were visualized by the LexA antibody. Coomassie Brilliant Blue-stained gels were used as loading controls. Arrows indicate lanes in which the amounts of AtMIN proteins are greatly reduced. AtMIN12 (a hypothetical protein predicted to be targeted to the chloroplast) is not destabilized. (C) Immunoblot analysis of 6×His-HopM1 and AtMIN::HA proteins in *N. benthamiana* leaves when AtMIN::HA proteins were transiently co-expressed with either full length 6×His::HopM1 or 6×His::HopM11-300. Total leaf proteins in these samples were visualized by Coomassie staining and used as loading controls (bottom panel). Arrows indicate lanes in which DEX-induced expression of full-length HopM1 destabilized AtMIN2, 7, and 10. (D) Immunoblot analysis of the stability of endogenous AtMIN7 in *Arabidopsis* leaves. Leaves of wild-type Col-0 gl1 plants were infiltrated with water or $1\times10^8$ CFU/ml ΔCEL mutant or ΔCEL mutant (pAVRE+pAVRF), which expresses AvrE but not HopM1 (FIG. 7). Treated leaves were harvested 10 hrs later. The endogenous AtMIN7 protein was detected using a rabbit polyclonal AtMIN7 antibody. AtMIN7 was not destabilized in leaves infiltrated with ΔCEL mutant (pAVRE+pAVRF). (E) Immunoblot analysis of HopM1-dependent destabilization of AtMIN10::HA in stable transgenic plants. Leaves of AtMIN10::HA transgenic plants were infiltrated with water or $1\times10^8$ CFU/ml ΔCEL mutant bacteria or ΔCEL mutant bacteria (pORF43) and harvested 10 hrs later. AtMIN10::HA was detected using the HA epitope antibody. Please note that membrane-associated AtMIN10::HA was preferably eliminated during bacterial infection.

AtMIN fusion proteins expressed from pB42AD were visualized by the HA epitope antibody, as was AtMIN10-HA. HopM1 fusion proteins expressed from pGilda were visualized by the LexA antibody. Coomassie Brilliant Blue-stained gels were used as loading controls. Arrows indicate lanes in which the amounts of AtMIN proteins are greatly reduced (FIG. 6A). AtMIN12 (a putative protein predicted to be targeted to the chloroplast) was not destabilized.

Brefeldin A (BFA) Treatment:

Leaves were infiltrated with $1\times10^6$ cfu/ml of bacteria, detached, and placed in microtiter wells with petioles immersed in the 36 μM BFA (Sigma Co.) solution. At 24 h intervals over 3 days, leaves were transferred to fresh BFA solutions. Bacterial populations and disease symptoms were determined on day 0 and day three.

Figure 4:
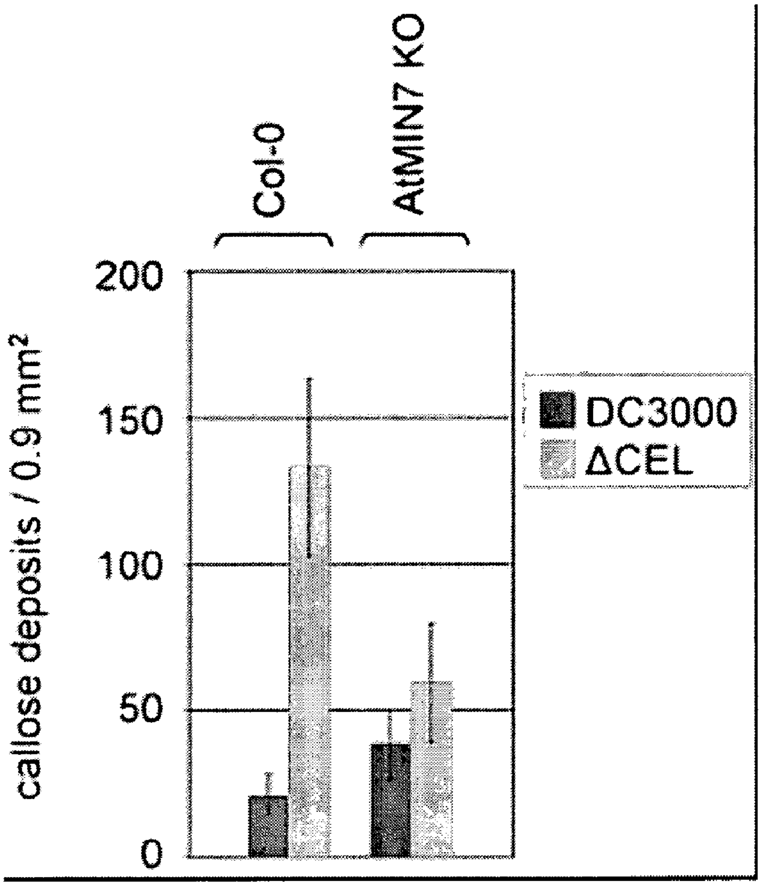
FIG. 4 shows exemplary callose deposition in leaves of Col-0 and AtMIN7 KO plants. *Arabidopsis* Col-0 and AtMIN7 KO leaves were stained to show callose deposition 7 h after inoculation with $1\times10^8$ CFU/ml DC3000 and ΔCEL mutant bacteria. Average numbers of callose depositions per field of view (0.9 $mm^2$) are presented with standard deviations displayed as errors.

Callose Staining:

Callose staining was performed 7-9 hours after bacterial inoculation as described previously (Hauck et al., Proc. Natl. Acad. Sci. USA 100:8577 (2003); herein incorporated by reference), with the exception of no application of DEX. Leaves were examined with a Zeiss Axiophot D-7082 Photomicroscope with an A3 fluorescence cube. The number of callose depositions was determined with ImagePro Plus software. The values presented in FIG. 4 are averages and standard deviations from at least four independent leaves evaluated for each treatment.

Reverse Transcription (RT)-PCR of *Arabidopsis* SALK Lines:

Total RNA was extracted using an RNeasy Plant Mini Kit (Qiagen) according to the manufacturer's instructions RNeasy® Mini Handbook, Fourth Edition April 2006, p. 52-55; herein incorporated by reference. First-strand cDNAs were synthesized from 200 ng of total RNA by using oligo dT primer and AMV reverse transcriptase from an RNA LA PCR Kit Ver. 1.1 (Takara) according to the manufacturer's instruction (see, RNA LA PCR Kit Ver. 1.1 Manual USA Version, v.02.08; herein incorporated by reference) in its entirety. PCR amplification was carried out using oligonucleotide primers specific to each AtMIN transcript. The following primers were used for obtaining an AtMIN7, described and used herein: sense primer, 5'-CGCCCAG CATATGCCAAGGATTGGTACTC-3' (NdeI site underlined) SEQ ID NO:78; antisense primer, 5'-T GAATTCTTACTGTTGCAAAAGTGGCTTC-3' (EcoRI site underlined) SEQ ID NO:79.

Example II

This example briefly describes plants with materials and methods used for growing plants and for providing and then analyzing transgenic plants (see, Katagiri et al., in The *Arabidopsis* Book, Somerville, Meyerowitz, Eds. (American Society of Plant Biologists, Rockville, Md., 2002), at website dx.doi.org/10.1199/tab.0039; herein incorporated by reference).

*Arabidopsis* and *Nicotiana* Plants:

*Arabidopsis thaliana* plant lines used for the present inventions were wild-type ecotype Columbia (Col-0) with a glabrous (gl1) morphological marker. *Arabidopsis thaliana* SALK lines were obtained that were previously transformed with *Agrobacterium* T-DNA with a kanamycin-resistance gene (NPTII) insertion in each of the AtMIN genes listed in Table 1 providing a knock-out (KO) line for each AtMIN gene (Alonso et al., Science 301:653 (2003); herein incorporated by reference) (see, *Arabidopsis* Biological Resource Center (ABRC) (website at: /signal.salk.edu/)).

*Nicotiana benthamiana* plants were obtained and grown under conditions similar to *Arabidopsis* plants.

Soil and Pot Preparation:

Soil mix was an equal mix of BACCTO Premium Potting Soil (Michigan Peat Company) high porosity professional plant mix, perlite and vermiculite. Moist soil mix was mounded into 3-inch square pots followed by a thin layer of fine vermiculite spread over the top of the soil that rose in the center about 0.5 to 1 inch above the edge of the pot. Pots that were destined for providing plants for bacterial inoculation were covered with mesh, such as plastic window screen, held firmly to the surface of the soil with a rubber band. The pots were placed in flats and soaked with a fertilizer solution. For syringe injection or spray inoculation no mesh was used in pots. For plants used for dipping or vacuum infiltration mesh was used in pots. This was important for helping contain the soil during inversion in the inoculum.

Growing Plants:

Seed was sown in the pots and covered with a screen and a plastic dome that maintained a high humidity for efficient germination. For synchronizing germination, the flats were placed in the cold (4° C.) for 2 days and then moved to a growth chamber. Growth chamber conditions were 30° C. and 70-80% relative humidity with 12 hours of fluorescent light (a light intensity of approximately 100 to 150 $\mu$Einstein/$m^2$/sec). After about 1 week, when seedlings emerged through the screen the plastic domes were opened slightly for a few days and then removed completely. At this time excess plants were removed from the pot to leave 4 to 6 well-distributed plants in each pot. The plants were watered, from the bottom up (adding water to the flat without overwatering) once or twice a week without letting the soil completely dry out between watering. Fertilizer was added during watering every two weeks. Plants 4 to 6 weeks old were used for inoculation (at this point they had numerous large leaves but did not have flowers).

*Agrobacterium: A. tumefaciens* C58.C1 (C58C1) used for these EXAMPLES were a derivative of *A. tumefaciens* C58 lacking a full Ti plasmid pAtC58. C58.C1 is a nonpathogenic *A. tumefaciens* strain lacking the Ti portion of pAtC58 and instead harbored a cryptic pAtC58 (Vaudequin-Dransart, et al. 1998 Mol. Plant-Microbe Interact. 11:583-591; herein incorporated by reference). *A. tumefaciens* bacteria were cultivated at 30° C. using standard *Agrobacterium* growth medium, such as a Trypticase soy agar.

*E. coli*: Routine cloning and gene expression for HOPM1 and AtMIN genes, including those destined for expression and transformation used standard *E. coli*, such as DHS$\alpha$ (Invitrogen, Corp.).

Plasmid Preparation:

Plasmids were isolated from *Pseudomonas* sp. and other bacteria using well-known methods (Kado and Liu (1981) J. Bacteriol. (1981) 145(3):1365-73; and Casse, et al., (1979) J. Gen. Microbiol. 113:229-242; all of which are herein incorporated by reference in their entirety).

Figure 16:
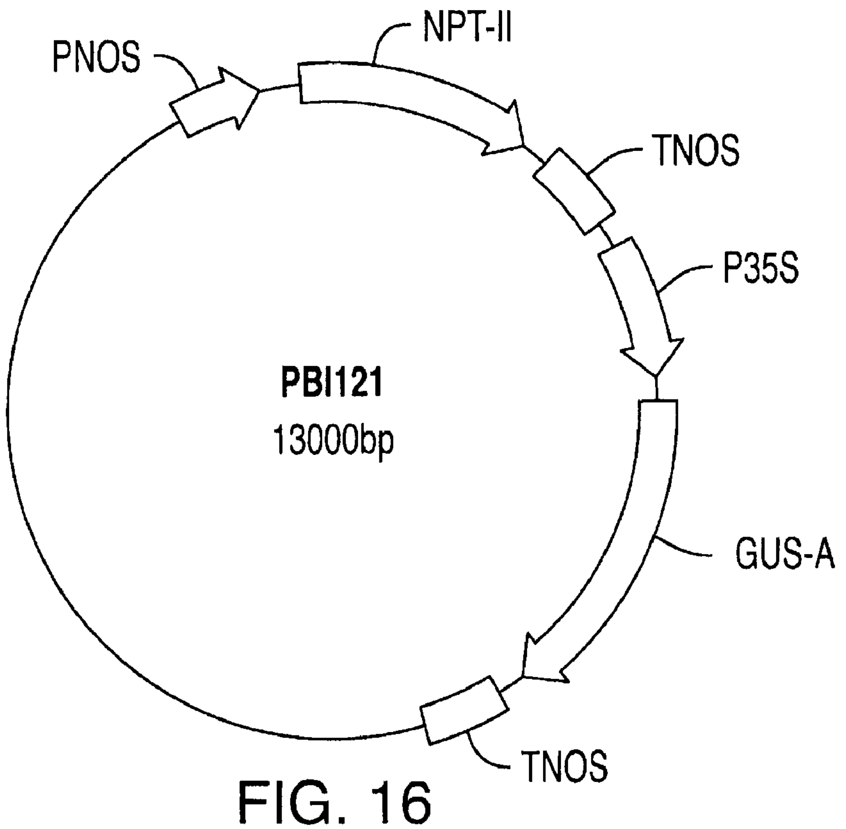
FIG. 16 shows plasmid pBI121.

Binary Plasmids (Vectors) for Inserting Heterologous Genes into *Agrobacterium:* pBI121: Shown in FIG. 16, originally obtained from Clontech Laboratories, Inc., was used for providing pBI121-AtMIN vectors using standard cloning methods.

pTA7002: a DEX-inducible expression vector, via an ava promoter, that expressed nucleotide inserts upon DEX exposure (see, Aoyama and Chua (1997) The Plant Journal 11:605; herein incorporated by reference in its entirety) that was used for providing pTA7002 deletion derivatives (for example, pTA7002-HopM$1_{1-300}$). Six× Histidine (6×His)-tagged proteins were provided by first cloning sequences, such as full-length HopM1 or HopM$1_{1-300}$, into pET-3 (publication TB095 December 1998, Novagen; herein incorporated by reference), for attaching the 6 Histidine coding regions, such as for providing expressed 6×His-HopM1 or 6×His-HopM$1_{1-300}$, then subcloning these nucleotide sequence comprising the HIS-tag into pTA7002 using standard molecular biology techniques. Transformation procedures are described below.

Transgenic Plants:

*Arabidopsis* plants were stably transformed with HopM1, HopM1 deletion fragments, and AtMIN genes. In brief, a floral dip *Agrobacterium*-mediated transformation protocol was used for inserting genes and gene fragments of HopM1 or AtMIN into *Arabidopsis* plants using methods, such as described by Clough and Bent (Clough et al., (1998) Plant J. 16:735; herein incorporated by reference).

*N. benthamiana* plants were transiently transformed with HopM1 and AtMIN proteins. In brief, fully expanded *N. benthamiana* leaves were co-infiltrated with *Agrobacterium tumefaciens* C58 C1 (for an example of co-infiltration techniques, see, Hellens, et al. (2005) Plant Methods, 1:13; herein incorporated by reference) comprising plasmids and genes described herein (for example, see, Bechtold, et al. (1993) Comptes Rendus De L Academie Des Sciences Serie Iii-Sciences De La Vie-Life Sciences 316(10):1194-1199; herein incorporated by reference).

[Western] Immunoblot Analysis of Leaf Discs:

In brief: leaf disc fractions were homogenized in 1×SDS-polyacrylamide gel electrophoresis (PAGE) sample buffer, boiled for 5 min, and centrifuged for 2 minutes. Proteins in the supernatant were separated on SDS-PAGE gels and transferred to Immobilon-P membrane for immunoblotting procedures (Millipore Corp., Bedford, Mass.).

Primary antibodies used were a mouse 6×His epitope antibody (to detect the 6×His-HopM1 proteins; purchased from Clontech Laboratories, Inc.), a chicken HA epitope antibody for recognizing AtMIN fusion proteins expressed from pB42AD (AtMIN-HA proteins) was purchased from Aves Labs, Inc., a rabbit LexA binding domain (BD) antibody to detect BD-HopM1 fusion proteins expressed by pGilda were purchased from Clontech Laboratories, Inc.), a rabbit AtMIN7 antibody was raised against recombinant AtMIN7 protein expressed in *E. coli* at Cocalico Biologicals, Inc., antibodies for recognizing PM-localized H+-ATPase (Dr. Marc Boutry), and antibodies for recognizing Golgi-localized xyloglucan xylosyltransferase (AtXT1) (Dr. Ken Keegstra). The secondary antibody used for detection of primary mouse antibody binding (for example, mouse 6×His epitope antibody and the like) was a goat anti-mouse IgG antibody conjugated with alkaline phosphatase (Sigma Co.); primary chicken antibody binding (for example, chicken HA epitope antibody and the like) was an alkaline Phosphatase (AP)-labeled anti-chicken IgY (Aves Labs, Inc.); and primary rabbit antibody binding (for example, mouse LexA antibody and the like) was a goat anti-rabbit IgG antibody conjugated with alkaline phosphatase (Sigma Co.).

Example III

This example demonstrates pathogen susceptibility of transgenic plants that expressed full-length HopM1 showing compensation for the virulence defect of a Pst DC3000 ΔCEL mutant.

Transgenic Expression of HopM1 and AtMIN Proteins in *Arabidopsis* and *Nicotiana:*

Transgenic *Arabidopsis* plants (Col-0 gl1) were produced that expressed a full-length 6×His tagged HopM1 using method described above. These transgenic HopM1 plants were highly susceptible to *Pseudomonas* infection as were certain transgenic plants expressing pTA7002 deletion derivatives, described below.

Specifically, 6×His tagged HopM1 transgenic plants were infected with one of Pst DC3000, Pst DC3000 ΔCEL, or Pst hrcC. *Arabidopsis* plants that expressed full-length HopM1 almost fully complemented the virulence defect of a Pst DC3000 ΔCEL mutant, see, FIG. 1A. Moreover, the complementation was specific to the Pst DC3000 ΔCEL mutant because multiplication of the TTSS-defective hrcC mutant (Yuan and He, (1996) J. Bacterial. 178:6399; herein incorporated by reference), which does not secrete any effectors, did not show this effect nor did Pst DC3000 (FIG. 1A).

Figure 1B:
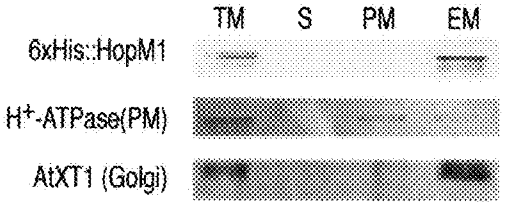

In order to determine where HopM1 protein was located within the transgenic plant cell, immunoblot studies were used to located the His tags of the expressed transgene in leaves collected from transgenic *Arabidopsis* plants that expressed 6×His HopM1. Subcellular fractionation experiments followed by immunoblotting, see below for procedure, revealed that HopM1 expression was enriched in the endomembrane fraction in the transgenic plants (FIG. 1B). Taken together, these results suggest that bacterial HopM1 acts in a host endomembrane compartment(s) to promote bacterial pathogenesis.

Subcellular Localization of HopM1:

Five-week-old HopM1 transgenic plants were sprayed with 30 μM DEX. The leaves were collected 6 hours later and homogenized in ice-cold homogenization buffer (0.5M sucrose, 0.6%[w/v] polyvinylpyrrolidone, 1.0 mM dithiothreitol, 5.0 mM ascorbic acid, 50 mM HEPES/KOH, pH 7.5, 1 mM PMSF). The homogenate was centrifuged at 4° C. for 10 min at 1,500×g and the supernatant was filtered through Miracloth (Calbiochem, San Diego, Calif.) to remove plant debris. The filtrate was centrifuged again at 13,000×g for 30 min at 4° C. The supernatant was collected and centrifuged for 30 min at 100,000×g to yield soluble (supernatant) and microsomal (pellet) protein fractions. An aqueous two-phase partitioning procedure was used to separate the plasma membrane (PM) and endomembranes (EMs) according to Larsson et al. (Larsson et al., Methods Enzymol. 228:451 (1994); herein incorporated by reference) with a polymer concentration of 6.2% (w/vol). The microsomal protein pellets were resuspended in buffer R (250 mM sucrose, 5 mM potassium phosphate, pH=7.5, 6.0 mM KCl) and subjected to phase partitioning. Both the upper phase (enriched for the PM) and the lower phase (enriched for the EM) were further partitioned for two more times with lower phase buffer and upper phase buffer, respectively. The PM and EM fractions were harvested at the end of the third partitioning from their corresponding upper and lower phases by centrifugation at 4° C. for 60 min at 150,000×g.

Fractions were applied to 12% SDS-PAGE gels for protein separation using standard methods, then transferred onto Immobilon-P membranes (Millipore Corp.) using standard protein transfer methods. Membranes were processed using immunoblot procedures briefly described herein, see Example II. The secondary antibody used was a goat-anti-rabbit antibody conjugated with alkaline-phosphatase (Sigma).

Example IV

This example demonstrates the discovery of a N-terminal truncated derivative of HopM1 that when expressed in transgenic plants interfered with the virulence function of full-length HopM1 during an infection with pathogenic *Pseudomonas* bacteria.

The inventors investigated the virulence function of HopM1 as defined by the following experiments using truncation derivatives of HopM1. Numerous transgenic *Arabidopsis* plant lines (12+) were produced where each line expressed one of at least 12 different C- and N-terminally truncated derivatives of HopM1 in a pTA7002 expression vector (see, FIG. 14 for primers used to produce sequences for HopM1 truncation derivatives).

Figure 1C:
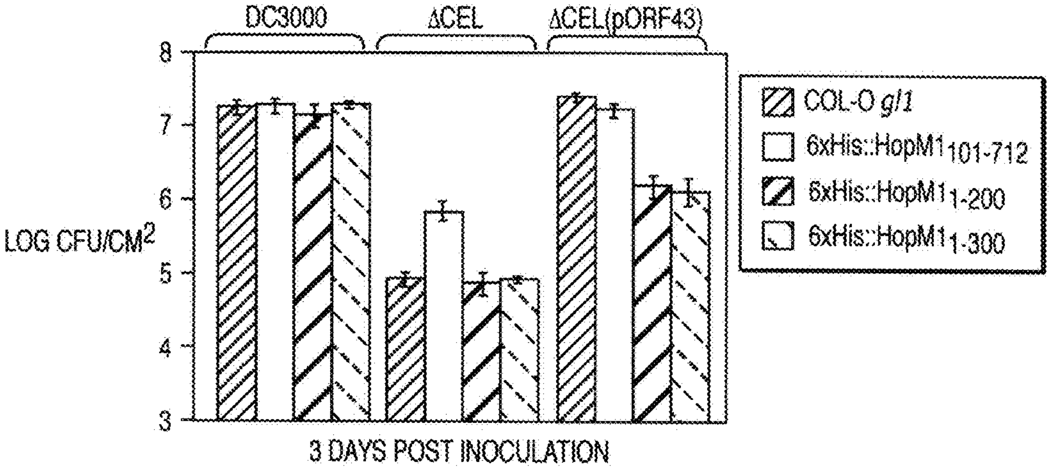
Figure 5:
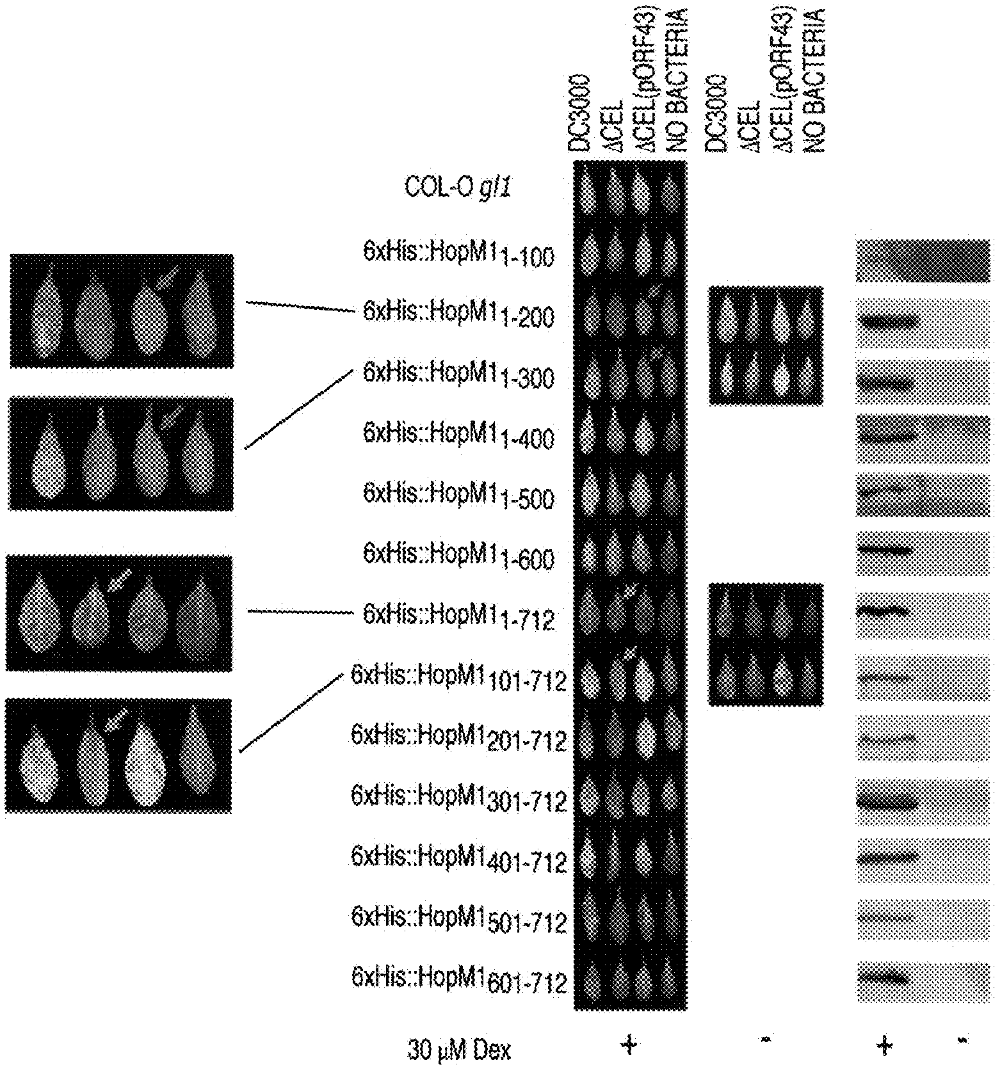
FIG. 5 shows exemplary bacterial disease symptoms on Col-0 gl1 and HopM1 transgenic plants inoculated with Pst DC3000, the ΔCEL mutant, and the ΔCEL mutant (pORF43) which expresses HopM1 and the cognate chaperone ShcM (Ma et al., (1991) Mol. Plant-Microbe Interact. 4:69; Badel et al., (2003) Mol. Microbiol. 49:1239; herein incorporated by reference). Pink arrows (upper left lines) indicate those leaves illustrating the dominant-negative effect of $HopM1_{1-200}$ and $HopM1_{1-300}$ on the ΔCEL mutant (pORF43), whereas blue arrows (lower left lines) indicate those leaves that illustrate the ability of full-length HopM1 or $HopM1_{101-712}$ to completely or partially complement the ΔCEL mutant (see, FIG. 1C for bacterial multiplication). Please note that leaves of $HopM1_{101-712}$ plants infected with the ΔCEL mutant were only slightly yellow (discolored). The right panels show HopM1 protein levels, revealed by immunoblotting, 24 hours after spraying plants with 30 μM DEX (immediately before bacterial inoculation).

Following evaluation of the HopM1 truncated deletion sequences of transgenic *Arabidopsis* plants, the inventors discovered that *Arabidopsis* plants expressing $HopM1_{101-712}$, SEQ ID NO:98 (produced using SEQ ID NOs:54 and 55 that lacked the coding region for the first 100 aa) partially restored the multiplication and disease chlorosis symptom of the Pst DC3000 ΔCEL mutant (FIG. 1C and FIG. 5). None of the other eleven truncated derivatives complemented the virulence defect of the Pst DC3000 ΔCEL mutant (FIG. 1C and FIG. 5).

Further analysis of the transgenic plants expressing truncation mutants revealed that when *Arabidopsis* plants expressed N-terminal regions of HopM1 ($HopM1_{1-200}$ and $HopM1_{1-300}$) there was a dominant-negative effect exerted on the function of full-length HopM1 delivered from the infecting Pst DC3000 ΔCEL mutant-pORF43 bacteria, expressing HopM1 and its cognate chaperone ShcM (i.e. no AvrE) (FIG. 1C and FIG. 5).

Thus, disease symptoms (necrosis and chlorosis) on plants and bacterial multiplication within plants were significantly reduced in $HopM1_{1-200}$ and $HopM1_{1-300}$ *Arabidopsis* transgenic plants, compared with those in Col-0 gl1 or *Arabidopsis* transgenic plants expressing other HopM1 truncated derivatives, such as truncated derivatives from the C-terminal regions (for example, $HopM1_{101-712}$ plants shown in FIG. 1C and FIG. 5). The dominant-negative effect was specific to HopM1 because $HopM1_{1-200}$ and $HopM1_{1-300}$ plants were still susceptible to Pst DC3000, which produces AvrE, in addition to HopM1 (FIG. 1C and FIG. 5). These results demonstrated that the $\text{N-terminal}_{100-300}$ aa (SEQ ID NO:82) of HopM1 functioned as an independent domain in vivo interfering with the virulence function of full-length HopM1 delivered from bacteria.

These results were replicated in *N. benthamiana* leaves that were co-infiltrated with *Agrobacterium tumefaciens* C58C1 carrying either pBI121-AtMIN or pBAR1-AtMIN and *A.*

*tumefaciens* C58C1 carrying either pTA7002-HopM$1_{1-712}$, pTA7002-HopM$1_{1-300}$, or pTA7002-HopM$1_{1-712}$. Oligonucleotide primers used for amplifying hopM1 and AtMIN genes from Pst DC3000 genomic DNA or *Arabidopsis* total cDNA, as applicable, used for creating these expression vectors are shown in FIG. 14. Two days after leaf infiltration, 0.3 μM DEX was applied to induce the expression of HopM$1_{1-712}$, or HopM$1_{1-300}$ or HopM$1_{1-712}$. Three hours after DEX treatment, leaf discs were taken for subsequent analyses using immunoblotting or co-immunoprecipitation experiments (see, EXAMPLES herein for procedures).

Example V

This example demonstrates using a yeast two-hybrid (Y2H) screening for obtaining HopM1 interacting proteins of the present invention, such as AtMIN genes and proteins that associated with either pathogen resistance or pathogen susceptibility in plants.

Yeast Two-Hybrid (Y2H) Screening Analysis:

A LexA-based yeast two-hybrid system was used for screening an *Arabidopsis* Y2H cDNA library using full-length HopM1 and the dominant-negative domain of HopM1 (HopM$1_{1-300}$) as bait, in separate screenings. This system was based upon a pGilda Lex A expression vector (CLONTECHniques, OCTOBER 1999 p. 26-27, Clontech Laboratories Inc.; herein incorporated by reference in its entirety) for expressing HopM1 proteins in combination with a lacZ reporter gene on a separate plasmid that autonomously replicated in yeast (CLONTECHniques, OCTOBER 1999 p. 26-27, Clontech Laboratories Inc.; herein incorporated by reference in its entirety), see below for addition information (see, MATCHMAKER LexA Two-Hybrid System Catalog #K1609-1 and MATCHMAKER LexA Libraries User Manual (PT3040-1) Version #PR67300 and (Yeast Protocols Handbook, Protocol #PT3024-1 Version #PR13103, published 14 Mar. 2001; herein incorporated by reference in its entirety).

hopM1 DNA fragments were amplified by PCR using the primers listed below and standard PCR procedures then fragments were isolated and cloned into a bait vector pGilda Lex A (resistance to ampicillin (100 μg/ml) to *E. coli* hosts; Protocol #PT3147-5; Version #PR81829; Clontech Laboratories, Inc.; herein incorporated by reference in its entirety). The following primers were used: Full-length hopM1: Sense primer, 5'-GGAATTCATGATCAGTTCGCGGATCGGC-3' (EcoRI site underlined) SEQ ID NO:74; Antisense primer, 5'-CCTGCTCGAGTGACGGATGTTATTCAAAG-3' (XhoI site underlined) SEQ ID NO:75; hopM$1_{1-300}$: Sense primer, 5'-GGAATTCATGATCAGTTCGCGGATCGGC-3' (EcoRI site underlined) SEQ ID NO:76; Antisense primer, 5'-GGCCCTCGAGCTTACCAGCCACCCACCG-3' (XhoI site underlined) SEQ ID NO:77.

Plasmid constructs were transformed into EGY48[p8op-lacZ] competent yeast cells (EGY48; Clontech Laboratories, Inc.) using standard yeast transformation procedures. Library screening procedures followed the instructions described in the Y2H manual provided by Clontech, (Yeast Protocols Handbook, Protocol #PT3024-1 Version #PR13103, published 14 Mar. 2001; herein incorporated by reference in its entirety).

However, yeast-2-hybrid (Y2H) screens of an *Arabidopsis* cDNA library failed to recover target interactor host proteins using full-length HopM1 bait. This failure to isolate interacting host proteins using full-length HopM1 was unexpected. However, a dominant-negative effect in a cellular process can be caused by unproductive protein-protein interactions as shown in Shpak et al. (2003) Plant Cell 15:1095 and Wang et al. (2005) Dev Cell 8:855; all of which are herein incorporated by reference. Therefore, the dominant-negative domains of HopM$1_{1-1200}$ and HopM$1_{1-300}$ were suspected to compete with full-length HopM1 for interaction with full-length HopM1 targeted host proteins.

In contrast to yeast screens using full-length HopM1 bait, Y2H screens using HopM$1_{1-300}$ as bait caught 21 strong interactors of HopM$1_{1-300}$. For the purpose of the present inventions, these 21 interactors were named "AtMIN" for *Arabidopsis thaliana* HopM interactors with at least 8 of the AtMIN genes listed in Table 1.

Example VI

This example demonstrates HopM1-dependent destabilization of AtMIN proteins by demonstrating protein-protein interactions between HopM1 and/or HopM$1_{1-300}$ with AtMIN proteins. In particular, this example demonstrates HopM1-dependent destabilization of AtMIN proteins in yeast cells and in *N. benthamiana* leaves transiently expressing HopM1 and AtMIN proteins. This example further demonstrates HopM1-dependent destabilization of AtMIN proteins in yeast two-hybrid (Y2H) systems (A) and in *N. benthamiana* leaves transiently expressing HopM1 and AtMIN proteins (B) and between HopM1 and AtMIN proteins in *Arabidopsis thaliana* cells and plants (C) of the present invention. These experiments contributed to the identification of AtMIN genes and proteins associated with whether a plant responded to a pathogen by resistance or allowing an infection (susceptibility).

Each AtMIN protein was amplified by PCR using primers, such as those shown in FIG. 14, isolated and then individually cloned into a pB42AD vector using standard methods.

A. Interactions Between HopM$1_{1-300}$ and AtMIN Proteins were Observed in Yeast Two-Hybrid (Y2H) Assays.

AtMIN proteins were destabilized in yeast when co-expressed with full length HopM1, but not with HopM$1_{1-300}$. AtMIN12 (a hypothetical protein predicted to be targeted to the chloroplast) was not destabilized.

Figure 2A:
FIG. 2 shows an exemplary analysis of physical interaction between HopM1 and AtMIN proteins and HopM1-dependent destabilization of AtMIN proteins. (A) Yeast two-hybrid (Y2H) assay of physical interaction between $HopM_{1-300}$ expressed from pGILDA (Clontech) and AtMIN proteins expressed from pB42AD (Clontech; shown for AtMIN2, 7, 10, 12). A blue (dark) color indicates interaction, whereas a white (light) color indicates no interaction. The "+" symbol indicates positive control strain containing pLexA-p53 and pB42AD-T; (B) Immunoblot analysis of the physical interaction between AtMIN7-HA and 6×His-$HopM1_{1-300}$ (lane 1) or between AtMIN7-HA and 6×His-$HopM1_{301-712}$ (lane 2) in *N. benthamiana* leaves using protein pull-down assay (see, Examples, Materials and Methods). AtMIN-HA and 6×His-HopM1 proteins were detected using the HA and 6×His epitope antibodies, respectively. AtMIN7-HA was pulled down with $HopM_{1-300}$ but not with 6×His-$HopM1_{301-712}$; and (C) Western blot and reverse transcription polymerase chain reaction analyses of HopM1-dependent destabilization of AtMIN7 in *Arabidopsis* plants. Leaves of Col-0 gl1 plants were infiltrated with water or $1\times10^8$ CFUs per milliliter of DCEL mutant bacteria with or without pORF43 and harvested 10 hours later. The endogenous AtMIN7 protein—detected with the use of a rabbit polyclonal AtMIN7 antibody—was absent in leaves infiltrated with DCEL mutant bacteria (pORF43) that produce HopM1; however, the AtMIN7 transcript level was not reduced. (D) Proteasome inhibitors (MG132 and epoxomicin) blocked the HopM1-mediated destabilization of AtMIN7 in *N. benthamiana* leaves, whereas a cocktail of inhibitors of serine-, cysteine-, aspartic-, and metallo-proteases did not. AtMIN7::HA and 6×His::HopM11-712 proteins were detected with HA and 6×His epitope antibodies, respectively.

A yeast two-hybrid (Y2H) assay was performed for determining the physical interaction between HopM$1_{1-300}$ compared to full-length HopM1 expressed by pGILDA and each AtMIN protein expressed by a pB42AD vector in yeast cells. HopM$1_{1-300}$ or full-length HopM1 pGILDA and each individual test AtMIN pB42AD were co-transformed into yeast cells as described in EXAMPLE III. Exemplary results showed a loss of AtMIN2, AtMIN7, and AtMIN10 in cells that co-expressed HopM1 (FIG. 2A). AtMIN proteins that were predicted to be chloroplast or mitochondrial proteins did not appear to be different between yeast strains that did or did not co-express full-length HopM1 (see, AtMIN12 in FIG. 2A).

Immunoblot analysis was then performed on yeast cells lines that expressed one each of the 21 AtMIN proteins co-expressed with either HopM$1_{1-300}$ or full-length HopM1(1-712). AtMIN proteins demonstrated destabilization in yeast when co-expressed with full length HopM1, but not with HopM$1_{1-300}$. For comparison, AtMIN12 (a hypothetical protein predicted to be targeted to the chloroplast) was not destabilized (FIG. 6A).

In yeast cells that expressed HopM$1_{1-300}$ with any one of eight of the following AtMIN proteins; AtMIN2, AtMIN3, AtMIN4, AtMIN6, AtMIN7, AtMIN9, AtMIN10, and AtMIN11, the inventors further observed an unexpected result. Eight AtMIN proteins (AtMIN2 represented by SEQ ID NOs:13 and 14; AtMIN3 represented by SEQ ID NOs:15 and 16; AtMIN4 represented by SEQ ID NOs:17 and 18; AtMIN6 represented by SEQ ID NOs:19 and 20; AtMIN7 represented by SEQ ID NOs:13 and 14; AtMIN9 represented by SEQ ID NOs:21 and 22; AtMIN10 represented by SEQ ID NOs:23 and 24; and AtMIN11 represented by SEQ ID NOs: 25 and 26) either disappeared or were present in much smaller amounts in yeast cells expressing full-length HopM1 as opposed to yeast cells co-expressing those proteins and $HopM1_{1-300}$.

B. Interactions Between $HopM1_{1-300}$ and AtMIN Proteins were Observed in *Nicotiana benthamiana* Plant Cells.

Figure 2B:
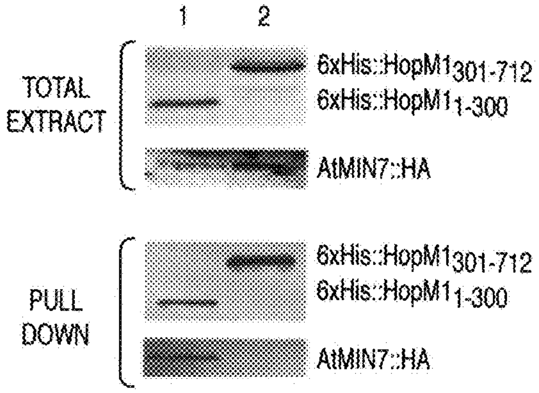
Figure 6B:
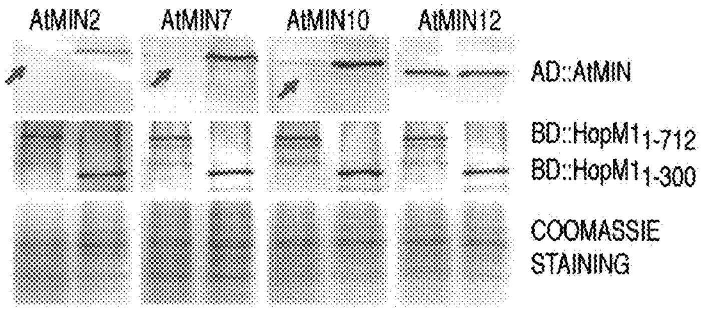
Figure 6C:
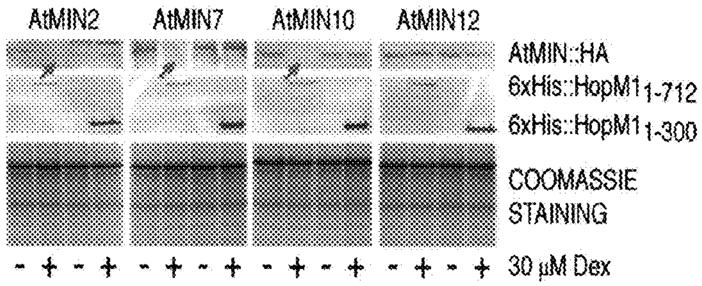
Figure 6D:
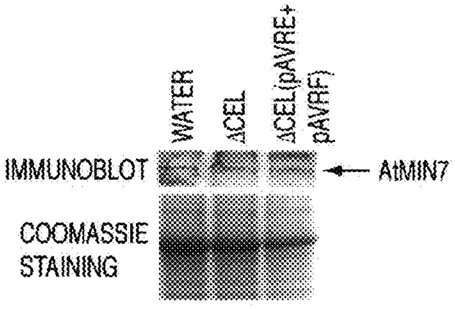
Figure 6E:
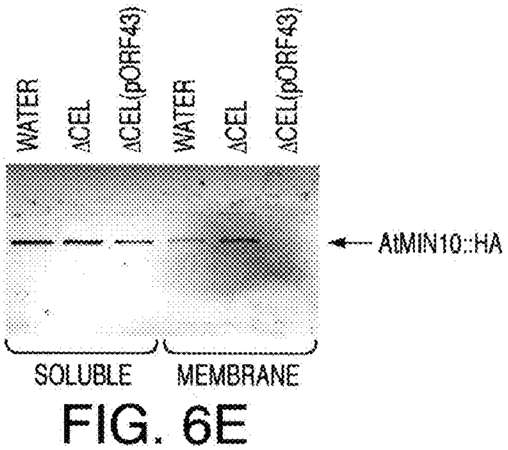
Figure 7:
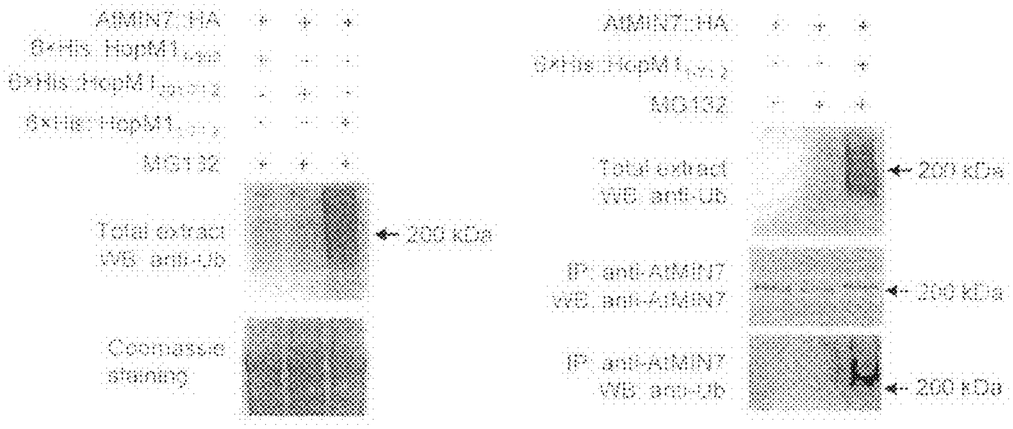
FIG. 7 shows exemplary detection of polyubiquitinated AtMIN7 in planta. Left: AtMIN7::HA and 6×His::$HopM_{1-300}$, 6×His::$HopM_{301-712}$ or 6×His::$HopM_{1-712}$ were transiently co-expressed in MG132-treated *N. benthamiana* leaves. Ubiquitinated proteins were detected by western blot (WB) with a polyclonal ubiquitin (Ub) antibody (Sigma Co.). Right: AtMIN7::HA and 6×His::$HopM_{1-712}$ were transiently co-expressed in 1% DMSO(−)- or MG132-treated *N. benthamiana* leaves. AtMIN7 was immunoprecipitated (IP) using a polyclonal AtMIN7 antibody. Ubiquitinated AtMIN7 protein was detected by western blot (WB) with a polyclonal ubiquitin (Ub) antibody (Sigma Co.). See Materials and Methods for transient expression and immunoprecipitation of AtMIN7 and HopM1 in *N. benthamiana* leaves. Taken together, these results showed that full-length HopM1, but not nonfunctional HopM1 fragments, enhanced the polyubiquitination of AtMIN7 in vivo.

Transient transgene expression of $HopM1_{1-300}$ or full-length HopM1 and AtMIN proteins in *Nicotiana benthamiana* cells showed that AtMIN7 interacted with $HopM1_{1-300}$ but not $HopM1_{301-712}$ These assays were based on transient expression experiments in *Nicotiana benthamiana* leaf cells followed by pull down assays and immunoblot analysis (see FIG. 2B for AtMIN7 and FIG. 6B for AtMINs 2, 7, and 10).

Plant cells expressing 6×His-HopM1 and AtMIN-HA proteins in *N. benthamiana* leaves were engineered to co-express a second transiently expressed protein, either full-length 6×His-HopM1 or 6×His-$HopM1_{1-300}$. Immunoblot analysis of leaves expressing protein pairs demonstrated a physical interaction between AtMIN7-HA and 6×His-$HopM1_{1-300}$ (lane 1) but no interaction between AtMIN7-HA and 6×His-$HopM1_{301-712}$ (lane 2) (FIG. 2B). Specifically, AtMIN7-HA was pulled down with $HopM_{1-300}$, but not with 6×His-$HopM1_{301-712}$. Please note that membrane associated AtMIN 10-HA was preferably eliminated during bacterial infection. Arrows indicate lanes in which DEX-induced expression of full-length HopM1 destabilized AtMIN2, AtMIN7, and AtMIN 10 (FIG. 6B).

Expression Plasmids for *Nicotiana* cells: For transient expression studies in *Nicotiana benthamiana*; expression plasmids were engineered to express C-terminal HA epitope-tagged AtMIN proteins using a constitutive CaMV 35S promoter operably linked to AtMIN sequences. Plasmids used were a pBAR1 provided by Jeff Dangl, University of North Carolina, Chapel Hill and a pBI121 (described in Jefferson et al. (1987) EMBO 6:3901; herein incorporated by reference). Leaves of AtMIN10-HA transgenic plants were infiltrated with water or $1\times10^8$ CFU/ml ΔCEL mutant bacteria or ΔCEL mutant bacteria (pORF43).

Protein pull-down analysis methods: *N. benthamiana* leaf discs were homogenized in lysis buffer (50 mM Tris-HCl pH=8.0, 250 mM NaCl, 10 mM β-mercaptoethanol, 1% Triton X100, 1 mM PMSF, plant protease inhibitor cocktail [Sigma Co.]). Total protein extracts were collected after centrifugation of the homogenate at 20,000-x g for 15 min at 4° C. to remove insoluble materials. The supernatant was incubated with Ni-NTA agarose beads (Qiagen) with gentle shaking for 1 hour at 4° C., followed by centrifugation at 15,000-x g for 1 min to pull down 6×His-HopM1 and its interacting proteins. Beads were then washed three times with lysis buffer and resuspended in 1×SDS-PAGE sample buffer for SDS-PAGE gel and/or immunoblot analyses. Equal amounts of total extracts were used for immunoblot analysis of HopM1 and AtMIN7, whereas the amount of pull-down sample used in the AtMIN7 blot was 15-fold higher than that used in the HopM1 blot. Total leaf proteins in these samples was visualized by Coomassie staining and used as loading controls (bottom panel). AtMIN10-HA was detected using the HA epitope antibody.

C. HopM1 Destabilizes AtMIN Proteins in *Arabidopsis* Transgenic Cells and Plants.

Western blot analysis of HopM1 transgenic *Arabidopsis* plants showed HopM1-dependent destabilization of AtMIN7 and transgene AtMIN10-HA.

Figure 2C:
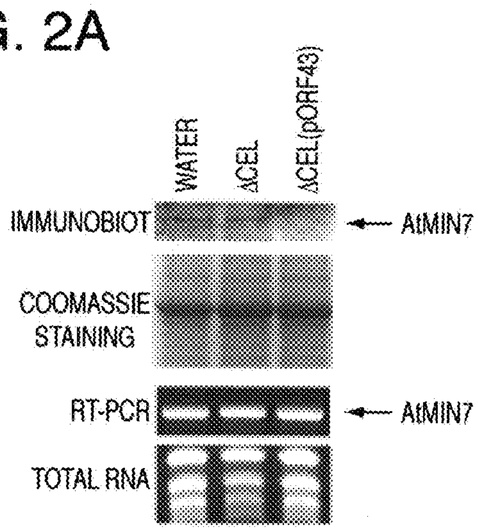
Figure 2D:
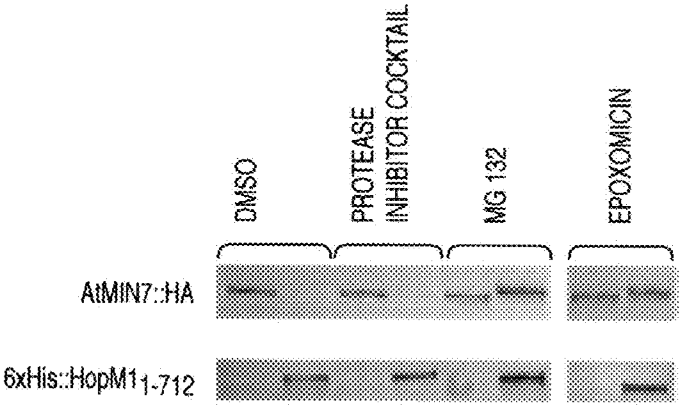

AtMIN7 is a low-abundance protein in *Arabidopsis* plants, however it is detected with a rabbit polyclonal antibody, described herein. In order to show that HopM1 destabilized AtMIN7, leaves of Col gl1 plants were infiltrated with water or $1\times10^8$ CFU/ml ΔCEL mutant bacteria or ΔCEL mutant bacteria (pORF43, expressing HopM1 and the cognate chaperone ShcM). AtMIN7 was absent on the immunoblots of leaves infiltrated with ΔCEL mutant bacteria (pORF43) but not the leaves infiltrated with water or ΔCEL mutant bacteria (FIG. 2C).

Furthermore AtMIN10-HA stably expressed in transgenic plants was also destabilized by HopM1. Leaves of AtMIN10-HA transgenic plants were infiltrated with water or $1\times10^8$ CFU/ml ΔCEL mutant bacteria or ΔCEL mutant bacteria (pORF43). AtMIN10-HA was detected using the HA epitope antibody. Moreover, subcellular fractionation analysis of AtMIN-HA transgenic plants, in which AtMIN-HA is localized in both soluble and membrane fractions, showed that membrane-associated AtMIN-HA was preferably eliminated during bacterial infection (FIG. 6). This result is consistent with the membrane localization of HopM1, as shown in FIG. 1B.

This example provides an explanation as to why these AtMIN proteins were not detected or isolated when full-length HopM1 was used in the previous Y2H screening (EXAMPLE V).

Example VII

This Example shows that destruction of specific AtMIN protein(s) is necessary for HopM1-mediated promotion of Pst DC3000 pathogenesis in *Arabidopsis* plants. This information was obtained by the inventors using *Arabidopsis* SALK lines carrying TDNA insertions in AtMIN genes and AtMIN KO plants, examples listed in Table 1.

Figure 8:
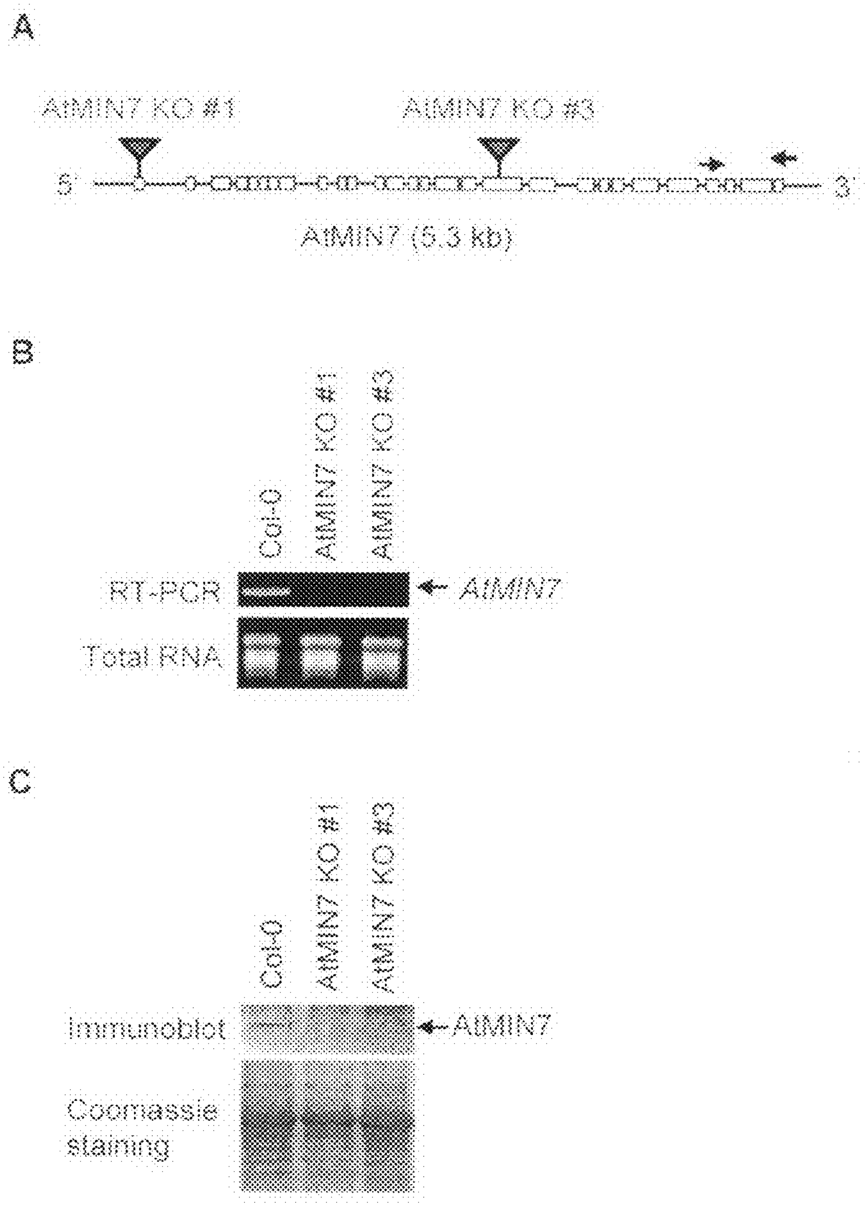
FIG. 8 shows exemplary characterization of *Arabidopsis* SALK lines carrying T-DNA insertions in the AtMIN7 gene. (A) The two T-DNA insertion lines used in this study carried T-DNA insertions in exon 1 (AtMIN7 KO #1) and exon 18 (AtMIN7 KO #3), respectively. (B) Reverse transcriptase-polymerase chain reaction (RT-PCR) analysis, using primers indicated in blue showed no full-length AtMIN7 transcript in either of the two AtMIN7 knockout (KO) lines. Col-0 plants were used as a positive control. Ethidium bromide-stained total RNA profiles were used as loading controls. (C) Western blot analysis of AtMIN7 in wild-type (Col-0) and two KO *Arabidopsis* plants. The endogenous AtMIN7 protein was detected using a rabbit polyclonal antibody.

The inventors analyzed *Arabidopsis* SALK lines (Alonso et al. (2003) Science 301:653; herein incorporated by reference) carrying T-DNA insertions in each of the AtMIN genes listed in Table 1. Col-0 plants were used as a positive control. For example, two T-DNA insertion lines used in this study carried T-DNA insertions in exon 1 (AtMIN7 KO #1) and exon 18 (AtMIN7 KO #3), respectively (FIG. 8A).

Figure 3:
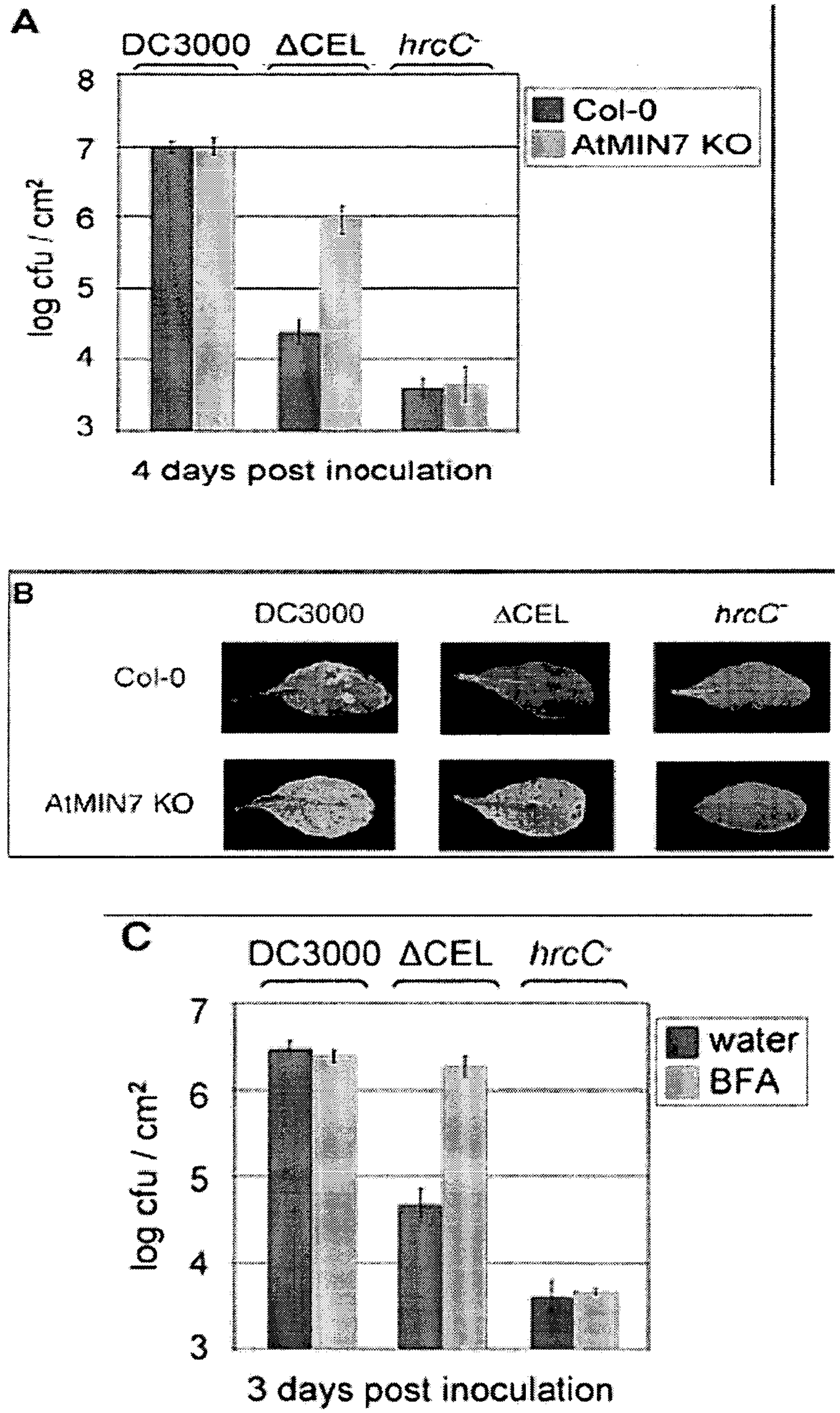
FIG. 3 shows an exemplary analysis of AtMIN7 knockout (KO) plants. (A) Growth of Pst DC3000, the ΔCEL mutant, and the hrcC mutant in AtMIN7 KO plants or in Col-O plants. Bacteria were inoculated by dipping with $1\times10^8$ cfu/ml. Bacterial populations were determined at day 4. Two independent T-DNA insertion lines were analyzed with similar results; results from line #1 are shown here. (B) Disease symptoms (chlorosis and necrosis) in Col-0 plants and AtMIN7 KO plants at day four. (C) Effect of brefeldin A (BFA) treatment on bacterial multiplication.

Plants from each AtMIN knockout (KO) line were infected with the Pst DC3000 ΔCEL mutant. When KO plants were infected with the ΔCEL mutant, the AtMIN knockout (KO) lines, except for the AtMIN7 KO line, restricted the growth of the ΔCEL mutant in a manner similar to the wild-type Col-0 plants. Unlike the other lines, the AtMIN7 KO plant line did not restrict growth of the Pst DC3000 ΔCEL mutant in a manner similar to the wild-type *Arabidopsis* Col-0 plants. Instead, AtMIN7 KO plants (FIG. 8) infected by the Pst DC3000 ΔCEL mutant showed markedly increased bacterial multiplication and chlorotic and necrotic disease symptoms when compared to wild-type *Arabidopsis* Col-0 plants (FIGS. 3A and 3B). Further, AtMIN7 KO plants responded to both Pst DC3000 bacteria and Pst hrcC mutant bacteria in a manner similar to the wild-type *Arabidopsis* Col-0 plants (FIG. 3, A and B). These demonstrations showed that increased susceptibility to bacterial infection in AtMIN7 KO plants is specific to Pst DC3000 ΔCEL mutant bacteria, mirroring the results shown in FIG. 1A, thus AtMIN7 is directly related to the virulence function of HopM1.

Specifically, reverse transcriptase-polymerase chain reaction (RT-PCR) analysis, that used primers indicated in blue showed no full-length AtMIN7 transcript in either of the two AtMIN7 knockout (KO) lines (FIG. 8B). Western blot analysis of AtMIN7 in wild-type (Col-0) and two KO *Arabidopsis* plants showed that AtMIN7 was absent in leaves of KO lines (FIG. 8C) where endogenous AtMIN7 protein in controls was detected using a rabbit polyclonal antibody.

This result demonstrates that the increased susceptibility to bacteria in AtMIN7 KO plants is specific to ΔCEL mutant bacteria, mirroring the results shown in FIG. 1A, and therefore is biologically relevant to the virulence function of HopM1. Further, the inventors believe this is the first demonstration of a host-target mutation specifically complementing the virulence loss of a plant-pathogen mutant lacking the cognate TTSS effector.

Example VIII

This example demonstrates that BFA treatment significantly enhanced the virulence (both multiplication and disease symptoms) of the Pst DC3000 ΔCEL mutant in wild-type Col-0 gl1 plants (FIG. 3C) that mimicked the results of similar experiments using $HopM1_{1-300}$.

In order to test whether the virulence defect of the Pst DC3000 ΔCEL mutant is caused by its inability to inhibit host vesicle traffic, BFA treatment was performed in order to observe whether the virulence of this bacterial mutant was restored when proteins were inhibited from translocation out of the Golgi apparatus.

The HopM1-mediated destruction of AtMIN7 and the ability of BFA to restore the virulence of the Pst DC3000 ΔCEL shows that HopM1 is involved in the inhibition of a host vesicle trafficking pathway. Accelerated vesicle traffic is associated with polarized cell wall-associated defense in plants (Bestwick et al. (1995) Plant Physiol. 108:503; Collins et al. (2003) Nature 425:973; all of which are herein incorporated by reference) previous studies by the inventors showed that a major function of HopM1 is suppression of this defense (DebRoy et al. (2004) Proc. Natl. Acad. Sci. U.S.A. 101:9927; herein incorporated by reference). This result is consistent with the demonstration of increased susceptibility of AtMIN7 KO plants to the Pst DC3000 ΔCEL mutant (FIG. 3) and establishes an active role of AtMIN7 in host immune response.

Unexpectedly, the restoration of bacterial virulence by BFA was also specific to the Pst DC3000 ΔCEL mutant, because there were no significant differences in the multiplication or disease symptoms caused by Pst DC3000 or the hrcC mutant in Col-0 gl1 plants treated with water or BFA (FIG. 3C).

Example IX

This example demonstrates that AtMIN7 is required for cell wall-associated defense in *Arabidopsis* plants.

Callose deposition (a cellular marker of this defense) in leaves of Col-0 and AtMIN7 KO plants infected by Pst DC3000 or the Pst DC3000 ΔCEL mutant. As observed previously (DebRoy et al. (2004) Proc. Natl. Acad. Sci. U.S.A. 101:9927; herein incorporated by reference), Col-0 leaves accumulated a high number of callose deposits in response to the ΔCEL mutant, whereas Pst DC3000 suppressed callose deposition in Col-0 leaves (FIG. 4).

Leaves of AtMIN7 KO plants were reduced in the ability to mount an active callose response to the ΔCEL mutant, whereas their response to Pst DC3000 was similar to that of Col-0 plants (FIG. 4).

Example X

This example demonstrates that several *Arabidopsis* plant factors may contribute to enhancing resistance to bacterial infections.

In EXAMPLE VIII, inhibition of vesicle trafficking in *Arabidopsis* AtMIN7 KO plants restored a lower level of virulence. Specifically, inhibition of vesicle trafficking in *Arabidopsis* plants significantly enhanced the virulence (both multiplication and disease symptoms) of the Pst DC3000 ΔCEL mutant in wild-type *Arabidopsis* Col-0 gl1 plants (FIG. 3C). Further, there were no significant differences in the multiplication or disease symptoms caused by Pst DC3000 or the hrcC mutant in wild-type *Arabidopsis* Col-0 gl1 plants treated with water or BFA (FIG. 3C) showing that BFA restoration of bacterial virulence was unique to the Pst DC3000 ΔCEL mutant bacteria.

The restoration of the virulence of the Pst DC3000 ΔCEL mutant in BFA-treated leaves was greater than that in the AtMIN7 KO plants, therefore the inventors contemplated that additional Arf GEFs are targeted by BFA that would represent proteins targeted by HopM1. One or more of these Arf GEFs are contemplated to be partially redundant in function to AtMIN7. Therefore, the inventors constructed an exemplary schematic phylogenetic tree showing the relationship among *Arabidopsis* Arf guanine nucleotide exchange factor (GEF) proteins (FIG. 9). Protein sequences were aligned using the ClustalW program (website at align.genome.jp) to construct this phylogenetic tree.

Example XI

Figure 10:
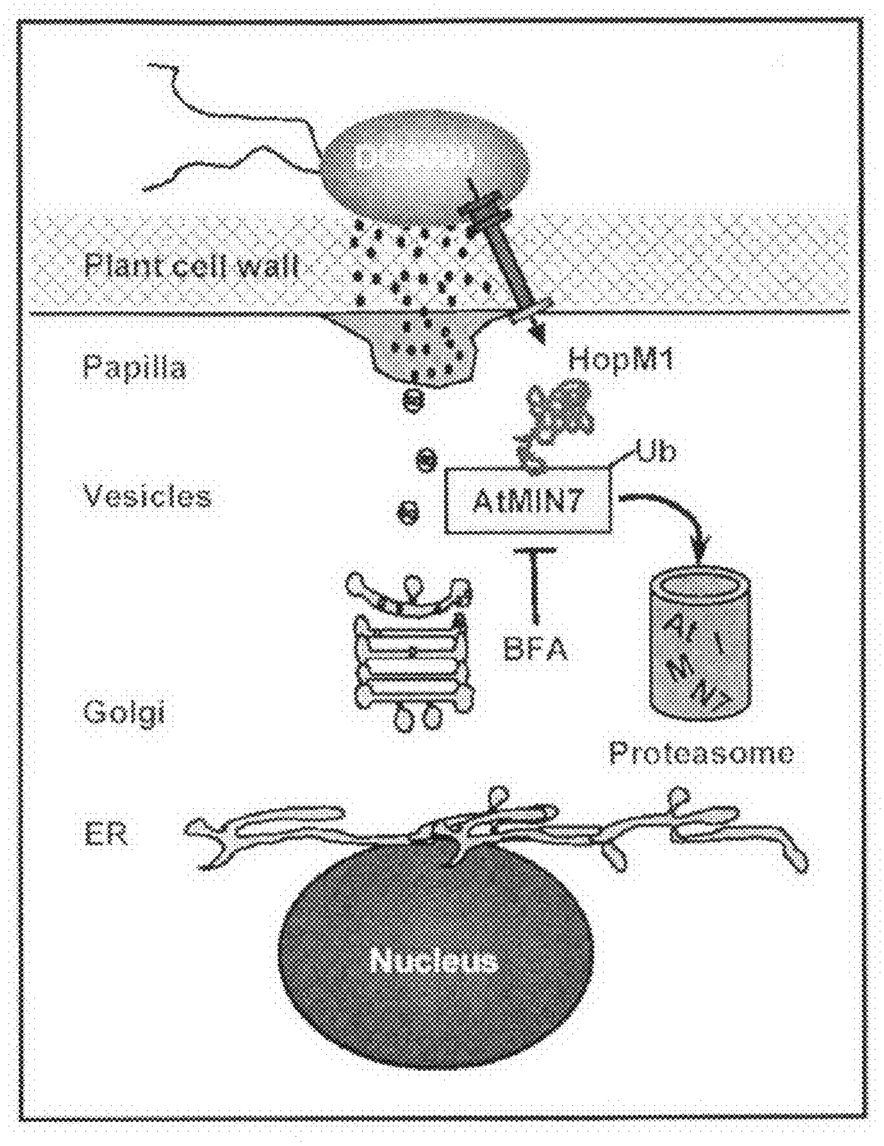
FIG. 10 shows a schematic diagram depicting a polarized vesicle trafficking pathway, in which AtMIN7 is a key component. The AtMIN7-dependent pathway is associated with plant immune responses, including the formation of callose deposits and probably release of antimicrobial phytoalexins (red dots in the papilla and plant cell wall). Pst DC3000 and presumably other *P. syringae* strains inject HopM1 into the host cell. Once inside the host cell, HopM1 is associated with an endomembrane compartment(s), binds to AtMIN7 through the N-terminus (in red), and destabilizes AtMIN7 and other AtMIN proteins. Brefeldin A (BFA) could mimic the effect of HopM1 by inhibiting the guanine nucleotide exchange factor (GEF) activity of the Sec7 protein family, of which AtMIN7 is a member.

The majority of plant pathogenic bacteria, including Pst DC3000, are extracellular pathogens that reproduce in apoplast areas of the plant after the bacterium has initially transversed the outermost layer of cell wall encased epidermal cells. However, the results obtained during the development of the inventions described herein, showed that *P. syringae* has an effective strategy to overcome a cell wall-associated host defense by suppression and/or elimination of AtMIN proteins that in turn are a component of an immunity-associated vesicle traffic pathway. Thus the inventors developed an exemplary model for demonstrating AtMIN protein function and interaction within a cell (see, an exemplary schematic diagram in FIG. 10).

In brief, the inventors contemplate a polarized vesicle trafficking pathway, in which AtMIN7 is a key component. By using the information from the examples described herein, an AtMIN7-dependent pathway is now associated with plant immune responses, including the formation of callose deposits and release of antimicrobial phytoalexins (red (darker) dots in the papilla and plant cell wall, FIG. 10). Thus, Pst DC3000, and likely other *P. syringae* strains, inject HopM1 into the host cell. Once inside the host cell, HopM1 is associated with an endomembrane compartment(s), binds to AtMIN7 through the N-terminus (in red/dark area), and destabilizes AtMIN7 and other AtMIN proteins. Brefeldin A (BFA) revealed further information when its use mimicked the effect of HopM1 by inhibiting the GEF activity of the Sec7 protein family, of which AtMIN7 is a member.

The HopM1-dependent elimination of a host plant AtMIN7 protein that is a member of the Sec7/Arf GEF family protein provides a bridge to the recent demonstrations that vesicle trafficking and extracellular secretion play important roles in plant immune response (Collins et al. (2003) Nature 425:973; Wang et al. (2005) Science 308:1036; all of which are herein incorporated by reference).

The results provided herein are in contrast to previously published studies that showed an intracellular human pathogen, *Salmonella enterica*, using TTSS effectors to interfere with host vesicle trafficking for bacterium induced biogenesis and established maintenance of a specialized membrane-bound compartment in which bacteria survived and multiplied (Cossart and Sansonetti (2004) Science 304:242; Knodler and Steele-Mortimer (2005) Mol. Biol. Cell 16:4108; all of which are herein incorporated by reference). Despite the difference in proposed mechanisms, the results shown herein showed that plant bacterial protein modulation of host vesicle trafficking is a goal of infectious pathogens for creating a host environment favorable for bacterial survival and multiplication; a type of modulation that is contemplated to be shared by human pathogens.

TABLE 2

AtMIN7 and Homolog identity.

| Genus sp. and gene/ protein name | SEQ ID NO: XX | Protein aa identity (%) | SEQ ID NO: XX | mRNA na identity (%) |
|---|---|---|---|---|
| *Arabidopsis thaliana* (AT3G43300) AtMIN7 Q9LXK4__ARATH | 1 | 100% | 2 | 100% |
| oilseed__rape homologue to UP\|Q9LXK4 (Q9LXK4) | 5 | 94% | 6 | 92% |
| *Arabidopsis thaliana* Guanine nucleotide-exchange-like protein | 3 | 93% | 4 | Not provided |
| *Oryza sativa* (japonica cultivar-group) Putative guanine nucleotide-exchange protein GEP2 | 11 | 69% | 12 | 76% |
| *Lycopersicon esculentum* tomato mixed elicitor, BTI | 7 | 61% | 8 | 68% |
| *Lycopersicon esculentum* cDNA clone LePU0380 similar to Acc# ref\|NP__195533.1\|; guanine nucleotide-exchange protein - like; protein id: At4g38200.1 | 9 | 38% | 10 | 57% |

TABLE 3

HopM1 and Homolog identity.

| Genus sp. and gene/ protein name | SEQ ID NO: XX | Protein aa identity (%) | SEQ ID NO: XX | mRNA na identity (%) |
|---|---|---|---|---|
| HopM1 | 34 | 100% | 35 | 100% |
| *Pseudomonas syringae* pv. *syringae* B728a, type III effector HopM1 | 36 | 64% | 37 | 75% |
| *Pseudomonas viridiflava* HopPtoM-like protein | 38 | 51% | 39 | 78% |

TABLE 4

$HopM1_{1-300}$ and Homolog identity.

| Genus sp. and gene/ protein name | SEQ ID NO: XX | Protein aa identity (%) | SEQ ID NO: XX | mRNA na identity (%) |
|---|---|---|---|---|
| $HopM1_{1-300}$ | 82 | 100% | 94 | 100% |
| *Pseudomonas syringae* pv. *phaseolicola* 1448A coding for 1-300 | 108 | 83% | 109 | 85% |
| *Pseudomonas syringae* pv. *syringae* B728a, type III effector HopM1 coding for 1-300 | 106 | 58% | 107 | 74% |
| *Pseudomonas viridiflava* HopPtoM-like protein coding for 1-300 | 105 | 46% | 110 | 79% |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in biochemistry, chemistry, molecular biology, plant biology, plant disease, and plant pathogens or related fields are intended to be within the scope of the following claims.

The invention claimed is:

1. An expression vector construct comprising a nucleic acid molecule at least 95% identical to SEQ ID NO:02, wherein said nucleic acid encodes a polypeptide that alters pathogen resistance in a plant.

2. The expression vector construct of claim 1, wherein said nucleic acid molecule encodes a polypeptide that is at least 95% identical to SEQ ID NO:01, wherein said polypeptide alters pathogen resistance in a plant.

3. The expression vector construct of claim 2, wherein said polypeptide increases pathogen resistance in a plant.

4. The expression vector construct of claim 1, wherein said nucleic acid is operably linked to an exogenous promoter.

5. The expression vector construct of claim 4, wherein said exogenous promoter is a eukaryotic promoter.

6. The expression vector construct of claim 5, wherein said eukaryotic promoter is active in a plant.

7. The expression vector construct of claim 1, wherein said vector is a eukaryotic vector.

8. The expression vector construct of claim 7, wherein said vector is a plant vector.

9. The expression vector construct of claim 8, wherein said plant vector is a prokaryotic vector.

10. The expression vector construct of claim 1, wherein said vector is a T-DNA vector.

11. A transgenic plant comprising a heterologous nucleic acid molecule encoding a polypeptide that is at least 95% identical to SEQ ID NO:01, wherein said polypeptide expression provides pathogen resistance.

12. The plant of claim 11, wherein said pathogen is a microbial pathogen.

13. The plant of claim 12, wherein said microbial pathogen is a bacterium.

14. The plant of claim 13, wherein said bacterium is a *Pseudomonas* species.

15. A transformed plant part of the plant of claim 11.

16. A transformed seed of the plant of claim 11.

17. A transformed tiller of the plant of claim 11.

18. The transgenic plant of claim 11, wherein said nucleic acid molecule is derived from the group consisting of Brassicaceae, Solanaceae, and Poaceae.

19. The transgenic plant of claim 11, wherein said plant is selected from the group consisting of a crop plant, a decorative plant, and a tree.

20. The expression vector construct of claim 1, wherein said nucleic acid molecule is 100% identical to SEQ ID NO:02.

21. The expression vector construct of claim 1, wherein said nucleic acid molecule encodes a polypeptide that is 100% identical to SEQ ID NO:01, wherein said polypeptide alters pathogen resistance in a plant.

22. The transgenic plant of claim 11, wherein said nucleic acid molecule is 100% identical to SEQ ID NO:02.

* * * * *

SEQUENCE LISTING

```
<160> NUMBER OF SEQ ID NOS: 113

<210> SEQ ID NO 1
<211> LENGTH: 1756
<212> TYPE: PRT
<213> ORGANISM: Arabidopsis thaliana

<400> SEQUENCE: 1
```

-continued

```
Met Ala Ala Gly Gly Phe Leu Thr Arg Ala Phe Asp Thr Met Leu Lys
1               5                   10                  15

Glu Ser Gly Gly Lys Lys Phe Pro Asp Leu Gln Lys Ala Ile Gln Ala
            20                  25                  30

Tyr Gln Asp Gly Ser Lys Val Val Thr Gln Ala Ala Pro Ser Ser Ile
        35                  40                  45

Val Glu Ser Ser Gln Ala Glu Gly Gly Gly Glu Lys Thr Gly Val Glu
    50                  55                  60

Ala Asp Glu Pro Gln Lys Val Thr Ser Ala Glu Val Ala Gln Gln Ala
65                  70                  75                  80

Ser Gln Ser Lys Ser Glu Thr Ile Asn Val Ser Leu Ala Asn Ala Gly
                85                  90                  95

His Thr Leu Gly Gly Ala Glu Val Glu Leu Val Leu Lys Pro Leu Arg
            100                 105                 110

Leu Ala Phe Glu Thr Lys Asn Leu Lys Ile Phe Asp Ala Ala Leu Asp
        115                 120                 125

Cys Leu His Lys Leu Ile Ala Tyr Asp His Leu Glu Gly Asp Pro Gly
    130                 135                 140

Leu Asp Gly Gly Lys Asn Ser Ala Pro Phe Thr Asp Ile Leu Asn Met
145                 150                 155                 160

Val Cys Ser Cys Val Asp Asn Ser Ser Pro Asp Ser Thr Val Leu Gln
                165                 170                 175

Val Leu Lys Val Leu Leu Thr Ala Val Ala Ser Gly Lys Phe Lys Val
            180                 185                 190

His Gly Glu Pro Leu Leu Gly Val Ile Arg Val Cys Tyr Asn Ile Ala
        195                 200                 205

Leu Asn Ser Pro Ile Asn Gln Ala Thr Ser Lys Ala Met Leu Thr Gln
    210                 215                 220

Met Ile Ser Ile Val Phe Arg Arg Met Glu Thr Asp Ile Val Ser Ala
225                 230                 235                 240

Ser Ser Thr Val Ser Gln Glu Glu His Val Ser Gly Asp Thr Ser Ser
                245                 250                 255

Pro Lys Asn Glu Glu Ile Thr Ala Ala Asp Glu Asn Glu Lys Glu Met
            260                 265                 270

Thr Leu Gly Asp Ala Leu Thr Gln Ala Lys Asp Thr Thr Leu Ala Ser
        275                 280                 285

Val Glu Glu Leu His Thr Leu Val Gly Gly Ala Asp Ile Lys Gly Leu
    290                 295                 300

Glu Ala Ala Leu Asp Lys Ala Val His Leu Glu Asp Gly Lys Lys Ile
305                 310                 315                 320

Lys Arg Gly Ile Glu Leu Glu Ser Met Ser Ile Gly Gln Arg Asp Ala
                325                 330                 335

Leu Leu Val Phe Arg Thr Leu Cys Lys Met Gly Met Lys Glu Asp Ser
            340                 345                 350

Asp Glu Val Thr Thr Lys Thr Arg Ile Leu Ser Leu Glu Leu Leu Gln
        355                 360                 365

Gly Met Leu Glu Gly Val Ser His Ser Phe Thr Lys Asn Phe His Phe
    370                 375                 380

Ile Asp Ser Val Lys Ala Tyr Leu Ser Tyr Ala Leu Leu Arg Ala Ser
385                 390                 395                 400

Val Ser Gln Ser Ser Val Ile Phe Gln Tyr Ala Ser Gly Ile Phe Ser
                405                 410                 415

Val Leu Leu Leu Arg Phe Arg Asp Ser Leu Lys Val Ser Met Asp Cys
```

-continued

```
            420                 425                 430

Tyr Leu Ser Pro Tyr Phe Ser Asp Pro Lys Ser His Ser Gln Gly Glu
        435                 440                 445

Ile Gly Ile Phe Phe Pro Ile Ile Val Leu Arg Ser Leu Asp Asn Ser
    450                 455                 460

Glu Cys Pro Asn Asp Gln Lys Met Gly Val Leu Arg Met Leu Glu Lys
465                 470                 475                 480

Val Cys Lys Asp Pro Gln Met Leu Val Asp Val Tyr Val Asn Tyr Asp
                485                 490                 495

Cys Asp Leu Glu Ala Pro Asn Leu Phe Glu Arg Met Val Thr Thr Leu
            500                 505                 510

Ser Lys Ile Ala Gln Gly Ser Gln Ser Ala Asp Pro Asn Pro Ala Met
        515                 520                 525

Ala Ser Gln Thr Ala Ser Val Lys Gly Ser Ser Leu Gln Cys Leu Val
    530                 535                 540

Asn Val Leu Lys Ser Leu Val Asp Trp Glu Lys Ile Arg Arg Glu Ala
545                 550                 555                 560

Glu Asn Ser Thr Arg Asn Ala Asn Glu Asp Ser Ala Ser Thr Gly Glu
                565                 570                 575

Pro Ile Glu Thr Lys Ser Arg Glu Asp Val Pro Ser Asn Phe Glu Lys
            580                 585                 590

Ala Lys Ala His Lys Ser Thr Met Glu Ala Ala Ile Ser Glu Phe Asn
        595                 600                 605

Arg Asn Ser Val Lys Gly Val Glu Tyr Leu Ile Ala Asn Lys Leu Val
    610                 615                 620

Glu Arg Asn Pro Ala Ser Val Ala Gln Phe Leu Arg Ser Thr Ser Ser
625                 630                 635                 640

Leu Ser Lys Val Met Ile Gly Asp Tyr Leu Gly Gln His Glu Glu Phe
                645                 650                 655

Pro Leu Ala Val Met His Ala Tyr Val Asp Ser Met Lys Phe Ser Glu
            660                 665                 670

Met Lys Phe His Ser Ala Ile Arg Glu Phe Leu Lys Gly Phe Arg Leu
        675                 680                 685

Pro Gly Glu Ala Gln Lys Ile Asp Arg Ile Met Glu Lys Phe Ala Glu
    690                 695                 700

Arg Tyr Cys Ala Asp Asn Pro Gly Leu Phe Lys Asn Ala Asp Thr Ala
705                 710                 715                 720

Tyr Val Leu Ala Tyr Ala Val Ile Met Leu Asn Thr Asp Ala His Asn
                725                 730                 735

Pro Met Val Trp Pro Lys Met Ser Lys Ser Asp Phe Thr Arg Met Asn
            740                 745                 750

Ala Thr Asn Asp Pro Glu Asp Cys Ala Pro Thr Glu Leu Leu Glu Glu
        755                 760                 765

Ile Tyr Asp Ser Ile Val Gln Glu Glu Ile Lys Leu Lys Asp Asp Asp
    770                 775                 780

Thr Met Lys Lys Leu Ser Ser Gln Arg Pro Gly Gly Glu Glu Arg Gly
785                 790                 795                 800

Gly Leu Val Ser Ile Leu Asn Leu Gly Leu Pro Lys Arg Ile Ser Ala
                805                 810                 815

Ala Asp Ala Lys Ser Glu Thr Glu Asp Ile Val Arg Lys Thr Gln Glu
            820                 825                 830

Ile Phe Arg Lys His Gly Val Lys Arg Gly Val Phe His Thr Val Glu
        835                 840                 845
```

-continued

```
Gln Val Asp Ile Ile Arg Pro Met Val Glu Ala Val Gly Trp Pro Leu
    850                 855                 860

Leu Ala Ala Phe Ser Val Thr Met Glu Val Gly Asp Asn Lys Pro Arg
865                 870                 875                 880

Ile Leu Leu Cys Met Glu Gly Phe Lys Ala Gly Ile His Ile Ala Tyr
                885                 890                 895

Val Leu Gly Met Asp Thr Met Arg Tyr Ala Phe Leu Thr Ser Leu Val
            900                 905                 910

Arg Phe Thr Phe Leu His Ala Pro Lys Glu Met Arg Ser Lys Asn Val
        915                 920                 925

Glu Ala Leu Arg Ile Leu Leu Gly Leu Cys Asp Ser Glu Pro Asp Thr
    930                 935                 940

Leu Gln Asp Thr Trp Asn Ala Val Leu Glu Cys Val Ser Arg Leu Glu
945                 950                 955                 960

Phe Ile Ile Ser Thr Pro Gly Ile Ala Ala Thr Val Met His Gly Ser
                965                 970                 975

Asn Gln Ile Ser Arg Asp Gly Val Val Gln Ser Leu Lys Glu Leu Ala
            980                 985                 990

Gly Arg Pro Ala Glu Gln Val Phe  Val Asn Ser Val Lys  Leu Pro Ser
        995                 1000                1005

Glu Ser  Val Val Glu Phe Phe  Thr Ala Leu Cys Gly  Val Ser Ala
    1010                 1015                1020

Glu Glu  Leu Lys Gln Ser Pro  Ala Arg Val Phe Ser  Leu Gln Lys
1025                 1030                1035

Leu Val  Glu Ile Ser Tyr Tyr  Asn Ile Ala Arg Ile  Arg Met Val
            1040                1045                1050

Trp Ala  Arg Ile Trp Ser Val  Leu Ala Glu His Phe  Val Ser Ala
        1055                1060                1065

Gly Ser  His His Asp Glu Lys  Ile Ala Met Tyr Ala  Ile Asp Ser
        1070                1075                1080

Leu Arg  Gln Leu Gly Met Lys  Tyr Leu Glu Arg Ala  Glu Leu Thr
    1085                 1090                1095

Asn Phe  Thr Phe Gln Asn Asp  Ile Leu Lys Pro Phe  Val Ile Ile
    1100                 1105                1110

Met Arg  Asn Thr Gln Ser Gln  Thr Ile Arg Ser Leu  Ile Val Asp
    1115                 1120                1125

Cys Ile  Val Gln Met Ile Lys  Ser Lys Val Gly Ser  Ile Lys Ser
    1130                 1135                1140

Gly Trp  Arg Ser Val Phe Met  Ile Phe Thr Ala Ala  Ala Asp Asp
    1145                 1150                1155

Glu Val  Glu Ser Ile Val Glu  Lys Ser Phe Glu Asn  Val Glu Gln
    1160                 1165                1170

Val Ile  Leu Glu His Phe Asp  Gln Val Ile Gly Asp  Cys Phe Met
    1175                 1180                1185

Asp Cys  Val Asn Cys Leu Ile  Arg Phe Ala Asn Asn  Lys Ala Ser
    1190                 1195                1200

Asp Arg  Ile Ser Leu Lys Ala  Ile Ala Leu Leu Arg  Ile Cys Glu
    1205                 1210                1215

Asp Arg  Leu Ala Glu Gly Leu  Ile Pro Gly Gly Val  Leu Lys Pro
    1220                 1225                1230

Val Asp  Gly Asn Glu Asp Glu  Thr Phe Asp Val Thr  Glu His Tyr
    1235                 1240                1245

Trp Phe  Pro Met Leu Ala Gly  Leu Ser Asp Leu Thr  Ser Asp Tyr
    1250                 1255                1260
```

```
Arg Pro  Glu Val Arg Asn Cys  Ala Leu Glu Val Leu  Phe Asp Leu
    1265                 1270                 1275

Leu Asn  Glu Arg Gly Asn Lys  Phe Ser Thr Pro Phe  Trp Glu Ser
    1280                 1285                 1290

Ile Phe  His Arg Ile Leu Phe  Pro Ile Phe Asp His  Val Ser His
    1295                 1300                 1305

Ala Gly  Lys Glu Ser Leu Ile  Ser Ser Gly Asp Val  Lys Phe Arg
    1310                 1315                 1320

Glu Thr  Ser Ile His Ser Leu  Gln Leu Leu Cys Asn  Leu Phe Asn
    1325                 1330                 1335

Thr Phe  Tyr Lys Glu Val Cys  Phe Met Leu Pro Pro  Leu Leu Ser
    1340                 1345                 1350

Leu Leu  Leu Asp Cys Ala Lys  Lys Ser Asp Gln Thr  Val Val Ser
    1355                 1360                 1365

Ile Ser  Leu Gly Ala Leu Val  His Leu Ile Glu Val  Gly Gly His
    1370                 1375                 1380

Gln Phe  Ser Glu Gly Asp Trp  Asp Met Leu Leu Lys  Ser Ile Arg
    1385                 1390                 1395

Asp Ala  Ser Tyr Thr Thr Gln  Pro Leu Glu Leu Leu  Asn Ala Leu
    1400                 1405                 1410

Ser Phe  Asp Asn Pro Lys Lys  Asn Leu Val Leu Ala  Gly Asp Ile
    1415                 1420                 1425

Glu Ala  Asp Ala Ser Asp Ser  Pro Arg Val Asp Arg  Asn Pro Asp
    1430                 1435                 1440

Asp Ile  Lys Asp Asn Gly Lys  Val Ser Ala Gln Ala  Ser Pro Arg
    1445                 1450                 1455

Ile Gly  Thr His Gly Thr Ser  Leu Glu Ser Gly Ile  Pro Pro Lys
    1460                 1465                 1470

Ala Asp  Gly Ser Glu Gly Arg  Pro Ser Ser Ser Gly  Arg Ala Gln
    1475                 1480                 1485

Lys Asp  Val Asp Asp Val Asn  Leu Gln Arg Ser Gln  Thr Phe Gly
    1490                 1495                 1500

Gln Arg  Phe Met Asp Asn Leu  Phe Leu Arg Asn Leu  Thr Ser Gln
    1505                 1510                 1515

Pro Lys  Ser Ser Val Ala Glu  Val Thr Val Pro Ser  Ser Pro Tyr
    1520                 1525                 1530

Lys His  Glu Asp Pro Thr Glu  Pro Asp Ser Arg Glu  Glu Glu Ser
    1535                 1540                 1545

Pro Ala  Leu Gly Ala Ile Arg  Gly Lys Cys Ile Thr  Gln Leu Leu
    1550                 1555                 1560

Leu Leu  Gly Ala Ile Asn Ser  Ile Gln Gln Lys Tyr  Trp Ser Asn
    1565                 1570                 1575

Leu Lys  Thr Pro Gln Lys Ile  Ala Ile Met Asp Ile  Leu Phe Ser
    1580                 1585                 1590

Phe Ile  Glu Phe Ala Ser Ser  Tyr Asn Ser Tyr Ser  Asn Leu Arg
    1595                 1600                 1605

Thr Arg  Met Asn His Ile Pro  Thr Glu Arg Pro Pro  Leu Asn Leu
    1610                 1615                 1620

Leu Arg  Gln Glu Leu Glu Gly  Thr Thr Ile Tyr Leu  Asp Val Leu
    1625                 1630                 1635

Gln Lys  Thr Thr Ser Gly Leu  Ala Asp Asp Ala Ser  Asn Ser Glu
    1640                 1645                 1650

Asp Arg  Leu Glu Gly Ala Ala  Glu Glu Lys Leu Val  Ser Phe Cys
```

```
    1655                1660                1665

Glu Gln  Val Leu Lys Glu Thr  Ser Asp Leu Gln Ser  Thr Leu Gly
    1670                1675                1680

Glu Thr  Thr Asn Met Asp Val  His Arg Val Leu Glu  Leu Arg Ser
    1685                1690                1695

Pro Val  Ile Val Lys Val Leu  Glu Gly Met Cys Phe  Met Asn Asn
    1700                1705                1710

Thr Ile  Phe Arg Lys His Met  Arg Glu Phe Tyr Pro  Leu Leu Thr
    1715                1720                1725

Arg Leu  Val Cys Cys Glu Gln  Met Glu Ile Arg Gly  Ala Leu Ala
    1730                1735                1740

Asn Leu  Phe Lys Ala Gln Leu  Lys Pro Leu Leu Gln  Gln
    1745                1750                1755


<210> SEQ ID NO 2
<211> LENGTH: 5610
<212> TYPE: DNA
<213> ORGANISM: Arabidopsis thaliana

<400> SEQUENCE: 2

atggcggctg gtggattttt gactcgagca tttgatacga tgcttaagga gtctggagga     60

aagaagtttc ctgatctcca gaaagctatt caagcttatc aagatggttc aaaggttgtt    120

acgcaggctg caccctcgag catagtggag agttcacaag ctgaaggtgg aggtgaaaaa    180

actggggtag aagcagatga accgcaaaaa gtcacgagtg ctgaagtagc gcagcaggct    240

agccagtcaa aaagtgagac tataaacgtt tccttagcaa atgctggaca cacattaggg    300

ggagcggaag tggagcttgt gctgaaacct ctacgccttg catttgagac aaagaactta    360

aaaatatttg atgctgcttt ggattgtctt cataaactca ttgcctatga tcatttggaa    420

ggggatccgg ggttggatgg tggaaaaaat tctgcacctt tcaccgacat tctgaacatg    480

gtttgcagct gtgttgataa ttcatcacca gacagcactg tactccaagt actgaaggtt    540

cttcttacag ctgttgcttc aggaaagttc aaagtgcatg gggagccatt gctgggagtt    600

attagagttt gctataacat tgctctaaac agcccaatta accaagcaac ttctaaagca    660

atgctgactc agatgataag cattgtattc aggagaatgg agactgacat tgtttccgca    720

tcatccacag tgtctcaaga agaacatgtt tcaggtgaca cttcaagccc taaaaatgaa    780

gaaataactg cagctgacga aaatgagaaa gaaatgacct taggagatgc actcactcag    840

gctaaagaca caactcttgc atctgttgaa gagctgcata cccttgtggg cggtgctgat    900

attaagggtt tagaagccgc ccttgacaaa gctgtgcatc ttgaagatgg caagaagata    960

aaacggggca tcgagctgga gagcatgagt attggacagc gtgatgcatt gcttgttttc   1020

cgtacccttt gcaagatggg tatgaaagaa gatagtgatg aagtcacaac caagacccgt   1080

atattgtctc ttgagcttct tcagggtatg ttagaaggag ttagtcactc atttacaaag   1140

aactttcact ttatagattc agtgaaagcc tacctctcat atgcattgtt gcgggcgtcg   1200

gtttctcagt cttctgtcat atttcagtat gcatctggta tcttctccgt gcttttgctg   1260

cggttcagag acagtttaaa agtaagcatg gattgttacc tttcaccata tttttctgat   1320

cctaaatctc actctcaggg tgaaattggt atatttttcc ccatcatcgt cttaagatca   1380

ttagataact ccgagtgtcc caatgaccaa aagatgggtg ttcttaggat gcttgagaaa   1440

gtctgcaaag atcctcagat gcttgttgat gtgtatgtaa actatgattg tgatctagag   1500

gccccaaact tgtttgagcg catggtaaca actttgtcta aaattgctca agggtctcag   1560
```

-continued

```
agtgctgatc caaatcctgc catggcttcg cagacagctt cggttaaagg ttcatccctt   1620
cagtgcctgg tcaacgttct taaatcacta gttgattggg agaaaataag gagagaggca   1680
gaaaatagta caagaaatgc aaacgaggac tctgcttcta ctggagagcc aattgaaacc   1740
aaaagcaggg aagatgtccc aagcaacttt gagaaggcta aagctcataa atccacaatg   1800
gaggctgcca tctccgagtt caacaggaat tcagtgaagg gtgtcgaata tctaattgca   1860
aacaagttgg ttgaaaggaa tcctgcttca gttgcacagt ttctgagaag tacttcgagt   1920
ctgagcaagg ttatgattgg cgattacctg ggccaacacg aggagtttcc tcttgctgtc   1980
atgcatgcat atgttgattc aatgaaattt tcagaaatga agtttcattc ggctattcgt   2040
gaatttctca aaggttttag acttcctgga gaggcccaaa aaattgatcg tattatggaa   2100
aagttcgcag aaagatattg cgcagacaat ccgggtcttt tcaagaatgc agatacagcc   2160
tacgttctag cctatgcagt tatcatgtta aatacagatg cgcataatcc tatggtttgg   2220
cctaagatgt caaaatcaga tttcacacgt atgaatgcca ctaatgatcc tgaagattgt   2280
gctccaactg aacttctgga agagatctat gattctattg tacaagaaga aattaaacta   2340
aaagacgatg acaccatgaa gaagctcagt agtcaaaggc caggaggaga agaaagaggt   2400
ggtcttgtca gcattcttaa tctgggtttg ccaaagagaa tatcagcagc tgatgctaaa   2460
tctgagactg aggacattgt taggaaaaca caggaaattt tccgaaagca tggagtgaaa   2520
agaggagtct ttcacacggt tgagcaagtg gacattataa ggcccatggt ggaagctgtt   2580
gggtggcctc tgcttgctgc tttctccgtt acaatggaag taggtgataa caaaccaagg   2640
attcttctct gcatggaggg atttaaagct ggaatacata ttgcttatgt tcttggaatg   2700
gatacaatgc gatatgcatt tctaacatcg cttgtcaggt tcactttctt gcatgctcca   2760
aaagaaatgc ggagcaaaaa tgttgaagca ttgaggatat tactggggtt gtgtgactca   2820
gaacctgaca cccttcaaga tacttggaat gcagttttag aatgtgtttc taggctggaa   2880
ttcattattt ctactcccgg aattgctgca acagtaatgc atggatcaaa ccagatctcc   2940
agggatgggg ttgttcaatc attgaaggag ttagccggga gacctgctga acaagttttt   3000
gtaaacagtg tcaagctgcc cagtgaatct gttgtggagt tttttactgc gctatgtggt   3060
gtttcagctg aagaattgaa gcagtctcct gcccgtgttt tcagcttgca gaagctagtt   3120
gagatcagtt attacaatat agcacgtatc cgaatggtct gggcaagaat atggtctgtc   3180
cttgccgaac atttcgtatc tgctggtagc catcatgatg aaaagattgc aatgtatgcc   3240
atagattctc tgagacagct cgggatgaag tatttagaac gtgctgagct caccaatttc   3300
actttccaaa atgatattct caaaccgttc gttattatca tgcggaatac tcaaagtcag   3360
accataagga gcctaattgt tgactgcatc gttcagatga taaaatctaa agttggaagt   3420
atcaaatcgg gatggaggag tgtttttatg atatttacag cagctgcaga tgacgaagtt   3480
gaatcgatag ttgaaaaatc atttgagaat gttgagcaag ttattctgga acactttgac   3540
caggtgatag gtgactgctt catggattgt gtcaattgtc tcatcaggtt tgccaataac   3600
aaagcttcag accggataag cctgaaagct attgcccttc tcagaatatg tgaggatcgg   3660
cttgcagagg gacttatacc cggtggtgtt cttaagcccg ttgatggcaa tgaggatgaa   3720
acttttgatg tgacagagca ttactggttt ccgatgcttg ccggtctatc tgatctcaca   3780
tctgattata ggcccgaagt tagaaactgt gctctggagg tgttgtttga tttgctaaat   3840
gaaaggggaa acaagttctc cacacctttc tgggagagta tcttccatcg catcttgttt   3900
ccaatttttg atcatgtgag tcatgctgga aaggaaagct taatatcttc cggggatgta   3960
```

-continued

```
aaatttcgtg aaacaagcat tcattccctt cagctcctct gcaatctctt caatacgttc   4020

tacaaggaag tatgttttat gctgcctcca cttttaagtt tgctcctaga ctgtgcgaag   4080

aaatcagatc agacagttgt ttcaatttca ttaggagcat tggttcacct catcgaggtt   4140

ggaggccacc aatttagtga gggagactgg gatatgctct tgaaaagcat aagagatgca   4200

tcatacacaa ctcaaccgct ggagctgttg aatgctttga gttttgacaa tccgaaaaag   4260

aacctagttt tggcaggaga catagaggcc gatgcctctg attctccacg agttgatcgt   4320

aatccggacg atattaaaga taatgggaaa gtgtccgccc aggcatctcc aaggattggt   4380

actcatggta cttccctaga atctgggata ccgcctaagg ctgatggttc ggaaggtcgt   4440

ccatcgtcat ctggaagggc tcaaaaggat gtggatgatg tgaatctgca gcggagtcag   4500

acttttggcc aaagattcat ggacaatctc ttcctccgga atctcacatc tcaaccaaaa   4560

agctctgttg cagaagtgac tgtaccctcc tctccatata agcatgaaga tcctacagag   4620

cctgacagca gagaagaaga gagtccagca ttgggagcta ttagaggaaa atgcatcaca   4680

caattactac tacttggtgc tatcaacagc atccagcaaa aatactggag taatttgaaa   4740

accccacaga agattgcgat tatggacatc ttattctctt tcatcgaatt tgcttcttcc   4800

tacaattcat attctaacct tagaacacgt atgaatcaca ttcccacaga gaggccacct   4860

ctaaaccttc tccggcaaga gctggaagga accaccatat atttggacgt cttgcaaaag   4920

acaacttctg ggcttgcgga tgatgcatct aactcggaag atagactaga aggtgcagca   4980

gaagaaaaat tggtatcgtt ctgtgaacag gttctgaaag aaacatctga tctccagtcc   5040

actttggggg agactactaa catggatgtt catcgggtac tggagctacg ttctcccgtg   5100

attgtgaagg ttttggaagg catgtgcttc atgaacaaca caatattcag gaagcacatg   5160

agagagttct accctctgct cacgaggctc gtttgctgtg aacagatgga gataagaggt   5220

gcactagcca accttttcaa agcacaattg aagccacttt tgcaacagta aatgatctat   5280

acgctatgat attgtggcaa agcaaaacac tctcaatgtc atttacttcc aacagttttt   5340

tttttttttt tttctacatt ggattgattt ttctcctgat taaagagcac atcccgatta   5400

aattgccagt ggtactcata cccgtatcag ttgttttttt ctttgcgatt ctttgctccc   5460

atcttatttt ggtttatttt tagtatgatg ttcgcaagtc tgttgttcag gcatcgttta   5520

gtcacctaaa aagtattatt tggtcacaga gtactggttg tttcttagac attgttaact   5580

tgaatggtgt tatcatagtt tcgatcaaac                                    5610
```

<210> SEQ ID NO 3
<211> LENGTH: 1669
<212> TYPE: PRT
<213> ORGANISM: Arabidopsis thaliana

<400> SEQUENCE: 3

```
Met Ala Ala Gly Gly Phe Leu Thr Arg Ala Phe Asp Thr Met Leu Lys
1               5                   10                  15

Glu Ser Gly Gly Lys Lys Phe Pro Asp Leu Gln Lys Ala Ile Gln Ala
            20                  25                  30

Tyr Gln Asp Gly Ser Lys Val Val Thr Gln Ala Ala Pro Ser Ser Ile
        35                  40                  45

Val Glu Ser Ser Gln Ala Glu Gly Gly Gly Glu Lys Thr Gly Val Glu
    50                  55                  60

Ala Asp Glu Pro Gln Lys Val Thr Ser Ala Glu Val Ala Gln Gln Ala
65                  70                  75                  80

Ser Gln Ser Lys Ser Glu Thr Ile Asn Val Ser Leu Ala Asn Ala Gly
```

-continued

```
                85                  90                  95

His Thr Leu Gly Gly Ala Glu Val Glu Leu Val Leu Lys Pro Leu Arg
            100                 105                 110

Leu Ala Phe Glu Thr Lys Asn Leu Lys Ile Phe Asp Ala Ala Leu Asp
        115                 120                 125

Cys Leu His Lys Leu Ile Ala Tyr Asp His Leu Glu Gly Asp Pro Gly
    130                 135                 140

Leu Asp Gly Gly Lys Asn Ser Ala Pro Phe Thr Asp Ile Leu Asn Met
145                 150                 155                 160

Val Cys Ser Cys Val Asp Asn Ser Ser Pro Asp Ser Thr Val Leu Gln
                165                 170                 175

Val Leu Lys Val Leu Leu Thr Ala Val Ala Ser Gly Lys Phe Lys Val
            180                 185                 190

His Gly Glu Pro Leu Leu Gly Val Ile Arg Val Cys Tyr Asn Ile Ala
        195                 200                 205

Leu Asn Ser Pro Ile Asn Gln Ala Thr Ser Lys Ala Met Leu Thr Gln
    210                 215                 220

Met Ile Ser Ile Val Phe Arg Arg Met Glu Thr Asp Ile Val Ser Ala
225                 230                 235                 240

Ser Ser Thr Val Ser Gln Glu Glu His Val Ser Gly Asp Thr Ser Ser
                245                 250                 255

Pro Lys Asn Glu Glu Ile Thr Ala Ala Asp Glu Asn Glu Lys Glu Met
            260                 265                 270

Thr Leu Gly Asp Ala Leu Thr Gln Ala Lys Asp Thr Thr Leu Ala Ser
        275                 280                 285

Val Glu Glu Leu His Thr Leu Val Gly Gly Ala Asp Ile Lys Gly Leu
    290                 295                 300

Glu Ala Ala Leu Asp Lys Ala Val His Leu Glu Asp Gly Lys Lys Ile
305                 310                 315                 320

Lys Arg Gly Ile Glu Leu Glu Ser Met Ser Ile Gly Gln Arg Asp Ala
                325                 330                 335

Leu Leu Val Phe Arg Thr Leu Cys Lys Met Gly Met Lys Glu Asp Ser
            340                 345                 350

Asp Glu Val Thr Thr Lys Thr Arg Ile Leu Ser Leu Glu Leu Leu Gln
        355                 360                 365

Gly Met Leu Glu Gly Val Ser His Ser Phe Thr Lys Asn Phe His Phe
    370                 375                 380

Ile Asp Ser Val Lys Ala Tyr Leu Ser Tyr Ala Leu Leu Arg Ala Ser
385                 390                 395                 400

Val Ser Gln Ser Ser Val Ile Phe Gln Tyr Ala Ser Gly Ile Phe Ser
                405                 410                 415

Val Leu Leu Leu Arg Phe Arg Asp Ser Leu Lys Gly Glu Ile Gly Ile
            420                 425                 430

Phe Phe Pro Ile Ile Val Leu Arg Ser Leu Asp Asn Ser Glu Cys Pro
        435                 440                 445

Asn Asp Gln Lys Met Gly Val Leu Arg Tyr Asn Ile Phe Leu Leu Val
    450                 455                 460

Gln Met Met Leu Glu Lys Val Cys Lys Asp Pro Gln Met Leu Val Asp
465                 470                 475                 480

Val Tyr Val Asn Tyr Asp Cys Asp Leu Glu Ala Pro Asn Leu Phe Glu
                485                 490                 495

Arg Met Val Thr Thr Leu Ser Lys Ile Ala Gln Gly Ser Gln Ser Ala
            500                 505                 510
```

```
Asp Pro Asn Pro Ala Met Ala Ser Gln Thr Ala Ser Val Lys Gly Ser
        515                 520                 525

Ser Leu Gln Ala Glu Asn Ser Thr Arg Asn Ala Asn Glu Asp Ser Ala
    530                 535                 540

Ser Thr Gly Glu Pro Ile Glu Thr Lys Ser Arg Glu Asp Val Pro Ser
545                 550                 555                 560

Asn Phe Glu Lys Ala Lys Ala His Lys Ser Thr Met Glu Ala Ala Ile
                565                 570                 575

Ser Glu Phe Asn Arg Asn Ser Val Lys Gly Val Glu Tyr Leu Ile Ala
            580                 585                 590

Asn Lys Leu Val Glu Arg Asn Pro Ala Ser Val Ala Gln Phe Leu Arg
        595                 600                 605

Ser Thr Ser Ser Leu Ser Lys Val Met Ile Gly Asp Tyr Leu Gly Gln
    610                 615                 620

His Glu Glu Phe Pro Leu Ala Val Met His Ala Tyr Val Asp Ser Met
625                 630                 635                 640

Lys Phe Ser Glu Met Lys Phe His Ser Ala Ile Arg Glu Phe Leu Lys
                645                 650                 655

Asp Asn Pro Gly Leu Phe Lys Asn Ala Asp Thr Ala Tyr Val Leu Ala
            660                 665                 670

Tyr Ala Val Ile Met Leu Asn Thr Asp Ala His Asn Pro Met Val Trp
        675                 680                 685

Pro Lys Met Ser Lys Ser Asp Phe Thr Arg Met Asn Ala Thr Asn Asp
    690                 695                 700

Pro Glu Asp Cys Ala Pro Thr Glu Leu Leu Glu Glu Ile Tyr Asp Ser
705                 710                 715                 720

Ile Val Gln Glu Glu Ile Lys Leu Lys Asp Asp Asp Thr Met Lys Lys
                725                 730                 735

Leu Ser Ser Gln Arg Pro Gly Gly Glu Glu Arg Gly Gly Leu Val Ser
            740                 745                 750

Ile Leu Asn Leu Gly Leu Pro Lys Arg Ile Ser Ala Ala Asp Ala Lys
        755                 760                 765

Ser Glu Thr Glu Asp Ile Val Arg Lys Thr Gln Glu Ile Phe Arg Lys
    770                 775                 780

His Gly Val Lys Arg Gly Val Phe His Thr Val Glu Gln Val Asp Ile
785                 790                 795                 800

Ile Arg Pro Met Val Glu Ala Val Gly Trp Pro Leu Leu Ala Ala Phe
                805                 810                 815

Ser Val Thr Met Glu Val Gly Asp Asn Lys Pro Arg Ile Leu Leu Cys
            820                 825                 830

Met Glu Gly Phe Lys Ala Gly Ile His Ile Ala Tyr Val Leu Gly Met
        835                 840                 845

Asp Thr Met Arg Tyr Ala Phe Leu Thr Ser Leu Val Arg Phe Thr Phe
    850                 855                 860

Leu His Ala Pro Lys Glu Met Arg Ser Lys Asn Val Glu Ala Leu Arg
865                 870                 875                 880

Ile Leu Leu Gly Leu Cys Asp Ser Glu Pro Asp Thr Leu Gln Asp Thr
                885                 890                 895

Trp Asn Ala Val Leu Glu Cys Val Ser Arg Leu Glu Phe Ile Ile Ser
            900                 905                 910

Thr Pro Gly Ile Ala Ala Thr Val Met His Gly Ser Asn Gln Ile Ser
        915                 920                 925

Arg Asp Gly Val Val Gln Ser Leu Lys Glu Leu Ala Gly Arg Pro Ala
    930                 935                 940
```

```
Glu Gln Val Phe Val Asn Ser Val Lys Leu Pro Ser Glu Ser Val Val
945                 950                 955                 960

Glu Phe Phe Thr Ala Leu Cys Gly Val Ser Ala Glu Glu Leu Lys Gln
                965                 970                 975

Ser Pro Ala Arg Val Phe Ser Leu Gln Lys Leu Val Glu Ile Ser Tyr
            980                 985                 990

Tyr Asn Ile Ala Arg Ile Arg Met  Val Trp Ala Arg Ile  Trp Ser Val
        995                 1000                 1005

Leu Ala  Glu His Phe Val Ser  Ala Gly Ser His His  Asp Glu Lys
    1010                 1015                 1020

Ile Ala  Met Tyr Ala Ile Asp  Ser Leu Arg Gln Leu  Gly Met Lys
    1025                 1030                 1035

Tyr Leu  Glu Arg Ala Glu Leu  Thr Asn Phe Thr Phe  Gln Asn Asp
    1040                 1045                 1050

Ile Leu  Lys Pro Phe Val Ile  Ile Met Arg Asn Thr  Gln Thr Ala
    1055                 1060                 1065

Ala Asp  Asp Glu Val Glu Ser  Ile Val Glu Lys Ser  Phe Glu Asn
    1070                 1075                 1080

Val Glu  Gln Val Ile Leu Glu  His Phe Asp Gln Val  Ile Gly Asp
    1085                 1090                 1095

Cys Phe  Met Asp Cys Val Asn  Cys Leu Ile Arg Phe  Ala Asn Asn
    1100                 1105                 1110

Lys Ala  Ser Asp Arg Ile Ser  Leu Lys Ala Ile Ala  Leu Leu Arg
    1115                 1120                 1125

Ile Cys  Glu Asp Arg Leu Ala  Glu Gly Leu Ile Pro  Gly Gly Val
    1130                 1135                 1140

Leu Lys  Pro Val Asp Gly Asn  Glu Asp Glu Thr Phe  Asp Val Thr
    1145                 1150                 1155

Glu His  Tyr Trp Phe Pro Met  Leu Ala Gly Leu Ser  Asp Leu Thr
    1160                 1165                 1170

Ser Asp  Tyr Arg Pro Glu Val  Arg Asn Cys Ala Leu  Glu Val Leu
    1175                 1180                 1185

Phe Asp  Leu Leu Asn Glu Arg  Gly Asn Lys Phe Ser  Thr Pro Phe
    1190                 1195                 1200

Trp Glu  Ser Ile Phe His Arg  Ile Leu Phe Pro Ile  Phe Asp His
    1205                 1210                 1215

Val Ser  His Ala Gly Lys Glu  Ser Leu Ile Ser Ser  Gly Asp Val
    1220                 1225                 1230

Lys Phe  Arg Glu Thr Ser Ile  His Ser Leu Gln Leu  Leu Cys Asn
    1235                 1240                 1245

Leu Phe  Asn Thr Phe Tyr Lys  Glu Val Cys Phe Met  Leu Pro Pro
    1250                 1255                 1260

Leu Leu  Ser Leu Leu Leu Asp  Cys Ala Lys Lys Ser  Asp Gln Thr
    1265                 1270                 1275

Val Val  Ser Ile Ser Leu Gly  Ala Leu Val His Leu  Ile Glu Val
    1280                 1285                 1290

Gly Gly  His Gln Phe Ser Glu  Gly Asp Trp Asp Met  Leu Leu Lys
    1295                 1300                 1305

Ser Ile  Arg Asp Ala Ser Tyr  Thr Thr Gln Pro Leu  Glu Leu Leu
    1310                 1315                 1320

Asn Ala  Leu Ser Phe Asp Asn  Pro Lys Lys Asn Leu  Val Leu Ala
    1325                 1330                 1335

Gly Asp  Ile Glu Ala Asp Ala  Ser Asp Ser Pro Arg  Val Asp Arg
```

1340 1345 1350

Asn Pro Asp Asp Ile Lys Asp Asn Gly Lys Val Ser Ala Gln Ala
1355 1360 1365

Ser Pro Arg Ile Gly Thr His Gly Thr Ser Leu Glu Ser Gly Ile
1370 1375 1380

Pro Pro Lys Ala Asp Gly Ser Glu Gly Arg Pro Ser Ser Ser Gly
1385 1390 1395

Arg Ala Gln Lys Asp Val Asp Asp Val Asn Leu Gln Arg Ser Gln
1400 1405 1410

Thr Phe Gly Gln Arg Phe Met Asp Asn Leu Phe Leu Arg Asn Leu
1415 1420 1425

Thr Ser Gln Pro Lys Ser Ser Val Ala Glu Val Thr Val Pro Ser
1430 1435 1440

Ser Pro Tyr Lys His Glu Asp Pro Thr Glu Pro Asp Ser Arg Glu
1445 1450 1455

Glu Glu Ser Pro Ala Leu Gly Ala Ile Arg Gly Lys Cys Ile Thr
1460 1465 1470

Gln Leu Leu Leu Leu Gly Ala Ile Asn Ser Ile Gln Gln Lys Tyr
1475 1480 1485

Trp Ser Asn Leu Lys Thr Pro Gln Lys Ile Ala Ile Met Asp Ile
1490 1495 1500

Leu Phe Ser Phe Ile Glu Phe Ala Ser Ser Tyr Asn Ser Tyr Ser
1505 1510 1515

Asn Leu Arg Thr Arg Met Asn His Ile Pro Thr Glu Arg Pro Pro
1520 1525 1530

Leu Asn Leu Leu Arg Gln Glu Leu Glu Gly Thr Thr Ile Tyr Leu
1535 1540 1545

Asp Val Leu Gln Lys Thr Thr Ser Gly Leu Ala Asp Asp Ala Ser
1550 1555 1560

Asn Ser Glu Asp Arg Leu Glu Gly Ala Ala Glu Glu Lys Leu Val
1565 1570 1575

Ser Phe Cys Glu Gln Val Leu Lys Glu Thr Ser Asp Leu Gln Ser
1580 1585 1590

Thr Leu Gly Glu Thr Thr Asn Met Asp Val His Arg Val Leu Glu
1595 1600 1605

Leu Arg Ser Pro Val Ile Val Lys Val Leu Glu Gly Met Cys Phe
1610 1615 1620

Met Asn Asn Thr Ile Phe Arg Lys His Met Arg Glu Phe Tyr Pro
1625 1630 1635

Leu Leu Thr Arg Leu Val Cys Cys Glu Gln Met Glu Ile Arg Gly
1640 1645 1650

Ala Leu Ala Asn Leu Phe Lys Ala Gln Leu Lys Pro Leu Leu Gln
1655 1660 1665

Gln

<210> SEQ ID NO 4
<211> LENGTH: 5009
<212> TYPE: DNA
<213> ORGANISM: Arabidopsis thaliana

<400> SEQUENCE: 4
cttgataagc ttgaatagct ttctggagat caggaaactt ctttcctcca gactccttaa 60
gcatcgtatc aaatgctcga gtcaaaaatc caccagccgc catctctcca ctatgctcga 120
gggtgcagcc tgcgtaacaa cctttgaacc atatgaagac aatccaaagc agcatcaaat 180

-continued

```
atttttaagt tctttgtctc aaatgcaagg cgtagaggtt tcagcacaag ctccacttcc    240
gctcccccta atgtgtgtcc agcatttgct aaggaaacgt ttatagtctc actttttgac    300
tggctagcct gctgcgctac ttcagcactc gtgacttttt gcggttcatc tgcttctacc    360
ccagtttttt cacctccacc ttcagcttgt gaactgtctg gtgatgaatt atcaacacag    420
ctgcaaacca tgttcagaat gtcggtgaaa ggtgcagaat tttttccacc atccaacccc    480
ggatcccctt ccaaatgatc ataggcaatg agtttctttg aactttcctg aagcaacagc    540
tgtaagaaga accttcagta cttggagtac agtgctgttt agagcaatgt tatagcaaac    600
tctaataact cccagcaatg gctccccatg caaatgtcag tctccattct cctgaataca    660
atgcttatca tctgagtcag cattgcttta gaagttgctt ggttaattgg gcttaatatc    720
agcaccgccc acaagggtat gcagctcttc aacagatgca agagttgtgt ctttagcctg    780
agtgagtgca tctcctaagg tcatttcttt ctcattttcg tcagctgcag ttatttcttc    840
atttttaggg cttgaagtgt cacctgaaac atgttcttct tgagacactg tggatgatgc    900
ggaaaccgtt ttatcttctt gccatcttca agatgcacag ctttgtcaag ggcggcttct    960
aaacccttgc aaagggtacg gaaaacaagc aatgcatcac gctgtccaat actcatgctc   1020
tccagctcga tgcccctgaa gaagctcaag agacaatata cgggtcttgg ttgtgacttc   1080
atcactatct tctttcatac ccatctgaaa tatgacagaa gactgagaaa ccgacgcccg   1140
caacaatgca tatgagaggt aggctttcac tgaatctata aagtgaaagt tctttgtaaa   1200
tgagtgacta actccttcta acataccttt taaactgtct ctgaaccgca gcaaaagcac   1260
ggagaagata ccagatgcat aatctggacg agcagaaaaa tattgtacct aagaacaccc   1320
atcttttggt cattgggaca ctcggagtta tctaatgatc ttaagacgat gatggggaaa   1380
aatataccaa tttcacccat gcgctcaaac aagtttgggg cctctagatc acaatcatag   1440
tttacataca catcaacaag catctgagga tctttgcaga ctttctcaag catcctgaag   1500
ggatgaacct ttaaccgaag ctgtctgcga agccatggca ggatttggat cagcactctg   1560
gacccttgag caattttaga caaagttgtt acctcggaga tggcagcctc cattgtggat   1620
ttatgagctt tagccttctc aaagttgctt gggacatctt ccctgctttt ggtttcaatt   1680
ggctctccag tagaagcaga gtcctcgttt gcatttcttg tactattttc tgccttgctc   1740
agactcgaag tacttctcag aaactgtgca actgaagcag gattcctttc aaccaacttg   1800
tttgcaatta gatattcgac acccttcact gaattcctgt tgaactttga gaaattcacg   1860
aatagccgaa tgaaacttca tttctgaaaa tttcattgaa tcaacatatg catgcatgac   1920
agcaagagga aactcctcgt gttggcccag gtaatcgcca atcataacct gacaagcgat   1980
gttagaaatg catatcgcat tgtatccatt ccaagaacat aagcaatatg tattccagct   2040
ttaaatccct ccatgcagag aagaatcctt ggtttgttat cacctacttc cattgtaacg   2100
gagaaagcag caagcagagg ccacccaaca gcttccacca tgggccttat aatgtccact   2160
tgctcaaccg tgtgaaagac tcctcttttc actccatgct ttcggaaaat ttcctgtgtt   2220
ttcctaacaa tgtcctcagt ctcagattta gcatcagctg ctgatattct ctttggcaaa   2280
cccagattaa gaatgctgac aagaccacct ctttcttctc ctcctggcct ttgactactg   2340
agcttcttca tggtgtcatc gtcttttagt ttaatttctt cttgtacaat agaatcatag   2400
atctcttcca gaagttcagt tggagcacaa tcttcaggat cattagtggc attcatacgt   2460
gtgaaatctg attttgacat cttaggccaa accataggat tatgcgcatc tgtatttaac   2520
atgataactg cataggctag aacgtaggct gtatctgcat tcttgaaaag acccggattg   2580
```

-continued

```
tcattcggat acgtgctata ttgtaataac tgatctcaac tagcttctgc aagctgaaaa   2640
cacgggcagg agactgcttc aattcttcag ctgaaacacc acatagcgca gtaaaaaact   2700
ccacaacaga ttcactgggc agcttgacac tgtttacaaa aacttgttca gcaggtctcc   2760
cggctaactc cttcaatgat tgaacaaccc catccctgga gatctggttt gatccatgca   2820
ttactgttgc agcaattccg ggagtagaaa taatgaattc cagcctagaa acacattcta   2880
aaactgcatt ccaagtatct tgaagggtgt caggttctga gtcacacaac cccagtaata   2940
tcctcaatgc ttcaacattt ttgctccgca tttcttttgg agcatgcaag aaagtgaact   3000
ttgagtattc cgcatgataa taacgaacgg tttgagaata tcattttgga aagtgaaatt   3060
ggtgagctca gcacgttcta aatacttcat cccgagctgt ctcagagaat ctatggcata   3120
cattgcaatc ttttcatcat gatggctacc agcagatacg aaatgttcgg caaggacaga   3180
ccatattctt gcccagacct tgctcaacat tctcaaatga tttttcaact atcgattcaa   3240
cttcgtcatc tgcagctgct ctgcaagccg atcctcacat attctgagaa gggcaatagc   3300
tttcaggctt atccggtctg aagctttgtt attggcaaac ctgatgagac aattgacaca   3360
atccatgaag cagtcaccta tcacctggtc aaagtgttcc agaataactt gtagaacgta   3420
ttgaagagat tgcagaggag ctgaagggaa tgaatgcttg tttcacgaaa ttttacatcc   3480
ccggaagata ttaagctttc ctttccagca tgactcacat gatcaaaaat tggaaacaag   3540
atgcgatgga agatactctc ccagaaaggt gtggagaact tgtttcccct ttcatttagc   3600
aaatcaaaca acacctccag agcacagttt ctaacttcgg gcctataatc agatgtgaga   3660
tcagatagac cggcaagcat cggaaaccag taatgctctg tcacatcaaa agtttcatcc   3720
tcattgccat caacgggctt aagaacacca ccgggtataa gtcccttatg cttttcaaga   3780
gcatatccca gtctccctca ctaaattggt ggcctccaac ctcgatgagg tgaaccaatg   3840
ctcctaatga aattgaaaca actgtctgat ctgatttctt cgcacagtct aggagcaaac   3900
ttaaaagtgg aggcagcata aaacatactt ccttccgaac catcagcctt aggcggtatc   3960
ccagattcta gggaagtacc atgagtacca atccttggag atgcctgggc ggacactttc   4020
ccattatctt taatatcgtc cggattacga tcaactcgtg gagaatcaga ggcatcggcc   4080
tctatgtctc ctgccaaaac taggttcttt ttcggattgt caaaactcaa agcattcaac   4140
agctccagcg gttgagttgt gtatgatgca tctcttatat ggagaggagg gtacagtcac   4200
ttctgcaaca gagctttttg gttgagatgt gagattccgg aggaagagat tgtccatgaa   4260
tctttggcca aaagtctgac tccgctgcag attcacatca tccacatcct tttgagccct   4320
tccagatgac gatggacgac ctggatgctg ttgatagcac caagtagtag taattgtgtg   4380
atgcattttc ctctaatagc tcccaatgct ggactctctt cttctctgct gtcaggctct   4440
gtaggatctt catgctctct gtgggaatgt gattcatacg tgttctaagg ttagaatatg   4500
aattgtagga agaagcaaat tcgatgaaag agaataagat gtccataatc gcaatcttct   4560
gtggggtttt caaattactc cagtattttt gcttcacaat cacgggagaa cgtagctcca   4620
gtacccgatg aacatccatg ttagtagtct cccccaaagt ggactggaga tcagatgttt   4680
ctttcagaac ctgttcacag aacgatacca atttttcttc tgctgcacct tctagtctat   4740
cttccgagtt agatgcatca tccgcaagcc cagaagttgt cttttgcaag acgtccaaat   4800
atatggtggt tccttccagc tcttgccgga gaaggtttag aggtggcctg ttcacagcaa   4860
acgagcctcg tgagcagagg gtagaactct ctcatgtgct tcctgaatat tgtgttgttc   4920
atgaagcaca tgccttccaa aacttactgt tgcaaaagtg gcttcaattg tgctttgaaa   4980
```

aggttggcta gtgcacctct tatctccat 5009

<210> SEQ ID NO 5
<211> LENGTH: 238
<212> TYPE: PRT
<213> ORGANISM: Brassica napus

<400> SEQUENCE: 5

Leu Leu Val Gln Met Ile Lys Ser Lys Val Gly Ser Ile Lys Ser Gly
1 5 10 15

Trp Arg Ser Val Phe Met Ile Phe Thr Ala Ala Ala Asp Asp Asp Val
20 25 30

Glu Ser Ile Val Glu Lys Ser Phe Glu Asn Val Glu Gln Val Ile Leu
35 40 45

Glu His Phe Asp Gln Val Ile Gly Asp Cys Phe Met Asp Cys Val Asn
50 55 60

Cys Leu Ile Arg Phe Ala Asn Asn Lys Ala Ser Asp Arg Ile Ser Leu
65 70 75 80

Lys Ala Ile Ala Phe Leu Arg Ile Cys Glu Asp Arg Leu Ala Glu Gly
85 90 95

Leu Ile Pro Gly Gly Val Leu Lys Pro Val Asn Thr Asn Glu Asp Glu
100 105 110

Thr Phe Asp Val Thr Glu His Tyr Trp Tyr Pro Met Leu Ala Gly Leu
115 120 125

Ser Asp Leu Thr Ser Asp Phe Arg Pro Glu Val Arg Asn Cys Ala Leu
130 135 140

Glu Val Leu Phe Asp Leu Leu Asn Glu Arg Gly Lys Lys Phe Ser Thr
145 150 155 160

Pro Phe Trp Glu Ser Ile Phe His Arg Ile Leu Phe Pro Ile Phe Asp
165 170 175

His Val Ser His Ala Gly Lys Glu Gly Leu Val Ser Ser Gly Asp Val
180 185 190

Gln Phe Arg Glu Thr Ser Ile His Ser Leu Gln Leu Leu Cys Asn Leu
195 200 205

Phe Asn Thr Phe Tyr Lys Glu Val Cys Phe Met Leu Pro Pro Leu Leu
210 215 220

Ser Leu Leu Leu Asp Cys Ala Lys Lys Ser Asp Gln Lys Val
225 230 235

<210> SEQ ID NO 6
<211> LENGTH: 724
<212> TYPE: DNA
<213> ORGANISM: Brassica napus

<400> SEQUENCE: 6
attgttgact gctcgttcag atgatcaaat ctaaagttgg aagtataaaa tcgggttgga 60
ggagtgtttt tatgatattt acagcagctg cagatgacga tgttgaatcc atagttgaaa 120
aatcatttga gaatgtggag caagttattc tggaacactt tgaccaggtg atcggtgact 180
gcttcatgga ttgcgtcaac tgtctcatcc gatttgccaa taacaaagct tcagaccgga 240
taagcctgaa agctattgcc tttctcagaa tatgcgagga tcggcttgca gagggactta 300
taccgggtgg tgttctcaag cctgtcaata ccaatgagga tgaaactttt gatgtgacag 360
agcattactg gtatccgatg cttgctggtt tatctgatct cacgtcagat tttagacctg 420
aagttagaaa ctgcgctctg gaggtgctgt ttgatttgct gaatgaaaga ggcaaaaagt 480

-continued

```
tctccacgcc tttctgggag agcatcttcc atcgcatctt gtttccaatt tttgatcatg    540

tgagtcatgc tggaaaggaa ggcttagtat cgtcggggga tgttcaattt cgtgaaacaa    600

gcattcattc ccttcagctt ctctgtaatc tctttaatac attctacaag gaagtttgtt    660

ttatgctacc tccactttta agcttgctcc tggactgtgc gaagaaatca gatcagaaag    720

ttgt                                                                 724


<210> SEQ ID NO 7
<211> LENGTH: 167
<212> TYPE: PRT
<213> ORGANISM: Lycopersicon esculentum

<400> SEQUENCE: 7

Val Pro Glu Gly Leu Asp Arg Ser Gln Thr Ile Gly Gln Lys Ile Met
1               5                   10                  15

Gly Asn Met Met Asp Asn Arg Phe Ile Arg Ser Phe Thr Ser Lys Pro
            20                  25                  30

Lys Ile Gln Ala Ser Asp Ile Leu Pro Thr Ser Pro Ser Lys Leu Leu
        35                  40                  45

Ala Asp Asp Ala Glu Pro Glu Ala Lys Asp Glu Asp Glu Ser Ser Met
    50                  55                  60

Leu Ala Thr Ile Arg Ser Lys Cys Ile Thr Gln Leu Leu Leu Leu Ser
65                  70                  75                  80

Ala Ile Asp Ser Ile Gln Lys Lys Tyr Trp Asn Lys Leu Lys Pro Thr
                85                  90                  95

His Lys Ile Thr Ile Met Asp Ile Leu Phe Ser Val Leu Glu Phe Ala
            100                 105                 110

Ala Ser Tyr Asn Ser Tyr Ser Asn Leu Arg Leu Arg Met Arg Gln Ile
        115                 120                 125

Pro Ala Glu Arg Pro Pro Phe Asn Leu Leu Arg Gln Glu Leu Ala Gly
    130                 135                 140

Thr Ser Ile Tyr Leu Asp Ile Leu Gln Lys Thr Thr Ala Gly Ile Asn
145                 150                 155                 160

Ser Val Arg Gly Arg Ile Asn
                165


<210> SEQ ID NO 8
<211> LENGTH: 511
<212> TYPE: DNA
<213> ORGANISM: Lycopersicon esculentum

<400> SEQUENCE: 8

gttccagaag gtcttgaccg tagtcaaaca ataggtcaga aaattatggg aaatatgatg     60

gacaaccgct tcatcagaag tttcacctct aaaccaaaga ttcaggcttc tgatatttta    120

ccaacttcac cgtcaaagct attagctgat gatgcggagc ctgaagcaaa agacgaggat    180

gaaagttcaa tgttggctac tattaggagc aaatgcatca cacagttgtt acttctcagt    240

gcaattgata gcattcagaa gaaatactgg aacaagttaa aaccaacaca caagataact    300

ataatggaca tcttgttctc tgtgttagag tttgctgcat catataattc gtattccaat    360

ctgagattgc ggatgcgcca aatacctgct gaaaggccac catttaatct tctccgccag    420

gaattagcag gaacttccat ctatcttgat atcttacaga agacgacagc tgggatcaat    480

tctgtaaggg gaagaatcaa ctgaaactac c                                   511


<210> SEQ ID NO 9
<211> LENGTH: 163
```

<212> TYPE: PRT
<213> ORGANISM: Lycopersicon esculentum

<400> SEQUENCE: 9

Tyr Ser Asp Gly Lys Asp Leu Pro Glu Asp Tyr Leu Gly Ala Leu Tyr
1 5 10 15

Asp Gln Ile Val Arg Asn Glu Ile Lys Met Lys Ala Asp Ser Ser Val
20 25 30

Pro Gln Asn Lys Gln Gly Asn Ser Leu Asn Lys Leu Leu Gly Leu Asp
35 40 45

Gly Ile Leu Asn Leu Val Trp Lys Gln Arg Glu Glu Lys Pro Leu Gly
50 55 60

Ala Asn Gly Val Leu Val Arg His Ile Gln Glu Gln Phe Lys Val Lys
65 70 75 80

Ser Gly Lys Ser Glu Ser Val Tyr Tyr Val Ile Ala Asp Pro Ala Ile
85 90 95

Leu Arg Phe Met Val Glu Val Cys Trp Gly Pro Met Leu Ala Ala Phe
100 105 110

Ser Val Thr Leu Asp Gln Ser Asp Asn Lys Asn Ala Thr Ser Gln Cys
115 120 125

Leu Leu Gly Phe Arg His Ala Val His Ile Thr Ala Val Met Gly Met
130 135 140

Gln Thr Gln Arg Asp Ala Phe Val Thr Ser Met Ala Lys Phe Thr Asn
145 150 155 160

Leu His Cys

<210> SEQ ID NO 10
<211> LENGTH: 490
<212> TYPE: DNA
<213> ORGANISM: Lycopersicon esculentum

<400> SEQUENCE: 10
gtactccgac gggaaggatt tacctgaaga ttatttgggt gctctttatg accaaattgt 60
gagaaacgag ataaagatga aagcagattc ttccgtgcca caaaacaagc aggggaatag 120
tcttaataag ctgttgggct tggatggtat actgaatcta gtatggaagc agagagagga 180
aaaaccactg ggtgcaaacg gagttctcgt gaggcatatt caagagcagt ttaaagtaaa 240
atctggaaaa tctgagtctg tctattatgt tattgcagat ccagctattt tgagatttat 300
ggtagaagtc tgctggggtc ccatgcttgc tgctttcagt gtcaccctag accagagtga 360
taataagaat gccacttctc aatgtttgct agggttcagg catgctgtgc atattacagc 420
tgtgatgggt atgcagacgc agagagatgc ttttgtcacc tctatggcaa agttcactaa 480
tcttcattgt 490

<210> SEQ ID NO 11
<211> LENGTH: 1256
<212> TYPE: PRT
<213> ORGANISM: Oryza sativa

<400> SEQUENCE: 11

Met Ala Gly Ala Ala Gly Gly Phe Val Thr Arg Ala Phe Glu Ala Met
1 5 10 15

Leu Lys Glu Cys Thr Ala Asn Arg Gly Lys Phe Ala Ala Leu Gln Gln
20 25 30

Ser Ile Gln Ser Tyr Leu Asp Ala Ile Lys Gly Ala Ala Ala Ala Gly
35 40 45

```
Gln Glu Glu Gly Gly Asp Ala Ala Ala Ala Pro Ile Thr Gln Val Leu
    50                  55                  60

Ala Ser Ala Gly Arg Val Leu Glu Gly Thr Gln Ala Glu Leu Val Leu
65                  70                  75                  80

Gln Pro Leu Arg Leu Ala Phe Glu Thr Lys His Val Lys Leu Val Glu
                85                  90                  95

Pro Ala Leu Asp Cys Leu His Lys Leu Ile Ala Tyr Asp His Leu Glu
            100                 105                 110

Gly Asp Pro Gly Leu Glu Gly Gly Lys Asn Ser Pro Leu Phe Thr Asp
        115                 120                 125

Ile Leu Asn Met Val Cys Gly Cys Val Asp Asn Thr Ser Ser Asp Ser
    130                 135                 140

Thr Val Leu Gln Val Leu Lys Val Leu Leu Asn Ala Val Ala Ser Asn
145                 150                 155                 160

Arg Phe Arg Val His Gly Glu Pro Leu Leu Gly Val Ile Arg Val Cys
                165                 170                 175

Tyr Asn Ile Ala Leu Asn Arg Arg Met Glu Ser Glu Gln Ala Lys Asn
            180                 185                 190

Phe Pro His Asn Phe Tyr Trp His Tyr Ala Lys Gly Asp Asp Leu Leu
        195                 200                 205

Lys Glu Arg Glu Ala Ser Pro Ala Ser Val Glu Glu Leu Gln Ser Leu
    210                 215                 220

Ala Gly Gly Ala Asp Ile Lys Gly Leu Glu Ala Val Leu Asp Lys Ala
225                 230                 235                 240

Val Glu Leu Glu Asp Gly Lys Lys Val Ser Gly Gly Ile Asp Leu Asp
                245                 250                 255

Thr Val Asn Ile Ile Gln Arg Asp Ala Leu Leu Leu Phe Arg Thr Leu
            260                 265                 270

Cys Lys Met Ser Met Lys Glu Glu Ser Asp Glu Val Ala Thr Lys Thr
        275                 280                 285

Arg Leu Leu Ser Leu Glu Leu Leu Gln Gly Leu Leu Glu Gly Val Ser
    290                 295                 300

Asp Ser Phe Thr Lys Asn Phe His Phe Ile Asp Ser Val Lys Ala Tyr
305                 310                 315                 320

Leu Ser Tyr Ala Ile Leu Arg Ala Ala Val Ser Ser Ser Ala Val Val
                325                 330                 335

Phe Gln Tyr Ala Cys Gly Ile Phe Ala Val Leu Leu Leu Arg Phe Arg
            340                 345                 350

Glu Ser Leu Lys Gly Glu Ile Gly Val Phe Phe Pro Leu Ile Val Leu
        355                 360                 365

Arg Ser Leu Asp Ser Ser Asp Ser Pro Leu Ser Gln Arg Ala Ser Val
    370                 375                 380

Leu Arg Met Leu Glu Lys Val Cys Lys Asp Ser Gln Met Leu Ala Asp
385                 390                 395                 400

Met Phe Val Asn Tyr Asp Cys Asp Leu Glu Gly Pro Asn Leu Phe Glu
                405                 410                 415

Arg Met Val Ser Ala Leu Ser Arg Ile Ala Gln Gly Ser Gln Asn Ala
            420                 425                 430

Asp Thr Asn Thr Ala Ala Ser Ser Gln Thr Val Ser Val Lys Gly Ser
        435                 440                 445

Ser Leu Gln Ser Leu Val Asp Trp Glu Gln Ala Arg Arg Asp Ser Leu
    450                 455                 460

Lys Gln Gly Ser Val Ala Glu Ala Cys Glu Asn Asp Ser Ser Ala Arg
465                 470                 475                 480
```

-continued

```
Ser Ile Thr Ser Asp Glu Ile Lys Ser Gln Glu Asp Gly Arg Asn Gln
                485                 490                 495

Phe Glu Ile Ala Lys Ala His Lys Ser Thr Met Glu Ala Ala Ile Ser
            500                 505                 510

Glu Phe Asn Arg Lys Pro Ala Arg Gly Ile Glu Tyr Leu Leu Asn
        515                 520                 525

Lys Leu Ile Glu Asn Asn Ala Thr Ser Val Ala His Phe Leu Lys Ser
    530                 535                 540

Asn Ser Ser Leu Asp Lys Ala Met Ile Gly Glu Tyr Leu Gly Gln His
545                 550                 555                 560

Glu Glu Phe Pro Leu Ala Val Met His Ala Tyr Val Asp Ser Met Lys
                565                 570                 575

Phe Ser Gly Leu Lys Phe Asp Ala Ala Ile Arg Glu Phe Leu Lys Gly
            580                 585                 590

Phe Arg Leu Pro Gly Glu Ala Gln Lys Ile Asp Arg Ile Met Glu Lys
        595                 600                 605

Phe Ala Glu Arg Tyr Cys Ala Asp Asn Pro Gly Leu Phe Lys Asn Ala
    610                 615                 620

Asp Thr Ala Tyr Val Leu Ala Tyr Ala Val Ile Met Leu Asn Thr Asp
625                 630                 635                 640

Ala His Asn Pro Met Val Trp Pro Lys Met Ser Lys Ser Asp Phe Val
                645                 650                 655

Arg Met Asn Thr Ala Ser Asp Ala Glu Glu Cys Ala Pro Lys Glu Leu
            660                 665                 670

Leu Glu Glu Ile Tyr Asp Ser Ile Val Gln Glu Glu Ile Lys Met Lys
        675                 680                 685

Asp Asp Phe Pro Asp Ser Ala Lys Thr Asn Lys Pro Arg Arg Glu Thr
    690                 695                 700

Glu Glu Arg Gly Val Val Asn Ile Leu Asn Leu Ala Leu Pro Arg Leu
705                 710                 715                 720

Lys Ser Ala Ser Asp Thr Lys Ala Glu Ser Glu Lys Ile Ile Lys Gln
                725                 730                 735

Thr Gln Ala Leu Phe Lys Asn Gln Gly Gln Lys Arg Gly Val Phe His
            740                 745                 750

Val Ala Gln Gln Val Glu Leu Val Arg Pro Met Leu Glu Ala Val Gly
        755                 760                 765

Trp Pro Leu Leu Ala Thr Phe Ser Val Thr Met Glu Glu Gly Asp Ser
    770                 775                 780

Lys Pro Arg Val Val Leu Cys Met Glu Gly Phe Arg Ala Gly Ile His
785                 790                 795                 800

Leu Thr Arg Val Leu Gly Met Asp Thr Met Arg Tyr Ala Phe Leu Thr
                805                 810                 815

Ser Leu Val Arg Phe Thr Phe Leu His Ala Pro Lys Glu Met Arg Ser
            820                 825                 830

Lys Asn Val Glu Ala Leu Arg Thr Leu Leu Gly Leu Ala Asp Thr Asp
        835                 840                 845

Met Asp Ala Leu Gln Asp Thr Trp Asn Ala Val Leu Glu Cys Val Ser
    850                 855                 860

Arg Leu Glu Tyr Ile Thr Ser Asn Pro Ser Ile Ala Ala Thr Val Met
865                 870                 875                 880

Gln Gly Ser Asn Gln Ile Ser Arg Glu Ser Val Val Gln Ser Leu Lys
                885                 890                 895

Glu Leu Ser Gly Lys Pro Ala Glu Gln Val Phe Val Asn Ser Val Lys
```

```
          900                 905                 910

Leu Pro Ser Asp Ser Ile Val Glu Phe Phe Thr Ala Leu Cys Gly Val
        915                 920                 925

Ser Ala Glu Glu Leu Lys Gln Thr Pro Ala Arg Val Phe Ser Leu Gln
    930                 935                 940

Lys Leu Val Glu Ile Ser Tyr Tyr Asn Met Ala Arg Ile Arg Leu Val
945                 950                 955                 960

Trp Ala Arg Ile Trp Ser Val Leu Ser Gln His Phe Ile Ala Ala Gly
                965                 970                 975

Ser His His Glu Glu Lys Val Ala Met Tyr Ala Ile Asp Ser Leu Arg
            980                 985                 990

Gln Leu Gly Met Lys Tyr Leu Glu  Arg Ala Glu Leu Asn  Lys Phe Thr
        995                 1000                1005

Phe Gln  Asn Asp Ile Leu Lys  Pro Phe Val Ile Leu  Met Arg Asn
    1010                 1015                 1020

Ser His  Ser Glu Lys Ile Arg  Gly Leu Ile Val Asp  Cys Ile Val
    1025                 1030                 1035

Gln Leu  Ile Lys Ser Lys Val  Gly Ser Ile Lys Ser  Gly Trp Arg
    1040                 1045                 1050

Cys Val  Phe Met Ile Phe Thr  Ala Ala Ala Asp Asp  Glu Asn Glu
    1055                 1060                 1065

His Ile  Val Glu Ser Ala Phe  Glu Asn Val Glu Gln  Val Ile Leu
    1070                 1075                 1080

Glu His  Phe Asp Gln Val Val  Gly Asp Cys Phe Met  Asp Cys Val
    1085                 1090                 1095

Asn Cys  Leu Ile Gly Phe Ala  Asn Asn Lys Cys Thr  Pro Arg Ile
    1100                 1105                 1110

Ser Leu  Lys Ala Ile Ala Leu  Leu Arg Ile Cys Glu  Asp Arg Leu
    1115                 1120                 1125

Ala Glu  Gly Cys Ile Pro Gly  Gly Ala Val Lys Pro  Val Asp Asp
    1130                 1135                 1140

Val Pro  Glu Ala His Phe Asp  Val Thr Glu His Tyr  Trp Phe Pro
    1145                 1150                 1155

Met Leu  Ala Gly Leu Ser Asp  Leu Thr Leu Asp Pro  Arg Pro Glu
    1160                 1165                 1170

Val Arg  His Cys Ala Leu Glu  Val Leu Phe Asp Leu  Leu Asn Glu
    1175                 1180                 1185

Arg Gly  His Lys Phe Ser Ser  Pro Phe Trp Glu Ser  Ile Phe His
    1190                 1195                 1200

Arg Val  Leu Phe Pro Ile Phe  Asp His Val Arg His  Ala Gly Arg
    1205                 1210                 1215

Asp Gly  Leu Ser Ser Gly Asp  Asp Trp Leu Arg Asp  Thr Ser Ile
    1220                 1225                 1230

His Ser  Leu Gln Leu Ile Cys  Asn Leu Phe Asn Thr  Phe Tyr Lys
    1235                 1240                 1245

Val Met  Tyr Val Val Leu Pro  Cys
    1250                 1255
```

<210> SEQ ID NO 12
<211> LENGTH: 3771
<212> TYPE: DNA
<213> ORGANISM: Oryza sativa

<400> SEQUENCE: 12
cgaggtagga ctggatggat tgctgcagcg cggcgaactt gccgcggttg gctgtgcact 60

-continued

```
ccttgagcat ggcctcgaag gcccgcgtga cgaaccctcc cgcggcgccc gccatatgga    120
ggcagtcgag cgcgggctcg acgagcttga cgtgcttggt ctcgaaggcg aggcggagcg    180
gctgcagcac cagctcggcc tgagtcccct ccagcacgcg ccccgccgac gccagcacct    240
gcgtgatggg cgccgccgcc gcgtcgccgc cctcctcctg tcccgccgcc gccgcccccct    300
tgatggcatc tgtcagagga ggtgttatca acacaaccgc agaccatgtt caggatgtca    360
gtaaatagag gggaattttt accaccctct aaaccagggt cgccttctag atggtcataa    420
gcaataagtt tctctaaatc tatttgaagc aacagcattg agaagcactt tcaagacttg    480
gagaacagtg ctgttgagag caatattata gcatactcta atcactccaa gcaaaggttc    540
tccatgtact cgttccttca gtaaatcatc tccctttgca taatgccaat agaagttatg    600
gggaaaattt tttgcctgct cagattccat ccgccttaat atcagctcct cctgcaagac    660
tctgaagctc ttcaacagat gctggagatg cttcctgata ctttctttcc atcctcaagt    720
tcaacagcct tgtcaagaac agcctccaac cccttgcaga gagtccggaa gagcaatagt    780
gcatcacgct gtattatgtt cacagtgtcc aggtctattc cactgtaaca gttcgagtga    840
tagcagcctt gtctttgtag caacctcatc actctcttcc ttcatgctca tctgaaaaac    900
aaccgcagat gaagacacag ccgctcgcag aatagcatag gaaagatagg ctttaactga    960
atcgatgaag tggaaatttt tggtaaatga atcactgact ccttctagca atcccttcag   1020
actctctcga aaacgaagca atagaactgc aaatatccca caagcgtact aaggacactg   1080
gccctttggc tgagtggact gtcagagcta tcgagagacc ttaaaactat cagaggaaag   1140
aagacaccga tctcacccat gcgttcaaaa aggtttggcc cctcaaggtc acaatcataa   1200
tttacaaaca tgtctgcaag catttgtgaa tccttgcaga ctttctccag catcctgaag   1260
agatgagcct ttcacagaaa ctgtttgaga agatgcggca gtgtttgtat ccgcattttg   1320
agatccttgt gcaatccttg agagtgcact gacctctgag attgcagcct ccattgttga   1380
cttatgagct ttagctatct caaactgatt gcgaccatcc tcttggctct ttatttcatc   1440
acttgttatg ctccttgcag aagaatcatt ttcacaagct tcggcaacac tcccctgttt   1500
caaggaatct cttcgagctt gctcccaatc aaccaatgac ttatccaagc tagaattgct   1560
cttgagaaag tgagctacag atgttgcatt attttcgatc aacttattta ataacaaata   1620
ctcaatcccc cttgctggtt tgcgattgaa cgctcagcaa acttttccat tatgcgatca   1680
atcttttgtg cctccccagg aaggcgaaac cctttcaaga actcacgaat tgcagcatca   1740
aacttcaatc ccgaaaattt cattgaatca acataagcat gcatcacagc aagagggaac   1800
tcctcatgtt gtcccaaata ttcaccaatc atagccgcac taaggatgtc aagaaagcat   1860
agcgcatggt gtccatccca agaacacgag taagatggat gccagcccta aacccttcca   1920
tgcatagcac aaccctaggc ttgctgtcac cttcctccat ggtaacagaa aatgttgcaa   1980
gcaaaggcca tcctacagct tcaagcattg gcctaacaag ctcgacctgc tgagcaacat   2040
gaaaaacacc tctcttctgt ccctgatttt tgaaaagtgc ttgagtctgc ttaatgattt   2100
tctcactttc tgctttggta tcacttgctg acttcagtct tggaagagct aaattgagga   2160
tattgacaac accccttct tctgtttctc gtctgggttt attagttttt gctgaatcag   2220
ggaaatcgtc tttcatcttt atctcttcct ggacaatgga atcataaatt tcctccaaga   2280
gctcctttgg ggcacattcc tctgcatcac tcgcagtgtt cattcgtacg aaatctgatt   2340
ttgacatttt aggccacacc attgggttgt gggcgtcagt attcaacatt ataacagcat   2400
aagcaagaac ataagcagta tctgcatttt tgaaaagtcc agggttatca gcacagtacc   2460
```

```
aaacgtatcc gagccatatt atagtagctt atctcgacaa gcttttgtaa gctaaagaca   2520

cgagcaggtg tctgtttcag ttcttctgca gaaacaccac aaagagcagt gaagaattca   2580

acaatggaat cacttggtag ttttacactg tttacaaaga cttgttcagc aggcttccca   2640

gacaactctt tcagtgactg gacaacagat tctctcgata tttgatttga tccctgcata   2700

acagttgcag caattgaagg atttgaagtg atatattcaa gcctggagac acattctaaa   2760

acagcattcc aagtatcttg caaagcatcc atatctgtgt cagctaagcc aaggagggtc   2820

cgtaaagcct caacattttt actacgcatt tccttaggag catgcaaaaa tgtaaacctg   2880

aacaatgcaa tcaacaatta gaccacggat tttttcactg tgactatttc tcattaaaat   2940

aacaaaaggc ttcaatatgt cattctgaaa tgtgaatttg ttcaattctg cacgttccaa   3000

gtacttcata ccaagctgcc tcaatgagtc aattgcatac atggcaactt tctcctcgtg   3060

gtggctccca gcggcaataa aatgctgtga caagacagac catattctcg cccacacctt   3120

gttctacatt ttcaaaagca ctttcaacaa tatgttcatt ctcatcatca gctgccgcgg   3180

tgaatatcat gaacacacaa cgccaacctg actttatgct gccaactttt gatttgatca   3240

actctgccaa acggtcttca catatgcgta ggagagcgat agcctttaaa ctaattcgag   3300

gtgtgcattt attatttgcg aaaccaataa gacagttgac gcagtccatg aagcaatcac   3360

caacaacttg atcaaaatgc tccaagataa tcagcagggg agaacaacat acattacctt   3420

gtagaaagta ttgaaaaggt tgcagattaa ctgcagagaa tgaatgctgg tatcacgaag   3480

ccagtcatcc ccagaagaaa ggccatccct tccagcatgc cttacatgat caaatatggg   3540

aaataataca cgatgaaaaa tgctctccca aaaaggtgag gagaatttat gacctctctc   3600

attcagaaga tcaaacaaca cttcaagtgc acagtgtcta acttctggtc tggggtctaa   3660

agttaaatct gatagcccag ctagcatagg aaaccaataa tgctcagtaa catcaaaatg   3720

ggcctctgga acatcatcaa caggtttaac agcaccacca ggaatgcaac c            3771
```

<210> SEQ ID NO 13
<211> LENGTH: 368
<212> TYPE: PRT
<213> ORGANISM: Arabidopsis thaliana

<400> SEQUENCE: 13

```
Met Lys Leu Thr Val Lys Thr Leu Lys Gly Ser His Phe Glu Ile Arg
1               5                   10                  15

Val Leu Pro Thr Asp Thr Ile Met Ala Val Lys Lys Asn Ile Glu Asp
            20                  25                  30

Ser Gln Ser Lys Asp Asn Tyr Pro Cys Gly Gln Gln Leu Leu Ile His
        35                  40                  45

Asn Gly Lys Val Leu Lys Asp Glu Thr Thr Leu Val Glu Asn Lys Val
    50                  55                  60

Thr Glu Glu Gly Phe Leu Val Val Met Leu Ser Lys Ser Lys Thr Ala
65                  70                  75                  80

Ser Ser Ala Gly Pro Ser Ser Thr Gln Pro Thr Ser Thr Thr Thr Ser
                85                  90                  95

Thr Ile Ser Ser Thr Thr Leu Ala Ala Pro Ser Thr Thr Gln Ser Ile
            100                 105                 110

Ala Val Pro Ala Ser Asn Ser Thr Pro Val Gln Glu Gln Pro Thr Ala
        115                 120                 125

Gln Ser Asp Thr Tyr Gly Gln Ala Ala Ser Thr Leu Val Ser Gly Ser
    130                 135                 140
```

-continued

```
Ser Ile Glu Gln Met Val Gln Gln Ile Met Glu Met Gly Gly Gly Ser
145                 150                 155                 160

Trp Asp Lys Glu Thr Val Thr Arg Ala Leu Arg Ala Ala Tyr Asn Asn
                165                 170                 175

Pro Glu Arg Ala Val Asp Tyr Leu Tyr Ser Gly Ile Pro Glu Thr Val
            180                 185                 190

Thr Ile Pro Ala Thr Asn Leu Ser Gly Val Gly Ser Gly Arg Glu Leu
        195                 200                 205

Thr Ala Pro Pro Pro Ser Gly Gly Pro Asn Ser Ser Pro Leu Asp Leu
    210                 215                 220

Phe Pro Gln Glu Ala Val Ser Asp Ala Ala Gly Gly Asp Leu Gly Thr
225                 230                 235                 240

Leu Glu Phe Leu Arg Gly Asn Asp Gln Phe Gln Gln Leu Arg Ser Met
                245                 250                 255

Val Asn Ser Asn Pro Gln Ile Leu Gln Pro Met Leu Gln Glu Leu Gly
            260                 265                 270

Lys Gln Asn Pro Gln Leu Leu Arg Leu Ile Gln Glu Asn Gln Ala Glu
        275                 280                 285

Phe Leu Gln Leu Leu Asn Glu Pro Tyr Glu Gly Ser Asp Gly Asp Val
    290                 295                 300

Asp Ile Phe Asp Gln Pro Asp Gln Glu Met Pro His Ser Val Asn Val
305                 310                 315                 320

Thr Pro Glu Glu Gln Glu Ser Ile Glu Arg Leu Glu Ala Met Gly Phe
                325                 330                 335

Asp Arg Ala Ile Val Ile Glu Ala Phe Leu Ser Cys Asp Arg Asn Glu
            340                 345                 350

Glu Leu Ala Ala Asn Tyr Leu Leu Glu His Ser Ala Asp Phe Glu Asp
        355                 360                 365
```

```
<210> SEQ ID NO 14
<211> LENGTH: 1107
<212> TYPE: DNA
<213> ORGANISM: Arabidopsis thaliana

<400> SEQUENCE: 14

atgaagctca ctgttaagac tctcaagggt agccattttg agattagggt tcttcccacc      60

gacacgataa tggcggtgaa gaagaatatt gaagattcac aaagcaaaga caactatcct     120

tgtgggcagc aattactgat tcacaatgga aaggttttga aagatgaaac taccttggtg     180

gagaacaagg ttaccgagga gggttttctt gtcgtgatgc ttagcaagag caaaactgca     240

agttcagctg gtccctcttc tactcagcct acttctacca cgacatctac catatcttca     300

accacgcttg cagctccgtc gacaacccag tctattgctg tgccggcttc aaattctact     360

cccgttcaag aacaaccaac ggcacaaagt gacacctatg gtcaagctgc ttcaacttta     420

gttagtggca gtagtattga gcaaatggtt caacaaataa tggaaatggg aggaggcagt     480

tgggacaaag aaacggttac tcgtgcactt cgtgcagcat ataacaaccc tgagagagca     540

gtggattatc tatattctgg aattcctgaa acagtaacca ttccagcaac taatttatct     600

ggagtaggat ctggtagaga acttactgct cctcctccct ctggaggccc taattcatct     660

cctctggatt tgtttcccca ggaagcagtt tctgatgcag caggtggaga tcttggaacg     720

cttgaattcc tcagaggcaa tgatcagttc caacaattac gctccatggt caattccaac     780

cccagattc tgcagcctat gcttcaagag ctcggaaagc agaaccccca acttctgagg     840

ctaattcaag agaaccaagc cgaatttctt cagttactaa acgagcccta cgaaggatct     900
```

gacggggatg tggatatctt cgatcaacct gatcaagaaa tgccccactc agtcaacgtt 960
acccctgaag agcaagaatc aattgaacgg cttgaggcaa tggggtttga tagagcaata 1020
gtcatagaag ccttcctttc ctgtgaccgt aacgaggaat tggctgcaaa ctatctacta 1080
gagcactcag cagattttga agactga 1107

<210> SEQ ID NO 15
<211> LENGTH: 282
<212> TYPE: PRT
<213> ORGANISM: Arabidopsis thaliana

<400> SEQUENCE: 15

Met Leu Ser Arg Leu Phe Lys Ala Gly Glu Lys Val Leu Ser Asn Leu
1 5 10 15

Val Ser Lys Lys Asp Ile Tyr Met Ala Ser Arg Asn Gln Glu Lys Ser
20 25 30

Pro Lys Val Gln Glu Leu Tyr Asp Leu Cys Lys Glu Thr Phe Thr Gly
35 40 45

Lys Ala Pro Ser Pro Ala Ser Met Ala Ile Gln Lys Leu Cys Ser Val
50 55 60

Leu Asp Ser Val Ser Pro Ala Asp Val Gly Leu Glu Glu Val Ser Gln
65 70 75 80

Asp Asp Asp Arg Gly Tyr Gly Val Ser Gly Val Ser Arg Phe Asn Arg
85 90 95

Val Gly Arg Trp Ala Gln Pro Ile Thr Phe Leu Asp Ile His Glu Cys
100 105 110

Asp Thr Phe Thr Met Cys Ile Phe Cys Phe Pro Thr Ser Ser Val Ile
115 120 125

Pro Leu His Asp His Pro Glu Met Ala Val Phe Ser Lys Ile Leu Tyr
130 135 140

Gly Ser Leu His Val Lys Ala Tyr Asp Trp Val Glu Pro Pro Cys Ile
145 150 155 160

Ile Thr Gln Asp Lys Gly Val Pro Gly Ser Leu Pro Ala Arg Leu Ala
165 170 175

Lys Leu Val Ser Asp Lys Val Ile Thr Pro Gln Ser Glu Ile Pro Ala
180 185 190

Leu Tyr Pro Lys Thr Gly Gly Asn Leu His Cys Phe Thr Ala Leu Thr
195 200 205

Pro Cys Ala Val Leu Asp Ile Leu Ser Pro Pro Tyr Lys Glu Ser Val
210 215 220

Gly Arg Ser Cys Ser Tyr Tyr Met Asp Tyr Pro Phe Ser Thr Phe Ala
225 230 235 240

Leu Glu Asn Gly Met Lys Lys Val Asp Glu Gly Lys Glu Asp Glu Tyr
245 250 255

Ala Trp Leu Val Gln Ile Asp Thr Pro Asp Asp Leu His Met Arg Pro
260 265 270

Gly Ser Tyr Thr Gly Pro Thr Ile Arg Val
275 280

<210> SEQ ID NO 16
<211> LENGTH: 1106
<212> TYPE: DNA
<213> ORGANISM: Arabidopsis thaliana

<400> SEQUENCE: 16
attcgaacaa ttaccgacac acaaaaagtt tgaagagaaa aacaaaaaat gttgtcgaga 60

-continued

```
ttgttcaagg caggtgaaaa ggttttgtcg aatctcgtta gcaagaaaga catttacatg    120

gcgtcgagga atcaggagaa atctcccaaa gtgcaagagc tttacgacct ctgcaaagag    180

actttcactg gcaaagctcc ttctcctgct tccatggcta tccaaaagct atgctctgtg    240

ttggactcag ttagtcctgc agatgttggg cttgaagagg tatctcaaga cgatgatcga    300

ggctatggag tttctggggt tagccgtttc aatagagtag gacgatgggc acaaccgata    360

acattcttag acattcatga atgtgatact tttacaatgt gtattttctg cttcccaacg    420

tcttcagtga tcccattgca tgatcatcca gagatggctg tgtttagtaa aatcctctat    480

ggatcacttc atgttaaagc ttacgattgg gtcgaacctc catgtattat cacacaagat    540

aaaggcgtcc ccggttctct tccagcaagg ttggcgaaat tggtgagtga caaagttata    600

acgcctcagt ctgagatacc ggcgttgtac ccaaagactg gaggcaatct ccattgcttc    660

actgcgttga ctccatgtgc tgtgctcgac attctctcac ctccttacaa agaaagtgtt    720

ggcaggagtt gcagttacta catggactat ccgttttcca ctttcgcatt ggagaacgga    780

atgaagaagg tggatgaagg aaaggaagac gaatacgcat ggcttgtaca gattgacacg    840

cccgatgatc ttcacatgcg tcccggatca tatactggtc caactatcag agtctagata    900

tttgtggttt gttttgtagc aaagtagagc aactcttgta acattccaag ataagtttct    960

ggagaagata tcaatacgat ttcagattaa agatgaactc tttgtttagt ccatgtccac   1020

ttctcagttc tcacacgcat tcaagcaaat gaaactgcgg aaaactacaa atagatcggc   1080

aatgagaaat gttaagattt catttc                                        1106
```

<210> SEQ ID NO 17
<211> LENGTH: 366
<212> TYPE: PRT
<213> ORGANISM: Arabidopsis thaliana

<400> SEQUENCE: 17

```
Met Ala Thr Thr Thr Leu Ser Ser Phe Ser Leu Ser Leu Pro Gln Leu
1               5                   10                  15

Leu His Lys Pro Thr Lys Pro Leu Pro Phe Leu Phe Leu Leu Pro Arg
            20                  25                  30

Phe Asn Arg Arg Phe Arg Ser Leu Thr Ile Thr Ser Ser Ser Thr Thr
        35                  40                  45

Ser Ser Asn Asn Phe Ser Ser Asn Cys Gly Asp Asp Gly Phe Ser Leu
    50                  55                  60

Asp Asp Phe Thr Leu His Ser Asp Ser Arg Ser Pro Lys Lys Cys Val
65                  70                  75                  80

Leu Ser Asp Leu Ile Gln Glu Ile Glu Pro Leu Asp Val Ser Leu Ile
                85                  90                  95

Gln Lys Asp Val Pro Val Thr Thr Leu Asp Ala Met Lys Arg Thr Ile
            100                 105                 110

Ser Gly Met Leu Gly Leu Leu Pro Ser Asp Arg Phe Gln Val His Ile
        115                 120                 125

Glu Ser Leu Trp Glu Pro Leu Ser Lys Leu Leu Val Ser Ser Met Met
    130                 135                 140

Thr Gly Tyr Thr Leu Arg Asn Ala Glu Tyr Arg Leu Phe Leu Glu Lys
145                 150                 155                 160

Asn Leu Asp Met Ser Gly Gly Gly Leu Asp Ser His Ala Ser Glu Asn
                165                 170                 175

Thr Glu Tyr Asp Met Glu Gly Thr Phe Pro Asp Glu Asp His Val Ser
            180                 185                 190
```

-continued

Ser Lys Arg Asp Ser Arg Thr Gln Asn Leu Ser Glu Thr Ile Asp Glu
        195                 200                 205

Glu Gly Leu Gly Arg Val Ser Ser Glu Ala Gln Glu Tyr Ile Leu Arg
    210                 215                 220

Leu Gln Ser Gln Leu Ser Ser Val Lys Lys Glu Leu Gln Glu Met Arg
225                 230                 235                 240

Arg Lys Asn Ala Ala Leu Gln Met Gln Gln Phe Val Gly Glu Glu Lys
                245                 250                 255

Asn Asp Leu Leu Asp Tyr Leu Arg Ser Leu Gln Pro Glu Lys Val Ala
            260                 265                 270

Glu Leu Ser Glu Pro Ala Ala Pro Glu Val Lys Glu Thr Ile His Ser
        275                 280                 285

Val Val His Gly Leu Leu Ala Thr Leu Ser Pro Lys Met His Ser Lys
    290                 295                 300

Phe Pro Ala Ser Glu Val Pro Pro Thr Glu Thr Val Lys Ala Lys Ser
305                 310                 315                 320

Asp Glu Asp Cys Ala Glu Leu Val Glu Asn Thr Ser Leu Gln Phe Gln
                325                 330                 335

Pro Leu Ile Ser Leu Thr Arg Asp Tyr Leu Ala Arg Leu Leu Phe Trp
            340                 345                 350

Leu Glu Glu Leu Pro Ser Ser Thr Ser Leu Ser Leu Ala Cys
        355                 360                 365

<210> SEQ ID NO 18
<211> LENGTH: 1957
<212> TYPE: DNA
<213> ORGANISM: Arabidopsis thaliana

<400> SEQUENCE: 18
gttccggatt gttttgtggc tgacgataaa acagagcaca aaagaagaaa aatctagggt 60
ttgtttgaga ctaagaggaa gagaaagaag aagaagagaa aattcgtaca attccgccat 120
taaagcttca acctttaatg gcgacaacga ctctttcttc cttctctctt tctcttcctc 180
aacttctcca taaacccaca aagcctcttc ctttcctctt ccttcttcct cgattcaatc 240
ggagatttcg aagtctcact atcacttctt cttctacaac ttcttcaaac aatttcagta 300
gtaattgtgg cgatgatggc ttctctcttg acgatttcac tctccattct gattctcgat 360
cacctaaaaa atgtgtcctt tctgatctta tacaagagat tgagccatta gatgtgagtt 420
tgattcagaa ggatgttcca gttactactt tggatgcaat gaaaagaaca atctcaggca 480
tgttgggtct tcttccatct gataggtttc aggttcatat tgagtcactt tgggaacctt 540
tgtctaagct tttggtatct tcaatgatga ctgggtatac attgaggaat gctgaatatc 600
ggctttttct tgaaaaaaac cttgatatga gtggtggagg cttggacagc cacgcttcgg 660
aaaacactga atatgatatg gaagggacgt ttcctgatga agatcatgtt tcatccaaaa 720
gggatagcag aactcagaac ctttctgaaa cgattgatga agaaggtttg ggcagagtat 780
cctctgaagc tcaagaatat atcttacgtt tgcagtcaca attgtcttct gtgaaaaagg 840
aattacaaga aatgagacga aagaacgctg ccctacaaat gcaacaattt gttggcgaag 900
agaagaatga tttgttggac tatttacgat ctttgcaacc tgagaaggta gctgagttgt 960
cagaacctgc ggctcctgag gtgaaagaga ctattcattc tgttgttcac ggtcttttgg 1020
caactctatc accgaagatg cactctaagt ttccagcatc agaagttcca cctactgaaa 1080
cggtgaaagc aaaaagtgat gaagattgtg ctgaacttgt agagaacact tcgttgcagt 1140
ttcagcctct tatctcactg actcgagact accttgctcg tcttctcttc tggttagaag 1200

```
aactgcctag ctctacctct ctttctcttg cttgctagga tttagatgga tatcgtatat   1260

ttacgtataa actacaaaca caaatagatc ctctcaaaag aaactttagt gtttctttgg   1320

ttgtattacc aaagacatct tataccacag tgtctgcttt ctattgctag gtgcatgcta   1380

ttgggacatt atctcagagg tttggaatat cgaatggaac tgatggaggt cctgtctttg   1440

acatgcgatg ccaatgggtc tgagaacgtc gcttgaagct atctttatac atctcaacat   1500

tgtcttacat gcgtatcagc ggccttgaca ctcttaaacc aacaaagtgg gcaagtgact   1560

aggagacagg ccagcctttg agctttagct cttgcacata tatgcagctt tgtgctggcc   1620

tgaaaattca tgggcgaggt aaagtgtaac ataagaaatc acttctacta aaattatttt   1680

tcgttgcatt atcgtgtgat ggatctgcaa agcaataaag ctaagtgtaa ttgtattcag   1740

gaatatactc gtttggtcat taagtatagt ttgtcctaca attattggct cagaaatagc   1800

aatctcgagc gggttcgttt ggcctggccc gtccctttta ggcttggctc aagagtttac   1860

cttagtcaag ccttagtttt atttttcgcc agtttacgct tgttggatac cgtaaacaaa   1920

atccaacact tccgttattc gataaacaag caatttt                            1957
```

<210> SEQ ID NO 19
<211> LENGTH: 162
<212> TYPE: PRT
<213> ORGANISM: Arabidopsis thaliana

<400> SEQUENCE: 19

```
Met Ala Thr Gly Asp Gly Lys Ser Val Met Val Val Gly Val Asp Asp
1               5                   10                  15

Ser Glu Gln Ser Thr Tyr Ala Leu Glu Trp Thr Leu Asp Arg Phe Phe
            20                  25                  30

Ala Pro Tyr Ala Pro Asn Tyr Pro Phe Lys Leu Phe Ile Val His Ala
        35                  40                  45

Lys Pro Asn Ala Val Ser Ala Val Gly Leu Ala Gly Pro Gly Thr Ala
    50                  55                  60

Glu Val Val Pro Tyr Val Asp Ala Asp Leu Lys His Thr Ala Ala Lys
65                  70                  75                  80

Val Val Glu Lys Ala Lys Ala Ile Cys Gln Ser Arg Ser Val His Gly
                85                  90                  95

Ala Val Ile Glu Val Phe Glu Gly Asp Ala Arg Asn Ile Leu Cys Glu
            100                 105                 110

Val Val Asp Lys His His Ala Ser Ile Leu Val Val Gly Ser His Gly
        115                 120                 125

Tyr Gly Ala Ile Lys Arg Ala Val Leu Gly Ser Thr Ser Asp Tyr Cys
    130                 135                 140

Ala His His Ala His Cys Ser Val Met Ile Val Lys Lys Pro Lys Ile
145                 150                 155                 160

Lys Val
```

<210> SEQ ID NO 20
<211> LENGTH: 809
<212> TYPE: DNA
<213> ORGANISM: Arabidopsis thaliana

<400> SEQUENCE: 20

```
accaaaactc tctttttctg tgcaaacact ttggaggatt cttctaggct tctttctacc     60

acaaacacaa gagcgcgttt tcttcacgcc ggcgaacaac gtcagagtca tggccaccgg    120

agatgggaaa tcggtgatgg tcgtcggagt tgacgacagc gagcagagca cttacgcctt    180
```

ggagtggacg ctcgatcgtt tcttcgctcc ttacgctccc aattatcctt ttaagctctt 240
catcgtccac gccaaaccta acgccgtctc cgccgttggt ctcgctggtc ccggaactgc 300
ggaggttgta ccttatgttg atgctgatct gaagcatacc gctgctaagg ttgtcgagaa 360
agccaaagca atttgtcaga gcagatcggt tcatggcgcg gtgatcgaag ttttcgaagg 420
tgatgcaagg aatatcctat gtgaagttgt agataagcat catgcttcta ttcttgttgt 480
gggaagccat ggatatggag ctatcaagag ggcggttctc gggagtacga gtgactactg 540
cgctcatcat gctcattgct cggtgatgat cgtgaagaag cctaagatca aggtctgaaa 600
cctaagggaa ggctactcgg tcaaagcaaa gtctctgcat agtcttctaa ttcagaagaa 660
taaagtgaaa taatattagc ttgatgtgaa acaacgattc aagacaatat acatttgcat 720
ctatatgtgt aattgtttac tacatacaat gttttggtat ccttagacaa tcaatattcg 780
tgtgttataa tatgctaatc tttctcata 809

<210> SEQ ID NO 21
<211> LENGTH: 158
<212> TYPE: PRT
<213> ORGANISM: Arabidopsis thaliana

<400> SEQUENCE: 21

Met Glu Glu Gln Phe Gly Gly Ser Asp Glu Arg Trp Lys Gly Ser Leu
1 5 10 15

Glu Asn Ile Thr Glu Met Ala Ser Asn Leu Asp Ser Leu Gln Lys Leu
20 25 30

Leu Leu Lys Lys Ala Val Phe Val Glu Glu Asp Thr Phe Ser Arg Ala
35 40 45

Ser Leu Val Ser Glu Gln Ala Arg Thr Ile Lys Val Leu Glu Gln Arg
50 55 60

Val Gln Thr Leu Glu Arg Glu Leu Asp Ala Ala Ile Thr Ala Ala Ala
65 70 75 80

His Ala Arg Ser Glu Lys Arg Gln Ala Glu Ser Ser Gln Lys Ala Ala
85 90 95

Glu Ser Arg Ala Gln Asp Val Thr Lys Glu Leu Glu Asn Thr Thr Lys
100 105 110

Val Phe Lys Leu His Met Glu Glu Leu Arg Gly Met Gln Glu Gln Ile
115 120 125

Ser Lys Arg Asp Asn Glu Ile Lys Leu Leu Glu Ala Ile Ile Gln Thr
130 135 140

Leu Gly Gly Lys Glu Arg Leu Gly Lys Ser Asp Val Asn Gly
145 150 155

<210> SEQ ID NO 22
<211> LENGTH: 648
<212> TYPE: DNA
<213> ORGANISM: Arabidopsis thaliana

<400> SEQUENCE: 22
tttagttgtt tttccgatcg atctgcgagt cgagtagttt ttttatttgc cggcgccggg 60
agagatcctt tgatcttttt ccgatggagg agcaattcgg cgggagcgat gagagatgga 120
aaggatcatt ggagaatata acggagatgg catcgaatct cgattcgctt cagaaacttc 180
tcctcaagaa agcagtcttc gttgaagaag acactttctc tagagcttct ctcgtctccg 240
agcaagcccg aacaatcaag gttcttgagc aaagagtaca aacactagaa agagaactag 300
atgctgccat tacagctgct gctcatgctc ggtctgagaa acgccaagct gagtcctctc 360

-continued

```
aaaaggctgc tgaatcacgt gcccaagatg tcacaaaaga gcttgaaaac accacaaagg    420

ttttcaagct gcatatggaa gagcttcgag gaatgcaaga acagatatcc aaacgcgata    480

acgagatcaa actcttagaa gctataatcc aaacgctcgg cggcaaagag cggttgggaa    540

aaagcgacgt gaatggatga tgatgatgcg ttttttcact tgtaaaggtt tgtactcctg    600

agtttgtgga gatgtatcac ttcgaagata aatgtatttt tgtctgtc                 648
```

```
<210> SEQ ID NO 23
<211> LENGTH: 248
<212> TYPE: PRT
<213> ORGANISM: Arabidopsis thaliana

<400> SEQUENCE: 23

Met Ala Thr Thr Leu Ser Arg Asp Gln Tyr Val Tyr Met Ala Lys Leu
1               5                   10                  15

Ala Glu Gln Ala Glu Arg Tyr Glu Glu Met Val Gln Phe Met Glu Gln
            20                  25                  30

Leu Val Ser Gly Ala Thr Pro Ala Gly Glu Leu Thr Val Glu Glu Arg
        35                  40                  45

Asn Leu Leu Ser Val Ala Tyr Lys Asn Val Ile Gly Ser Leu Arg Ala
    50                  55                  60

Ala Trp Arg Ile Val Ser Ser Ile Glu Gln Lys Glu Glu Ser Arg Lys
65                  70                  75                  80

Asn Glu Glu His Val Ser Leu Val Lys Asp Tyr Arg Ser Lys Val Glu
                85                  90                  95

Thr Glu Leu Ser Ser Ile Cys Ser Gly Ile Leu Arg Leu Leu Asp Ser
            100                 105                 110

His Leu Ile Pro Ser Ala Thr Ala Ser Glu Ser Lys Val Phe Tyr Leu
        115                 120                 125

Lys Met Lys Gly Asp Tyr His Arg Tyr Leu Ala Glu Phe Lys Ser Gly
    130                 135                 140

Asp Glu Arg Lys Thr Ala Ala Glu Asp Thr Met Ile Ala Tyr Lys Ala
145                 150                 155                 160

Ala Gln Asp Val Ala Val Ala Asp Leu Ala Pro Thr His Pro Ile Arg
                165                 170                 175

Leu Gly Leu Ala Leu Asn Phe Ser Val Phe Tyr Tyr Glu Ile Leu Asn
            180                 185                 190

Ser Ser Glu Lys Ala Cys Ser Met Ala Lys Gln Ala Phe Glu Glu Ala
        195                 200                 205

Ile Ala Glu Leu Asp Thr Leu Gly Glu Glu Ser Tyr Lys Asp Ser Thr
    210                 215                 220

Leu Ile Met Gln Leu Leu Arg Asp Asn Leu Thr Leu Trp Thr Ser Asp
225                 230                 235                 240

Met Gln Glu Gln Met Asp Glu Ala
                245
```

```
<210> SEQ ID NO 24
<211> LENGTH: 1029
<212> TYPE: DNA
<213> ORGANISM: Arabidopsis thaliana

<400> SEQUENCE: 24

cagaaatttc ctccgatttc aaaattttcc ggtgaaatcg aaaaaaaaag cgagatcttc     60

ttctctaatg gcgacgacct taagcagaga tcaatatgtc tacatggcga agctcgccga    120

gcaagccgag cgttacgaag agatggttca attcatggaa cagctcgtaa gtggagctac    180
```

```
accggccggt gagctgaccg tagaagagag gaatcttctc tcggtcgcgt ataagaacgt    240

gattggatct cttcgtgcgg catggagaat cgtgtcttcg attgagcaaa aggaagagag    300

caggaagaac gaagaacacg tgtcgcttgt taaggattac agatctaaag ttgagactga    360

gctttcttcg atctgttctg ggattctcag gttacttgat tcgcatctaa ttccttcagc    420

tactgccagt gagtctaagg ttttttacct gaagatgaaa ggagattatc atcgttattt    480

ggctgagttt aaatctggtg atgagaggaa aactgctgct gaagatacta tgatcgctta    540

caaagctgct caggacgttg cagttgctga tctagcacct acacatccga tcaggcttgg    600

tttggctctt aacttctcag tgttttacta cgagattctc aactcttcag agaaagcttg    660

tagcatggcg aaacaggctt ttgaagaagc cattgctgag ctggacacat tgggagagga    720

gtcatacaag gacagtactc tcatcatgca gttgctaagg gacaatctaa ccctttggac    780

ctccgatatg caggagcaga tggatgaggc ctgaaggtct aatggaagaa aagacggtta    840

tgtaatgtac ctgcaaccgt aaccgaaaat ctgagttcaa cctcctttgc tgtaaaactt    900

gtcgaaaaga aaagtttgtt tttttatgac agattatgtg cacagctttg gtgttatctg    960

ctgctctgta tcaactctgt ttttgtttgg taatttatcc tcatctttgc tccaaaaaaa   1020

aaaaaaaaa                                                           1029


<210> SEQ ID NO 25
<211> LENGTH: 259
<212> TYPE: PRT
<213> ORGANISM: Arabidopsis thaliana

<400> SEQUENCE: 25

Gly Ile Pro Ile Ile Gly Gly Gly Ala Gly Thr Gly Ile Ser Ala Lys
1               5                   10                  15

Phe Glu Glu Ala Gly Gly Ile Asp Leu Ile Val Ile Tyr Asn Ser Gly
            20                  25                  30

Arg Phe Arg Met Ala Gly Arg Gly Ser Leu Ala Gly Leu Leu Pro Phe
        35                  40                  45

Ala Asp Ala Asn Ala Val Val Leu Glu Met Ala Asn Glu Val Leu Pro
    50                  55                  60

Val Val Lys Ala Val Pro Val Leu Ala Gly Val Cys Ala Thr Asp Pro
65                  70                  75                  80

Phe Arg Arg Met Asp Tyr Phe Leu Lys Gln Leu Glu Ser Ile Gly Phe
                85                  90                  95

Val Gly Val Gln Asn Phe Pro Thr Val Gly Leu Phe Asp Gly Asn Phe
            100                 105                 110

Arg Gln Asn Leu Glu Glu Thr Gly Met Gly Tyr Gly Leu Glu Val Lys
        115                 120                 125

Met Ile Ser Glu Ala His Lys Met Gly Leu Leu Thr Thr Pro Tyr Ala
    130                 135                 140

Phe Asn Pro Lys Glu Gly Glu Glu Met Ala Lys Ala Gly Ala Asp Ile
145                 150                 155                 160

Ile Val Ala His Met Gly Leu Thr Thr Ser Gly Asn Ile Gly Ala Lys
                165                 170                 175

Thr Ala Val Ser Val Glu Glu Ser Val Val Arg Val Gln Ala Ile Ala
            180                 185                 190

Asp Ala Ala Arg Arg Phe Asn Pro Asp Ile Ile Val Leu Cys His Gly
        195                 200                 205

Gly Pro Ile Ser Gly Pro Glu Glu Ala Glu Phe Val Leu Lys Arg Thr
    210                 215                 220
```

Gln Gly Cys Val His Gly Phe Tyr Gly Ala Ser Ser Met Glu Arg Leu
225 230 235 240

Pro Val Glu Gln Ala Ile Thr Asn Thr Val Gln Lys Tyr Lys Ser Ile
245 250 255

Ser Ile Lys

<210> SEQ ID NO 26
<211> LENGTH: 1003
<212> TYPE: DNA
<213> ORGANISM: Arabidopsis thaliana

<400> SEQUENCE: 26
ggaataccaa taattggggg aggtgctggt actggaatat ctgcaaagtt tgaggaagct 60
ggtgggattg atttgatagt gatatacaac tctggacgtt ttcgtatggc tggaagagga 120
tccttagcag gcttacttcc atttgctgat gccaatgcag tcgtgcttga aatggcaaat 180
gaagttttac ctgtagtgaa ggcggtgcct gttctggctg ggtgtgcgc aacagatcca 240 tttcgtcgta tggactattt cctgaagcag ttggagtcca ttgggttcgt tggtgtccag 300
aactttccaa ctgttggtct ctttgatggt aattttagac aaaatcttga ggagacagga 360
atgggatatg gtcttgaagt taaaatgatc tcagaagcgc acaaaatggg gctgttgacc 420
actccatatg ctttcaaccc aaaagaagga gaagaaatgg caaaagcggg agctgatatc 480
atagtagccc acatgggtct aacgacatcc ggaaatattg gggcgaaaac cgcagtttca 540
gtggaagaaa gcgttgttcg tgtacaagct attgcagatg ctgctcgtag attcaaccca 600
gacattatcg tcctctgcca cggaggtccg atatcgggtc cagaagaggc agagtttgtg 660
ttgaagagaa cacagggttg tgtccatggc ttctacggag catcaagcat ggaaaggcta 720
cctgtagaac aagcaataac aaacactgtt caaaaataca agtccatatc gatcaagtga 780
agtcaaaata ataagttcac ttagaaacct ttatctttgg tgtttctagt atatttgcat 840
gtgttgtggc ctatgggtgt ggatgtttcc ttttgttgca tggttttttt tttctggtca 900
tctttgattg cctctgcagg atcttatatg atctctagtt ctgtattaca cgtttttgta 960
ttttaataaa gttcatagtg ctcaactctt atcaaataaa aaa 1003

<210> SEQ ID NO 27
<211> LENGTH: 1700
<212> TYPE: PRT
<213> ORGANISM: Arabidopsis thaliana

<400> SEQUENCE: 27

Met Ala Ser Thr Glu Val Asp Ser Arg Leu Gly Arg Val Val Ile Pro
1 5 10 15

Ala Leu Asp Lys Val Ile Lys Asn Ala Ser Trp Arg Lys His Ser Lys
20 25 30

Leu Ala His Glu Cys Lys Ser Val Ile Glu Arg Leu Arg Ser Pro Glu
35 40 45

Asn Ser Ser Pro Val Ala Asp Ser Glu Ser Gly Ser Ser Ile Pro Gly
50 55 60

Pro Leu His Asp Gly Gly Ala Ala Glu Tyr Ser Leu Ala Glu Ser Glu
65 70 75 80

Ile Ile Leu Ser Pro Leu Ile Asn Ala Ser Ser Thr Gly Val Leu Lys
85 90 95

Ile Val Asp Pro Ala Val Asp Cys Ile Gln Lys Leu Ile Ala His Gly
100 105 110

```
Tyr Val Arg Gly Glu Ala Asp Pro Thr Gly Gly Pro Glu Ala Leu Leu
        115                 120                 125

Leu Ser Lys Leu Ile Glu Thr Ile Cys Lys Cys His Glu Leu Asp Asp
    130                 135                 140

Glu Gly Leu Glu Leu Leu Val Leu Lys Thr Leu Leu Thr Ala Val Thr
145                 150                 155                 160

Ser Ile Ser Leu Arg Ile His Gly Asp Ser Leu Leu Gln Ile Val Arg
                165                 170                 175

Thr Cys Tyr Gly Ile Tyr Leu Gly Ser Arg Asn Val Val Asn Gln Ala
            180                 185                 190

Thr Ala Lys Ala Ser Leu Val Gln Met Ser Val Ile Val Phe Arg Arg
        195                 200                 205

Met Glu Ala Asp Ser Ser Thr Val Pro Ile Gln Pro Ile Val Val Ala
    210                 215                 220

Glu Leu Met Glu Pro Met Asp Lys Ser Glu Ser Asp Pro Ser Thr Thr
225                 230                 235                 240

Gln Ser Val Gln Gly Phe Ile Thr Lys Ile Met Gln Asp Ile Asp Gly
                245                 250                 255

Val Phe Asn Ser Ala Asn Ala Lys Gly Thr Phe Gly Gly His Asp Gly
            260                 265                 270

Ala Phe Glu Thr Ser Leu Pro Gly Thr Ala Asn Pro Thr Asp Leu Leu
        275                 280                 285

Asp Ser Thr Asp Lys Asp Met Leu Asp Ala Lys Tyr Trp Glu Ile Ser
    290                 295                 300

Met Tyr Lys Ser Ala Leu Glu Gly Arg Lys Gly Glu Leu Ala Asp Gly
305                 310                 315                 320

Glu Val Glu Lys Asp Asp Asp Ser Glu Val Gln Ile Gly Asn Lys Leu
                325                 330                 335

Arg Arg Asp Ala Phe Leu Val Phe Arg Ala Leu Cys Lys Leu Ser Met
            340                 345                 350

Lys Thr Pro Pro Lys Glu Asp Pro Glu Leu Met Arg Gly Lys Ile Val
        355                 360                 365

Ala Leu Glu Leu Leu Lys Ile Leu Leu Glu Asn Ala Gly Ala Val Phe
    370                 375                 380

Arg Thr Ser Asp Arg Phe Leu Gly Ala Ile Lys Gln Tyr Leu Cys Leu
385                 390                 395                 400

Ser Leu Leu Lys Asn Ser Ala Ser Asn Leu Met Ile Ile Phe Gln Leu
                405                 410                 415

Ser Cys Ser Ile Leu Leu Ser Leu Val Ser Arg Phe Arg Ala Gly Leu
            420                 425                 430

Lys Ala Glu Ile Gly Val Phe Phe Pro Met Ile Val Leu Arg Val Leu
        435                 440                 445

Glu Asn Val Ala Gln Pro Asp Phe Gln Gln Lys Met Ile Val Leu Arg
    450                 455                 460

Phe Leu Asp Lys Leu Cys Val Asp Ser Gln Ile Leu Val Asp Ile Phe
465                 470                 475                 480

Ile Asn Tyr Asp Cys Asp Val Asn Ser Ser Asn Ile Phe Glu Arg Met
                485                 490                 495

Val Asn Gly Leu Leu Lys Thr Ala Gln Gly Val Pro Ile Val Asp Arg
            500                 505                 510

Asn Leu Glu Glu Gly Ser His Pro Val Glu Asn Gly Lys Gly Asp Gly
        515                 520                 525

Gly His Gly Gly Phe Glu Arg Ser Asp Ser Gln Ser Glu Leu Ser Ser
    530                 535                 540
```

```
Gly Asn Ser Asp Ala Leu Ala Ile Glu Gln Arg Arg Ala Tyr Lys Leu
545                 550                 555                 560

Glu Leu Gln Glu Gly Ile Ser Ile Phe Asn Gln Lys Pro Lys Lys Gly
                565                 570                 575

Ile Glu Phe Leu Ile Lys Ala Asn Lys Val Gly Asp Ser Pro Glu Glu
            580                 585                 590

Ile Ala Ala Phe Leu Lys Asp Ala Ser Gly Leu Asn Lys Thr Leu Ile
        595                 600                 605

Gly Asp Tyr Leu Gly Glu Arg Glu Asp Leu Ser Leu Lys Val Met His
    610                 615                 620

Ala Tyr Val Asp Ser Phe Glu Phe Gln Gly Met Glu Phe Asp Glu Ala
625                 630                 635                 640

Ile Arg Ala Phe Leu Arg Gly Phe Arg Leu Pro Gly Glu Ala Gln Lys
                645                 650                 655

Ile Asp Arg Ile Met Glu Lys Phe Ala Glu Arg Phe Cys Lys Cys Asn
            660                 665                 670

Pro Lys Asp Phe Ser Ser Ala Asp Thr Ala Tyr Val Leu Ala Tyr Ser
        675                 680                 685

Val Ile Leu Leu Asn Thr Asp Ala His Asn Pro Met Val Lys Ser Lys
    690                 695                 700

Met Thr Ala Asp Gly Phe Ile Arg Asn Asn Arg Gly Ile Asp Asp Gly
705                 710                 715                 720

Lys Asp Leu Pro Glu Glu Tyr Leu Arg Ala Leu Tyr Glu Arg Ile Ser
                725                 730                 735

Arg Asn Glu Ile Lys Met Lys Asp Asp Gly Leu Gly Pro Gln Gln Lys
            740                 745                 750

Gln Pro Thr Asn Ser Ser Arg Leu Leu Gly Leu Asp Thr Ile Leu Asn
        755                 760                 765

Ile Val Val Pro Arg Arg Gly Asp Asp Met Asn Met Glu Thr Ser Asp
    770                 775                 780

Asp Leu Ile Arg His Met Gln Glu Arg Phe Lys Glu Lys Ala Arg Lys
785                 790                 795                 800

Ser Glu Ser Val Tyr Tyr Ala Ala Ser Asp Val Ile Ile Leu Arg Phe
                805                 810                 815

Met Val Glu Val Cys Trp Ala Pro Met Leu Ala Ala Phe Ser Val Pro
            820                 825                 830

Leu Asp Gln Ser Asp Asp Ala Val Ile Thr Thr Leu Cys Leu Glu Gly
        835                 840                 845

Phe His His Ala Ile His Val Thr Ser Val Met Ser Leu Lys Thr His
    850                 855                 860

Arg Asp Ala Phe Val Thr Ser Leu Ala Lys Phe Thr Ser Leu His Ser
865                 870                 875                 880

Pro Ala Asp Ile Lys Gln Lys Asn Ile Glu Ala Ile Lys Ala Ile Val
                885                 890                 895

Lys Leu Ala Glu Glu Glu Gly Asn Tyr Leu Gln Asp Ala Trp Glu His
            900                 905                 910

Ile Leu Thr Cys Val Ser Arg Phe Glu His Leu His Leu Leu Gly Glu
        915                 920                 925

Gly Ala Pro Pro Asp Ala Thr Phe Phe Ala Phe Pro Gln Thr Glu Ser
    930                 935                 940

Gly Asn Ser Pro Leu Ala Lys Pro Asn Ser Val Pro Ala Ile Lys Glu
945                 950                 955                 960

Arg Ala Pro Gly Lys Leu Gln Tyr Ala Ala Ser Ala Met Ile Arg Gly
```

-continued 965 970 975

Ser Tyr Asp Gly Ser Gly Val Ala Gly Lys Ala Ser Asn Thr Val Thr
980 985 990

Ser Glu Gln Met Asn Asn Leu Ile Ser Asn Leu Asn Leu Leu Glu Gln
995 1000 1005

Val Gly Asp Met Ser Arg Ile Phe Thr Arg Ser Gln Arg Leu Asn
1010 1015 1020

Ser Glu Ala Ile Ile Asp Phe Val Lys Ala Leu Cys Lys Val Ser
1025 1030 1035

Met Asp Glu Leu Arg Ser Pro Ser Asp Pro Arg Val Phe Ser Leu
1040 1045 1050

Thr Lys Ile Val Glu Ile Ala His Tyr Asn Met Asn Arg Ile Arg
1055 1060 1065

Leu Val Trp Ser Ser Ile Trp His Val Leu Ser Asp Phe Phe Val
1070 1075 1080

Thr Ile Gly Cys Ser Asp Asn Leu Ser Ile Ala Ile Phe Ala Met
1085 1090 1095

Asp Ser Leu Arg Gln Leu Ser Met Lys Phe Leu Glu Arg Glu Glu
1100 1105 1110

Leu Ala Asn Tyr Asn Phe Gln Asn Glu Phe Met Lys Pro Phe Val
1115 1120 1125

Val Val Met Arg Lys Ser Gly Ala Val Glu Ile Arg Glu Leu Ile
1130 1135 1140

Ile Arg Cys Val Ser Gln Met Val Leu Ser Arg Val Asp Asn Val
1145 1150 1155

Lys Ser Gly Trp Lys Ser Met Phe Met Ile Phe Thr Thr Ala Ala
1160 1165 1170

His Asp Ala His Lys Asn Ile Val Phe Leu Ser Phe Glu Met Val
1175 1180 1185

Glu Lys Ile Ile Arg Asp Tyr Phe Pro His Ile Thr Glu Thr Glu
1190 1195 1200

Thr Thr Thr Phe Thr Asp Cys Val Asn Cys Leu Val Ala Phe Thr
1205 1210 1215

Asn Cys Lys Phe Glu Lys Asp Ile Ser Leu Gln Ala Ile Ala Phe
1220 1225 1230

Leu Gln Tyr Cys Ala Arg Lys Leu Ala Glu Gly Tyr Val Gly Ser
1235 1240 1245

Ser Leu Arg Arg Asn Pro Pro Leu Ser Pro Gln Gly Gly Lys Ile
1250 1255 1260

Gly Lys Gln Asp Ser Gly Lys Phe Leu Glu Ser Asp Glu His Leu
1265 1270 1275

Tyr Ser Trp Phe Pro Leu Leu Ala Gly Leu Ser Glu Leu Ser Phe
1280 1285 1290

Asp Pro Arg Ala Glu Ile Arg Lys Val Ala Leu Lys Val Leu Phe
1295 1300 1305

Asp Thr Leu Arg Asn His Gly Asp His Phe Ser Leu Ala Leu Trp
1310 1315 1320

Glu Arg Val Phe Glu Ser Val Leu Phe Arg Ile Phe Asp Tyr Val
1325 1330 1335

Arg Gln Asp Val Asp Pro Ser Glu Asp Asp Ser Thr Asp Gln Arg
1340 1345 1350

Gly Tyr Asn Gly Glu Val Asp Gln Glu Ser Trp Leu Tyr Glu Thr
1355 1360 1365

-continued

```
Cys Ser  Leu Ala Leu Gln Leu  Val Val Asp Leu Phe  Val Asn Phe
    1370                 1375                 1380

Tyr Lys  Thr Val Asn Pro Leu  Leu Lys Lys Val Leu  Met Leu Phe
    1385                 1390                 1395

Val Ser  Leu Ile Lys Arg Pro  His Gln Ser Leu Ala  Gly Ala Gly
    1400                 1405                 1410

Ile Ala  Ala Leu Val Arg Leu  Met Arg Asp Val Gly  His Gln Phe
    1415                 1420                 1425

Ser Asn  Glu Gln Trp Leu Glu  Val Val Ser Cys Ile  Lys Glu Ala
    1430                 1435                 1440

Ala Asp  Ala Thr Ser Pro Asp  Phe Ser Tyr Val Thr  Ser Glu Asp
    1445                 1450                 1455

Leu Met  Glu Asp Val Ser Asn  Glu Asp Glu Thr Asn  Asp Asn Ser
    1460                 1465                 1470

Asn Asp  Ala Leu Arg Arg Arg  Asn Arg Gln Leu His  Ala Val Val
    1475                 1480                 1485

Thr Asp  Ala Lys Ser Lys Ala  Ser Ile Gln Ile Phe  Val Ile Gln
    1490                 1495                 1500

Ala Val  Thr Asp Ile Tyr Asp  Met Tyr Arg Met Ser  Leu Thr Ala
    1505                 1510                 1515

Asn His  Met Leu Met Leu Phe  Asp Ala Met His Gly  Ile Gly Ser
    1520                 1525                 1530

Asn Ala  His Lys Ile Asn Ala  Asp Leu Leu Leu Arg  Ser Lys Leu
    1535                 1540                 1545

Gln Glu  Leu Gly Ser Ser Leu  Glu Ser Gln Glu Ala  Pro Leu Leu
    1550                 1555                 1560

Arg Leu  Glu Asn Glu Ser Phe  Gln Thr Cys Met Thr  Phe Leu Asp
    1565                 1570                 1575

Asn Leu  Ile Ser Asp Gln Pro  Val Gly Tyr Asn Glu  Ala Glu Ile
    1580                 1585                 1590

Glu Ser  His Leu Ile Ser Leu  Cys Arg Glu Val Leu  Glu Phe Tyr
    1595                 1600                 1605

Ile Asn  Ile Ser Cys Ser Lys  Glu Gln Ser Ser Arg  Trp Ala Val
    1610                 1615                 1620

Pro Ser  Gly Ser Gly Lys Lys  Lys Glu Leu Thr Ala  Arg Ala Pro
    1625                 1630                 1635

Leu Val  Val Ala Ala Ile Gln  Thr Leu Gly Asn Met  Gly Glu Ser
    1640                 1645                 1650

Leu Phe  Lys Lys Asn Leu Pro  Glu Leu Phe Pro Leu  Ile Ala Thr
    1655                 1660                 1665

Leu Ile  Ser Cys Glu His Gly  Ser Gly Glu Val Gln  Val Ala Leu
    1670                 1675                 1680

Ser Asp  Met Leu Gln Thr Ser  Met Gly Pro Val Leu  Leu Arg Ser
    1685                 1690                 1695

Cys Cys
    1700


<210> SEQ ID NO 28
<211> LENGTH: 521
<212> TYPE: PRT
<213> ORGANISM: Arabidopsis thaliana

<400> SEQUENCE: 28

Pro Leu Gly Asp Glu Ser Ile Glu Leu Pro Val Leu Lys Thr Leu Leu
1               5                   10                  15
```

-continued

```
Ser Ala Ile Asn Ser Ile Ser Leu Arg Ile His Gly Lys Cys Leu Leu
            20                  25                  30

Leu Val Val Arg Thr Cys Tyr Asp Ile Tyr Leu Gly Ser Lys Asn Val
        35                  40                  45

Val Asn Gln Thr Thr Ala Lys Ala Ser Leu Ile Gln Ile Leu Val Ile
    50                  55                  60

Val Phe Arg Arg Met Glu Ala Asp Ser Ser Thr Val Pro Ile Gln Pro
65                  70                  75                  80

Ile Val Val Ala Glu Leu Met Glu Pro Leu Glu Lys Ser Asp Ala Asp
                85                  90                  95

Gly Thr Met Thr Gln Phe Val Gln Gly Phe Ile Thr Lys Ile Met Gln
            100                 105                 110

Asp Ile Asp Gly Val Leu Asn Pro Thr Met Ser Gly Ser Gly Ser Gly
        115                 120                 125

Ser Gly Ser Gly Gly Gln Asp Gly Ala Tyr Gly Thr Thr Thr Val Glu
    130                 135                 140

Thr Thr Asn Pro Thr Asp Leu Leu Asp Ser Thr Asp Lys Asp Met Leu
145                 150                 155                 160

Asp Ala Lys Tyr Trp Glu Ile Ser Met Tyr Lys Ser Ala Leu Glu Gly
                165                 170                 175

Arg Lys Gly Glu Leu Thr Asp Gly Asp Ala Glu Arg Asp Asp Asp Leu
            180                 185                 190

Glu Val Gln Ile Glu Asn Lys Leu Arg Arg Asp Ala Cys Leu Val Phe
        195                 200                 205

Arg Ala Leu Cys Lys Leu Ser Met Lys Ala Pro Pro Lys Glu Ser Ser
    210                 215                 220

Ala Asp Pro Gln Ser Met Arg Gly Lys Ile Leu Ala Leu Glu Leu Leu
225                 230                 235                 240

Lys Ile Leu Leu Glu Asn Ala Gly Ala Val Phe Arg Thr Ser Glu Lys
                245                 250                 255

Phe Ser Ala Asp Ile Lys Gln Phe Leu Cys Leu Ser Leu Leu Lys Asn
            260                 265                 270

Ser Ala Ser Thr Leu Met Ile Ile Phe Gln Leu Ser Cys Ser Ile Phe
        275                 280                 285

Ile Ser Leu Val Ala Arg Phe Arg Ala Gly Leu Lys Ala Glu Ile Gly
    290                 295                 300

Val Phe Phe Pro Met Ile Val Leu Arg Val Val Glu Asn Val Ala Gln
305                 310                 315                 320

Pro Asn Phe Gln Gln Lys Met Ile Val Leu Arg Phe Leu Asp Lys Leu
                325                 330                 335

Cys Leu Asp Ser Gln Ile Leu Val Asp Ile Phe Leu Asn Tyr Asp Cys
            340                 345                 350

Asp Val Asn Ser Ser Asn Ile Phe Glu Arg Met Val Asn Gly Leu Leu
        355                 360                 365

Lys Thr Ala Gln Gly Val Pro Pro Gly Thr Ala Thr Thr Leu Met Pro
    370                 375                 380

Pro Gln Glu Ala Ala Met Lys Leu Glu Ala Met Lys Cys Leu Val Ala
385                 390                 395                 400

Ile Leu Lys Ser Met Gly Asp Trp Leu Asn Lys Gln Leu Arg Leu Pro
                405                 410                 415

Val Ser Asn Ser Leu Asn Lys Ser Asp Val Ile Glu Ile Asp Leu Gly
            420                 425                 430

Pro Gly Ser Pro Gln Leu Ala Asn Gly Asn Ala Asp Glu Ser Ala Asp
        435                 440                 445
```

```
Gly Ser Asp Thr Tyr Ser Glu Ser Ser Gly Gly Thr Ser Asp Ala Leu
    450                 455                 460

Ala Ile Glu Gln Arg Arg Ala Tyr Lys Leu Glu Leu Gln Glu Gly Ile
465                 470                 475                 480

Ser Leu Phe Asn Arg Lys Pro Thr Lys Gly Ile Glu Phe Leu Ile Asn
                485                 490                 495

Ala Gly Lys Val Gly Glu Ser Pro Glu Glu Ile Ala Gly Phe Leu Lys
            500                 505                 510

Asp Ala Ser Val Met Thr Pro Thr Tyr
        515                 520


<210> SEQ ID NO 29
<211> LENGTH: 791
<212> TYPE: PRT
<213> ORGANISM: Arabidopsis thaliana

<400> SEQUENCE: 29

Cys Leu Ser Arg Ile Glu His Leu Gln Leu Leu Gly Glu Gly Ala Pro
1               5                   10                  15

Ser Asp Ala Ser Tyr Phe Ala Ser Thr Glu Thr Glu Glu Lys Lys Ala
            20                  25                  30

Leu Gly Phe Pro Asn Leu Lys Lys Lys Gly Ala Leu Gln Asn Pro Val
        35                  40                  45

Met Met Ala Val Val Arg Gly Gly Ser Tyr Asp Ser Ser Thr Ile Gly
    50                  55                  60

Pro Asn Met Pro Gly Leu Val Lys Gln Asp Gln Ile Asn Asn Phe Ile
65                  70                  75                  80

Ala Asn Leu Asn Leu Leu Asp Gln Ile Gly Ser Phe Gln Leu Asn Asn
                85                  90                  95

Val Tyr Ala His Ser Gln Arg Leu Lys Thr Glu Ala Ile Val Ala Phe
            100                 105                 110

Val Lys Ala Leu Cys Lys Val Ser Met Ser Glu Leu Gln Ser Pro Thr
        115                 120                 125

Asp Pro Arg Val Phe Ser Leu Thr Lys Leu Val Glu Ile Ala His Tyr
    130                 135                 140

Asn Met Asn Arg Ile Arg Leu Val Trp Ser Arg Ile Trp Ser Ile Leu
145                 150                 155                 160

Ser Asp Phe Phe Val Ser Val Gly Leu Ser Glu Asn Leu Ser Val Ala
                165                 170                 175

Ile Phe Val Met Asp Ser Leu Arg Gln Leu Ser Met Lys Phe Leu Glu
            180                 185                 190

Arg Glu Glu Leu Ala Asn Tyr Asn Phe Gln Asn Glu Phe Leu Arg Pro
        195                 200                 205

Phe Val Ile Val Met Gln Lys Ser Ser Ser Ala Glu Ile Arg Glu Leu
    210                 215                 220

Ile Val Arg Cys Ile Ser Gln Met Val Leu Ser Arg Val Ser Asn Val
225                 230                 235                 240

Lys Ser Gly Trp Lys Ser Val Phe Lys Val Phe Thr Thr Ala Ala Ala
                245                 250                 255

Asp Glu Arg Lys Asn Ile Val Leu Leu Ala Phe Glu Thr Met Glu Lys
            260                 265                 270

Ile Val Arg Glu Tyr Phe Ser Tyr Ile Thr Glu Thr Glu Ala Thr Thr
        275                 280                 285

Phe Thr Asp Cys Val Arg Cys Leu Ile Thr Phe Thr Asn Ser Thr Phe
    290                 295                 300
```

```
Thr Ser Asp Val Ser Leu Asn Ala Ile Ala Phe Leu Arg Phe Cys Ala
305                 310                 315                 320

Leu Lys Leu Ala Asp Gly Gly Leu Val Trp Asn Glu Lys Gly Arg Ser
                325                 330                 335

Ser Ser Pro Ser Thr Pro Val Thr Asp Asp His Ser Pro Ser Thr Gln
            340                 345                 350

Asn Phe Met Asp Ala Asp Glu Asn Ile Ser Tyr Trp Val Pro Leu Leu
        355                 360                 365

Thr Gly Leu Ser Lys Leu Thr Ser Asp Ser Arg Ser Ala Ile Arg Lys
    370                 375                 380

Ser Ser Leu Glu Val Leu Phe Asn Ile Leu Lys Asp His Gly His Ile
385                 390                 395                 400

Phe Ser Arg Thr Phe Trp Ile Gly Val Phe Ser Ser Val Ile Tyr Pro
                405                 410                 415

Ile Phe Asn Ser Val Trp Gly Glu Asn Asp Leu Leu Ser Lys Asp Glu
            420                 425                 430

His Ser Ser Phe Pro Ser Thr Phe Ser Ser His Pro Ser Glu Val Ser
        435                 440                 445

Trp Asp Ala Glu Thr Ser Ala Met Ala Ala Gln Tyr Leu Val Asp Leu
    450                 455                 460

Phe Val Ser Phe Phe Thr Val Ile Arg Ser Gln Leu Ser Ser Val Val
465                 470                 475                 480

Ser Leu Leu Ala Gly Leu Ile Arg Ser Pro Ala Gln Gly Pro Thr Val
                485                 490                 495

Ala Gly Val Gly Ala Leu Leu Arg Leu Ala Asp Glu Leu Gly Asp Arg
            500                 505                 510

Phe Ser Glu Asn Glu Trp Lys Glu Ile Phe Leu Ala Val Asn Glu Ala
        515                 520                 525

Ala Ser Leu Thr Leu Ser Ser Phe Met Lys Thr Leu Arg Thr Met Asp
    530                 535                 540

Asp Ile Pro Asp Glu Asp Thr Leu Ser Asp Gln Asp Phe Ser Asn Glu
545                 550                 555                 560

Asp Asp Ile Asp Glu Asp Ser Leu Gln Thr Met Ser Tyr Val Val Ala
                565                 570                 575

Arg Thr Lys Ser His Ile Thr Val Gln Leu Gln Val Val Gln Val Val
            580                 585                 590

Thr Asp Leu Tyr Arg Ile His Gln Gln Ser Leu Leu Ala Ser His Val
        595                 600                 605

Thr Val Ile Leu Glu Ile Leu Ser Ser Ile Ser Ser His Ala His Gln
    610                 615                 620

Leu Asn Ser Asp Leu Ile Leu Gln Lys Lys Val Arg Arg Ala Cys Ser
625                 630                 635                 640

Ile Leu Glu Leu Ser Glu Pro Pro Met Leu His Phe Glu Asn Asp Thr
                645                 650                 655

Phe Gln Asn Tyr Leu Asp Ile Leu Gln Ala Ile Val Thr Asn Asn Pro
            660                 665                 670

Gly Val Ser Leu Glu Leu Asn Val Glu Ser Gln Leu Met Thr Val Cys
        675                 680                 685

Met Gln Ile Leu Lys Met Tyr Leu Lys Cys Thr Leu Phe Gln Gly Asp
    690                 695                 700

Glu Leu Glu Glu Thr Arg Gln Pro Lys Asn Trp Ile Leu Pro Met Gly
705                 710                 715                 720

Ala Ala Ser Lys Glu Glu Ala Ala Ala Arg Ser Pro Leu Val Val Ala
```

```
                725                 730                 735

Val Leu Lys Ala Leu Arg Glu Leu Lys Arg Asp Ser Phe Lys Arg Tyr
            740                 745                 750

Ala Pro Asn Phe Phe Pro Leu Leu Val Glu Leu Val Arg Ser Glu His
        755                 760                 765

Ser Ser Ser Gln Val Pro Gln Val Leu Ser Thr Val Phe His Thr Cys
    770                 775                 780

Met Gly Ala Met Met Asp Glu
785                 790


<210> SEQ ID NO 30
<211> LENGTH: 1706
<212> TYPE: PRT
<213> ORGANISM: Arabidopsis thaliana

<400> SEQUENCE: 30

Met Ser Thr Ser Gln Thr Leu Gly Gly Ala Thr Arg Cys Gly Arg Ile
1               5                   10                  15

Ile Gly Pro Ser Leu Asp Lys Ile Ile Lys Asn Ala Ala Trp Arg Lys
            20                  25                  30

His Thr Tyr Leu Val Ser Ser Cys Lys Ser Val Leu Asp Lys Leu Glu
        35                  40                  45

Ser Leu Pro Asp Asp Phe His Asp Pro Ser Ser Val Val Ser Gly Leu
    50                  55                  60

Ala Ala Ser Asp Ala Asp Ser Val Leu Gln Pro Phe Leu Leu Ser Leu
65                  70                  75                  80

Glu Thr Ala Tyr Ser Lys Val Val Glu Pro Ser Leu Asp Cys Ala Phe
                85                  90                  95

Lys Leu Phe Ser Leu Ser Ile Leu Arg Gly Glu Ile Gln Ser Ser Lys
            100                 105                 110

Gln Asp Ser Ile Leu Phe Lys Leu Val Asn Ala Val Ser Lys Val Gly
        115                 120                 125

Ala Ile Ala Glu Glu Pro Ile Gln Leu Ala Val Leu Arg Val Leu Leu
    130                 135                 140

Ala Ala Val Arg Ser Pro Cys Ile Leu Ile Arg Gly Asp Cys Leu Leu
145                 150                 155                 160

His Val Val Lys Thr Cys Tyr Asn Ile Tyr Leu Gly Gly Leu Ser Gly
                165                 170                 175

Thr Thr Gln Ile Cys Ala Lys Ser Val Leu Ala Gln Met Met Leu Val
            180                 185                 190

Ile Phe Thr Arg Ser Glu Glu Asp Ser Leu Asp Val Ser Val Lys Thr
        195                 200                 205

Ile Tyr Val Asn Glu Leu Leu Thr Phe Thr Asp Lys Ser Val Asn Glu
    210                 215                 220

Gly Ser Ser Val Tyr Phe Cys Gln Gly Phe Val Asn Glu Val Met Ala
225                 230                 235                 240

Ala Gly Gln Gly Ser Pro Leu Pro Pro Pro Asp Val Ile Gln Ile Leu
                245                 250                 255

Leu Gln Asn Pro Glu Thr Glu Thr Val Met Thr Pro Asp Ser Pro Ser
            260                 265                 270

Phe Arg Gly Tyr Val Ala Asn Gly Glu Gly Asp Ser Glu Thr Gly Asp
        275                 280                 285

Met Ser Lys Val Arg Gln Asp Ala Phe Leu Leu Phe Lys Asn Leu Cys
    290                 295                 300

Lys Leu Ser Met Arg Phe Ser Ser Lys Glu Asn Asn Asp Asp Gln Ile
```

-continued 305 310 315 320

Met Val Arg Gly Lys Thr Leu Ser Leu Glu Leu Leu Lys Val Ile Ile
325 330 335

Asp Asn Gly Gly Ser Val Trp Arg Thr Asn Glu Ser Phe Ile Asn Ala
340 345 350

Val Lys Gln Tyr Leu Cys Leu Ser Leu Leu Lys Asn Ser Ala Val Ser
355 360 365

Ile Met Ser Ile Phe Gln Leu Gln Cys Ala Ile Phe Met Ser Leu Leu
370 375 380

Ser Lys Leu Arg Ser Val Leu Lys Ala Glu Ile Gly Ile Phe Phe Pro
385 390 395 400

Met Ile Val Leu Arg Val Leu Glu Asn Val Leu Gln Pro Ser Tyr Leu
405 410 415

Gln Lys Met Thr Val Leu Asn Leu Leu Asp Lys Met Ser Gln Asp Pro
420 425 430

Gln Leu Met Val Asp Ile Phe Val Asn Tyr Asp Cys Asp Val Glu Ser
435 440 445

Ser Asn Ile Leu Glu Arg Ile Val Asn Gly Leu Leu Lys Thr Ala Leu
450 455 460

Gly Pro Pro Thr Gly Ser Ser Thr Thr Leu Ser Pro Ala Gln Asp Ser
465 470 475 480

Thr Phe Arg Asn Asp Ser Val Lys Cys Leu Val Asn Leu Ala Lys Ala
485 490 495

Met Gly Asn Trp Met Asp Gln Gln Leu Lys Val Asn Glu Thr Val Trp
500 505 510

Pro Lys Gly Ser Gln Val Tyr Ala Ser Met Asp Ser Asn Ala Ser Gln
515 520 525

Ile Ser Glu Leu Glu Gly Thr Ile Ser Asp Cys Asp Ser Gln Pro Asp
530 535 540

Thr Ser Asn Pro Glu Ala Tyr Asp Ala Ser Met Leu Glu Gln Arg Arg
545 550 555 560

Ala Tyr Lys Ile Glu Leu Gln Lys Gly Ile Ser Leu Phe Asn Arg Lys
565 570 575

Pro Ser Lys Gly Val Glu Phe Leu Ile Ser Thr Lys Lys Ile Gly Ser
580 585 590

Ser Pro Glu Glu Val Ala Ser Phe Leu Met Lys Thr Ala Gly Leu Asn
595 600 605

Gly Thr Val Ile Gly Asp Tyr Leu Gly Glu Arg Asp Glu Leu Pro Leu
610 615 620

Lys Val Met His Ala Tyr Val Asp Ser Phe Asn Phe Glu Lys Lys Asp
625 630 635 640

Phe Val Glu Ala Ile Arg Phe Phe Leu Arg Gly Phe Arg Leu Pro Gly
645 650 655

Glu Ala Gln Lys Ile Asp Arg Ile Met Glu Lys Phe Ala Glu His Tyr
660 665 670

Trp Lys Cys Asn Pro Gly Ser Phe Thr Ser Ala Asp Thr Ala Tyr Val
675 680 685

Leu Ala Tyr Ser Val Ile Met Leu Asn Thr Asp Ala His Asn Asn Met
690 695 700

Val Lys Asp Lys Met Thr Lys Ala Asp Phe Val Arg Asn Asn Arg Gly
705 710 715 720

Ile Asp Asp Gly Lys Asp Leu Pro Glu Glu Tyr Leu Gly Ser Leu Tyr
725 730 735

-continued

```
Asp Arg Val Val Lys Glu Glu Ile Arg Met Asn Ser Asp Thr Leu Ala
            740                 745                 750

Pro Gln Asn Lys Gln Val Asn Gly Leu Asn Lys Leu Leu Gly Leu Asp
        755                 760                 765

Gly Ile Leu Asn Leu Val Ser Trp Met Gln Pro Asp Glu Lys Pro His
    770                 775                 780

Gly Ala Asn Gly Arg Leu Ile Arg Asp Ile Gln Glu Gln Phe Gln Ala
785                 790                 795                 800

Lys Pro Glu Lys Ser Glu Ser Val Tyr His Thr Val Thr Asp Ile Ser
                805                 810                 815

Ile Leu Arg Phe Ile Leu Glu Val Ser Trp Gly Pro Met Leu Ala Ala
            820                 825                 830

Phe Ser Val Thr Ile Asp Gln Ser Asp Asp Arg Leu Ala Thr Ser Leu
        835                 840                 845

Cys Leu Gln Gly Phe Arg Tyr Ala Val His Val Thr Ala Val Met Gly
    850                 855                 860

Met Gln Thr Gln Arg Asp Ala Phe Val Thr Ser Met Ala Lys Phe Thr
865                 870                 875                 880

Asn Leu His Cys Ala Ala Asp Met Lys Gln Lys Asn Val Asp Ala Val
                885                 890                 895

Lys Ala Ile Ile Thr Ile Ala Ile Glu Asp Gly Asn His Leu His Gly
            900                 905                 910

Ser Trp Glu His Ile Leu Thr Cys Leu Ser Arg Ile Glu His Leu Gln
        915                 920                 925

Leu Leu Gly Glu Val Ser Pro Ser Glu Lys Arg Tyr Val Pro Thr Lys
    930                 935                 940

Lys Ala Glu Val Asp Asp Lys Lys Ala Leu Gly Phe Pro Asn Leu Lys
945                 950                 955                 960

Lys Arg Gly Ser Phe Gln Asn Pro Ser Val Met Ala Val Val Arg Gly
                965                 970                 975

Gly Ser Tyr Asp Ser Thr Ser Leu Val Lys Ser Val Pro Lys Leu Val
            980                 985                 990

Thr Pro Glu Gln Ile Lys Ser Phe  Ile Ala Asn Leu Asn  Leu Leu Asp
        995                 1000                1005

Gln Ile  Gly Asn Phe Glu Leu  Asn His Val Tyr Ala  Asn Ser Gln
    1010                1015                1020

Arg Leu  Asn Ser Glu Ala Ile  Val Ser Phe Val Lys  Ala Leu Cys
    1025                1030                1035

Lys Val  Ser Met Ser Glu Leu  Gln Ser Pro Thr Asp  Pro Arg Val
    1040                1045                1050

Phe Ser  Leu Thr Lys Leu Val  Glu Thr Ala His Tyr  Asn Met Asn
    1055                1060                1065

Arg Ile  Arg Leu Val Trp Ser  Arg Ile Trp Asn Val  Leu Ser Asp
    1070                1075                1080

Phe Phe  Val Ser Val Gly Leu  Ser Glu Asn Leu Ser  Val Ala Ile
    1085                1090                1095

Phe Val  Met Asp Ser Leu Arg  Gln Leu Ser Met Lys  Phe Leu Glu
    1100                1105                1110

Arg Glu  Glu Leu Ala Asn Tyr  His Phe Gln His Glu  Phe Leu Arg
    1115                1120                1125

Pro Phe  Val Val Val Met Gln  Lys Ser Ser Ser Ala  Glu Ile Arg
    1130                1135                1140

Glu Leu  Ile Val Arg Cys Val  Ser Gln Met Val Leu  Ser Arg Val
    1145                1150                1155
```

```
Ser Asn  Val Lys Ser Gly Trp  Lys Asn Val Phe Thr  Val Phe Thr
    1160                 1165                 1170

Thr Ala  Ala Leu Asp Glu Arg  Lys Asn Ile Val Leu  Leu Ala Phe
    1175                 1180                 1185

Glu Thr  Ile Glu Lys Ile Val  Arg Asp His Phe His  Cys Ile Ile
    1190                 1195                 1200

Glu Thr  Glu Ile Thr Val Tyr  Ala Asp Cys Ile Arg  Cys Leu Ile
    1205                 1210                 1215

Thr Phe  Thr Asn Ser Lys Phe  Glu Gly Asp Ile Gly  Phe Asn Thr
    1220                 1225                 1230

Ile Glu  Phe Leu Arg Phe Cys  Ala Leu Lys Leu Glu  Glu Gly Gly
    1235                 1240                 1245

Leu Val  Leu Asn Glu Lys Leu  Lys Asn Asn Thr Ile  Ser Ala Leu
    1250                 1255                 1260

Lys Glu  Asp Phe Ser Asp Thr  Gln Ser Phe Thr Asp  Leu Asp Glu
    1265                 1270                 1275

Gln Val  Ser Tyr Trp Ile Pro  Leu Leu Thr Gly Leu  Cys Lys Gln
    1280                 1285                 1290

Val Ser  Asp Pro Arg Pro Ala  Ile Arg Lys Arg Ser  Ile Glu Val
    1295                 1300                 1305

Leu Phe  His Ile Leu Met Asp  His Gly His Leu Phe  Thr Arg Pro
    1310                 1315                 1320

Phe Trp  Thr Gly Ile Phe Ser  Ser Ile Ile Leu Pro  Val Phe Asn
    1325                 1330                 1335

Asn Ile  Arg Ser Lys Thr Asp  Met Leu Phe Glu Glu  Ser Val Asp
    1340                 1345                 1350

Ser Pro  Ser Ser Ala Ser Leu  Asp Thr Glu Glu Thr  Thr Trp Asp
    1355                 1360                 1365

Val Glu  Thr Ser Thr Leu Ala  Leu Gln Leu Leu Val  Asp Leu Leu
    1370                 1375                 1380

Val Lys  Phe Phe Arg Ser Val  Arg Ser Gln Leu Pro  Ser Val Val
    1385                 1390                 1395

Ser Ile  Ile Val Gly Phe Ile  Lys Ser Pro Phe Gln  Gly Ser Thr
    1400                 1405                 1410

Gly Ser  Gly Ile Ser Val Leu  Leu His Leu Ala Asp  Gly Leu Ala
    1415                 1420                 1425

Arg Ser  Ala Ser Glu Asp Glu  Trp Arg Glu Ile Phe  Leu Ala Leu
    1430                 1435                 1440

Lys Glu  Ala Ala Ser Leu Thr  Phe Ala Gly Phe Met  Lys Val Leu
    1445                 1450                 1455

Arg Thr  Met Asp Asp Ile Glu  Asp Val Glu Thr Leu  Ser Gly Gln
    1460                 1465                 1470

Ser Val  Asn Ile Gly Asp Leu  Asp Asp Asp Ser Leu  His Ile Met
    1475                 1480                 1485

Ser Tyr  Val Val Ser Arg Thr  Lys Lys His Ile Asp  Val Leu Ser
    1490                 1495                 1500

Gln Ile  Val Glu Val Val Ser  Asp Leu Tyr Arg Arg  Asn Gln Phe
    1505                 1510                 1515

Ser Leu  Ser Ala Ser His Val  Asp Ile Leu Ala Asp  Ile Phe Ser
    1520                 1525                 1530

Cys Ile  Ala Ser His Ala Gln  Gln Leu Asn Thr Asp  Thr Val Leu
    1535                 1540                 1545

Arg Arg  Lys Phe Lys Arg Ala  Cys Ser Val Gln Asn  Leu Thr Glu
```

```
    1550                1555                1560

Pro Gln  Leu Leu Asn Phe Glu  Asn Glu Ala Tyr Lys  Ser Tyr Met
    1565                1570                1575

Met Phe  Leu Gln Asp Met Val  Thr Cys Asn Pro Asn  Val Ser Lys
    1580                1585                1590

Glu Leu  Asp Leu Glu Ser Arg  Leu Val Thr Glu Cys  Ala Lys Ile
    1595                1600                1605

Val Lys  Ile Tyr Leu Lys Cys  Thr Asp Pro Gln Gln  Gln Glu Gln
    1610                1615                1620

Gln Gln  Arg Lys Pro Val Leu  Trp Val Leu Pro Met  Glu Ser Asp
    1625                1630                1635

Arg Val  Glu Glu Ala Thr Ala  Arg Thr Ser Leu Leu  Val Ser Ser
    1640                1645                1650

Leu Glu  Ala Leu Cys Ser Leu  Glu Ala Glu Ser Leu  Lys Lys His
    1655                1660                1665

Val Ser  Ser Phe Phe Pro Leu  Leu Val Asp Leu Val  Arg Thr Glu
    1670                1675                1680

His Cys  Ser Pro Gln Val Pro  Tyr Val Leu Ser Asn  Val Leu Lys
    1685                1690                1695

Ser Cys  Ile Gly Pro Ile Leu  Ala
    1700                1705


<210> SEQ ID NO 31
<211> LENGTH: 1451
<212> TYPE: PRT
<213> ORGANISM: Arabidopsis thaliana

<400> SEQUENCE: 31

Met Gly Arg Leu Lys Leu His Ser Gly Ile Lys Ala Ile Glu Glu Glu
1               5                   10                  15

Pro Glu Asp Phe Glu Cys Thr Asp Ser Ser Asn Thr Thr Thr Leu Ala
            20                  25                  30

Cys Met Ile Asp Thr Glu Ile Ala Ala Val Leu Ala Val Met Arg Arg
        35                  40                  45

Asn Val Arg Trp Gly Gly Arg Tyr Met Ser Gly Asp Asp Gln Leu Glu
    50                  55                  60

His Ser Leu Ile Gln Ser Leu Lys Ala Leu Arg Lys Gln Val Phe Ser
65                  70                  75                  80

Trp Asn Gln Pro Trp His Thr Ile Ser Pro Met Leu Tyr Leu Gln Pro
                85                  90                  95

Phe Leu Asp Val Ile Arg Ser Asp Glu Thr Gly Ala Pro Ile Thr Ser
            100                 105                 110

Ile Ala Leu Ser Ser Val Tyr Lys Ile Leu Asn Leu Asn Val Ile Asp
        115                 120                 125

Gln Asn Thr Ala Asn Ile Glu Asp Ala Met His Leu Val Val Asp Ser
    130                 135                 140

Val Thr Ser Cys Arg Phe Glu Val Thr Asp Pro Ala Ser Glu Glu Val
145                 150                 155                 160

Val Leu Met Lys Ile Leu Gln Val Leu Leu Ala Cys Met Lys Asn Lys
                165                 170                 175

Ala Ser Val Met Leu Ser Asn Gln His Val Cys Thr Val Val Asn Thr
            180                 185                 190

Cys Phe Arg Val Val His Gln Ala Gly Met Lys Gly Glu Leu Leu Gln
        195                 200                 205

Arg Val Ala Arg His Thr Met His Glu Leu Val Arg Cys Ile Phe Ser
```

```
    210                 215                 220

His Leu Pro Asp Val Glu Arg Thr Glu Thr Thr Leu Val Asn Arg Ala
225                 230                 235                 240

Gly Ser Ile Lys Gln Glu Lys Ala Gly Val Asp Ser Asp Tyr Ala Ile
                245                 250                 255

Val Ser Lys Pro Val Glu Asp Gly Asn Ala Asn Ser Glu Tyr Asp Val
            260                 265                 270

Glu Asn Ser Met Ala Thr Phe Ala Thr Gly Ala Gln Ser Leu Met Asp
        275                 280                 285

Asp Gly Pro Val Gly Pro Gly Ser Arg Lys Pro Ala Ser Pro Tyr Asp
    290                 295                 300

Leu His Ile Met Thr Glu Pro Tyr Gly Val Pro Ser Met Val Glu Ile
305                 310                 315                 320

Phe His Phe Leu Cys Ser Leu Leu Asn Val Val Glu His Val Gly Met
                325                 330                 335

Gly Ser Arg Ser Asn Thr Ile Ala Phe Asp Glu Asp Val Pro Leu Phe
            340                 345                 350

Ala Leu Asn Leu Ile Asn Ser Ala Ile Glu Leu Gly Gly Ser Ser Ile
        355                 360                 365

Arg His His Pro Arg Leu Leu Ser Leu Ile Gln Asp Glu Leu Phe Arg
    370                 375                 380

Asn Leu Met Gln Phe Gly Leu Ser Met Ser Pro Leu Ile Leu Ser Met
385                 390                 395                 400

Val Cys Ser Ile Val Leu Asn Leu Tyr Gln His Leu Arg Thr Glu Leu
                405                 410                 415

Lys Leu Gln Leu Glu Ala Phe Phe Ser Cys Val Ile Leu Arg Leu Ala
            420                 425                 430

Gln Gly Lys Tyr Gly Pro Ser Tyr Gln Gln Gln Glu Val Ala Met Glu
        435                 440                 445

Ala Leu Val Asn Phe Cys Arg Gln Lys Ser Phe Met Val Glu Met Tyr
    450                 455                 460

Ala Asn Leu Asp Cys Asp Ile Thr Cys Ser Asn Val Phe Glu Glu Leu
465                 470                 475                 480

Ser Asn Leu Leu Ser Lys Ser Thr Phe Pro Val Asn Cys Pro Leu Ser
                485                 490                 495

Ala Met His Ile Leu Ala Leu Asp Gly Leu Ile Ala Val Ile Gln Gly
            500                 505                 510

Met Ala Glu Arg Ile Ser Asn Gly Leu Thr Gly Leu Asp Leu Gly Pro
        515                 520                 525

Val His Leu Asp Glu Tyr Thr Pro Phe Trp Met Val Lys Cys Asp Asn
    530                 535                 540

Tyr Ser Asp Pro Asn His Trp Val Ser Phe Val Arg Arg Arg Lys Tyr
545                 550                 555                 560

Ile Lys Arg Arg Leu Met Ile Gly Ala Asp His Phe Asn Arg Asp Pro
                565                 570                 575

Lys Lys Gly Leu Glu Phe Leu Gln Gly Thr His Leu Leu Pro Asp Lys
            580                 585                 590

Leu Asp Pro Gln Ser Val Ala Cys Phe Phe Arg Tyr Thr Ala Gly Leu
        595                 600                 605

Asp Lys Asn Leu Val Gly Asp Phe Leu Gly Asn His Asp Glu Phe Cys
    610                 615                 620

Val Gln Val Leu Asn Glu Phe Ala Gly Thr Phe Asp Phe Gln Tyr Met
625                 630                 635                 640
```

```
Asn Leu Asp Thr Ala Leu Arg Leu Phe Leu Glu Thr Phe Arg Leu Pro
                645                 650                 655

Gly Glu Ser Gln Lys Ile Gln Arg Val Leu Glu Ala Phe Ser Glu Arg
            660                 665                 670

Tyr Tyr Met Gln Ser Pro Glu Ile Leu Ala Asn Lys Asp Ala Ala Leu
        675                 680                 685

Val Leu Ser Tyr Ser Ile Ile Met Leu Asn Thr Asp Gln His Asn Val
    690                 695                 700

Gln Val Lys Lys Lys Met Thr Glu Glu Asp Phe Ile Arg Asn Asn Arg
705                 710                 715                 720

His Ile Asn Gly Gly Asn Asp Leu Pro Arg Glu Phe Leu Ser Glu Leu
                725                 730                 735

Phe His Ser Ile Cys Asn Asn Glu Ile Arg Thr Thr Pro Glu Gln Gly
            740                 745                 750

Ala Gly Phe Pro Glu Met Thr Pro Ser Arg Trp Ile Asp Leu Met His
        755                 760                 765

Lys Ser Lys Lys Thr Ala Pro Tyr Ile Leu Ala Asp Ser Arg Ala Tyr
    770                 775                 780

Leu Asp His Asp Met Phe Ala Ile Met Ser Gly Pro Thr Ile Ala Ala
785                 790                 795                 800

Ile Ser Val Val Phe Asp His Ala Glu His Glu Asp Val Tyr Gln Thr
                805                 810                 815

Cys Ile Asp Gly Phe Leu Ala Ile Ala Lys Ile Ser Ala Cys His His
            820                 825                 830

Leu Glu Asp Val Leu Asp Asp Leu Val Val Ser Leu Cys Lys Phe Thr
        835                 840                 845

Thr Leu Leu Asn Pro Ser Ser Val Asp Glu Pro Val Leu Ala Phe Gly
    850                 855                 860

Asp Asp Ala Lys Ala Arg Met Ala Thr Ile Thr Ile Phe Thr Ile Ala
865                 870                 875                 880

Asn Lys Tyr Gly Asp Tyr Ile Arg Thr Gly Trp Arg Asn Ile Leu Asp
                885                 890                 895

Cys Ile Leu Arg Leu His Lys Leu Gly Leu Leu Pro Ala Arg Val Ala
            900                 905                 910

Ser Asp Ala Ala Asp Glu Ser Glu His Ser Ser Glu Gln Gly Gln Gly
        915                 920                 925

Lys Pro Leu Ala Asn Ser Leu Ser Ser Ala His Leu Gln Ser Met Gly
    930                 935                 940

Thr Pro Arg Arg Ser Ser Gly Leu Met Gly Arg Phe Ser Gln Leu Leu
945                 950                 955                 960

Ser Leu Asp Thr Glu Glu Pro Arg Ser Gln Pro Thr Glu Gln Gln Leu
                965                 970                 975

Ala Ala His Gln Arg Thr Leu Gln Thr Ile Gln Lys Cys His Ile Asp
            980                 985                 990

Ser Ile Phe Thr Glu Ser Lys Phe  Leu Gln Ala Glu Ser  Leu Leu Gln
        995                 1000                1005

Leu Ala  Arg Ala Leu Ile Trp  Ala Ala Gly Arg Pro  Gln Lys Gly
    1010                1015                1020

Thr Ser  Ser Pro Glu Asp Glu  Asp Thr Ala Val Phe  Cys Leu Glu
    1025                1030                1035

Leu Leu  Ile Ala Ile Thr Leu  Asn Asn Arg Asp Arg  Ile Val Leu
    1040                1045                1050

Leu Trp  Gln Gly Val Tyr Glu  His Ile Ala Thr Ile  Ala Gln Ser
    1055                1060                1065
```

Thr Val Met Pro Cys Asn Leu Val Asp Lys Ala Ile Phe Gly Leu
1070 1075 1080

Leu Arg Ile Cys Gln Arg Leu Leu Pro Tyr Lys Glu Ser Leu Ala
1085 1090 1095

Asp Glu Leu Leu Arg Ser Leu Gln Leu Val Leu Lys Leu Asp Ala
1100 1105 1110

Arg Val Ala Asp Ala Tyr Cys Glu Gln Ile Ala Ile Glu Val Ser
1115 1120 1125

Arg Leu Val Lys Ala Asn Ala Asn His Ile Arg Ser Gln Ala Gly
1130 1135 1140

Trp Arg Thr Ile Thr Ser Leu Leu Ser Ile Thr Ala Arg His Pro
1145 1150 1155

Glu Ala Ser Glu Ser Gly Phe Asp Ala Val Ser Phe Val Met Ser
1160 1165 1170

Glu Gly Thr His Leu Tyr Pro Ala Asn Tyr Val Leu Cys Val Asp
1175 1180 1185

Ala Ala Arg Gln Phe Ala Glu Ser Arg Val Gly Gln Ser Glu Arg
1190 1195 1200

Ser Ile Arg Ala Leu Asp Leu Met Gly Asp Ser Leu Glu Phe Leu
1205 1210 1215

Ala Lys Trp Ala Leu Ser Ala Lys Glu Asn Met Gly Glu Glu Asp
1220 1225 1230

Phe Gly Lys Met Ser Gln Asp Ile Gly Glu Met Trp Leu Arg Leu
1235 1240 1245

Val Gln Gly Leu Arg Lys Val Cys Leu Asp Gln Arg Glu Asp Val
1250 1255 1260

Arg Asn His Ala Leu Gln Ser Leu Gln Lys Cys Leu Gly Gly Val
1265 1270 1275

Asp Gly Ile Asn Leu Ala His Ser Met Trp Ser Gln Cys Phe Asp
1280 1285 1290

Lys Val Ile Phe Thr Val Leu Asp Asp Leu Leu Glu Ile Ala Ala
1295 1300 1305

Gly Ser Gln Lys Asp Tyr Arg Asn Met Glu Gly Thr Leu Leu Leu
1310 1315 1320

Ala Ile Lys Leu Leu Ser Lys Val Phe Leu Gln Gln Leu Gln Glu
1325 1330 1335

Leu Ser Gln Leu Ser Thr Phe Cys Lys Leu Trp Leu Gly Val Leu
1340 1345 1350

Thr Arg Met Glu Lys Tyr Met Lys Val Lys Val Arg Gly Lys Lys
1355 1360 1365

Ser Asp Lys Leu Gln Glu Ser Val Pro Glu Leu Leu Lys Asn Ile
1370 1375 1380

Leu Leu Val Met Lys Thr Lys Gly Val Leu Leu Gln Arg Ser Ala
1385 1390 1395

Leu Gly Gly Asp Ser Leu Trp Glu Leu Thr Trp Leu His Val Asn
1400 1405 1410

Asn Ile Ala Pro Ser Met Arg Leu Glu Leu Phe Pro Asp Gln Glu
1415 1420 1425

Ser Ser Gln Leu Gly Asp Asp Glu Thr Val Ser Asn Gly Leu Ser
1430 1435 1440

Ser Pro Glu Asn Thr Thr Gly Ser
1445 1450

-continued

<210> SEQ ID NO 32
<211> LENGTH: 1443
<212> TYPE: PRT
<213> ORGANISM: Arabidopsis thaliana

<400> SEQUENCE: 32

Met Gly Tyr Gln Asn His Pro Ser Gly Ser Asn Ser Phe His Gly Glu
1               5                   10                  15

Phe Lys Arg Cys His Ser Lys Pro Ser Lys Gly Ala Val Ala Ser Met
            20                  25                  30

Ile Asn Ser Glu Ile Gly Ala Val Leu Ala Val Met Arg Arg Asn Val
        35                  40                  45

Arg Trp Gly Val Arg Tyr Ile Ala Asp Asp Asp Gln Leu Glu His Ser
    50                  55                  60

Leu Ile His Ser Leu Lys Glu Leu Arg Lys Gln Ile Phe Ser Trp Gln
65                  70                  75                  80

Ser Asn Trp Gln Tyr Val Asp Pro Arg Leu Tyr Ile Gln Pro Phe Leu
                85                  90                  95

Asp Val Ile Leu Ser Asp Glu Thr Gly Ala Pro Ile Thr Gly Val Ala
            100                 105                 110

Leu Ser Ser Val Tyr Lys Ile Leu Thr Leu Glu Val Phe Thr Leu Glu
        115                 120                 125

Thr Val Asn Val Gly Glu Ala Met His Ile Ile Val Asp Ala Val Lys
    130                 135                 140

Ser Cys Arg Phe Glu Val Thr Asp Pro Ala Ser Glu Glu Val Val Leu
145                 150                 155                 160

Met Lys Ile Leu Gln Val Leu Leu Ala Cys Val Lys Ser Lys Ala Ser
                165                 170                 175

Asn Gly Leu Ser Asn Gln Asp Ile Cys Thr Ile Val Asn Thr Cys Leu
            180                 185                 190

Arg Val Val His Gln Ser Ser Ser Lys Ser Glu Leu Leu Gln Arg Ile
        195                 200                 205

Ala Arg His Thr Met His Glu Leu Ile Arg Cys Ile Phe Ser Gln Leu
    210                 215                 220

Pro Phe Ile Ser Pro Leu Ala Asn Glu Cys Glu Leu His Val Asp Asn
225                 230                 235                 240

Lys Val Gly Thr Val Asp Trp Asp Pro Asn Ser Gly Glu Lys Arg Val
                245                 250                 255

Glu Asn Gly Asn Ile Ala Ser Ile Ser Asp Thr Leu Gly Thr Asp Lys
            260                 265                 270

Asp Asp Pro Ser Ser Glu Met Val Ile Pro Glu Thr Asp Leu Arg Asn
        275                 280                 285

Asp Glu Lys Lys Thr Glu Val Ser Asp Asp Leu Asn Ala Ala Ala Asn
    290                 295                 300

Gly Glu Asn Ala Met Met Ala Pro Tyr Gly Ile Pro Cys Met Val Glu
305                 310                 315                 320

Ile Phe His Phe Leu Cys Thr Leu Leu Asn Val Gly Glu Asn Gly Glu
                325                 330                 335

Val Asn Ser Arg Ser Asn Pro Ile Ala Phe Asp Glu Asp Val Pro Leu
            340                 345                 350

Phe Ala Leu Gly Leu Ile Asn Ser Ala Ile Glu Leu Gly Gly Pro Ser
        355                 360                 365

Phe Arg Glu His Pro Lys Leu Leu Thr Leu Ile Gln Asp Asp Leu Phe
    370                 375                 380

Cys Asn Leu Met Gln Phe Gly Met Ser Met Ser Pro Leu Ile Leu Ser

-continued 385 390 395 400

Thr Val Cys Ser Ile Val Leu Asn Leu Tyr Leu Asn Leu Arg Thr Glu
405 410 415

Leu Lys Val Gln Leu Glu Ala Phe Phe Ser Tyr Val Leu Leu Arg Ile
420 425 430

Ala Gln Ser Lys His Gly Ser Ser Tyr Gln Gln Gln Glu Val Ala Met
435 440 445

Glu Ala Leu Val Asp Leu Cys Arg Gln His Thr Phe Ile Ala Glu Val
450 455 460

Phe Ala Asn Phe Asp Cys Asp Ile Thr Cys Ser Asn Val Phe Glu Asp
465 470 475 480

Val Ser Asn Leu Leu Ser Lys Asn Ala Phe Pro Val Asn Gly Pro Leu
485 490 495

Ser Ala Met His Ile Leu Ala Leu Asp Gly Leu Ile Ser Met Val Gln
500 505 510

Gly Met Ala Glu Arg Val Gly Glu Glu Leu Pro Ala Ser Asp Val Pro
515 520 525

Thr His Glu Glu Arg Tyr Glu Glu Phe Trp Thr Val Arg Cys Glu Asn
530 535 540

Tyr Gly Asp Pro Asn Phe Trp Val Pro Phe Val Arg Lys Val Lys His
545 550 555 560

Ile Lys Lys Lys Leu Met Leu Gly Ala Asp Arg Phe Asn Arg Asp Pro
565 570 575

Asn Lys Gly Leu Gln Tyr Leu Gln Gly Val His Leu Leu Pro Glu Lys
580 585 590

Leu Asp Pro Lys Ser Val Ala Cys Phe Phe Arg Tyr Thr Cys Gly Leu
595 600 605

Asp Lys Asn Val Met Gly Asp Phe Leu Gly Asn His Asp Gln Phe Cys
610 615 620

Ile Gln Val Leu His Glu Phe Ala Lys Thr Phe Asp Phe Gln Asn Met
625 630 635 640

Asn Leu Ala Thr Ala Leu Arg Leu Phe Val Gly Thr Phe Lys Leu Ser
645 650 655

Gly Glu Ala Gln Lys Ile His Arg Val Leu Glu Ala Phe Ser Glu Arg
660 665 670

Tyr Tyr Glu Gln Ser Pro His Ile Leu Ile Asp Lys Asp Ala Ala Phe
675 680 685

Val Leu Ala Tyr Ser Ile Ile Leu Leu Asn Thr Asp Gln His Asn Ala
690 695 700

Gln Val Lys Thr Arg Met Thr Glu Glu Asp Phe Ile Arg Asn Asn Arg
705 710 715 720

Thr Ile Asn Gly Gly Ala Asp Leu Pro Arg Glu Tyr Leu Ser Glu Ile
725 730 735

Tyr His Ser Ile Arg His Ser Glu Ile Gln Met Asp Glu Asp Lys Gly
740 745 750

Thr Gly Phe Gln Leu Met Thr Ala Ser Arg Trp Ile Ser Val Ile Tyr
755 760 765

Lys Ser Lys Glu Thr Ser Pro Tyr Ile Gln Cys Asp Ala Ala Ser His
770 775 780

Leu Asp Arg Asp Met Phe Tyr Ile Val Ser Gly Pro Thr Ile Ala Ala
785 790 795 800

Thr Ser Val Val Phe Glu Gln Ala Glu Gln Glu Asp Val Leu Arg Arg
805 810 815

-continued

Cys Ile Asp Gly Leu Leu Ala Ile Ala Lys Leu Ser Ala Tyr Tyr His
820 825 830

Leu Asn Ser Val Leu Asp Asp Leu Val Val Ser Leu Cys Lys Phe Thr
835 840 845

Pro Phe Phe Ala Pro Leu Ser Ala Asp Glu Ala Val Leu Val Leu Gly
850 855 860

Glu Asp Ala Arg Ala Arg Met Ala Thr Glu Ala Val Phe Leu Ile Ala
865 870 875 880

Asn Lys Tyr Gly Asp Tyr Ile Ser Ala Gly Trp Lys Asn Ile Leu Glu
885 890 895

Cys Val Leu Ser Leu Asn Lys Leu His Ile Leu Pro Asp His Ile Ala
900 905 910

Ser Asp Ala Ala Asp Asp Pro Glu Leu Ser Thr Ser Asn Leu Glu Gln
915 920 925

Glu Lys Pro Ser Ala Asn Pro Val Pro Val Val Ser Gln Ser Gln Pro
930 935 940

Ser Ala Met Pro Arg Lys Ser Ser Ser Phe Ile Gly Arg Phe Leu Leu
945 950 955 960

Ser Phe Asp Ser Glu Glu Thr Lys Pro Leu Pro Ser Glu Glu Glu Leu
965 970 975

Ala Ala Tyr Lys His Ala Arg Gly Ile Val Lys Asp Cys His Ile Asp
980 985 990

Ser Ile Phe Ser Asp Ser Lys Phe Leu Gln Ala Glu Ser Leu Gln Gln
995 1000 1005

Leu Val Asn Ser Leu Ile Arg Ala Ser Gly Lys Asp Glu Ala Ser
1010 1015 1020

Ser Val Phe Cys Leu Glu Leu Leu Ile Ala Val Thr Leu Asn Asn
1025 1030 1035

Arg Asp Arg Ile Leu Leu Ile Trp Pro Thr Val Tyr Glu His Ile
1040 1045 1050

Leu Gly Ile Val Gln Leu Thr Leu Thr Pro Cys Thr Leu Val Glu
1055 1060 1065

Lys Ala Val Phe Gly Val Leu Lys Ile Cys Gln Arg Leu Leu Pro
1070 1075 1080

Tyr Lys Glu Asn Leu Thr Asp Glu Leu Leu Lys Ser Leu Gln Leu
1085 1090 1095

Val Leu Lys Leu Lys Ala Lys Val Ala Asp Ala Tyr Cys Glu Arg
1100 1105 1110

Ile Ala Gln Glu Val Val Arg Leu Val Lys Ala Asn Ala Ser His
1115 1120 1125

Val Arg Ser Arg Thr Gly Trp Arg Thr Ile Ile Ser Leu Leu Ser
1130 1135 1140

Ile Thr Ala Arg His Pro Glu Ala Ser Glu Ala Gly Phe Glu Ala
1145 1150 1155

Leu Arg Phe Ile Met Ser Glu Gly Ala His Leu Leu Pro Ser Asn
1160 1165 1170

Tyr Glu Leu Cys Leu Asp Ala Ala Ser His Phe Ala Glu Ser Arg
1175 1180 1185

Val Gly Glu Val Asp Arg Ser Ile Ser Ala Ile Asp Leu Met Ser
1190 1195 1200

Asn Ser Val Phe Cys Leu Ala Arg Trp Ser Gln Glu Ala Lys Asn
1205 1210 1215

Ser Ile Gly Glu Thr Asp Ala Met Met Lys Leu Ser Glu Asp Ile
1220 1225 1230

```
Gly Lys  Met Trp Leu Lys Leu  Val Lys Asn Leu Lys  Lys Val Cys
    1235                 1240                 1245

Leu Asp  Gln Arg Asp Glu Val  Arg Asn His Ala Ile  Ser Met Leu
    1250                 1255                 1260

Gln Arg  Ala Ile Ala Gly Ala  Asp Gly Ile Met Leu  Pro Gln Pro
    1265                 1270                 1275

Leu Trp  Phe Gln Cys Phe Asp  Ser Ala Val Phe Ile  Leu Leu Asp
    1280                 1285                 1290

Asp Val  Leu Thr Phe Ser Ile  Glu Asn Ser Arg Lys  Thr Leu Lys
    1295                 1300                 1305

Lys Thr  Val Glu Glu Thr Leu  Val Leu Ala Thr Lys  Leu Met Ser
    1310                 1315                 1320

Lys Ala  Phe Leu Gln Ser Leu  Gln Asp Ile Ser Gln  Gln Pro Ser
    1325                 1330                 1335

Phe Cys  Arg Leu Trp Val Gly  Val Leu Asn Arg Leu  Glu Thr Tyr
    1340                 1345                 1350

Met Ser  Thr Glu Phe Arg Gly  Lys Arg Ser Glu Lys  Val Asn Glu
    1355                 1360                 1365

Leu Ile  Pro Glu Leu Leu Lys  Asn Thr Leu Leu Val  Met Lys Ala
    1370                 1375                 1380

Thr Gly  Val Leu Leu Pro Gly  Asp Asp Ile Gly Ser  Asp Ser Phe
    1385                 1390                 1395

Trp Gln  Leu Thr Trp Leu His  Val Asn Lys Ile Ser  Pro Ser Leu
    1400                 1405                 1410

Gln Ser  Glu Val Phe Pro Gln  Glu Glu Leu Asp Gln  Phe Gln Arg
    1415                 1420                 1425

Arg Asn  Ala Lys Pro Glu Asp  Pro Pro Val Pro Gly  Asn Glu Val
    1430                 1435                 1440


<210> SEQ ID NO 33
<211> LENGTH: 1375
<212> TYPE: PRT
<213> ORGANISM: Arabidopsis thaliana

<400> SEQUENCE: 33

Met Asp Arg Ile Ala Val Arg Ala Lys Arg Lys Glu Leu Gly Ile Ser
1               5                   10                  15

Cys Met Leu Asn Thr Glu Val Gly Ala Val Leu Ala Val Ile Arg Arg
            20                  25                  30

Pro Leu Ser Glu Ser Tyr Leu Ser Pro Gln Glu Thr Asp His Cys Asp
        35                  40                  45

Ser Ser Val Gln Gln Ser Leu Lys Ser Leu Arg Ala Leu Ile Phe Asn
    50                  55                  60

Pro Gln Gln Asp Trp Arg Thr Ile Asp Pro Ser Val Tyr Leu Ser Pro
65                  70                  75                  80

Phe Leu Glu Val Ile Gln Ser Asp Glu Ile Pro Ala Ser Ala Thr Ala
                85                  90                  95

Val Ala Leu Ser Ser Ile Leu Lys Ile Leu Lys Ile Glu Ile Phe Asp
            100                 105                 110

Glu Lys Thr Pro Gly Ala Lys Asp Ala Met Asn Ser Ile Val Ser Gly
        115                 120                 125

Ile Thr Ser Cys Arg Leu Glu Lys Thr Asp Leu Val Ser Glu Asp Ala
    130                 135                 140

Val Met Met Arg Ile Leu Gln Val Leu Thr Gly Ile Met Lys His Pro
145                 150                 155                 160
```

```
Ser Ser Glu Leu Leu Glu Asp Gln Ala Val Cys Thr Ile Val Asn Thr
                165                 170                 175

Cys Phe Gln Val Val Gln Gln Ser Thr Gly Arg Gly Asp Leu Leu Gln
            180                 185                 190

Arg Asn Gly Arg Tyr Thr Met His Glu Leu Ile Gln Ile Ile Phe Ser
        195                 200                 205

Arg Leu Pro Asp Phe Glu Val Arg Gly Asp Glu Gly Gly Glu Asp Ser
    210                 215                 220

Glu Ser Asp Thr Asp Glu Ile Asp Met Ser Gly Gly Tyr Gly Ile Arg
225                 230                 235                 240

Cys Cys Ile Asp Ile Phe His Phe Leu Cys Ser Leu Leu Asn Val Val
                245                 250                 255

Glu Val Val Glu Asn Leu Glu Gly Thr Asn Val His Thr Ala Asp Glu
            260                 265                 270

Asp Val Gln Ile Phe Ala Leu Val Leu Ile Asn Ser Ala Ile Glu Leu
        275                 280                 285

Ser Gly Asp Ala Ile Gly Gln His Pro Lys Leu Leu Arg Met Val Gln
    290                 295                 300

Asp Asp Leu Phe His His Leu Ile His Tyr Gly Ala Ser Ser Ser Pro
305                 310                 315                 320

Leu Val Leu Ser Met Ile Cys Ser Cys Ile Leu Asn Ile Tyr His Phe
                325                 330                 335

Leu Arg Lys Phe Met Arg Leu Gln Leu Glu Ala Phe Phe Ser Phe Val
            340                 345                 350

Leu Leu Arg Val Thr Ala Phe Thr Gly Phe Leu Pro Leu Gln Glu Val
        355                 360                 365

Ala Leu Glu Gly Leu Ile Asn Phe Cys Arg Gln Pro Ala Phe Ile Val
    370                 375                 380

Glu Ala Tyr Val Asn Tyr Asp Cys Asp Pro Met Cys Arg Asn Ile Phe
385                 390                 395                 400

Glu Glu Thr Gly Lys Val Leu Cys Arg His Thr Phe Pro Thr Ser Gly
                405                 410                 415

Pro Leu Thr Ser Ile Gln Ile Gln Ala Phe Glu Gly Leu Val Ile Leu
            420                 425                 430

Ile His Asn Ile Ala Asp Asn Met Asp Arg Glu Glu Asp Glu Gly Asn
        435                 440                 445

Glu Glu Asp Asp Asn Asn Ser Asn Val Ile Lys Pro Ser Pro Val Glu
    450                 455                 460

Ile His Glu Tyr Ile Pro Phe Trp Ile Asp Lys Pro Lys Glu Asp Phe
465                 470                 475                 480

Glu Thr Trp Val Asp His Ile Arg Val Arg Lys Ala Gln Lys Arg Lys
                485                 490                 495

Leu Ala Ile Ala Ala Asn His Phe Asn Arg Asp Glu Lys Lys Gly Leu
            500                 505                 510

Glu Tyr Leu Lys Tyr Asn Tyr Leu Val Ser Asp Pro Leu Asp Pro Met
        515                 520                 525

Ala Leu Ala Ser Phe Phe Arg Phe Thr Pro Gly Leu Asp Lys Thr Met
    530                 535                 540

Ile Gly Asp Tyr Leu Gly Asp Pro Asp Glu Leu His Leu Ser Val Leu
545                 550                 555                 560

Arg Ser Phe Thr His Thr Phe Glu Phe Thr Gly Met Asn Leu Asp Thr
                565                 570                 575

Ala Leu Arg Thr Phe Leu Glu Ser Phe Arg Leu Pro Gly Glu Ser Gln
```

```
            580                 585                 590

Lys Ile Glu Arg Met Ile Glu Ala Phe Ser Glu Arg Phe Tyr Asp Gln
        595                 600                 605

Gln Ser Ser Asp Ile Phe Ala Ser Lys Asp Thr Val His Ile Leu Cys
    610                 615                 620

Tyr Ser Leu Ile Met Leu Asn Thr Asp Gln His Asn Pro Gln Val Arg
625                 630                 635                 640

Arg Lys Met Thr Glu Asp Glu Phe Ile Arg Asn Asn Arg Ala Ile Asn
                645                 650                 655

Ala Gly Asn Asp Leu Pro Lys Glu Tyr Leu Ser Glu Leu Phe Gln Ser
            660                 665                 670

Ile Ala Thr Asn Ala Phe Ala Leu Ser Thr His Ser Gly Pro Val Glu
        675                 680                 685

Met Asn Pro Asn Arg Trp Ile Glu Leu Met Asn Arg Thr Lys Thr Thr
    690                 695                 700

Gln Pro Phe Ser Leu Cys Gln Phe Asp Arg Arg Ile Gly Arg Asp Met
705                 710                 715                 720

Phe Ala Thr Ile Ala Gly Pro Ser Ile Ala Ala Val Ser Ala Phe Phe
                725                 730                 735

Glu His Ser Asp Asp Asp Glu Val Leu His Glu Cys Val Asp Ala Met
            740                 745                 750

Ile Ser Ile Ala Arg Val Ala Gln Tyr Gly Leu Glu Asp Ile Leu Asp
        755                 760                 765

Glu Leu Ile Ala Ser Phe Cys Lys Phe Thr Thr Leu Leu Asn Pro Tyr
    770                 775                 780

Thr Thr Pro Glu Glu Thr Leu Phe Ala Phe Ser His Asp Met Lys Pro
785                 790                 795                 800

Arg Met Ala Thr Leu Ala Val Phe Thr Leu Ala Asn Thr Phe Gly Asp
                805                 810                 815

Ser Ile Arg Gly Gly Trp Arg Asn Ile Val Asp Cys Leu Leu Lys Leu
            820                 825                 830

Arg Lys Leu Gln Leu Leu Pro Gln Ser Val Ile Glu Phe Glu Ile Asn
        835                 840                 845

Glu Glu Asn Gly Gly Ser Glu Ser Asp Met Asn Asn Val Ser Ser Gln
    850                 855                 860

Asp Thr Lys Phe Asn Arg Arg Gln Gly Ser Ser Leu Met Gly Arg Phe
865                 870                 875                 880

Ser His Phe Leu Ala Leu Asp Asn Val Glu Glu Ser Val Ala Leu Gly
                885                 890                 895

Met Ser Glu Phe Glu Gln Asn Leu Lys Val Ile Lys Gln Cys Arg Ile
            900                 905                 910

Gly Gln Ile Phe Ser Lys Ser Ser Val Leu Pro Asp Val Ala Val Leu
        915                 920                 925

Asn Leu Gly Arg Ser Leu Ile Tyr Ala Ala Ala Gly Lys Gly Gln Lys
    930                 935                 940

Phe Ser Thr Ala Ile Glu Glu Glu Glu Thr Val Lys Phe Cys Trp Asp
945                 950                 955                 960

Leu Ile Ile Thr Ile Ala Leu Ser Asn Val His Arg Phe Asn Met Phe
                965                 970                 975

Trp Pro Ser Tyr His Glu Tyr Leu Leu Asn Val Ala Asn Phe Pro Leu
            980                 985                 990

Phe Ser Pro Ile Pro Phe Val Glu  Lys Gly Leu Pro Gly  Leu Phe Arg
        995                 1000                1005
```

```
Val Cys  Ile Lys Ile Leu Ala  Ser Asn Leu Gln Asp  His Leu Pro
    1010                 1015                 1020

Glu Glu  Leu Ile Phe Arg Ser  Leu Thr Ile Met Trp  Lys Ile Asp
    1025                 1030                 1035

Lys Glu  Ile Ile Glu Thr Cys  Tyr Asp Thr Ile Thr  Glu Phe Val
    1040                 1045                 1050

Ser Lys  Ile Ile Ile Asp Tyr  Ser Ala Asn Leu His  Thr Asn Ile
    1055                 1060                 1065

Gly Trp  Lys Ser Val Leu Gln  Leu Leu Ser Leu Cys  Gly Arg His
    1070                 1075                 1080

Pro Glu  Thr Lys Glu Gln Ala  Val Asp Ala Leu Ile  Gly Leu Met
    1085                 1090                 1095

Ser Phe  Asn Ala Ser His Leu  Ser Gln Ser Ser Tyr  Ala Tyr Cys
    1100                 1105                 1110

Ile Asp  Cys Ala Phe Ser Phe  Val Ala Leu Arg Asn  Ser Ser Val
    1115                 1120                 1125

Glu Lys  Asn Leu Lys Ile Leu  Asp Leu Met Ala Asp  Ser Val Thr
    1130                 1135                 1140

Met Leu  Val Lys Trp Tyr Lys  Thr Ala Ser Thr Asp  Thr Ala Asn
    1145                 1150                 1155

Ser Tyr  Ser Pro Ala Ser Asn  Thr Ser Ser Ser Ser  Ser Met Glu
    1160                 1165                 1170

Glu Asn  Asn Leu Arg Gly Val  Asn Phe Val His His  Leu Phe Leu
    1175                 1180                 1185

Lys Leu  Ser Glu Ala Phe Arg  Lys Thr Thr Leu Ala  Arg Arg Glu
    1190                 1195                 1200

Glu Ile  Arg Asn Arg Ala Val  Thr Ser Leu Glu Lys  Ser Phe Thr
    1205                 1210                 1215

Met Gly  His Glu Asp Leu Gly  Phe Thr Pro Ser Gly  Cys Ile Tyr
    1220                 1225                 1230

Cys Ile  Asp His Val Ile Phe  Pro Thr Ile Asp Asp  Leu His Glu
    1235                 1240                 1245

Lys Leu  Leu Asp Tyr Ser Arg  Arg Glu Asn Ala Glu  Arg Glu Met
    1250                 1255                 1260

Arg Ser  Met Glu Gly Thr Leu  Lys Ile Ala Met Lys  Val Leu Met
    1265                 1270                 1275

Asn Val  Phe Leu Val Tyr Leu  Glu Gln Ile Val Glu  Ser Ala Glu
    1280                 1285                 1290

Phe Arg  Thr Phe Trp Leu Gly  Val Leu Arg Arg Met  Asp Thr Cys
    1295                 1300                 1305

Met Lys  Ala Asp Leu Gly Glu  Tyr Gly Asp Asn Lys  Leu Gln Glu
    1310                 1315                 1320

Val Val  Pro Glu Leu Leu Thr  Thr Met Ile Gly Thr  Met Lys Glu
    1325                 1330                 1335

Lys Glu  Ile Leu Val Gln Lys  Glu Asp Asp Asp Leu  Trp Glu Ile
    1340                 1345                 1350

Thr Tyr  Ile Gln Ile Gln Trp  Ile Ala Pro Ala Leu  Lys Asp Glu
    1355                 1360                 1365

Leu Phe  Pro Asp Glu Glu Ile
    1370                 1375
```

<210> SEQ ID NO 34
<211> LENGTH: 712
<212> TYPE: PRT
<213> ORGANISM: Pseudomonas syringae pv. tomato str. DC3000

<400> SEQUENCE: 34

Met Ile Ser Ser Arg Ile Gly Gly Ala Gly Gly Val Glu Leu Ser Arg
1               5                   10                  15

Val Asn Gln Gln His Asp Thr Val Pro Ala Gln Thr Ala His Pro Asn
            20                  25                  30

Ala Val Thr Ala Gly Met Asn Pro Pro Leu Thr Pro Asp Gln Ser Gly
        35                  40                  45

Ser His Ala Thr Glu Ser Ser Ser Ala Gly Ala Ala Arg Leu Asn Val
    50                  55                  60

Ala Ala Arg His Thr Gln Leu Leu Gln Ala Phe Lys Ala Glu His Gly
65                  70                  75                  80

Thr Ala Pro Val Ser Gly Ala Pro Met Ile Ser Ser Arg Ala Ala Leu
                85                  90                  95

Leu Ile Gly Ser Leu Leu Gln Ala Glu Pro Leu Pro Phe Glu Val Met
            100                 105                 110

Ala Glu Lys Leu Ser Pro Glu Arg Tyr Gln Leu Lys Gln Phe Gln Gly
        115                 120                 125

Ser Asp Leu Gln Gln Arg Leu Glu Lys Phe Ala Gln Pro Gly Gln Ile
    130                 135                 140

Pro Asp Lys Ala Glu Val Gly Gln Leu Ile Lys Gly Phe Ala Gln Ser
145                 150                 155                 160

Val Ala Asp Gln Leu Glu His Phe Gln Leu Met His Asp Ala Ser Pro
                165                 170                 175

Ala Thr Val Gly Gln His Ala Lys Ala Asp Lys Ala Thr Leu Ala Val
            180                 185                 190

Ser Gln Thr Ala Leu Gly Glu Tyr Ala Gly Arg Ala Ser Lys Ala Ile
        195                 200                 205

Gly Glu Gly Leu Ser Asn Ser Ile Ala Ser Leu Asp Glu His Ile Ser
    210                 215                 220

Ala Leu Asp Leu Thr Leu Gln Asp Ala Glu Gln Gly Asn Lys Glu Ser
225                 230                 235                 240

Leu His Ala Asp Arg Gln Ala Leu Val Asp Ala Lys Thr Thr Leu Val
                245                 250                 255

Gly Leu His Ala Asp Phe Val Lys Ser Pro Glu Ala Lys Arg Leu Ala
            260                 265                 270

Ser Val Ala Ala His Thr Gln Leu Asp Asn Val Val Ser Asp Leu Val
        275                 280                 285

Thr Ala Arg Asn Thr Val Gly Gly Trp Lys Gly Ala Gly Pro Ile Val
    290                 295                 300

Ala Ala Ala Val Pro Gln Phe Leu Ser Ser Met Thr His Leu Gly Tyr
305                 310                 315                 320

Val Arg Leu Ser Thr Ser Asp Lys Leu Arg Asp Thr Ile Pro Glu Thr
                325                 330                 335

Ser Ser Asp Ala Asn Met Leu Lys Ala Ser Ile Ile Gly Met Val Ala
            340                 345                 350

Gly Ile Ala His Glu Thr Val Asn Ser Val Val Lys Pro Met Phe Gln
        355                 360                 365

Ala Ala Leu Gln Lys Thr Gly Leu Asn Glu Arg Leu Asn Met Val Pro
    370                 375                 380

Met Lys Ala Val Asp Thr Asn Thr Val Ile Pro Asp Pro Phe Glu Leu
385                 390                 395                 400

Lys Ser Glu His Gly Glu Leu Val Lys Lys Thr Pro Glu Glu Val Ala
                405                 410                 415

```
Gln Asp Lys Ala Phe Val Lys Ser Glu Arg Ala Leu Leu Asn Gln Lys
            420                 425                 430

Lys Val Gln Gly Ser Ser Thr His Pro Val Gly Glu Leu Met Ala Tyr
        435                 440                 445

Ser Ala Phe Gly Gly Ser Gln Ala Val Arg Gln Met Leu Asn Asp Val
    450                 455                 460

His Gln Ile Asn Gly Gln Thr Leu Ser Ala Arg Ala Leu Ala Ser Gly
465                 470                 475                 480

Phe Gly Gly Ala Val Ser Ala Ser Ser Gln Thr Leu Leu Gln Leu Lys
                485                 490                 495

Ser Asn Tyr Val Asp Pro Gln Gly Arg Lys Ile Pro Val Phe Thr Pro
            500                 505                 510

Asp Arg Ala Glu Ser Asp Leu Lys Lys Asp Leu Leu Lys Gly Met Asp
        515                 520                 525

Leu Arg Glu Pro Ser Val Arg Thr Thr Phe Tyr Ser Lys Ala Leu Ser
    530                 535                 540

Gly Ile Gln Ser Ser Ala Leu Thr Ser Ala Leu Pro Pro Val Thr Ala
545                 550                 555                 560

Gln Ala Glu Gly Ala Ser Gly Thr Leu Ser Ala Gly Ala Ile Leu Arg
                565                 570                 575

Asn Met Ala Leu Ala Ala Thr Gly Ser Val Ser Tyr Leu Ser Thr Leu
            580                 585                 590

Tyr Thr Asn Gln Ser Val Thr Ala Glu Ala Lys Ala Leu Lys Ala Ala
        595                 600                 605

Gly Met Gly Gly Ala Thr Pro Met Leu Asp Arg Thr Glu Thr Ala Leu
    610                 615                 620

Asn Asn Ile Arg His Pro Asn Arg Glu Ser Leu Pro His Thr Phe Gln
625                 630                 635                 640

Lys Ser Thr Leu Ser Gly Ile Pro Arg Val Ala Glu Asn Ala Tyr His
                645                 650                 655

Met Gly Arg Gly Ala Leu Gln Leu Pro Thr Gln Met Ala Val Asp Thr
            660                 665                 670

Val Arg Val Val Asp Glu Gly Val Leu Asn Ala Val Ala Ser Ala Arg
        675                 680                 685

Glu Ala Leu Lys Gln Pro Thr Lys Asp Asp Asp Ala Leu Arg Ala Leu
    690                 695                 700

Glu Glu Gly Leu Leu Asp Pro Arg
705                 710
```

<210> SEQ ID NO 35
<211> LENGTH: 2139
<212> TYPE: DNA
<213> ORGANISM: Pseudomonas syringae pv. tomato str. DC3000

<400> SEQUENCE: 35

```
atgatcagtt cgcggatcgg cggggccggt ggcgtcgaac tcagccgggt aaaccagcag     60

cacgatactg ttcccgccca gacagctcac ccaaatgcag tcactgcagg catgaatccg    120

ccgctgactc ccgatcagtc agggtcacac gcgacagaaa gctcgtctgc cggcgcggcg    180

cggctgaatg tcgcggctcg acacacacag cttttgcagg ccttcaaggc tgagcatggg    240

acggctccgg tcagcggcgc gccgatgatc agttcgcgtg ctgcgttgtt gatcggtagt    300

ctgctgcagg ccgagccttt gccttttgaa gtcatggccg agaaattgtc tcctgagcgc    360

tatcaactga agcagtttca gggctcggac ttgcagcagc ggctggaaaa attcgcccag    420
```

-continued

```
ccgggtcaga taccggataa agccgaggtc gggcaactga tcaagggttt tgctcagtcg    480

gtcgctgatc aactggagca ctttcaactg atgcatgacg cttcgcccgc aacggtaggc    540

cagcatgcaa aagcggacaa ggcgacgctt gccgtcagtc agactgccct tggcgaatac    600

gccggtcgtg caagcaaggc aatcggcgaa ggcctgagca acagcatcgc gtcgctggat    660

gagcacatca gtgcgctgga tctcactctg caagatgccg aacagggcaa caaggagtct    720

ctgcacgctg acaggcaggc gctggtcgac gccaaaacca ccctggtagg tttgcacgcc    780

gatttcgtca agtcgccgga ggccaagcgc cttgcttcgg tcgccgcaca tacgcaactg    840

gacaacgtcg tcagcgatct cgtcactgcc cgtaacacgg tgggtggctg gaaaggtgca    900

gggccgattg tcgcggctgc ggttccgcag ttcttgtctt caatgacaca cttgggttat    960

gtgcgtttgt ccaccagcga caagctgcga gacacgattc ccgagaccag cagcgacgcc   1020

aacatgctca aggcttcgat aatcgggatg gtggcgggca ttgctcacga gacggtcaac   1080

agcgtggtca agccgatgtt tcaggccgcc ttgcagaaga ctggcctcaa cgaacgcctg   1140

aacatggtgc caatgaaggc tgtggatacc aatacggtta ttcctgaccc cttcgagctg   1200

aaaagcgaac acggtgagct ggtcaaaaaa acgcccgagg aagtcgctca ggacaaggcg   1260

ttcgtgaaaa gtgaacgcgc gctgctgaac cagaagaagg ttcagggttc gtccacccat   1320

ccggtaggtg agctgatggc ttacagtgcc ttcggtggtt ctcaggctgt gcgccagatg   1380

ctcaacgatg ttcaccagat caatgggcag acgctgagtg caagagctct ggcatccggt   1440

tttggcgggg cggtgtctgc cagttcgcaa acgctgctgc aattgaagtc gaattatgtc   1500

gacccgcaag ggcgcaaaat tccggtattt accccggacc gcgccgagag cgatctgaaa   1560

aaggacctgc tcaaaggtat ggacctgcgc gagccgtcgg tacgcaccac gttctacagc   1620

aaggctcttt cgggtattca gagttctgca ctgacctcgg cactgccgcc tgtgaccgct   1680

caggctgaag gcgcaagtgg cacgctcagt gcgggggcta ttttgcgcaa catggccctg   1740

gcagcgacgg gttcggtgtc ctatctgtcc acgttgtaca ccaaccagtc ggttaccgca   1800

gaagccaagg cgttgaaagc ggcaggcatg ggcggtgcaa cacctatgct ggaccgtacc   1860

gagacggctt tgaataacat ccgtcatccg aacagggagt ctctgccaca tacgttccag   1920

aagagcacgt tgagcggtat cccacgagtc gcggaaaacg cctatcacat gggacgaggc   1980

gcattgcagt tgcctaccca gatggccgtg gatacggttc gggtcgtgga tgaaggtgtg   2040

ttgaacgcag tcgcgtcagc acgcgaggcg cttaagcagc cgacaaaaga cgatgacgca   2100

ttgagggcac ttgaagaggg cttgcttgac ccgcgttaa                           2139
```

<210> SEQ ID NO 36
<211> LENGTH: 718
<212> TYPE: PRT
<213> ORGANISM: Pseudomonas syringae pv. syringae B728a

<400> SEQUENCE: 36

```
Met Ile Gly Thr Arg Val Gly Gly Ser Gly Ser Thr Glu Ile Val Gln
1               5                   10                  15

Ala Asn Gln Pro Gln Pro Ser Ala Ala Val Ala Gln Ala His Pro His
            20                  25                  30

Ala Val Ser Pro Ser Ser Asn Pro Pro Leu Thr Ala Ser Gln Ser Ala
        35                  40                  45

Ala Gln Ala Pro Glu Ser Ser Ala Ala Gly Ala Ala Arg Leu Pro Val
    50                  55                  60

Ala Pro Arg His Leu Pro Thr Leu Glu Lys Phe Arg Ala Glu Gln Pro
65                  70                  75                  80
```

```
Thr Val Gln Gly Thr Ser Thr Pro Thr Ile Ser Ala Asn Ala Ala Leu
                85                  90                  95

Leu Ile Gly Ser Leu Leu Gln Ser Glu Lys Leu Pro Phe Glu Val Met
            100                 105                 110

Ala Ala Arg Leu Ser Pro Glu Arg Tyr Ala Leu Gln Gln Phe His Gly
        115                 120                 125

Ser Asp Leu Gln Gln Met Leu Gly Arg Phe Ala Glu Pro Gly His Leu
    130                 135                 140

Pro Gly Lys Ala Glu Thr Glu Gln Leu Ile Lys Gly Phe Ala Arg Ser
145                 150                 155                 160

Leu Ala Asp Gln Leu Glu His Phe Gln Leu Met His Asp Ala Thr Ala
                165                 170                 175

Glu Ala Phe Gly Pro Gly Gly Leu Arg Asp Arg Asn Thr Leu Ala Val
            180                 185                 190

Ser Gln Ala Ala Leu Gly Glu Tyr Ala Gly Arg Ala Ser Lys Ser Ile
        195                 200                 205

Glu Ala Gly Leu Asn His Ser Leu Ala Val Leu Asp Glu Arg Ile Ala
    210                 215                 220

Ala Leu Asp Ser Gln Leu Glu Gly Ala Thr Glu Asp Ser Arg Pro Val
225                 230                 235                 240

Leu Leu Met Asp Arg Gln Ala Leu Glu Thr Ala Arg Ala Met Leu Ser
                245                 250                 255

Asp Leu His Val Asp Phe Cys Lys Ser Pro Glu Ala Lys Arg Leu Ser
            260                 265                 270

Ala Val Ala Ala His Thr Gln Met Asp Ala Leu Ile Asp Lys Leu Asn
        275                 280                 285

Val Asp Arg Ser Ser Val Gly Gly Trp Lys Gly Ile Gly Pro Ile Val
    290                 295                 300

Ala Ala Ala Val Pro Gln Phe Met Val Ser Met Leu His Leu Gly Tyr
305                 310                 315                 320

Ile Arg Thr Ala Thr Ser Asp Ala Met Lys Asp Ala Val Pro Glu Lys
                325                 330                 335

Ser Ala Asp Ala Ser Met Lys Arg Ala Leu Ala Val Gly Leu Thr Ala
            340                 345                 350

Gly Val Ala His Glu Gly Val Thr Asn Leu Leu Lys Pro Met Val Gln
        355                 360                 365

Ala Gly Phe Gln Lys Ala Gly Leu Asn Glu Arg Leu Asn Met Val Pro
    370                 375                 380

Leu Lys Gly Ile Asp Thr Asp Ser Val Ile Pro Asp Pro Phe Glu Leu
385                 390                 395                 400

Lys Asn Asp Asn Gly Ala Leu Val Arg Lys Thr Pro Glu Glu Ala Ala
                405                 410                 415

Glu Asp Lys Ala Phe Val Ala Ser Glu Arg Ala Val Leu Asn Gln Lys
            420                 425                 430

Lys Val Gln Val Ser Ser Thr His Pro Leu Gly Glu Met Ile Pro Tyr
        435                 440                 445

Gly Ala Phe Gly Gly Gly Gln Ala Val Arg Gln Met Leu Asn Asp Phe
    450                 455                 460

Asn Leu Leu Asn Gly Gln Thr Leu Ser Ala Arg Ala Val Thr Ser Gly
465                 470                 475                 480

Ile Ala Gly Ala Ile Ser Ala Thr Thr Gln Thr Ile Ala Gln Leu Asn
                485                 490                 495

Ser Thr Tyr Val Asp Pro Arg Gly Arg Lys Ile Pro Val Phe Thr Pro
```

```
            500                 505                 510

Asp Arg Ala Asn Ala Asp Leu Gly Lys Asp Leu Ala Lys Gly Leu Asp
        515                 520                 525

Leu Arg Glu Pro Ala Val Arg Thr Ala Phe Tyr Ser Lys Ala Val Ser
    530                 535                 540

Gly Val Gln Ser Ala Ala Leu Asn Gly Ala Leu Pro Ser Val Ala Val
545                 550                 555                 560

Gln Pro Gln Gly Ala Ser Gly Thr Leu Ser Ala Gly Asn Ile Met Arg
                565                 570                 575

Asn Met Ala Leu Ala Ala Thr Gly Ser Val Ser Tyr Leu Ser Thr Leu
            580                 585                 590

Tyr Ala Asn Gln Ser Val Thr Ala Glu Ala Lys Ala Leu Lys Glu Ala
        595                 600                 605

Gly Met Gly Gly Ala Thr Pro Met Val Ala Arg Thr Glu Thr Ala Leu
    610                 615                 620

Ser Asn Ile Arg His Pro Asp Arg Ala Ser Leu Pro His Thr Phe Gln
625                 630                 635                 640

Pro Asp Thr Leu Gly Gly Val Pro Arg Ala Val Glu Asn Ala Tyr His
                645                 650                 655

Met Ala Arg Gly Ala Leu Gln Leu Pro Thr Gln Val Val Val Asp Thr
            660                 665                 670

Val Arg Val Val Glu Asp Gly Val Ala Ser Gly Val Ser Ser Leu Arg
        675                 680                 685

Asp Ala His Lys Pro Ala Glu Thr Ser Ser Pro Thr Ala Asp Asp Ala
    690                 695                 700

Ala Ala Val Glu Leu Thr Ala Met Glu Glu Gly Arg Arg Arg
705                 710                 715


<210> SEQ ID NO 37
<211> LENGTH: 2157
<212> TYPE: DNA
<213> ORGANISM: Pseudomonas syringae pv. syringae B728a

<400> SEQUENCE: 37

atgattggca cacgagtcgg cggatcaggc agtaccgaaa tcgttcaggc gaaccagccg      60

cagccgtctg ccgctgtcgc ccaggctcat ccacacgcgg taagcccgag cagcaacccg     120

ccgctgaccg ccagccagtc ggccgcgcaa gcgccggaaa gctcggcggc cggtgccgct     180

cgcctgccag tcgcgccgcg acatctgccg acattggaga agtttcgtgc cgaacagccc     240

accgtacaag gcacttccac gccgactatc agcgctaacg cggccctgct gatcggcagt     300

ctgttgcagt ctgaaaaact gcccttcgag gtcatggccg cccgtttgtc gcctgagcgt     360

tatgcgttgc agcagtttca cggctccgat ttacagcaaa tgctcggacg attcgctgag     420

ccagggcatc tgccaggcaa ggccgagacc gaacaactga tcaagggctt tgcccggtcg     480

ctcgcagacc agctggagca cttccagctc atgcatgacg cgacggctga ggcattcggc     540

cccggagggc tgcgcgaccg caacacactg gcggtcagtc aagcggcgct tggcgaatac     600

gccggtcggg cgagtaaatc catcgaagcg gggctgaacc acagtctcgc ggtgctggac     660

gagcgcatcg ccgcgctgga cagccagttg gagggcgcca ctgaggacag cagaccggtt     720

ttgctgatgg acaggcaggc gctggaaacg gccagggcga tgctgagcga cctgcacgtc     780

gacttctgca aatcgcctga agccaagcgg ttgagtgccg ttgccgctca cacgcaaatg     840

gatgctctga tcgacaagct gaacgttgat cgcagctcgg tcggcggctg gaaggggatc     900

ggtccgatcg tcgcggcagc ggtgccgcag tttatggtgt ccatgctcca cctggggtat     960
```

```
atccgcacgg ccaccagtga cgcgatgaaa gatgccgttc ccgaaaaaag cgccgacgcc   1020

agcatgaaga gggccctggc cgtaggactg actgccgggg tggctcacga gggcgttacc   1080

aacctcttga agccgatggt gcaggccggg tttcagaaag ccggcctcaa cgagcggctg   1140

aatatggtgc cgctcaaggg tattgatacc gactcggtga ttcccgaccc tttcgagttg   1200

aagaacgaca acggcgcact ggtcagaaaa acgcctgagg aagccgctga ggacaaagcc   1260

ttcgtcgcaa gcgagcgagc ggttttgaat cagaaaaagg ttcaggtttc gtctacccat   1320

ccactgggtg agatgatccc ctacggcgcc tttggtggcg ggcaggcggt acgccagatg   1380

ctcaatgatt tcaatctgct caatggccag accctgtcgg ccagagcggt gacctccggg   1440

atcgccgggg ccatatcagc caccacccag accattgcac agctgaactc gacctatgtc   1500

gatccgcgcg ggcgcaagat cccggtcttc accccggacc gcgccaatgc cgacctgggc   1560

aaggacctgg ccaaaggcct ggaccttcgc gaaccggcgg tacgcaccgc gttctacagc   1620

aaggctgttt caggtgtgca gagcgcagcg ctgaacggcg cgctaccatc ggttgccgtc   1680

cagccccaag gtgcatccgg cacgctcagc gcggggaata tcatgcgcaa catggcgctg   1740

gcggcaaccg gttcggtgtc ttacctgtcg accctgtatg ccaaccagtc ggtcacggcc   1800

gaggccaagg ccctgaaaga ggcgggcatg ggcggcgcaa cgccaatggt agctcgcact   1860

gaaaccgccc tgagcaacat ccgccatccg gacagagctt cactgccgca tacgttccag   1920

ccggataccc tgggtggcgt ccccagggcc gtggaaaacg cctatcacat ggcccggggc   1980

gcgctgcaat taccgaccca ggtggtggtc gatacggtgc gtgtcgtgga agacggcgta   2040

gcaagcgggg tgtcctcgtt gcgcgatgca cataaaccag cggaaacatc atcgccaaca   2100

gctgatgacg ccgctgctgt cgaactgacg gcgatggagg agggccgccg acgctga      2157
```

<210> SEQ ID NO 38
<211> LENGTH: 826
<212> TYPE: PRT
<213> ORGANISM: Pseudomonas viridiflava

<400> SEQUENCE: 38

```
Met Ile Asn Ser Arg Val Gly Gly Ser Gly Asp Ile Gln Met Val Ala
1               5                   10                  15

Val Arg Thr Glu Glu Gly Asn Pro Ser Ile Thr Ser Ala His Pro Asn
            20                  25                  30

Ala Val Thr Pro Ser Asn Asn Pro Pro Leu Leu Pro Arg Gln Met Gly
        35                  40                  45

Gln His Leu Glu Pro Ser Leu Glu Ser His Ala Ala Asn Leu Gly Ile
    50                  55                  60

Ala Leu Arg His Thr Glu Leu Leu Ala Thr Phe Gln Ala Glu Gln Ala
65                  70                  75                  80

Ser Thr Arg Ser Thr Asp Ala Pro Gln Val Ser Ala His Ala Ala Leu
                85                  90                  95

Leu Ile Gly Gly Met Leu Glu Glu Ala Asn Gly His Ala Ser Glu Thr
            100                 105                 110

Gly Lys Val Gly Phe Glu Val Met Ala Glu Arg Leu Cys Gly Pro His
        115                 120                 125

Leu Ala Leu Glu Ser Phe Gln Ser Ser Asp Val Lys Leu Leu Leu Glu
    130                 135                 140

Lys Leu Thr Asn Lys Asp Glu Ile Pro Asp Lys Ala Glu Val Gly Gln
145                 150                 155                 160

Leu Leu Lys Gly His Ala Gly Ala Ile Ala Asp Gln Leu Glu His Phe
```

-continued

```
                165                 170                 175

Gln Leu Met His Asn Ala Ser Ser Val His Gln Gly Glu Cys Ser Ala
            180                 185                 190

Pro Asp Arg Lys Thr Phe Glu Val Ser Gln Ala Ala Leu Gly Glu Tyr
        195                 200                 205

Ala Gly Arg Ala Ser Lys Ala Ile Ser Ser Val Leu Ser Glu Lys Thr
    210                 215                 220

Ala Asp Leu Asp Lys Arg Leu Ala Asp Val Asp Lys Gln Leu Glu Gly
225                 230                 235                 240

Met Ala Glu Gly Gly Glu Lys Ser Arg Leu Leu Thr Gln Lys Glu Thr
                245                 250                 255

Leu Gly Glu Ala Lys Thr Met Leu Ala Asp Ile Gln Asn Asp Phe Ser
            260                 265                 270

Lys Ser Pro Gln Ala Lys His Leu Lys Ser Val Ala Ala His Ala Arg
        275                 280                 285

Phe Asp Ala Gln Leu Lys Glu Leu Asn Ala Asp Arg Ala Gly Met Gly
    290                 295                 300

Phe Leu Gln Gly Ser Gly Arg Val Ile Ala Ala Ala Ile Pro Gln Phe
305                 310                 315                 320

Leu Ser Ser Met Thr His Leu Gly Phe Ile Arg Ser Ala Thr Asn Asp
                325                 330                 335

Glu Phe Arg Ala Ala Val Pro Gly Ser Ser Ser Asp Ala Ser Met Leu
            340                 345                 350

Glu Ala Thr Val Ile Gly Leu Val Ala Gly Ile Ala His Glu Gly Val
        355                 360                 365

Thr Asn Leu Val Lys Pro Met Val Gln Ser Gly Leu Gln Ala Ser Gly
    370                 375                 380

Leu Asp Lys Arg Leu Gly Met Ala Pro Leu Lys Gly Val Asp Thr Glu
385                 390                 395                 400

Ser Val Ile Pro Asp Pro Leu Glu Phe Lys Ser Gln Asp Gly Val Met
                405                 410                 415

Val Lys Lys Ser Asp Glu Glu Leu Thr Ala Glu Lys Ala Gln Val Lys
            420                 425                 430

Ala Gln Arg Ala Val Phe Glu Gln Lys Lys Val Gln Val Ser Ser Thr
        435                 440                 445

His Pro Leu Gly Glu Leu Ile Pro Tyr Met Ser Phe Gly Gly Gly Gln
    450                 455                 460

Ala Ile Arg Gln Leu Leu His Asp Phe Asn Gln Ile Asn Gly Gln Thr
465                 470                 475                 480

Val Thr Ala Arg Ala Leu Ala Ser Gly Met Ala Gly Ala Val Ser Ala
                485                 490                 495

Ser Ala Gln Ala Leu Tyr Gln Met Lys Ala Thr Tyr Thr Asp Pro Gln
            500                 505                 510

Gly Arg Gln Ile Pro Val Phe Thr Thr Asp Lys Ala Thr Ser Glu Leu
        515                 520                 525

Gly Lys Glu Leu Ala Lys Gly Leu Asp Pro Arg Asp Ala Thr Val Arg
    530                 535                 540

Thr Ser Phe Tyr Ser Lys Ala Val Ser Gly Ile Gln Ser Ala Ala Leu
545                 550                 555                 560

Thr Ala Glu Leu Pro Ala Ile Ala Ala Ala Gly Val Asn Ser Gly Leu
                565                 570                 575

Ser Ala Gly Arg Ile Ala Gly Asn Met Ala Leu Ala Ala Leu Gly Ser
            580                 585                 590
```

-continued

```
Val Ser Tyr Leu Ser Ser Leu Tyr Ala Asn Gln Ser Val Thr Ala Glu
        595                 600                 605

Gly Lys Ala Leu Lys Ala Ala Gly Glu Gly Gly Ala Thr Pro Ile Leu
    610                 615                 620

Glu Arg Thr Glu Val Ala Phe Thr Asn Val Arg Arg Pro Asn Arg Glu
625                 630                 635                 640

Ser Leu Pro His Thr Phe Ser Ser Asp Gln Leu Val Gly Leu Pro Arg
                645                 650                 655

Met Ala Glu Asn Thr Tyr His Arg Ala Arg Gly Val Leu Gln Ala Pro
            660                 665                 670

Ser Gln Ile Ala Val Asp Val Leu Arg Ala Val Asp Asp Gly Val Arg
        675                 680                 685

Ser Ser Phe Ser Ser Leu Gln Asp Lys Leu Thr Ser Gln Phe Gln Arg
    690                 695                 700

Gln Thr Thr Ala Thr Pro Pro Pro His Glu Ala Ala Val Asp Asn Pro
705                 710                 715                 720

Val Val Thr Glu Ser Val Val Ser Pro Glu Pro Glu Pro Gly Pro Lys
                725                 730                 735

Met Met Asn Val Gln Gln Pro Arg Asn Gly Ala Ile Asp Asp Asp Ala
            740                 745                 750

Leu Arg Met Leu Glu Glu Gly Ile Leu Pro Gln Thr Thr Ser Gln Pro
        755                 760                 765

Gln Arg Thr Pro Gln Gln Gln Arg Thr Pro Gln Pro Pro Arg Thr Ala
    770                 775                 780

Gln Pro Gln Arg Ala Pro Gln Pro Arg Ala Gln Gln Ser Ala Pro Val
785                 790                 795                 800

Ala Pro Pro Tyr Asp Pro Pro Leu Glu Ala Met Glu Ala Gly Phe Leu
                805                 810                 815

Lys Pro Ala Pro Ser Asn Asp Pro Ser Arg
            820                 825


<210> SEQ ID NO 39
<211> LENGTH: 2481
<212> TYPE: DNA
<213> ORGANISM: Pseudomonas viridiflava

<400> SEQUENCE: 39

atgattaatt cacgcgtagg gggatcaggc gacatacaaa tggttgcggt gagaacggag      60

gagggtaatc cgtccattac ctctgctcac ccgaatgcgg tcactcccag caacaatccc     120

ccgttactcc caaggcaaat gggtcaacac cttgagccct ctctggagtc gcatgcggcg     180

aacctgggta tagcgttgcg ccacactgag ttgctggcga cgtttcaggc tgagcaggcg     240

agcacacgct caaccgatgc accacaggtc agtgcgcatg cggcgctatt gattggaggc     300

atgctcgaag aggccaacgg tcacgcttcc gaaaccggca aggtgggctt tgaggtcatg     360

gcagagcgct tgtgcgggcc gcaccttgcg ctggagagtt tccagtccag tgacgtcaaa     420

ctcctgctcg agaagctcac taataaggac gagataccgg acaaggcaga ggtcgggcaa     480

ctgctcaaag gccatgccgg tgcgatcgcc gatcaacttg agcattttca gctgatgcac     540

aacgcttcca gcgtgcacca aggtgaatgc tcggctcccg accgaaagac ctttgaagtc     600

agccaggctg cgttgggcga atacgctgga cgtgcgagca aagcgatttc cagcgtactg     660

agcgagaaaa ctgcagatct ggacaagcgc cttgcggacg tggacaaaca gctcgagggt     720

atggctgaag gcggggaaaa atccagactt ttgacccaga aagagacgct tggcgaagcc     780

aaaaccatgc tggccgacat tcagaacgat tttcgaaat cgcctcaggc aaagcatctg      840
```

```
aaatccgttg ctgctcatgc gcgattcgac gcgcagctca aagagctgaa cgcggatcgt    900

gccggaatgg gatttctgca aggctcggga cgggtcatag ccgctgcgat tccccagttt    960

ctttcatcaa tgacgcactt gggctttatc cgctctgcca ccaacgatga gttcagagcg   1020

gcggtgccag gctcaagcag cgacgccagt atgctggaag ccactgtgat agggctggtc   1080

gcagggatcg ctcatgaagg cgtcaccaac ctggtgaagc cgatggtgca atccggcttg   1140

caggcgtcag gccttgataa gcgcctgggc atggcgccgc tcaaaggcgt cgataccgaa   1200

tcggtgattc ctgatccgct tgaattcaag tcgcaagacg gtgtgatggt caaaaagtcc   1260

gacgaggaac tgacggccga gaaagcgcag gtcaaagcgc agcgcgcggt gtttgaacag   1320

aagaaggttc aagtgtcttc tacgcatccg ctcggcgaac tgatccccta tatgagtttt   1380

ggcggcggtc aggcaatacg ccaactgttg catgatttca atcagatcaa cggtcagacg   1440

gtcactgcca gggcgttggc ttcagggatg gccggtgcag tgtcggcctc ggctcaggcg   1500

ctttatcaga tgaaggccac ctacaccgat ccgcaagggc gacagattcc ggtattcacc   1560

accgacaaag ccaccagtga actgggcaag gaactggcca agggattgga cccgcgcgat   1620

gccaccgttc ggacttcgtt ctacagcaag gctgtttcgg gtatccagag tgctgcgttg   1680

actgcagagc tgccagcaat agcggcggct ggcgtcaata gtgggctgag tgcaggcagg   1740

atcgcgggca atatggctct ggccgcgctg ggttcggtat cttatttgtc ctcgctgtac   1800

gccaatcagt cggttacggc tgaaggaaag gcgttgaagg ccgctggcga gggcggagcg   1860

accccgattc tggagcgtac cgaagtcgcg tttaccaacg ttcgtcgtcc gaacagagag   1920

tcactcccgc atacgttctc ttctgatcag ttggtaggct tgcctcgtat ggcagagaac   1980

acctaccacc gtgccagggg cgtgttgcaa gcacccagtc aaattgctgt cgacgtgctg   2040

cgcgctgttg acgatggcgt gcgcagcagc ttctcgtcgc tgcaggataa actcacgagc   2100

cagtttcaac gccagacgac ggcgacgcca cctccccacg aagcggctgt cgacaacccg   2160

gtcgtcacag agtccgttgt atcgcctgaa cctgagccag ggccaaaaat gatgaacgtt   2220

cagcagccga gaaacggtgc gatcgacgac gacgctttac gaatgctcga agaggggatc   2280

ctgccgcaga caacgtcgca gccacagcgc acgccacagc aacaacgaac gccacagccg   2340

ccacgaacgg cgcagccaca gcgtgcgcct cagcccaggg cgcaacaatc tgctccagtc   2400

gcacctccct atgacccgcc gctggaggcc atggaagcgg gctttttaaa gccagcccca   2460

agcaatgatc cttcacgttg a                                             2481
```

<210> SEQ ID NO 40
<211> LENGTH: 53
<212> TYPE: DNA
<213> ORGANISM: Artificial Sequence
<220> FEATURE:
<223> OTHER INFORMATION: Synthetic

<400> SEQUENCE: 40

```
ggctcgagac catggggcat catcatcatc atcatatcag ttcgcggatc ggc            53
```

<210> SEQ ID NO 41
<211> LENGTH: 35
<212> TYPE: DNA
<213> ORGANISM: Artificial Sequence
<220> FEATURE:
<223> OTHER INFORMATION: Synthetic

<400> SEQUENCE: 41

```
ggactagttt aggccatgac ttcaaaaggc aaagg                                35
```

<210> SEQ ID NO 42
<211> LENGTH: 53
<212> TYPE: DNA
<213> ORGANISM: Artificial Sequence
<220> FEATURE:
<223> OTHER INFORMATION: Synthetic

<400> SEQUENCE: 42
ggctcgagac catggggcat catcatcatc atcatatcag ttcgcggatc ggc 53

<210> SEQ ID NO 43
<211> LENGTH: 33
<212> TYPE: DNA
<213> ORGANISM: Artificial Sequence
<220> FEATURE:
<223> OTHER INFORMATION: Synthetic

<400> SEQUENCE: 43
ggactagttt agctcaggcc ttcgccgatt gcc 33

<210> SEQ ID NO 44
<211> LENGTH: 53
<212> TYPE: DNA
<213> ORGANISM: Artificial Sequence
<220> FEATURE:
<223> OTHER INFORMATION: Synthetic

<400> SEQUENCE: 44
ggctcgagac catggggcat catcatcatc atcatatcag ttcgcggatc ggc 53

<210> SEQ ID NO 45
<211> LENGTH: 32
<212> TYPE: DNA
<213> ORGANISM: Artificial Sequence
<220> FEATURE:
<223> OTHER INFORMATION: Synthetic

<400> SEQUENCE: 45
ggactagttt aagacaagaa ctgcggaacc gc 32

<210> SEQ ID NO 46
<211> LENGTH: 53
<212> TYPE: DNA
<213> ORGANISM: Artificial Sequence
<220> FEATURE:
<223> OTHER INFORMATION: Synthetic

<400> SEQUENCE: 46
ggctcgagac catggggcat catcatcatc atcatatcag ttcgcggatc ggc 53

<210> SEQ ID NO 47
<211> LENGTH: 35
<212> TYPE: DNA
<213> ORGANISM: Artificial Sequence
<220> FEATURE:
<223> OTHER INFORMATION: Synthetic

<400> SEQUENCE: 47
ggactagttt actcgggcgt ttttttgacc agctc 35

<210> SEQ ID NO 48
<211> LENGTH: 53
<212> TYPE: DNA
<213> ORGANISM: Artificial Sequence
<220> FEATURE:
<223> OTHER INFORMATION: Synthetic

<400> SEQUENCE: 48
ggctcgagac catggggcat catcatcatc atcatatcag ttcgcggatc ggc 53

<210> SEQ ID NO 49
<211> LENGTH: 29
<212> TYPE: DNA
<213> ORGANISM: Artificial Sequence
<220> FEATURE:
<223> OTHER INFORMATION: Synthetic

<400> SEQUENCE: 49
ggactagttt agtccggggt aaataccgg 29

<210> SEQ ID NO 50
<211> LENGTH: 53
<212> TYPE: DNA
<213> ORGANISM: Artificial Sequence
<220> FEATURE:
<223> OTHER INFORMATION: Synthetic

<400> SEQUENCE: 50
ggctcgagac catggggcat catcatcatc atcatatcag ttcgcggatc ggc 53

<210> SEQ ID NO 51
<211> LENGTH: 32
<212> TYPE: DNA
<213> ORGANISM: Artificial Sequence
<220> FEATURE:
<223> OTHER INFORMATION: Synthetic

<400> SEQUENCE: 51
ggactagttt atgcaccgcc catgcctgcc gc 32

<210> SEQ ID NO 52
<211> LENGTH: 53
<212> TYPE: DNA
<213> ORGANISM: Artificial Sequence
<220> FEATURE:
<223> OTHER INFORMATION: Synthetic

<400> SEQUENCE: 52
ggctcgagac catggggcat catcatcatc atcatatcag ttcgcggatc ggc 53

<210> SEQ ID NO 53
<211> LENGTH: 31
<212> TYPE: DNA
<213> ORGANISM: Artificial Sequence
<220> FEATURE:
<223> OTHER INFORMATION: Synthetic

<400> SEQUENCE: 53
ggactagttt aacgcgggtc aagcagccct c 31

<210> SEQ ID NO 54
<211> LENGTH: 58
<212> TYPE: DNA
<213> ORGANISM: Artificial Sequence
<220> FEATURE:
<223> OTHER INFORMATION: Synthetic

<400> SEQUENCE: 54
ggctcgagac catggggcat catcatcatc atcatctgct gcaggccgag cctttgcc 58

<210> SEQ ID NO 55
<211> LENGTH: 32

<212> TYPE: DNA
<213> ORGANISM: Artificial Sequence
<220> FEATURE:
<223> OTHER INFORMATION: Synthetic

<400> SEQUENCE: 55
gcactagttt aacgcgggtc aagcaagccc tc 32

<210> SEQ ID NO 56
<211> LENGTH: 55
<212> TYPE: DNA
<213> ORGANISM: Artificial Sequence
<220> FEATURE:
<223> OTHER INFORMATION: Synthetic

<400> SEQUENCE: 56
ggctcgagac catggggcat catcatcatc atcatgccgg tcgtgcaagc aaggc 55

<210> SEQ ID NO 57
<211> LENGTH: 32
<212> TYPE: DNA
<213> ORGANISM: Artificial Sequence
<220> FEATURE:
<223> OTHER INFORMATION: Synthetic

<400> SEQUENCE: 57
gcactagttt aacgcgggtc aagcaagccc tc 32

<210> SEQ ID NO 58
<211> LENGTH: 56
<212> TYPE: DNA
<213> ORGANISM: Artificial Sequence
<220> FEATURE:
<223> OTHER INFORMATION: Synthetic

<400> SEQUENCE: 58
ggctcgagac catggggcat catcatcatc atcatgggcc gattgtcgcg gctgcg 56

<210> SEQ ID NO 59
<211> LENGTH: 32
<212> TYPE: DNA
<213> ORGANISM: Artificial Sequence
<220> FEATURE:
<223> OTHER INFORMATION: Synthetic

<400> SEQUENCE: 59
gcactagttt aacgcgggtc aagcaagccc tc 32

<210> SEQ ID NO 60
<211> LENGTH: 57
<212> TYPE: DNA
<213> ORGANISM: Artificial Sequence
<220> FEATURE:
<223> OTHER INFORMATION: Synthetic

<400> SEQUENCE: 60
ggctcgagac catggggcat catcatcatc atcataaaag cgaacacggt gagctgg 57

<210> SEQ ID NO 61
<211> LENGTH: 32
<212> TYPE: DNA
<213> ORGANISM: Artificial Sequence
<220> FEATURE:
<223> OTHER INFORMATION: Synthetic

<400> SEQUENCE: 61
gcactagttt aacgcgggtc aagcaagccc tc 32

<210> SEQ ID NO 62
<211> LENGTH: 59
<212> TYPE: DNA
<213> ORGANISM: Artificial Sequence
<220> FEATURE:
<223> OTHER INFORMATION: Synthetic

<400> SEQUENCE: 62
ggctcgagac catggggcat catcatcatc atcatgaccc gcaagggcgc aaaattccg 59

<210> SEQ ID NO 63
<211> LENGTH: 32
<212> TYPE: DNA
<213> ORGANISM: Artificial Sequence
<220> FEATURE:
<223> OTHER INFORMATION: Synthetic

<400> SEQUENCE: 63
gcactagttt aacgcgggtc aagcaagccc tc 32

<210> SEQ ID NO 64
<211> LENGTH: 58
<212> TYPE: DNA
<213> ORGANISM: Artificial Sequence
<220> FEATURE:
<223> OTHER INFORMATION: Synthetic

<400> SEQUENCE: 64
ggctcgagac catggggcat catcatcatc atcatgaagc caaggcgttg aaagcggc 58

<210> SEQ ID NO 65
<211> LENGTH: 32
<212> TYPE: DNA
<213> ORGANISM: Artificial Sequence
<220> FEATURE:
<223> OTHER INFORMATION: Synthetic

<400> SEQUENCE: 65
gcactagttt aacgcgggtc aagcaagccc tc 32

<210> SEQ ID NO 66
<211> LENGTH: 32
<212> TYPE: DNA
<213> ORGANISM: Artificial Sequence
<220> FEATURE:
<223> OTHER INFORMATION: Synthetic

<400> SEQUENCE: 66
aattctcgag atgaagctca ctgttaagac tc 32

<210> SEQ ID NO 67
<211> LENGTH: 60
<212> TYPE: DNA
<213> ORGANISM: Artificial Sequence
<220> FEATURE:
<223> OTHER INFORMATION: Synthetic

<400> SEQUENCE: 67
atactagtct aggcataatc tggcacatca taagggtagt cttcaaaatc tgctgagtgc 60

<210> SEQ ID NO 68
<211> LENGTH: 33
<212> TYPE: DNA
<213> ORGANISM: Artificial Sequence
<220> FEATURE:
<223> OTHER INFORMATION: Synthetic

<400> SEQUENCE: 68
aattgtcgac atggcggctg gtggattttt gac 33

<210> SEQ ID NO 69
<211> LENGTH: 62
<212> TYPE: DNA
<213> ORGANISM: Artificial Sequence
<220> FEATURE:
<223> OTHER INFORMATION: Synthetic

<400> SEQUENCE: 69
taggtaccct aggcataatc tggcacatca taagggtact gttgcaaaag tggcttcaat 60
tg 62

<210> SEQ ID NO 70
<211> LENGTH: 32
<212> TYPE: DNA
<213> ORGANISM: Artificial Sequence
<220> FEATURE:
<223> OTHER INFORMATION: Synthetic

<400> SEQUENCE: 70
ttccctcgag ttcaaaattt tccggtgaaa tc 32

<210> SEQ ID NO 71
<211> LENGTH: 60
<212> TYPE: DNA
<213> ORGANISM: Artificial Sequence
<220> FEATURE:
<223> OTHER INFORMATION: Synthetic

<400> SEQUENCE: 71
ttactagtct aggcataatc tggcacatca taagggtagg cctcatccat ctgcatatcg 60

<210> SEQ ID NO 72
<211> LENGTH: 32
<212> TYPE: DNA
<213> ORGANISM: Artificial Sequence
<220> FEATURE:
<223> OTHER INFORMATION: Synthetic

<400> SEQUENCE: 72
aattctcgag tcgaagcaca cttctctgtt tc 32

<210> SEQ ID NO 73
<211> LENGTH: 60
<212> TYPE: DNA
<213> ORGANISM: Artificial Sequence
<220> FEATURE:
<223> OTHER INFORMATION: Synthetic

<400> SEQUENCE: 73
aaactagtct aggcataatc tggcacatca taagggtact ttaatccatc aaggcctggt 60

<210> SEQ ID NO 74
<211> LENGTH: 28
<212> TYPE: DNA
<213> ORGANISM: Artificial Sequence
<220> FEATURE:
<223> OTHER INFORMATION: Synthetic

<400> SEQUENCE: 74
ggaattcatg atcagttcgc ggatcggc 28

<210> SEQ ID NO 75
<211> LENGTH: 29
<212> TYPE: DNA
<213> ORGANISM: Artificial Sequence
<220> FEATURE:
<223> OTHER INFORMATION: Synthetic

<400> SEQUENCE: 75
cctgctcgag tgacggatgt tattcaaag 29

<210> SEQ ID NO 76
<211> LENGTH: 28
<212> TYPE: DNA
<213> ORGANISM: Artificial Sequence
<220> FEATURE:
<223> OTHER INFORMATION: Synthetic

<400> SEQUENCE: 76
ggaattcatg atcagttcgc ggatcggc 28

<210> SEQ ID NO 77
<211> LENGTH: 28
<212> TYPE: DNA
<213> ORGANISM: Artificial Sequence
<220> FEATURE:
<223> OTHER INFORMATION: Synthetic

<400> SEQUENCE: 77
ggccctcgag cttaccagcc acccaccg 28

<210> SEQ ID NO 78
<211> LENGTH: 29
<212> TYPE: DNA
<213> ORGANISM: Artificial Sequence
<220> FEATURE:
<223> OTHER INFORMATION: Synthetic

<400> SEQUENCE: 78
cgcccagcat atgccaagga ttggtactc 29

<210> SEQ ID NO 79
<211> LENGTH: 29
<212> TYPE: DNA
<213> ORGANISM: Artificial Sequence
<220> FEATURE:
<223> OTHER INFORMATION: Synthetic

<400> SEQUENCE: 79
tgaattctta ctgttgcaaa agtggcttc 29

<210> SEQ ID NO 80
<211> LENGTH: 100
<212> TYPE: PRT
<213> ORGANISM: Pseudomonas syringae

<400> SEQUENCE: 80

```
Met Ile Ser Ser Arg Ile Gly Gly Ala Gly Gly Val Glu Leu Ser Arg
1               5                   10                  15

Val Asn Gln Gln His Asp Thr Val Pro Ala Gln Thr Ala His Pro Asn
            20                  25                  30

Ala Val Thr Ala Gly Met Asn Pro Pro Leu Thr Pro Asp Gln Ser Gly
        35                  40                  45

Ser His Ala Thr Glu Ser Ser Ser Ala Gly Ala Ala Arg Leu Asn Val
    50                  55                  60

Ala Ala Arg His Thr Gln Leu Leu Gln Ala Phe Lys Ala Glu His Gly
```

65 70 75 80

Thr Ala Pro Val Ser Gly Ala Pro Met Ile Ser Ser Arg Ala Ala Leu
85 90 95

Leu Ile Gly Ser
100

<210> SEQ ID NO 81
<211> LENGTH: 200
<212> TYPE: PRT
<213> ORGANISM: Pseudomonas syringae

<400> SEQUENCE: 81

Met Ile Ser Ser Arg Ile Gly Gly Ala Gly Gly Val Glu Leu Ser Arg
1 5 10 15

Val Asn Gln Gln His Asp Thr Val Pro Ala Gln Thr Ala His Pro Asn
20 25 30

Ala Val Thr Ala Gly Met Asn Pro Pro Leu Thr Pro Asp Gln Ser Gly
35 40 45

Ser His Ala Thr Glu Ser Ser Ser Ala Gly Ala Ala Arg Leu Asn Val
50 55 60

Ala Ala Arg His Thr Gln Leu Leu Gln Ala Phe Lys Ala Glu His Gly
65 70 75 80

Thr Ala Pro Val Ser Gly Ala Pro Met Ile Ser Ser Arg Ala Ala Leu
85 90 95

Leu Ile Gly Ser Leu Leu Gln Ala Glu Pro Leu Pro Phe Glu Val Met
100 105 110

Ala Glu Lys Leu Ser Pro Glu Arg Tyr Gln Leu Lys Gln Phe Gln Gly
115 120 125

Ser Asp Leu Gln Gln Arg Leu Glu Lys Phe Ala Gln Pro Gly Gln Ile
130 135 140

Pro Asp Lys Ala Glu Val Gly Gln Leu Ile Lys Gly Phe Ala Gln Ser
145 150 155 160

Val Ala Asp Gln Leu Glu His Phe Gln Leu Met His Asp Ala Ser Pro
165 170 175

Ala Thr Val Gly Gln His Ala Lys Ala Asp Lys Ala Thr Leu Ala Val
180 185 190

Ser Gln Thr Ala Leu Gly Glu Tyr
195 200

<210> SEQ ID NO 82
<211> LENGTH: 300
<212> TYPE: PRT
<213> ORGANISM: Pseudomonas syringae

<400> SEQUENCE: 82

Met Ile Ser Ser Arg Ile Gly Gly Ala Gly Gly Val Glu Leu Ser Arg
1 5 10 15

Val Asn Gln Gln His Asp Thr Val Pro Ala Gln Thr Ala His Pro Asn
20 25 30

Ala Val Thr Ala Gly Met Asn Pro Pro Leu Thr Pro Asp Gln Ser Gly
35 40 45

Ser His Ala Thr Glu Ser Ser Ser Ala Gly Ala Ala Arg Leu Asn Val
50 55 60

Ala Ala Arg His Thr Gln Leu Leu Gln Ala Phe Lys Ala Glu His Gly
65 70 75 80

Thr Ala Pro Val Ser Gly Ala Pro Met Ile Ser Ser Arg Ala Ala Leu
85 90 95

Leu Ile Gly Ser Leu Leu Gln Ala Glu Pro Leu Pro Phe Glu Val Met
100 105 110

Ala Glu Lys Leu Ser Pro Glu Arg Tyr Gln Leu Lys Gln Phe Gln Gly
115 120 125

Ser Asp Leu Gln Gln Arg Leu Glu Lys Phe Ala Gln Pro Gly Gln Ile
130 135 140

Pro Asp Lys Ala Glu Val Gly Gln Leu Ile Lys Gly Phe Ala Gln Ser
145 150 155 160

Val Ala Asp Gln Leu Glu His Phe Gln Leu Met His Asp Ala Ser Pro
165 170 175

Ala Thr Val Gly Gln His Ala Lys Ala Asp Lys Ala Thr Leu Ala Val
180 185 190

Ser Gln Thr Ala Leu Gly Glu Tyr Ala Gly Arg Ala Ser Lys Ala Ile
195 200 205

Gly Glu Gly Leu Ser Asn Ser Ile Ala Ser Leu Asp Glu His Ile Ser
210 215 220

Ala Leu Asp Leu Thr Leu Gln Asp Ala Glu Gln Gly Asn Lys Glu Ser
225 230 235 240

Leu His Ala Asp Arg Gln Ala Leu Val Asp Ala Lys Thr Thr Leu Val
245 250 255

Gly Leu His Ala Asp Phe Val Lys Ser Pro Glu Ala Lys Arg Leu Ala
260 265 270

Ser Val Ala Ala His Thr Gln Leu Asp Asn Val Val Ser Asp Leu Val
275 280 285

Thr Ala Arg Asn Thr Val Gly Gly Trp Lys Gly Ala
290 295 300

<210> SEQ ID NO 83
<211> LENGTH: 400
<212> TYPE: PRT
<213> ORGANISM: Pseudomonas syringae

<400> SEQUENCE: 83

Met Ile Ser Ser Arg Ile Gly Gly Ala Gly Gly Val Glu Leu Ser Arg
1 5 10 15

Val Asn Gln Gln His Asp Thr Val Pro Ala Gln Thr Ala His Pro Asn
20 25 30

Ala Val Thr Ala Gly Met Asn Pro Pro Leu Thr Pro Asp Gln Ser Gly
35 40 45

Ser His Ala Thr Glu Ser Ser Ser Ala Gly Ala Ala Arg Leu Asn Val
50 55 60

Ala Ala Arg His Thr Gln Leu Leu Gln Ala Phe Lys Ala Glu His Gly
65 70 75 80

Thr Ala Pro Val Ser Gly Ala Pro Met Ile Ser Ser Arg Ala Ala Leu
85 90 95

Leu Ile Gly Ser Leu Leu Gln Ala Glu Pro Leu Pro Phe Glu Val Met
100 105 110

Ala Glu Lys Leu Ser Pro Glu Arg Tyr Gln Leu Lys Gln Phe Gln Gly
115 120 125

Ser Asp Leu Gln Gln Arg Leu Glu Lys Phe Ala Gln Pro Gly Gln Ile
130 135 140

Pro Asp Lys Ala Glu Val Gly Gln Leu Ile Lys Gly Phe Ala Gln Ser
145 150 155 160

Val Ala Asp Gln Leu Glu His Phe Gln Leu Met His Asp Ala Ser Pro
165 170 175

Ala Thr Val Gly Gln His Ala Lys Ala Asp Lys Ala Thr Leu Ala Val
180 185 190

Ser Gln Thr Ala Leu Gly Glu Tyr Ala Gly Arg Ala Ser Lys Ala Ile
195 200 205

Gly Glu Gly Leu Ser Asn Ser Ile Ala Ser Leu Asp Glu His Ile Ser
210 215 220

Ala Leu Asp Leu Thr Leu Gln Asp Ala Glu Gln Gly Asn Lys Glu Ser
225 230 235 240

Leu His Ala Asp Arg Gln Ala Leu Val Asp Ala Lys Thr Thr Leu Val
245 250 255

Gly Leu His Ala Asp Phe Val Lys Ser Pro Glu Ala Lys Arg Leu Ala
260 265 270

Ser Val Ala Ala His Thr Gln Leu Asp Asn Val Val Ser Asp Leu Val
275 280 285

Thr Ala Arg Asn Thr Val Gly Gly Trp Lys Gly Ala Gly Pro Ile Val
290 295 300

Ala Ala Ala Val Pro Gln Phe Leu Ser Ser Met Thr His Leu Gly Tyr
305 310 315 320

Val Arg Leu Ser Thr Ser Asp Lys Leu Arg Asp Thr Ile Pro Glu Thr
325 330 335

Ser Ser Asp Ala Asn Met Leu Lys Ala Ser Ile Ile Gly Met Val Ala
340 345 350

Gly Ile Ala His Glu Thr Val Asn Ser Val Val Lys Pro Met Phe Gln
355 360 365

Ala Ala Leu Gln Lys Thr Gly Leu Asn Glu Arg Leu Asn Met Val Pro
370 375 380

Met Lys Ala Val Asp Thr Asn Thr Val Ile Pro Asp Pro Phe Glu Leu
385 390 395 400

<210> SEQ ID NO 84
<211> LENGTH: 500
<212> TYPE: PRT
<213> ORGANISM: Pseudomonas syringae

<400> SEQUENCE: 84

Met Ile Ser Ser Arg Ile Gly Gly Ala Gly Gly Val Glu Leu Ser Arg
1 5 10 15

Val Asn Gln Gln His Asp Thr Val Pro Ala Gln Thr Ala His Pro Asn
20 25 30

Ala Val Thr Ala Gly Met Asn Pro Pro Leu Thr Pro Asp Gln Ser Gly
35 40 45

Ser His Ala Thr Glu Ser Ser Ser Ala Gly Ala Ala Arg Leu Asn Val
50 55 60

Ala Ala Arg His Thr Gln Leu Leu Gln Ala Phe Lys Ala Glu His Gly
65 70 75 80

Thr Ala Pro Val Ser Gly Ala Pro Met Ile Ser Ser Arg Ala Ala Leu
85 90 95

Leu Ile Gly Ser Leu Leu Gln Ala Glu Pro Leu Pro Phe Glu Val Met
100 105 110

Ala Glu Lys Leu Ser Pro Glu Arg Tyr Gln Leu Lys Gln Phe Gln Gly
115 120 125

Ser Asp Leu Gln Gln Arg Leu Glu Lys Phe Ala Gln Pro Gly Gln Ile
130 135 140

Pro Asp Lys Ala Glu Val Gly Gln Leu Ile Lys Gly Phe Ala Gln Ser
145 150 155 160

Val Ala Asp Gln Leu Glu His Phe Gln Leu Met His Asp Ala Ser Pro
165 170 175

Ala Thr Val Gly Gln His Ala Lys Ala Asp Lys Ala Thr Leu Ala Val
180 185 190

Ser Gln Thr Ala Leu Gly Glu Tyr Ala Gly Arg Ala Ser Lys Ala Ile
195 200 205

Gly Glu Gly Leu Ser Asn Ser Ile Ala Ser Leu Asp Glu His Ile Ser
210 215 220

Ala Leu Asp Leu Thr Leu Gln Asp Ala Glu Gln Gly Asn Lys Glu Ser
225 230 235 240

Leu His Ala Asp Arg Gln Ala Leu Val Asp Ala Lys Thr Thr Leu Val
245 250 255

Gly Leu His Ala Asp Phe Val Lys Ser Pro Glu Ala Lys Arg Leu Ala
260 265 270

Ser Val Ala Ala His Thr Gln Leu Asp Asn Val Val Ser Asp Leu Val
275 280 285

Thr Ala Arg Asn Thr Val Gly Gly Trp Lys Gly Ala Gly Pro Ile Val
290 295 300

Ala Ala Ala Val Pro Gln Phe Leu Ser Ser Met Thr His Leu Gly Tyr
305 310 315 320

Val Arg Leu Ser Thr Ser Asp Lys Leu Arg Asp Thr Ile Pro Glu Thr
325 330 335

Ser Ser Asp Ala Asn Met Leu Lys Ala Ser Ile Ile Gly Met Val Ala
340 345 350

Gly Ile Ala His Glu Thr Val Asn Ser Val Val Lys Pro Met Phe Gln
355 360 365

Ala Ala Leu Gln Lys Thr Gly Leu Asn Glu Arg Leu Asn Met Val Pro
370 375 380

Met Lys Ala Val Asp Thr Asn Thr Val Ile Pro Asp Pro Phe Glu Leu
385 390 395 400

Lys Ser Glu His Gly Glu Leu Val Lys Lys Thr Pro Glu Glu Val Ala
405 410 415

Gln Asp Lys Ala Phe Val Lys Ser Glu Arg Ala Leu Leu Asn Gln Lys
420 425 430

Lys Val Gln Gly Ser Ser Thr His Pro Val Gly Glu Leu Met Ala Tyr
435 440 445

Ser Ala Phe Gly Gly Ser Gln Ala Val Arg Gln Met Leu Asn Asp Val
450 455 460

His Gln Ile Asn Gly Gln Thr Leu Ser Ala Arg Ala Leu Ala Ser Gly
465 470 475 480

Phe Gly Gly Ala Val Ser Ala Ser Ser Gln Thr Leu Leu Gln Leu Lys
485 490 495

Ser Asn Tyr Val
500

<210> SEQ ID NO 85
<211> LENGTH: 600
<212> TYPE: PRT
<213> ORGANISM: Pseudomonas syringae

<400> SEQUENCE: 85

Met Ile Ser Ser Arg Ile Gly Gly Ala Gly Gly Val Glu Leu Ser Arg
1 5 10 15

Val Asn Gln Gln His Asp Thr Val Pro Ala Gln Thr Ala His Pro Asn
20 25 30

```
Ala Val Thr Ala Gly Met Asn Pro Pro Leu Thr Pro Asp Gln Ser Gly
        35                  40                  45

Ser His Ala Thr Glu Ser Ser Ser Ala Gly Ala Ala Arg Leu Asn Val
    50                  55                  60

Ala Ala Arg His Thr Gln Leu Leu Gln Ala Phe Lys Ala Glu His Gly
65                  70                  75                  80

Thr Ala Pro Val Ser Gly Ala Pro Met Ile Ser Ser Arg Ala Ala Leu
                85                  90                  95

Leu Ile Gly Ser Leu Leu Gln Ala Glu Pro Leu Pro Phe Glu Val Met
            100                 105                 110

Ala Glu Lys Leu Ser Pro Glu Arg Tyr Gln Leu Lys Gln Phe Gln Gly
        115                 120                 125

Ser Asp Leu Gln Gln Arg Leu Glu Lys Phe Ala Gln Pro Gly Gln Ile
    130                 135                 140

Pro Asp Lys Ala Glu Val Gly Gln Leu Ile Lys Gly Phe Ala Gln Ser
145                 150                 155                 160

Val Ala Asp Gln Leu Glu His Phe Gln Leu Met His Asp Ala Ser Pro
                165                 170                 175

Ala Thr Val Gly Gln His Ala Lys Ala Asp Lys Ala Thr Leu Ala Val
            180                 185                 190

Ser Gln Thr Ala Leu Gly Glu Tyr Ala Gly Arg Ala Ser Lys Ala Ile
        195                 200                 205

Gly Glu Gly Leu Ser Asn Ser Ile Ala Ser Leu Asp Glu His Ile Ser
    210                 215                 220

Ala Leu Asp Leu Thr Leu Gln Asp Ala Glu Gln Gly Asn Lys Glu Ser
225                 230                 235                 240

Leu His Ala Asp Arg Gln Ala Leu Val Asp Ala Lys Thr Thr Leu Val
                245                 250                 255

Gly Leu His Ala Asp Phe Val Lys Ser Pro Glu Ala Lys Arg Leu Ala
            260                 265                 270

Ser Val Ala Ala His Thr Gln Leu Asp Asn Val Val Ser Asp Leu Val
        275                 280                 285

Thr Ala Arg Asn Thr Val Gly Gly Trp Lys Gly Ala Gly Pro Ile Val
    290                 295                 300

Ala Ala Ala Val Pro Gln Phe Leu Ser Ser Met Thr His Leu Gly Tyr
305                 310                 315                 320

Val Arg Leu Ser Thr Ser Asp Lys Leu Arg Asp Thr Ile Pro Glu Thr
                325                 330                 335

Ser Ser Asp Ala Asn Met Leu Lys Ala Ser Ile Ile Gly Met Val Ala
            340                 345                 350

Gly Ile Ala His Glu Thr Val Asn Ser Val Val Lys Pro Met Phe Gln
        355                 360                 365

Ala Ala Leu Gln Lys Thr Gly Leu Asn Glu Arg Leu Asn Met Val Pro
    370                 375                 380

Met Lys Ala Val Asp Thr Asn Thr Val Ile Pro Asp Pro Phe Glu Leu
385                 390                 395                 400

Lys Ser Glu His Gly Glu Leu Val Lys Lys Thr Pro Glu Glu Val Ala
                405                 410                 415

Gln Asp Lys Ala Phe Val Lys Ser Glu Arg Ala Leu Leu Asn Gln Lys
            420                 425                 430

Lys Val Gln Gly Ser Ser Thr His Pro Val Gly Glu Leu Met Ala Tyr
        435                 440                 445

Ser Ala Phe Gly Gly Ser Gln Ala Val Arg Gln Met Leu Asn Asp Val
```

```
    450                 455                 460

His Gln Ile Asn Gly Gln Thr Leu Ser Ala Arg Ala Leu Ala Ser Gly
465                 470                 475                 480

Phe Gly Gly Ala Val Ser Ala Ser Ser Gln Thr Leu Leu Gln Leu Lys
                485                 490                 495

Ser Asn Tyr Val Asp Pro Gln Gly Arg Lys Ile Pro Val Phe Thr Pro
            500                 505                 510

Asp Arg Ala Glu Ser Asp Leu Lys Lys Asp Leu Leu Lys Gly Met Asp
        515                 520                 525

Leu Arg Glu Pro Ser Val Arg Thr Thr Phe Tyr Ser Lys Ala Leu Ser
    530                 535                 540

Gly Ile Gln Ser Ser Ala Leu Thr Ser Ala Leu Pro Pro Val Thr Ala
545                 550                 555                 560

Gln Ala Glu Gly Ala Ser Gly Thr Leu Ser Ala Gly Ala Ile Leu Arg
                565                 570                 575

Asn Met Ala Leu Ala Ala Thr Gly Ser Val Ser Tyr Leu Ser Thr Leu
            580                 585                 590

Tyr Thr Asn Gln Ser Val Thr Ala
        595                 600


<210> SEQ ID NO 86
<211> LENGTH: 612
<212> TYPE: PRT
<213> ORGANISM: Pseudomonas syringae

<400> SEQUENCE: 86

Leu Leu Gln Ala Glu Pro Leu Pro Phe Glu Val Met Ala Glu Lys Leu
1               5                   10                  15

Ser Pro Glu Arg Tyr Gln Leu Lys Gln Phe Gln Gly Ser Asp Leu Gln
            20                  25                  30

Gln Arg Leu Glu Lys Phe Ala Gln Pro Gly Gln Ile Pro Asp Lys Ala
        35                  40                  45

Glu Val Gly Gln Leu Ile Lys Gly Phe Ala Gln Ser Val Ala Asp Gln
    50                  55                  60

Leu Glu His Phe Gln Leu Met His Asp Ala Ser Pro Ala Thr Val Gly
65                  70                  75                  80

Gln His Ala Lys Ala Asp Lys Ala Thr Leu Ala Val Ser Gln Thr Ala
                85                  90                  95

Leu Gly Glu Tyr Ala Gly Arg Ala Ser Lys Ala Ile Gly Glu Gly Leu
            100                 105                 110

Ser Asn Ser Ile Ala Ser Leu Asp Glu His Ile Ser Ala Leu Asp Leu
        115                 120                 125

Thr Leu Gln Asp Ala Glu Gln Gly Asn Lys Glu Ser Leu His Ala Asp
    130                 135                 140

Arg Gln Ala Leu Val Asp Ala Lys Thr Thr Leu Val Gly Leu His Ala
145                 150                 155                 160

Asp Phe Val Lys Ser Pro Glu Ala Lys Arg Leu Ala Ser Val Ala Ala
                165                 170                 175

His Thr Gln Leu Asp Asn Val Val Ser Asp Leu Val Thr Ala Arg Asn
            180                 185                 190

Thr Val Gly Gly Trp Lys Gly Ala Gly Pro Ile Val Ala Ala Ala Val
        195                 200                 205

Pro Gln Phe Leu Ser Ser Met Thr His Leu Gly Tyr Val Arg Leu Ser
    210                 215                 220

Thr Ser Asp Lys Leu Arg Asp Thr Ile Pro Glu Thr Ser Ser Asp Ala
```

```
225                 230                 235                 240

Asn Met Leu Lys Ala Ser Ile Ile Gly Met Val Ala Gly Ile Ala His
                245                 250                 255

Glu Thr Val Asn Ser Val Val Lys Pro Met Phe Gln Ala Ala Leu Gln
            260                 265                 270

Lys Thr Gly Leu Asn Glu Arg Leu Asn Met Val Pro Met Lys Ala Val
        275                 280                 285

Asp Thr Asn Thr Val Ile Pro Asp Pro Phe Glu Leu Lys Ser Glu His
    290                 295                 300

Gly Glu Leu Val Lys Lys Thr Pro Glu Glu Val Ala Gln Asp Lys Ala
305                 310                 315                 320

Phe Val Lys Ser Glu Arg Ala Leu Leu Asn Gln Lys Lys Val Gln Gly
                325                 330                 335

Ser Ser Thr His Pro Val Gly Glu Leu Met Ala Tyr Ser Ala Phe Gly
            340                 345                 350

Gly Ser Gln Ala Val Arg Gln Met Leu Asn Asp Val His Gln Ile Asn
        355                 360                 365

Gly Gln Thr Leu Ser Ala Arg Ala Leu Ala Ser Gly Phe Gly Gly Ala
    370                 375                 380

Val Ser Ala Ser Ser Gln Thr Leu Leu Gln Leu Lys Ser Asn Tyr Val
385                 390                 395                 400

Asp Pro Gln Gly Arg Lys Ile Pro Val Phe Thr Pro Asp Arg Ala Glu
                405                 410                 415

Ser Asp Leu Lys Lys Asp Leu Leu Lys Gly Met Asp Leu Arg Glu Pro
            420                 425                 430

Ser Val Arg Thr Thr Phe Tyr Ser Lys Ala Leu Ser Gly Ile Gln Ser
        435                 440                 445

Ser Ala Leu Thr Ser Ala Leu Pro Pro Val Thr Ala Gln Ala Glu Gly
    450                 455                 460

Ala Ser Gly Thr Leu Ser Ala Gly Ala Ile Leu Arg Asn Met Ala Leu
465                 470                 475                 480

Ala Ala Thr Gly Ser Val Ser Tyr Leu Ser Thr Leu Tyr Thr Asn Gln
                485                 490                 495

Ser Val Thr Ala Glu Ala Lys Ala Leu Lys Ala Ala Gly Met Gly Gly
            500                 505                 510

Ala Thr Pro Met Leu Asp Arg Thr Glu Thr Ala Leu Asn Asn Ile Arg
        515                 520                 525

His Pro Asn Arg Glu Ser Leu Pro His Thr Phe Gln Lys Ser Thr Leu
    530                 535                 540

Ser Gly Ile Pro Arg Val Ala Glu Asn Ala Tyr His Met Gly Arg Gly
545                 550                 555                 560

Ala Leu Gln Leu Pro Thr Gln Met Ala Val Asp Thr Val Arg Val Val
                565                 570                 575

Asp Glu Gly Val Leu Asn Ala Val Ala Ser Ala Arg Glu Ala Leu Lys
            580                 585                 590

Gln Pro Thr Lys Asp Asp Asp Ala Leu Arg Ala Leu Glu Glu Gly Leu
        595                 600                 605

Leu Asp Pro Arg
    610
```

<210> SEQ ID NO 87
<211> LENGTH: 512
<212> TYPE: PRT
<213> ORGANISM: Pseudomonas syringae

<400> SEQUENCE: 87

Ala Gly Arg Ala Ser Lys Ala Ile Gly Glu Gly Leu Ser Asn Ser Ile
1 5 10 15

Ala Ser Leu Asp Glu His Ile Ser Ala Leu Asp Leu Thr Leu Gln Asp
20 25 30

Ala Glu Gln Gly Asn Lys Glu Ser Leu His Ala Asp Arg Gln Ala Leu
35 40 45

Val Asp Ala Lys Thr Thr Leu Val Gly Leu His Ala Asp Phe Val Lys
50 55 60

Ser Pro Glu Ala Lys Arg Leu Ala Ser Val Ala Ala His Thr Gln Leu
65 70 75 80

Asp Asn Val Val Ser Asp Leu Val Thr Ala Arg Asn Thr Val Gly Gly
85 90 95

Trp Lys Gly Ala Gly Pro Ile Val Ala Ala Ala Val Pro Gln Phe Leu
100 105 110

Ser Ser Met Thr His Leu Gly Tyr Val Arg Leu Ser Thr Ser Asp Lys
115 120 125

Leu Arg Asp Thr Ile Pro Glu Thr Ser Ser Asp Ala Asn Met Leu Lys
130 135 140

Ala Ser Ile Ile Gly Met Val Ala Gly Ile Ala His Glu Thr Val Asn
145 150 155 160

Ser Val Val Lys Pro Met Phe Gln Ala Ala Leu Gln Lys Thr Gly Leu
165 170 175

Asn Glu Arg Leu Asn Met Val Pro Met Lys Ala Val Asp Thr Asn Thr
180 185 190

Val Ile Pro Asp Pro Phe Glu Leu Lys Ser Glu His Gly Glu Leu Val
195 200 205

Lys Lys Thr Pro Glu Glu Val Ala Gln Asp Lys Ala Phe Val Lys Ser
210 215 220

Glu Arg Ala Leu Leu Asn Gln Lys Lys Val Gln Gly Ser Ser Thr His
225 230 235 240

Pro Val Gly Glu Leu Met Ala Tyr Ser Ala Phe Gly Gly Ser Gln Ala
245 250 255

Val Arg Gln Met Leu Asn Asp Val His Gln Ile Asn Gly Gln Thr Leu
260 265 270

Ser Ala Arg Ala Leu Ala Ser Gly Phe Gly Gly Ala Val Ser Ala Ser
275 280 285

Ser Gln Thr Leu Leu Gln Leu Lys Ser Asn Tyr Val Asp Pro Gln Gly
290 295 300

Arg Lys Ile Pro Val Phe Thr Pro Asp Arg Ala Glu Ser Asp Leu Lys
305 310 315 320

Lys Asp Leu Leu Lys Gly Met Asp Leu Arg Glu Pro Ser Val Arg Thr
325 330 335

Thr Phe Tyr Ser Lys Ala Leu Ser Gly Ile Gln Ser Ser Ala Leu Thr
340 345 350

Ser Ala Leu Pro Pro Val Thr Ala Gln Ala Glu Gly Ala Ser Gly Thr
355 360 365

Leu Ser Ala Gly Ala Ile Leu Arg Asn Met Ala Leu Ala Ala Thr Gly
370 375 380

Ser Val Ser Tyr Leu Ser Thr Leu Tyr Thr Asn Gln Ser Val Thr Ala
385 390 395 400

Glu Ala Lys Ala Leu Lys Ala Ala Gly Met Gly Gly Ala Thr Pro Met
405 410 415

```
Leu Asp Arg Thr Glu Thr Ala Leu Asn Asn Ile Arg His Pro Asn Arg
            420                 425                 430

Glu Ser Leu Pro His Thr Phe Gln Lys Ser Thr Leu Ser Gly Ile Pro
        435                 440                 445

Arg Val Ala Glu Asn Ala Tyr His Met Gly Arg Gly Ala Leu Gln Leu
    450                 455                 460

Pro Thr Gln Met Ala Val Asp Thr Val Arg Val Val Asp Glu Gly Val
465                 470                 475                 480

Leu Asn Ala Val Ala Ser Ala Arg Glu Ala Leu Lys Gln Pro Thr Lys
                485                 490                 495

Asp Asp Asp Ala Leu Arg Ala Leu Glu Glu Gly Leu Leu Asp Pro Arg
            500                 505                 510


<210> SEQ ID NO 88
<211> LENGTH: 412
<212> TYPE: PRT
<213> ORGANISM: Pseudomonas syringae

<400> SEQUENCE: 88

Gly Pro Ile Val Ala Ala Ala Val Pro Gln Phe Leu Ser Ser Met Thr
1               5                   10                  15

His Leu Gly Tyr Val Arg Leu Ser Thr Ser Asp Lys Leu Arg Asp Thr
            20                  25                  30

Ile Pro Glu Thr Ser Ser Asp Ala Asn Met Leu Lys Ala Ser Ile Ile
        35                  40                  45

Gly Met Val Ala Gly Ile Ala His Glu Thr Val Asn Ser Val Val Lys
    50                  55                  60

Pro Met Phe Gln Ala Ala Leu Gln Lys Thr Gly Leu Asn Glu Arg Leu
65                  70                  75                  80

Asn Met Val Pro Met Lys Ala Val Asp Thr Asn Thr Val Ile Pro Asp
                85                  90                  95

Pro Phe Glu Leu Lys Ser Glu His Gly Glu Leu Val Lys Lys Thr Pro
            100                 105                 110

Glu Glu Val Ala Gln Asp Lys Ala Phe Val Lys Ser Glu Arg Ala Leu
        115                 120                 125

Leu Asn Gln Lys Lys Val Gln Gly Ser Ser Thr His Pro Val Gly Glu
    130                 135                 140

Leu Met Ala Tyr Ser Ala Phe Gly Gly Ser Gln Ala Val Arg Gln Met
145                 150                 155                 160

Leu Asn Asp Val His Gln Ile Asn Gly Gln Thr Leu Ser Ala Arg Ala
                165                 170                 175

Leu Ala Ser Gly Phe Gly Gly Ala Val Ser Ala Ser Ser Gln Thr Leu
            180                 185                 190

Leu Gln Leu Lys Ser Asn Tyr Val Asp Pro Gln Gly Arg Lys Ile Pro
        195                 200                 205

Val Phe Thr Pro Asp Arg Ala Glu Ser Asp Leu Lys Lys Asp Leu Leu
    210                 215                 220

Lys Gly Met Asp Leu Arg Glu Pro Ser Val Arg Thr Thr Phe Tyr Ser
225                 230                 235                 240

Lys Ala Leu Ser Gly Ile Gln Ser Ser Ala Leu Thr Ser Ala Leu Pro
                245                 250                 255

Pro Val Thr Ala Gln Ala Glu Gly Ala Ser Gly Thr Leu Ser Ala Gly
            260                 265                 270

Ala Ile Leu Arg Asn Met Ala Leu Ala Ala Thr Gly Ser Val Ser Tyr
        275                 280                 285
```

```
Leu Ser Thr Leu Tyr Thr Asn Gln Ser Val Thr Ala Glu Ala Lys Ala
    290                 295                 300

Leu Lys Ala Ala Gly Met Gly Gly Ala Thr Pro Met Leu Asp Arg Thr
305                 310                 315                 320

Glu Thr Ala Leu Asn Asn Ile Arg His Pro Asn Arg Glu Ser Leu Pro
                325                 330                 335

His Thr Phe Gln Lys Ser Thr Leu Ser Gly Ile Pro Arg Val Ala Glu
            340                 345                 350

Asn Ala Tyr His Met Gly Arg Gly Ala Leu Gln Leu Pro Thr Gln Met
        355                 360                 365

Ala Val Asp Thr Val Arg Val Val Asp Glu Gly Val Leu Asn Ala Val
    370                 375                 380

Ala Ser Ala Arg Glu Ala Leu Lys Gln Pro Thr Lys Asp Asp Asp Ala
385                 390                 395                 400

Leu Arg Ala Leu Glu Glu Gly Leu Leu Asp Pro Arg
                405                 410


<210> SEQ ID NO 89
<211> LENGTH: 312
<212> TYPE: PRT
<213> ORGANISM: Pseudomonas syringae

<400> SEQUENCE: 89

Lys Ser Glu His Gly Glu Leu Val Lys Lys Thr Pro Glu Glu Val Ala
1               5                   10                  15

Gln Asp Lys Ala Phe Val Lys Ser Glu Arg Ala Leu Leu Asn Gln Lys
            20                  25                  30

Lys Val Gln Gly Ser Ser Thr His Pro Val Gly Glu Leu Met Ala Tyr
        35                  40                  45

Ser Ala Phe Gly Gly Ser Gln Ala Val Arg Gln Met Leu Asn Asp Val
    50                  55                  60

His Gln Ile Asn Gly Gln Thr Leu Ser Ala Arg Ala Leu Ala Ser Gly
65                  70                  75                  80

Phe Gly Gly Ala Val Ser Ala Ser Ser Gln Thr Leu Leu Gln Leu Lys
                85                  90                  95

Ser Asn Tyr Val Asp Pro Gln Gly Arg Lys Ile Pro Val Phe Thr Pro
            100                 105                 110

Asp Arg Ala Glu Ser Asp Leu Lys Lys Asp Leu Leu Lys Gly Met Asp
        115                 120                 125

Leu Arg Glu Pro Ser Val Arg Thr Thr Phe Tyr Ser Lys Ala Leu Ser
    130                 135                 140

Gly Ile Gln Ser Ser Ala Leu Thr Ser Ala Leu Pro Pro Val Thr Ala
145                 150                 155                 160

Gln Ala Glu Gly Ala Ser Gly Thr Leu Ser Ala Gly Ala Ile Leu Arg
                165                 170                 175

Asn Met Ala Leu Ala Ala Thr Gly Ser Val Ser Tyr Leu Ser Thr Leu
            180                 185                 190

Tyr Thr Asn Gln Ser Val Thr Ala Glu Ala Lys Ala Leu Lys Ala Ala
        195                 200                 205

Gly Met Gly Gly Ala Thr Pro Met Leu Asp Arg Thr Glu Thr Ala Leu
    210                 215                 220

Asn Asn Ile Arg His Pro Asn Arg Glu Ser Leu Pro His Thr Phe Gln
225                 230                 235                 240

Lys Ser Thr Leu Ser Gly Ile Pro Arg Val Ala Glu Asn Ala Tyr His
                245                 250                 255
```

Met Gly Arg Gly Ala Leu Gln Leu Pro Thr Gln Met Ala Val Asp Thr
260 265 270

Val Arg Val Val Asp Glu Gly Val Leu Asn Ala Val Ala Ser Ala Arg
275 280 285

Glu Ala Leu Lys Gln Pro Thr Lys Asp Asp Asp Ala Leu Arg Ala Leu
290 295 300

Glu Glu Gly Leu Leu Asp Pro Arg
305 310

<210> SEQ ID NO 90
<211> LENGTH: 212
<212> TYPE: PRT
<213> ORGANISM: Pseudomonas syringae

<400> SEQUENCE: 90

Asp Pro Gln Gly Arg Lys Ile Pro Val Phe Thr Pro Asp Arg Ala Glu
1 5 10 15

Ser Asp Leu Lys Lys Asp Leu Leu Lys Gly Met Asp Leu Arg Glu Pro
20 25 30

Ser Val Arg Thr Thr Phe Tyr Ser Lys Ala Leu Ser Gly Ile Gln Ser
35 40 45

Ser Ala Leu Thr Ser Ala Leu Pro Pro Val Thr Ala Gln Ala Glu Gly
50 55 60

Ala Ser Gly Thr Leu Ser Ala Gly Ala Ile Leu Arg Asn Met Ala Leu
65 70 75 80

Ala Ala Thr Gly Ser Val Ser Tyr Leu Ser Thr Leu Tyr Thr Asn Gln
85 90 95

Ser Val Thr Ala Glu Ala Lys Ala Leu Lys Ala Ala Gly Met Gly Gly
100 105 110

Ala Thr Pro Met Leu Asp Arg Thr Glu Thr Ala Leu Asn Asn Ile Arg
115 120 125

His Pro Asn Arg Glu Ser Leu Pro His Thr Phe Gln Lys Ser Thr Leu
130 135 140

Ser Gly Ile Pro Arg Val Ala Glu Asn Ala Tyr His Met Gly Arg Gly
145 150 155 160

Ala Leu Gln Leu Pro Thr Gln Met Ala Val Asp Thr Val Arg Val Val
165 170 175

Asp Glu Gly Val Leu Asn Ala Val Ala Ser Ala Arg Glu Ala Leu Lys
180 185 190

Gln Pro Thr Lys Asp Asp Asp Ala Leu Arg Ala Leu Glu Glu Gly Leu
195 200 205

Leu Asp Pro Arg
210

<210> SEQ ID NO 91
<211> LENGTH: 152
<212> TYPE: PRT
<213> ORGANISM: Pseudomonas syringae

<400> SEQUENCE: 91

Gln Ala Glu Gly Ala Ser Gly Thr Leu Ser Ala Gly Ala Ile Leu Arg
1 5 10 15

Asn Met Ala Leu Ala Ala Thr Gly Ser Val Ser Tyr Leu Ser Thr Leu
20 25 30

Tyr Thr Asn Gln Ser Val Thr Ala Glu Ala Lys Ala Leu Lys Ala Ala
35 40 45

Gly Met Gly Gly Ala Thr Pro Met Leu Asp Arg Thr Glu Thr Ala Leu

```
    50                  55                  60

Asn Asn Ile Arg His Pro Asn Arg Glu Ser Leu Pro His Thr Phe Gln
65                  70                  75                  80

Lys Ser Thr Leu Ser Gly Ile Pro Arg Val Ala Glu Asn Ala Tyr His
                85                  90                  95

Met Gly Arg Gly Ala Leu Gln Leu Pro Thr Gln Met Ala Val Asp Thr
            100                 105                 110

Val Arg Val Val Asp Glu Gly Val Leu Asn Ala Val Ala Ser Ala Arg
        115                 120                 125

Glu Ala Leu Lys Gln Pro Thr Lys Asp Asp Asp Ala Leu Arg Ala Leu
    130                 135                 140

Glu Glu Gly Leu Leu Asp Pro Arg
145                 150


<210> SEQ ID NO 92
<211> LENGTH: 300
<212> TYPE: DNA
<213> ORGANISM: Pseudomonas syringae

<400> SEQUENCE: 92

atgatcagtt cgcggatcgg cggggccggt ggcgtcgaac tcagccgggt aaaccagcag      60

cacgatactg ttcccgccca gacagctcac ccaaatgcag tcactgcagg catgaatccg     120

ccgctgactc ccgatcagtc agggtcacac gcgacagaaa gctcgtctgc cggcgcggcg     180

cggctgaatg tcgcggctcg acacacacag cttttgcagg ccttcaaggc tgagcatggg     240

acggctccgg tcagcggcgc gccgatgatc agttcgcgtg ctgcgttgtt gatcggtagt     300


<210> SEQ ID NO 93
<211> LENGTH: 600
<212> TYPE: DNA
<213> ORGANISM: Pseudomonas syringae

<400> SEQUENCE: 93

atgatcagtt cgcggatcgg cggggccggt ggcgtcgaac tcagccgggt aaaccagcag      60

cacgatactg ttcccgccca gacagctcac ccaaatgcag tcactgcagg catgaatccg     120

ccgctgactc ccgatcagtc agggtcacac gcgacagaaa gctcgtctgc cggcgcggcg     180

cggctgaatg tcgcggctcg acacacacag cttttgcagg ccttcaaggc tgagcatggg     240

acggctccgg tcagcggcgc gccgatgatc agttcgcgtg ctgcgttgtt gatcggtagt     300

ctgctgcagg ccgagccttt gccttttgaa gtcatggccg agaaattgtc tcctgagcgc     360

tatcaactga agcagtttca gggctcggac ttgcagcagc ggctggaaaa attcgcccag     420

ccgggtcaga taccggataa agccgaggtc gggcaactga tcaagggttt tgctcagtcg     480

gtcgctgatc aactggagca ctttcaactg atgcatgacg cttcgcccgc aacggtaggc     540

cagcatgcaa aagcggacaa ggcgacgctt gccgtcagtc agactgccct tggcgaatac     600


<210> SEQ ID NO 94
<211> LENGTH: 900
<212> TYPE: DNA
<213> ORGANISM: Pseudomonas syringae

<400> SEQUENCE: 94

atgatcagtt cgcggatcgg cggggccggt ggcgtcgaac tcagccgggt aaaccagcag      60

cacgatactg ttcccgccca gacagctcac ccaaatgcag tcactgcagg catgaatccg     120

ccgctgactc ccgatcagtc agggtcacac gcgacagaaa gctcgtctgc cggcgcggcg     180
```

```
cggctgaatg tcgcggctcg acacacacag cttttgcagg ccttcaaggc tgagcatggg    240

acggctccgg tcagcggcgc gccgatgatc agttcgcgtg ctgcgttgtt gatcggtagt    300

ctgctgcagg ccgagccttt gccttttgaa gtcatggccg agaaattgtc tcctgagcgc    360

tatcaactga agcagtttca gggctcggac ttgcagcagc ggctggaaaa attcgcccag    420

ccgggtcaga taccggataa agccgaggtc gggcaactga tcaagggttt tgctcagtcg    480

gtcgctgatc aactggagca ctttcaactg atgcatgacg cttcgcccgc aacggtaggc    540

cagcatgcaa aagcggacaa ggcgacgctt gccgtcagtc agactgccct tggcgaatac    600

gccggtcgtg caagcaaggc aatcggcgaa ggcctgagca acagcatcgc gtcgctggat    660

gagcacatca gtgcgctgga tctcactctg caagatgccg aacagggcaa caaggagtct    720

ctgcacgctg acaggcaggc gctggtcgac gccaaaacca ccctggtagg tttgcacgcc    780

gatttcgtca agtcgccgga ggccaagcgc cttgcttcgg tcgccgcaca tacgcaactg    840

gacaacgtcg tcagcgatct cgtcactgcc cgtaacacgg tgggtggctg gaaaggtgca    900
```

<210> SEQ ID NO 95
<211> LENGTH: 1200
<212> TYPE: DNA
<213> ORGANISM: Pseudomonas syringae

<400> SEQUENCE: 95

```
atgatcagtt cgcggatcgg cggggccggt ggcgtcgaac tcagccgggt aaaccagcag     60

cacgatactg ttcccgccca gacagctcac ccaaatgcag tcactgcagg catgaatccg    120

ccgctgactc ccgatcagtc agggtcacac gcgacagaaa gctcgtctgc cggcgcggcg    180

cggctgaatg tcgcggctcg acacacacag cttttgcagg ccttcaaggc tgagcatggg    240

acggctccgg tcagcggcgc gccgatgatc agttcgcgtg ctgcgttgtt gatcggtagt    300

ctgctgcagg ccgagccttt gccttttgaa gtcatggccg agaaattgtc tcctgagcgc    360

tatcaactga agcagtttca gggctcggac ttgcagcagc ggctggaaaa attcgcccag    420

ccgggtcaga taccggataa agccgaggtc gggcaactga tcaagggttt tgctcagtcg    480

gtcgctgatc aactggagca ctttcaactg atgcatgacg cttcgcccgc aacggtaggc    540

cagcatgcaa aagcggacaa ggcgacgctt gccgtcagtc agactgccct tggcgaatac    600

gccggtcgtg caagcaaggc aatcggcgaa ggcctgagca acagcatcgc gtcgctggat    660

gagcacatca gtgcgctgga tctcactctg caagatgccg aacagggcaa caaggagtct    720

ctgcacgctg acaggcaggc gctggtcgac gccaaaacca ccctggtagg tttgcacgcc    780

gatttcgtca agtcgccgga ggccaagcgc cttgcttcgg tcgccgcaca tacgcaactg    840

gacaacgtcg tcagcgatct cgtcactgcc cgtaacacgg tgggtggctg gaaaggtgca    900

gggccgattg tcgcggctgc ggttccgcag ttcttgtctt caatgacaca cttgggttat    960

gtgcgtttgt ccaccagcga caagctgcga gacacgattc ccgagaccag cagcgacgcc   1020

aacatgctca aggcttcgat aatcgggatg gtggcgggca ttgctcacga gacggtcaac   1080

agcgtggtca agccgatgtt tcaggccgcc ttgcagaaga ctggcctcaa cgaacgcctg   1140

aacatggtgc caatgaaggc tgtggatacc aatacggtta ttcctgaccc cttcgagctg   1200
```

<210> SEQ ID NO 96
<211> LENGTH: 1500
<212> TYPE: DNA
<213> ORGANISM: Pseudomonas syringae

<400> SEQUENCE: 96
atgatcagtt cgcggatcgg cggggccggt ggcgtcgaac tcagccgggt aaaccagcag 60
cacgatactg ttcccgccca gacagctcac ccaaatgcag tcactgcagg catgaatccg 120
ccgctgactc ccgatcagtc agggtcacac gcgacagaaa gctcgtctgc cggcgcggcg 180
cggctgaatg tcgcggctcg acacacacag cttttgcagg ccttcaaggc tgagcatggg 240
acggctccgg tcagcggcgc gccgatgatc agttcgcgtg ctgcgttgtt gatcggtagt 300
ctgctgcagg ccgagccttt gccttttgaa gtcatggccg agaaattgtc tcctgagcgc 360
tatcaactga agcagtttca gggctcggac ttgcagcagc ggctggaaaa attcgcccag 420
ccgggtcaga taccggataa agccgaggtc gggcaactga tcaagggttt tgctcagtcg 480
gtcgctgatc aactggagca ctttcaactg atgcatgacg cttcgcccgc aacggtaggc 540
cagcatgcaa aagcggacaa ggcgacgctt gccgtcagtc agactgccct tggcgaatac 600
gccggtcgtg caagcaaggc aatcggcgaa ggcctgagca acagcatcgc gtcgctggat 660
gagcacatca gtgcgctgga tctcactctg caagatgccg aacagggcaa caaggagtct 720
ctgcacgctg acaggcaggc gctggtcgac gccaaaacca ccctggtagg tttgcacgcc 780
gatttcgtca agtcgccgga ggccaagcgc cttgcttcgg tcgccgcaca tacgcaactg 840
gacaacgtcg tcagcgatct cgtcactgcc cgtaacacgg tgggtggctg gaaaggtgca 900
gggccgattg tcgcggctgc ggttccgcag ttcttgtctt caatgacaca cttgggttat 960
gtgcgtttgt ccaccagcga caagctgcga gacacgattc ccgagaccag cagcgacgcc 1020
aacatgctca aggcttcgat aatcgggatg gtggcgggca ttgctcacga gacggtcaac 1080
agcgtggtca agccgatgtt tcaggccgcc ttgcagaaga ctggcctcaa cgaacgcctg 1140
aacatggtgc caatgaaggc tgtggatacc aatacggtta ttcctgaccc cttcgagctg 1200
aaaagcgaac acggtgagct ggtcaaaaaa acgcccgagg aagtcgctca ggacaaggcg 1260
ttcgtgaaaa gtgaacgcgc gctgctgaac cagaagaagg ttcagggttc gtccacccat 1320
ccggtaggtg agctgatggc ttacagtgcc ttcggtggtt ctcaggctgt gcgccagatg 1380
ctcaacgatg ttcaccagat caatgggcag acgctgagtg caagagctct ggcatccggt 1440
tttggcgggg cggtgtctgc cagttcgcaa acgctgctgc aattgaagtc gaattatgtc 1500

<210> SEQ ID NO 97
<211> LENGTH: 1800
<212> TYPE: DNA
<213> ORGANISM: Pseudomonas syringae

<400> SEQUENCE: 97
atgatcagtt cgcggatcgg cggggccggt ggcgtcgaac tcagccgggt aaaccagcag 60
cacgatactg ttcccgccca gacagctcac ccaaatgcag tcactgcagg catgaatccg 120
ccgctgactc ccgatcagtc agggtcacac gcgacagaaa gctcgtctgc cggcgcggcg 180
cggctgaatg tcgcggctcg acacacacag cttttgcagg ccttcaaggc tgagcatggg 240
acggctccgg tcagcggcgc gccgatgatc agttcgcgtg ctgcgttgtt gatcggtagt 300
ctgctgcagg ccgagccttt gccttttgaa gtcatggccg agaaattgtc tcctgagcgc 360
tatcaactga agcagtttca gggctcggac ttgcagcagc ggctggaaaa attcgcccag 420
ccgggtcaga taccggataa agccgaggtc gggcaactga tcaagggttt tgctcagtcg 480
gtcgctgatc aactggagca ctttcaactg atgcatgacg cttcgcccgc aacggtaggc 540
cagcatgcaa aagcggacaa ggcgacgctt gccgtcagtc agactgccct tggcgaatac 600
gccggtcgtg caagcaaggc aatcggcgaa ggcctgagca acagcatcgc gtcgctggat 660
gagcacatca gtgcgctgga tctcactctg caagatgccg aacagggcaa caaggagtct 720
ctgcacgctg acaggcaggc gctggtcgac gccaaaacca ccctggtagg tttgcacgcc 780
gatttcgtca agtcgccgga ggccaagcgc cttgcttcgg tcgccgcaca tacgcaactg 840
gacaacgtcg tcagcgatct cgtcactgcc cgtaacacgg tgggtggctg gaaaggtgca 900
gggccgattg tcgcggctgc ggttccgcag ttcttgtctt caatgacaca cttgggttat 960
gtgcgtttgt ccaccagcga caagctgcga gacacgattc ccgagaccag cagcgacgcc 1020
aacatgctca aggcttcgat aatcgggatg gtggcgggca ttgctcacga gacggtcaac 1080
agcgtggtca agccgatgtt tcaggccgcc ttgcagaaga ctggcctcaa cgaacgcctg 1140
aacatggtgc caatgaaggc tgtggatacc aatacggtta ttcctgaccc cttcgagctg 1200
aaaagcgaac acggtgagct ggtcaaaaaa acgcccgagg aagtcgctca ggacaaggcg 1260
ttcgtgaaaa gtgaacgcgc gctgctgaac cagaagaagg ttcagggttc gtccacccat 1320
ccggtaggtg agctgatggc ttacagtgcc ttcggtggtt ctcaggctgt gcgccagatg 1380
ctcaacgatg ttcaccagat caatgggcag acgctgagtg caagagctct ggcatccggt 1440
tttggcgggg cggtgtctgc cagttcgcaa acgctgctgc aattgaagtc gaattatgtc 1500
gacccgcaag ggcgcaaaat tccggtattt accccggacc gcgccgagag cgatctgaaa 1560
aaggacctgc tcaaaggtat ggacctgcgc gagccgtcgg tacgcaccac gttctacagc 1620
aaggctcttt cgggtattca gagttctgca ctgacctcgg cactgccgcc tgtgaccgct 1680
caggctgaag gcgcaagtgg cacgctcagt gcgggggcta ttttgcgcaa catggccctg 1740
gcagcgacgg gttcggtgtc ctatctgtcc acgttgtaca ccaaccagtc ggttaccgca 1800

<210> SEQ ID NO 98
<211> LENGTH: 1926
<212> TYPE: DNA
<213> ORGANISM: Pseudomonas syringae

<400> SEQUENCE: 98
cttttgcagg ccttcaaggc tgagcatggg acggctccgg tcagcggcgc gccgatgatc 60
agttcgcgtg ctgcgttgtt gatcggtagt ctgctgcagg ccgagccttt gccttttgaa 120
gtcatggccg agaaattgtc tcctgagcgc tatcaactga agcagtttca gggctcggac 180
ttgcagcagc ggctggaaaa attcgcccag ccgggtcaga taccggataa agccgaggtc 240
gggcaactga tcaagggttt tgctcagtcg gtcgctgatc aactggagca ctttcaactg 300
atgcatgacg cttcgcccgc aacggtaggc cagcatgcaa aagcggacaa ggcgacgctt 360
gccgtcagtc agactgccct tggcgaatac gccggtcgtg caagcaaggc aatcggcgaa 420
ggcctgagca acagcatcgc gtcgctggat gagcacatca gtgcgctgga tctcactctg 480
caagatgccg aacagggcaa caaggagtct ctgcacgctg acaggcaggc gctggtcgac 540
gccaaaacca ccctggtagg tttgcacgcc gatttcgtca agtcgccgga ggccaagcgc 600
cttgcttcgg tcgccgcaca tacgcaactg gacaacgtcg tcagcgatct cgtcactgcc 660
cgtaacacgg tgggtggctg gaaaggtgca gggccgattg tcgcggctgc ggttccgcag 720
ttcttgtctt caatgacaca cttgggttat gtgcgtttgt ccaccagcga caagctgcga 780
gacacgattc ccgagaccag cagcgacgcc aacatgctca aggcttcgat aatcgggatg 840
gtggcgggca ttgctcacga gacggtcaac agcgtggtca agccgatgtt tcaggccgcc 900
ttgcagaaga ctggcctcaa cgaacgcctg aacatggtgc caatgaaggc tgtggatacc 960
aatacggtta ttcctgaccc cttcgagctg aaaagcgaac acggtgagct ggtcaaaaaa 1020
acgcccgagg aagtcgctca ggacaaggcg ttcgtgaaaa gtgaacgcgc gctgctgaac 1080
cagaagaagg ttcagggttc gtccacccat ccggtaggtg agctgatggc ttacagtgcc 1140
ttcggtggtt ctcaggctgt gcgccagatg ctcaacgatg ttcaccagat caatgggcag 1200
acgctgagtg caagagctct ggcatccggt tttggcgggg cggtgtctgc cagttcgcaa 1260
acgctgctgc aattgaagtc gaattatgtc gacccgcaag ggcgcaaaat tccggtattt 1320
accccggacc gcgccgagag cgatctgaaa aaggacctgc tcaaaggtat ggacctgcgc 1380
gagccgtcgg tacgcaccac gttctacagc aaggctcttt cgggtattca gagttctgca 1440
ctgacctcgg cactgccgcc tgtgaccgct caggctgaag gcgcaagtgg cacgctcagt 1500
gcgggggcta ttttgcgcaa catggccctg gcagcgacgg gttcggtgtc ctatctgtcc 1560
acgttgtaca ccaaccagtc ggttaccgca gaagccaagg cgttgaaagc ggcaggcatg 1620
ggcggtgcaa cacctatgct ggaccgtacc gagacggctt tgaataacat ccgtcatccg 1680
aacagggagt ctctgccaca tacgttccag aagagcacgt tgagcggtat cccacgagtc 1740
gcggaaaacg cctatcacat gggacgaggc gcattgcagt tgcctaccca gatggccgtg 1800
gatacggttc gggtcgtgga tgaaggtgtg ttgaacgcag tcgcgtcagc acgcgaggcg 1860
cttaagcagc cgacaaaaga cgatgacgca ttgagggcac ttgaagaggg cttgcttgac 1920
ccgcgt 1926

<210> SEQ ID NO 99
<211> LENGTH: 1536
<212> TYPE: DNA
<213> ORGANISM: Pseudomonas syringae

<400> SEQUENCE: 99
gccggtcgtg caagcaaggc aatcggcgaa ggcctgagca acagcatcgc gtcgctggat 60
gagcacatca gtgcgctgga tctcactctg caagatgccg aacagggcaa caaggagtct 120
ctgcacgctg acaggcaggc gctggtcgac gccaaaacca ccctggtagg tttgcacgcc 180
gatttcgtca agtcgccgga ggccaagcgc cttgcttcgg tcgccgcaca tacgcaactg 240
gacaacgtcg tcagcgatct cgtcactgcc cgtaacacgg tgggtggctg gaaaggtgca 300
gggccgattg tcgcggctgc ggttccgcag ttcttgtctt caatgacaca cttgggttat 360
gtgcgtttgt ccaccagcga caagctgcga gacacgattc ccgagaccag cagcgacgcc 420
aacatgctca aggcttcgat aatcgggatg gtggcgggca ttgctcacga gacggtcaac 480
agcgtggtca agccgatgtt tcaggccgcc ttgcagaaga ctggcctcaa cgaacgcctg 540
aacatggtgc caatgaaggc tgtggatacc aatacggtta ttcctgaccc cttcgagctg 600
aaaagcgaac acggtgagct ggtcaaaaaa acgcccgagg aagtcgctca ggacaaggcg 660
ttcgtgaaaa gtgaacgcgc gctgctgaac cagaagaagg ttcagggttc gtccacccat 720
ccggtaggtg agctgatggc ttacagtgcc ttcggtggtt ctcaggctgt gcgccagatg 780
ctcaacgatg ttcaccagat caatgggcag acgctgagtg caagagctct ggcatccggt 840
tttggcgggg cggtgtctgc cagttcgcaa acgctgctgc aattgaagtc gaattatgtc 900
gacccgcaag ggcgcaaaat tccggtattt accccggacc gcgccgagag cgatctgaaa 960
aaggacctgc tcaaaggtat ggacctgcgc gagccgtcgg tacgcaccac gttctacagc 1020
aaggctcttt cgggtattca gagttctgca ctgacctcgg cactgccgcc tgtgaccgct 1080
caggctgaag gcgcaagtgg cacgctcagt gcgggggcta ttttgcgcaa catggccctg 1140
gcagcgacgg gttcggtgtc ctatctgtcc acgttgtaca ccaaccagtc ggttaccgca 1200

```
gaagccaagg cgttgaaagc ggcaggcatg ggcggtgcaa cacctatgct ggaccgtacc   1260

gagacggctt tgaataacat ccgtcatccg aacagggagt ctctgccaca tacgttccag   1320

aagagcacgt tgagcggtat cccacgagtc gcggaaaacg cctatcacat gggacgaggc   1380

gcattgcagt tgcctaccca gatggccgtg gatacggttc gggtcgtgga tgaaggtgtg   1440

ttgaacgcag tcgcgtcagc acgcgaggcg cttaagcagc cgacaaaaga cgatgacgca   1500

ttgagggcac ttgaagaggg cttgcttgac ccgcgt                              1536


<210> SEQ ID NO 100
<211> LENGTH: 1236
<212> TYPE: DNA
<213> ORGANISM: Pseudomonas syringae

<400> SEQUENCE: 100

gggccgattg tcgcggctgc ggttccgcag ttcttgtctt caatgacaca cttgggttat     60

gtgcgtttgt ccaccagcga caagctgcga gacacgattc ccgagaccag cagcgacgcc    120

aacatgctca aggcttcgat aatcgggatg gtggcgggca ttgctcacga gacggtcaac    180

agcgtggtca agccgatgtt tcaggccgcc ttgcagaaga ctggcctcaa cgaacgcctg    240

aacatggtgc caatgaaggc tgtggatacc aatacggtta ttcctgaccc cttcgagctg    300

aaaagcgaac acggtgagct ggtcaaaaaa acgcccgagg aagtcgctca ggacaaggcg    360

ttcgtgaaaa gtgaacgcgc gctgctgaac cagaagaagg ttcagggttc gtccacccat    420

ccggtaggtg agctgatggc ttacagtgcc ttcggtggtt ctcaggctgt gcgccagatg    480

ctcaacgatg ttcaccagat caatgggcag acgctgagtg caagagctct ggcatccggt    540

tttggcgggg cggtgtctgc cagttcgcaa acgctgctgc aattgaagtc gaattatgtc    600

gacccgcaag ggcgcaaaat tccggtattt accccggacc gcgccgagag cgatctgaaa    660

aaggacctgc tcaaaggtat ggacctgcgc gagccgtcgg tacgcaccac gttctacagc    720

aaggctcttt cgggtattca gagttctgca ctgacctcgg cactgccgcc tgtgaccgct    780

caggctgaag gcgcaagtgg cacgctcagt gcgggggcta ttttgcgcaa catggccctg    840

gcagcgacgg gttcggtgtc ctatctgtcc acgttgtaca ccaaccagtc ggttaccgca    900

gaagccaagg cgttgaaagc ggcaggcatg ggcggtgcaa cacctatgct ggaccgtacc    960

gagacggctt tgaataacat ccgtcatccg aacagggagt ctctgccaca tacgttccag   1020

aagagcacgt tgagcggtat cccacgagtc gcggaaaacg cctatcacat gggacgaggc   1080

gcattgcagt tgcctaccca gatggccgtg gatacggttc gggtcgtgga tgaaggtgtg   1140

ttgaacgcag tcgcgtcagc acgcgaggcg cttaagcagc cgacaaaaga cgatgacgca   1200

ttgagggcac ttgaagaggg cttgcttgac ccgcgt                              1236


<210> SEQ ID NO 101
<211> LENGTH: 936
<212> TYPE: DNA
<213> ORGANISM: Pseudomonas syringae

<400> SEQUENCE: 101

aaaagcgaac acggtgagct ggtcaaaaaa acgcccgagg aagtcgctca ggacaaggcg     60

ttcgtgaaaa gtgaacgcgc gctgctgaac cagaagaagg ttcagggttc gtccacccat    120

ccggtaggtg agctgatggc ttacagtgcc ttcggtggtt ctcaggctgt gcgccagatg    180

ctcaacgatg ttcaccagat caatgggcag acgctgagtg caagagctct ggcatccggt    240

tttggcgggg cggtgtctgc cagttcgcaa acgctgctgc aattgaagtc gaattatgtc    300
```

gacccgcaag ggcgcaaaat tccggtattt accccggacc gcgccgagag cgatctgaaa 360
aaggacctgc tcaaaggtat ggacctgcgc gagccgtcgg tacgcaccac gttctacagc 420
aaggctcttt cgggtattca gagttctgca ctgacctcgg cactgccgcc tgtgaccgct 480
caggctgaag gcgcaagtgg cacgctcagt gcgggggcta ttttgcgcaa catggccctg 540
gcagcgacgg gttcggtgtc ctatctgtcc acgttgtaca ccaaccagtc ggttaccgca 600
gaagccaagg cgttgaaagc ggcaggcatg ggcggtgcaa cacctatgct ggaccgtacc 660
gagacggctt tgaataacat ccgtcatccg aacagggagt ctctgccaca tacgttccag 720
aagagcacgt tgagcggtat cccacgagtc gcggaaaacg cctatcacat gggacgaggc 780
gcattgcagt tgcctaccca gatggccgtg gatacggttc gggtcgtgga tgaaggtgtg 840
ttgaacgcag tcgcgtcagc acgcgaggcg cttaagcagc cgacaaaaga cgatgacgca 900
ttgagggcac ttgaagaggg cttgcttgac ccgcgt 936

<210> SEQ ID NO 102
<211> LENGTH: 636
<212> TYPE: DNA
<213> ORGANISM: Pseudomonas syringae

<400> SEQUENCE: 102
gacccgcaag ggcgcaaaat tccggtattt accccggacc gcgccgagag cgatctgaaa 60
aaggacctgc tcaaaggtat ggacctgcgc gagccgtcgg tacgcaccac gttctacagc 120
aaggctcttt cgggtattca gagttctgca ctgacctcgg cactgccgcc tgtgaccgct 180
caggctgaag gcgcaagtgg cacgctcagt gcgggggcta ttttgcgcaa catggccctg 240
gcagcgacgg gttcggtgtc ctatctgtcc acgttgtaca ccaaccagtc ggttaccgca 300
gaagccaagg cgttgaaagc ggcaggcatg ggcggtgcaa cacctatgct ggaccgtacc 360
gagacggctt tgaataacat ccgtcatccg aacagggagt ctctgccaca tacgttccag 420
aagagcacgt tgagcggtat cccacgagtc gcggaaaacg cctatcacat gggacgaggc 480
gcattgcagt tgcctaccca gatggccgtg gatacggttc gggtcgtgga tgaaggtgtg 540
ttgaacgcag tcgcgtcagc acgcgaggcg cttaagcagc cgacaaaaga cgatgacgca 600
ttgagggcac ttgaagaggg cttgcttgac ccgcgt 636

<210> SEQ ID NO 103
<211> LENGTH: 456
<212> TYPE: DNA
<213> ORGANISM: Pseudomonas syringae

<400> SEQUENCE: 103
caggctgaag gcgcaagtgg cacgctcagt gcgggggcta ttttgcgcaa catggccctg 60
gcagcgacgg gttcggtgtc ctatctgtcc acgttgtaca ccaaccagtc ggttaccgca 120
gaagccaagg cgttgaaagc ggcaggcatg ggcggtgcaa cacctatgct ggaccgtacc 180
gagacggctt tgaataacat ccgtcatccg aacagggagt ctctgccaca tacgttccag 240
aagagcacgt tgagcggtat cccacgagtc gcggaaaacg cctatcacat gggacgaggc 300
gcattgcagt tgcctaccca gatggccgtg gatacggttc gggtcgtgga tgaaggtgtg 360
ttgaacgcag tcgcgtcagc acgcgaggcg cttaagcagc cgacaaaaga cgatgacgca 420
ttgagggcac ttgaagaggg cttgcttgac ccgcgt 456

<210> SEQ ID NO 104
<211> LENGTH: 1763
<212> TYPE: DNA

<213> ORGANISM: Arabidopsis thaliana

<400> SEQUENCE: 104
aaaatttaaa tcttcattga atgctttttc tgaagcttta tctaataaat ctcttcgttg 60
atccttcctt tccattaacg aggtagaaat tccaaaacgc gtaataatct tgtcgtcatt 120
acaaattaca ataaaaagaa gacattttta tttagatttc cctctgatcc tctcttttag 180
atttcgaatc gagaccagat ctgcgtgaag atgatagaga agtgtatagg agcgcatcgg 240
tttcggagat tacagagatt catgcgtcaa gggaaagtga cgattctttg tctcgttctc 300
accgtcatcg tcttacgtgg cacaatcgga gccggtaagt ttggtacgcc ggagaaagat 360
atcgaggaga tccgtgagca tttcttctac acgcgtaaac gcggcgagcc tcaccgtgtc 420
ctcgtcgagg tctcttccaa aacgacgtcg tccgaagacg gaggaaatgg tggtaacagc 480
tacgagacct tcgatatcaa caagctattc gttgatgaag gagacgaaga gaaatctcga 540
gaccggacta ataaacctta ttctcttggt cccaagatct ctgattggga tgagcagaga 600
cgtgattggc tcaaacaaaa ccctagcttc cctaatttcg tggcgccaaa caagcctagg 660
gttcttcttg tcacaggttc agctcctaaa ccgtgtgaga atcctgtagg agaccattac 720
ctcttgaaat cgattaagaa caaaatcgat tactgtagaa tacacggaat cgagatcttc 780
tacaacatgg cgttgctcga tgctgagatg gctggattct gggctaagct tccgttgatt 840
aggaagttac tcttgtcaca tcctgagatt gagtttctat ggtggatgga tagtgatgcc 900
atgttcacgg acatggtgtt cgagcttcca tgggagaggt acaaagatta caacttggtg 960
atgcatggtt ggaacgagat ggtttatgac cagaagaatt ggattggtct caacacggga 1020
agtttcttgc tcaggaactc acagtggtcg cttgatcttc ttgacgcttg ggctcctatg 1080
ggcccaaaag ggaagatccg agaagaagcg ggtaaagtct tgacccggga acttaaagac 1140
cgacccgctt tcgaagctga cgatcaatcg gcgatggttt atctgctggc gacggagaga 1200
gagaaatggg gaggcaaagt ttatctagag agtggttatt acttgcacgg ttattggggg 1260
attttggtag accggtacga ggagatgatt gagaatcata aaccgggttt tggagaccat 1320
cggtggccat tggttacgca tttcgtcggg tgtaaaccgt gcgggaaatt tggagattat 1380
ccggtggaac ggtgtctacg gcagatggat agagcgttta atttcggaga caatcagatc 1440
cttcaaatgt atggtttcac gcataaatcg cttgggagcc ggcgcgtgaa acccacgcgc 1500
aatcagacgg ataggccgct cgatgccaag gacgagtttg ggctgcttca tccgccgttc 1560
aaagcggcca agcttagtac gacgacgacg tgagtgagtg agaggatata ttgttttgta 1620
tcttttaatt ttgcgtttag gggacacacg tttatttgtt ttattcaatt ttatttgttt 1680
gtagtttact taattgtttt gatctcccat tcatggtgga gtcgtgtatg gagtatttaa 1740
tgatttattg tagacgttat ttc 1763

<210> SEQ ID NO 105
<211> LENGTH: 300
<212> TYPE: PRT
<213> ORGANISM: Pseudomonas viridiflava

<400> SEQUENCE: 105

Met Ile Asn Ser Arg Val Gly Gly Ser Gly Asp Ile Gln Met Val Ala
1 5 10 15

Val Arg Thr Glu Glu Gly Asn Pro Ser Ile Thr Ser Ala His Pro Asn
20 25 30

Ala Val Thr Pro Ser Asn Asn Pro Pro Leu Leu Pro Arg Gln Met Gly
35 40 45

```
Gln His Leu Glu Pro Ser Leu Glu Ser His Ala Ala Asn Leu Gly Ile
    50                  55                  60

Ala Leu Arg His Thr Glu Leu Leu Ala Thr Phe Gln Ala Glu Gln Ala
65                  70                  75                  80

Ser Thr Arg Ser Thr Asp Ala Pro Gln Val Ser Ala His Ala Ala Leu
                85                  90                  95

Leu Ile Gly Gly Met Leu Glu Glu Ala Asn Gly His Ala Ser Glu Thr
            100                 105                 110

Gly Lys Val Gly Phe Glu Val Met Ala Glu Arg Leu Cys Gly Pro His
        115                 120                 125

Leu Ala Leu Glu Ser Phe Gln Ser Ser Asp Val Lys Leu Leu Leu Glu
    130                 135                 140

Lys Leu Thr Asn Lys Asp Glu Ile Pro Asp Lys Ala Glu Val Gly Gln
145                 150                 155                 160

Leu Leu Lys Gly His Ala Gly Ala Ile Ala Asp Gln Leu Glu His Phe
                165                 170                 175

Gln Leu Met His Asn Ala Ser Ser Val His Gln Gly Glu Cys Ser Ala
            180                 185                 190

Pro Asp Arg Lys Thr Phe Glu Val Ser Gln Ala Ala Leu Gly Glu Tyr
        195                 200                 205

Ala Gly Arg Ala Ser Lys Ala Ile Ser Ser Val Leu Ser Glu Lys Thr
    210                 215                 220

Ala Asp Leu Asp Lys Arg Leu Ala Asp Val Asp Lys Gln Leu Glu Gly
225                 230                 235                 240

Met Ala Glu Gly Gly Glu Lys Ser Arg Leu Leu Thr Gln Lys Glu Thr
                245                 250                 255

Leu Gly Glu Ala Lys Thr Met Leu Ala Asp Ile Gln Asn Asp Phe Ser
            260                 265                 270

Lys Ser Pro Gln Ala Lys His Leu Lys Ser Val Ala Ala His Ala Arg
        275                 280                 285

Phe Asp Ala Gln Leu Lys Glu Leu Asn Ala Asp Arg
    290                 295                 300
```

<210> SEQ ID NO 106
<211> LENGTH: 300
<212> TYPE: PRT
<213> ORGANISM: Pseudomonas syringae pv. syringae B728a

<400> SEQUENCE: 106

```
Met Ile Gly Thr Arg Val Gly Gly Ser Gly Ser Thr Glu Ile Val Gln
1               5                   10                  15

Ala Asn Gln Pro Gln Pro Ser Ala Ala Val Ala Gln Ala His Pro His
            20                  25                  30

Ala Val Ser Pro Ser Ser Asn Pro Pro Leu Thr Ala Ser Gln Ser Ala
        35                  40                  45

Ala Gln Ala Pro Glu Ser Ser Ala Ala Gly Ala Ala Arg Leu Pro Val
    50                  55                  60

Ala Pro Arg His Leu Pro Thr Leu Glu Lys Phe Arg Ala Glu Gln Pro
65                  70                  75                  80

Thr Val Gln Gly Thr Ser Thr Pro Thr Ile Ser Ala Asn Ala Ala Leu
                85                  90                  95

Leu Ile Gly Ser Leu Leu Gln Ser Glu Lys Leu Pro Phe Glu Val Met
            100                 105                 110

Ala Ala Arg Leu Ser Pro Glu Arg Tyr Ala Leu Gln Gln Phe His Gly
        115                 120                 125
```

```
Ser Asp Leu Gln Gln Met Leu Gly Arg Phe Ala Glu Pro Gly His Leu
    130                 135                 140

Pro Gly Lys Ala Glu Thr Glu Gln Leu Ile Lys Gly Phe Ala Arg Ser
145                 150                 155                 160

Leu Ala Asp Gln Leu Glu His Phe Gln Leu Met His Asp Ala Thr Ala
                165                 170                 175

Glu Ala Phe Gly Pro Gly Gly Leu Arg Asp Arg Asn Thr Leu Ala Val
            180                 185                 190

Ser Gln Ala Ala Leu Gly Glu Tyr Ala Gly Arg Ala Ser Lys Ser Ile
        195                 200                 205

Glu Ala Gly Leu Asn His Ser Leu Ala Val Leu Asp Glu Arg Ile Ala
    210                 215                 220

Ala Leu Asp Ser Gln Leu Glu Gly Ala Thr Glu Asp Ser Arg Pro Val
225                 230                 235                 240

Leu Leu Met Asp Arg Gln Ala Leu Glu Thr Ala Arg Ala Met Leu Ser
                245                 250                 255

Asp Leu His Val Asp Phe Cys Lys Ser Pro Glu Ala Lys Arg Leu Ser
            260                 265                 270

Ala Val Ala Ala His Thr Gln Met Asp Ala Leu Ile Asp Lys Leu Asn
        275                 280                 285

Val Asp Arg Ser Ser Val Gly Gly Trp Lys Gly Ile
    290                 295                 300
```

<210> SEQ ID NO 107
<211> LENGTH: 900
<212> TYPE: DNA
<213> ORGANISM: Pseudomonas syringae pv. syringae B728a

<400> SEQUENCE: 107

```
atgattggca cacgagtcgg cggatcaggc agtaccgaaa tcgttcaggc gaaccagccg     60

cagccgtctg ccgctgtcgc ccaggctcat ccacacgcgg taagcccgag cagcaacccg    120

ccgctgaccg ccagccagtc ggccgcgcaa gcgccggaaa gctcggcggc cggtgccgct    180

cgcctgccag tcgcgccgcg acatctgccg acattggaga agtttcgtgc cgaacagccc    240

accgtacaag gcacttccac gccgactatc agcgctaacg cggccctgct gatcggcagt    300

ctgttgcagt ctgaaaaact gcccttcgag gtcatggccg cccgtttgtc gcctgagcgt    360

tatgcgttgc agcagtttca cggctccgat ttacagcaaa tgctcggacg attcgctgag    420

ccagggcatc tgccaggcaa ggccgagacc gaacaactga tcaagggctt tgcccggtcg    480

ctcgcagacc agctggagca cttccagctc atgcatgacg cgacggctga ggcattcggc    540

cccggagggc tgcgcgaccg caacacactg gcggtcagtc aagcggcgct tggcgaatac    600

gccggtcggg cgagtaaatc catcgaagcg gggctgaacc acagtctcgc ggtgctggac    660

gagcgcatcg ccgcgctgga cagccagttg gagggcgcca ctgaggacag cagaccggtt    720

ttgctgatgg acaggcaggc gctggaaacg gccagggcga tgctgagcga cctgcacgtc    780

gacttctgca aatcgcctga agccaagcgg ttgagtgccg ttgccgctca cacgcaaatg    840

gatgctctga tcgacaagct gaacgttgat cgcagctcgg tcggcggctg gaaggggatc    900
```

<210> SEQ ID NO 108
<211> LENGTH: 300
<212> TYPE: PRT
<213> ORGANISM: Pseudomonas syringae pv. phaseolicola 1448A

<400> SEQUENCE: 108

-continued

```
Met Asn Thr Pro Arg Ile Gly Gly Ser Gly Ala Ile Glu Leu Ser Arg
1               5                   10                  15

Ile Asn Gln Gln Pro Asp Ala Ile Pro Ala Gln Thr Ala His Pro Asn
            20                  25                  30

Ala Val Thr Pro Gly Met Asn Pro Pro Leu Thr Pro Asn Gln Ala Gly
        35                  40                  45

Pro His Ala Ala Glu Ser Ser Ala Thr Gly Ala Ala Arg Leu Asn Val
    50                  55                  60

Ala Ala Arg His Thr Gln Leu Leu Gln Ala Phe Lys Ala Glu Gln Ala
65                  70                  75                  80

Thr Ala Pro Val Ser Gly Ala Pro Met Ile Ser Ser Arg Ala Ala Leu
                85                  90                  95

Leu Ile Gly Ser Leu Leu Gln Ala Glu Lys Leu Pro Phe Glu Val Met
            100                 105                 110

Ala Glu Arg Leu Ser Pro Glu Arg Tyr Gln Leu Lys Gln Phe His Gly
        115                 120                 125

Ser Asp Leu Gln Gln Leu Leu Asp Lys Phe Thr Gln Pro Gly Gln Val
    130                 135                 140

Pro Asp Lys Ala Glu Val Gly Gln Leu Ile Lys Gly Phe Ala Gln Ser
145                 150                 155                 160

Val Ala Asp Gln Leu Glu His Phe Gln Leu Met His Asp Ala Thr Pro
                165                 170                 175

Thr Lys Thr Gly Pro His Ala Asn Glu Asp Arg Ala Thr Leu Ala Val
            180                 185                 190

Ser Gln Thr Ala Leu Gly Glu Tyr Ala Gly Arg Ala Ser Lys Ala Ile
        195                 200                 205

Gly Glu Gly Leu Ser Lys Gly Ile Val Ser Leu Asp Asp His Ile Ala
    210                 215                 220

Ala Leu Asp Val Ser Leu Gln Ser Ala Glu Glu Gly Ala Lys Asp Ala
225                 230                 235                 240

Leu His Ser Asn Arg Gln Ala Leu Val Asp Ala Lys Thr Thr Leu Val
                245                 250                 255

Gly Leu His Ala Asp Phe Val Lys Ser Pro Glu Ala Lys Arg Leu Ala
            260                 265                 270

Ser Val Ala Ala His Thr Gln Leu Asp Thr Val Val Ser Asp Leu Val
        275                 280                 285

Thr Ala Arg Asn Ser Val Gly Gly Trp Lys Gly Ala
    290                 295                 300
```

<210> SEQ ID NO 109
<211> LENGTH: 900
<212> TYPE: DNA
<213> ORGANISM: Pseudomonas syringae pv. phaseolicola 1448A

<400> SEQUENCE: 109

```
atgaacactc cgcgaatcgg tggatcgggc gccatcgagc tctcccggat aaaccagcag     60

cccgatgcta ttcccgccca gaccgctcac ccgaatgcag tgacgccagg catgaatccg    120

ccgctgactc ccaatcaggc agggccgcac gcagcagaaa gctcggctac cggtgccgcg    180

cggctgaatg ttgcggcgcg acacacgcag cttttgcagg ccttcaaggc tgagcaggcg    240

acagctccgg tcagcggcgc gccgatgatc agctcgcgtg ccgcgttatt gattggcagc    300

ttgctgcagg ctgaaaagct gccttttgaa gtcatggccg agcgtctctc ccctgagcgc    360

tatcaactga agcagtttca tggttcggac ttgcaacaac tgctggacaa gtttacccag    420

ccgggtcagg tacccgacaa agccgaagtc ggtcaactga tcaagggctt cgcgcaatcg    480
```

gtcgccgatc aactggagca ctttcagttg atgcatgacg ctacgcccac caagacaggc 540
ccgcatgcca acgaggatcg ggcgacgctt gccgtcagtc agacagccct tggcgagtac 600
gccggtcgtg cgagcaaggc aatcggcgaa gggctgagca aaggcatcgt gtcgctggat 660
gatcacatcg ctgcactgga tgtgagcctg caaagtgccg aagagggcgc caaggacgct 720
ttgcactcta acagacaggc gctggttgat gcgaaaacca ctctggtcgg cctgcacgcc 780
gatttcgtca aatcgccaga ggctaaacgc cttgcttcgg tcgccgcaca tacacaactg 840
gacaccgtcg tcagtgatct tgtcactgcc cgcaactcgg ttggcggctg gaaaggtgcc 900

<210> SEQ ID NO 110
<211> LENGTH: 900
<212> TYPE: DNA
<213> ORGANISM: Pseudomonas viridiflava

<400> SEQUENCE: 110
atgattaatt cacgcgtagg gggatcaggc gacatacaaa tggttgcggt gagaacggag 60
gagggtaatc cgtccattac ctctgctcac ccgaatgcgg tcactcccag caacaatccc 120
ccgttactcc caaggcaaat gggtcaacac cttgagccct ctctggagtc gcatgcggcg 180
aacctgggta tagcgttgcg ccacactgag ttgctggcga cgtttcaggc tgagcaggcg 240
agcacacgct caaccgatgc accacaggtc agtgcgcatg cggcgctatt gattggaggc 300
atgctcgaag aggccaacgg tcacgcttcc gaaaccggca aggtgggctt tgaggtcatg 360
gcagagcgct tgtgcgggcc gcaccttgcg ctggagagtt tccagtccag tgacgtcaaa 420
ctcctgctcg agaagctcac taataaggac gagataccgg acaaggcaga ggtcgggcaa 480
ctgctcaaag gccatgccgg tgcgatcgcc gatcaacttg agcattttca gctgatgcac 540
aacgcttcca gcgtgcacca aggtgaatgc tcggctcccg accgaaagac ctttgaagtc 600
agccaggctg cgttgggcga atacgctgga cgtgcgagca aagcgatttc cagcgtactg 660
agcgagaaaa ctgcagatct ggacaagcgc cttgcggacg tggacaaaca gctcgagggt 720
atggctgaag gcggggaaaa atccagactt ttgacccaga aagagacgct tggcgaagcc 780
aaaaccatgc tggccgacat tcagaacgat ttttcgaaat cgcctcaggc aaagcatctg 840
aaatccgttg ctgctcatgc gcgattcgac gcgcagctca aagagctgaa cgcggatcgt 900

<210> SEQ ID NO 111
<211> LENGTH: 697
<212> TYPE: PRT
<213> ORGANISM: Pseudomonas syringae pv. phaseolicola 1448A

<400> SEQUENCE: 111

Met Asn Thr Pro Arg Ile Gly Gly Ser Gly Ala Ile Glu Leu Ser Arg
1               5                   10                  15

Ile Asn Gln Gln Pro Asp Ala Ile Pro Ala Gln Thr Ala His Pro Asn
            20                  25                  30

Ala Val Thr Pro Gly Met Asn Pro Pro Leu Thr Pro Asn Gln Ala Gly
        35                  40                  45

Pro His Ala Ala Glu Ser Ser Ala Thr Gly Ala Ala Arg Leu Asn Val
    50                  55                  60

Ala Ala Arg His Thr Gln Leu Leu Gln Ala Phe Lys Ala Glu Gln Ala
65                  70                  75                  80

Thr Ala Pro Val Ser Gly Ala Pro Met Ile Ser Ser Arg Ala Ala Leu
                85                  90                  95

Leu Ile Gly Ser Leu Leu Gln Ala Glu Lys Leu Pro Phe Glu Val Met

```
            100                 105                 110

Ala Glu Arg Leu Ser Pro Glu Arg Tyr Gln Leu Lys Gln Phe His Gly
        115                 120                 125

Ser Asp Leu Gln Gln Leu Leu Asp Lys Phe Thr Gln Pro Gly Gln Val
    130                 135                 140

Pro Asp Lys Ala Glu Val Gly Gln Leu Ile Lys Gly Phe Ala Gln Ser
145                 150                 155                 160

Val Ala Asp Gln Leu Glu His Phe Gln Leu Met His Asp Ala Thr Pro
                165                 170                 175

Thr Lys Thr Gly Pro His Ala Asn Glu Asp Arg Ala Thr Leu Ala Val
            180                 185                 190

Ser Gln Thr Ala Leu Gly Glu Tyr Ala Gly Arg Ala Ser Lys Ala Ile
        195                 200                 205

Gly Glu Gly Leu Ser Lys Gly Ile Val Ser Leu Asp Asp His Ile Ala
    210                 215                 220

Ala Leu Asp Val Ser Leu Gln Ser Ala Glu Glu Gly Ala Lys Asp Ala
225                 230                 235                 240

Leu His Ser Asn Arg Gln Ala Leu Val Asp Ala Lys Thr Thr Leu Val
                245                 250                 255

Gly Leu His Ala Asp Phe Val Lys Ser Pro Glu Ala Lys Arg Leu Ala
            260                 265                 270

Ser Val Ala Ala His Thr Gln Leu Asp Thr Val Val Ser Asp Leu Val
        275                 280                 285

Thr Ala Arg Asn Ser Val Gly Gly Trp Lys Gly Ala Gly Pro Ile Val
    290                 295                 300

Ala Ala Ala Val Pro Gln Phe Leu Ser Ser Met Thr His Leu Gly Tyr
305                 310                 315                 320

Val Arg Leu Ser Thr Ser Asp Lys Leu Arg Glu Glu Val Pro Glu Thr
                325                 330                 335

Ser Ser Asp Ala Ser Met Leu Lys Ala Ala Ile Thr Gly Met Val Thr
            340                 345                 350

Gly Ile Ala His Glu Thr Val Asn Ser Val Val Lys Pro Val Phe Gln
        355                 360                 365

Ala Thr Phe Gln Lys Thr Gly Leu Asn Glu Arg Leu Asn Met Val Pro
    370                 375                 380

Leu Lys Ala Ile Asp Thr Asn Ser Val Ile Pro Asp Pro Phe Glu Leu
385                 390                 395                 400

Lys Ser Glu His Gly Glu Leu Ile Arg Lys Thr Pro Glu Glu Ile Ala
                405                 410                 415

Gln Asp Lys Ala Phe Val Lys Gly Glu Arg Ala Val Leu Asn Gln Lys
            420                 425                 430

Lys Val Gln Gly Ser Ser Thr His Pro Leu Gly Glu Met Ile Gly Tyr
        435                 440                 445

Ser Ala Phe Gly Gly Ser His Ala Val Arg Gln Met Leu Asn Asp Leu
    450                 455                 460

His Gln Ile Asn Gly Gln Thr Leu Ser Ala Arg Ala Leu Ala Ser Gly
465                 470                 475                 480

Phe Gly Gly Ala Val Ser Val Ser Ser Gln Thr Leu Leu Gln Leu Lys
                485                 490                 495

Ser Thr Tyr Val Asp Pro Ala Gly Arg Lys Ile Pro Val Phe Thr Pro
            500                 505                 510

Asp Arg Ala Glu Thr Glu Leu Lys Lys Asp Leu Ala Lys Gly Met Asp
        515                 520                 525
```

```
Leu Arg Glu Ala Ser Val Arg Thr Thr Phe Tyr Ser Lys Ala Ile Ser
    530                 535                 540

Gly Tyr Ser Glu Leu Gly Ala Asp Leu Gly Thr Ala Ala Cys Asp Ser
545                 550                 555                 560

Pro Ala Gly Arg Arg Ala Arg Tyr Ala Gln Cys Gly Glu Tyr Pro Ala
                565                 570                 575

Gln Tyr Gly Ser Gly Arg Asn Gly Leu Asp Phe Leu Ser Val His Ala
            580                 585                 590

Leu Arg Gln Pro Val Cys His Arg Arg Ser Gln Gly Val Glu Gly Cys
        595                 600                 605

Gly Asp Gly Gly Arg Asn Ala Asp Ala Gly Ser Tyr Arg Asn Ser Leu
    610                 615                 620

Glu Gln His Pro Pro Ser Glu Gln Gly Ile Ala Ala Thr Tyr Leu Pro
625                 630                 635                 640

Ala Glu His Val Glu Arg Tyr Ser Lys Gly Tyr Gly Lys Arg Leu Ser
                645                 650                 655

His Gly Thr Arg Arg Val Ala Ala Ala Asn Pro Asp Gly Arg Gly His
            660                 665                 670

Gly Ser Ser Val Gly Arg Arg Cys Ala Glu Arg Arg Val Val Ser Thr
        675                 680                 685

Arg Cys Ala Tyr Ala Ser Lys Thr Ala
    690                 695
```

<210> SEQ ID NO 112
<211> LENGTH: 2236
<212> TYPE: DNA
<213> ORGANISM: Pseudomonas syringae pv. phaseolicola 1448A

<400> SEQUENCE: 112

```
atgaacactc cgcgaatcgg tggatcgggc gccatcgagc tctcccggat aaaccagcag     60

cccgatgcta ttcccgccca gaccgctcac ccgaatgcag tgacgccagg catgaatccg    120

ccgctgactc ccaatcaggc agggccgcac gcagcagaaa gctcggctac cggtgccgcg    180

cggctgaatg ttgcggcgcg acacacgcag cttttgcagg ccttcaaggc tgagcaggcg    240

acagctccgg tcagcggcgc gccgatgatc agctcgcgtg ccgcgttatt gattggcagc    300

ttgctgcagg ctgaaaagct gccttttgaa gtcatggccg agcgtctctc ccctgagcgc    360

tatcaactga agcagtttca tggttcggac ttgcaacaac tgctggacaa gtttacccag    420

ccgggtcagg tacccgacaa agccgaagtc ggtcaactga tcaagggctt cgcgcaatcg    480

gtcgccgatc aactggagca ctttcagttg atgcatgacg ctacgcccac caagacaggc    540

ccgcatgcca acgaggatcg ggcgacgctt gccgtcagtc agacagccct tggcgagtac    600

gccggtcgtg cgagcaaggc aatcggcgaa gggctgagca aaggcatcgt gtcgctggat    660

gatcacatcg ctgcactgga tgtgagcctg caaagtgccg aagagggcgc caaggacgct    720

ttgcactcta acagacaggc gctggttgat gcgaaaacca ctctggtcgg cctgcacgcc    780

gatttcgtca aatcgccaga ggctaaacgc cttgcttcgg tcgccgcaca tacacaactg    840

gacaccgtcg tcagtgatct tgtcactgcc cgcaactcgg ttggcggctg gaaaggtgcc    900

gggccgattg tcgcagctgc ggttccacag ttcctgtcgt caatgacgca cctgggttat    960

gtgcgtttgt ccaccagtga caagctgcga gaggaggtgc ctgagaccag cagcgacgcc   1020

agtatgctca aggcggcgat aaccggaatg gtcacgggca ttgcccacga gacagtcaac   1080

agcgtagtga aaccggtgtt tcaggctact tttcagaaaa ctggcctgaa cgaacggctg   1140

aacatggtgc cactcaaggc tatcgatacc aattcggtga ttcctgaccc cttcgaactg   1200
```

aaaagcgagc acggtgagct gatcagaaaa acgcccgagg aaatcgctca ggacaaggca 1260
ttcgtcaagg gcgaacgcgc ggtgctgaat cagaagaagg tccagggttc gtccacccac 1320
ccgttgggtg aaatgatagg ttacagtgcc tttggtggtt cacatgccgt gcgccagatg 1380
ctcaacgatt tacaccagat caatggtcag acgctgagtg caagagcctt ggcatccggc 1440
tttggcgggg cggtgtctgt cagttcgcaa acgcttttgc agttgaagtc gacgtatgtc 1500
gatcccgcag ggcgcaaaat tccggtattc acgccagacc gagccgagac agagctgaaa 1560
aaggatctgg ccaaaggtat ggacctgcgc gaagcctcgg tacgtaccac gttctacagc 1620
aaggcaatat ccgggtattc agagctcggc gctgacctcg gcactgccgc ctgtgacagc 1680
ccagctggaa ggcgcgcgcg gtacgctcag tgcggggaat atcctgcgca atatggctct 1740
ggtcgcaacg ggctcgattt cctatctgtc cacgctttac gccaaccagt ctgtcaccgc 1800
cgaagccaag gcgttgaagg atgcggggat gggggcgca acgccgatgc tggatcgtac 1860
cgaaacagcc ttgaacaaca tccgccatcc gaacagggca tcgctgccac ataccttcca 1920
gccgagcacg ttgagcggta ttccaagggc tatggaaagc gcttatcaca tgggacgagg 1980
cgcgttgcag ctgccaaccc agatggccgt ggacacggtt cgagtgttgg cagacggtgc 2040
gctgaacggc gtgtcgtcag cacgcgctgc gcttacgcca gcaaaaccgc ctgaagctcg 2100
cgtgtccgtc gacgagctcc ggaacacggc cccaacgccg ccatccagcc ccacagtgca 2160
gcggccggca ccctccgttc cgcttgacga cgagcagttg cgggcgctcg aagaaagctt 2220
gctcgctccg cgttga 2236

<210> SEQ ID NO 113
<211> LENGTH: 460
<212> TYPE: PRT
<213> ORGANISM: Arabidopsis thaliana

<400> SEQUENCE: 113

Met Ile Glu Lys Cys Ile Gly Ala His Arg Phe Arg Arg Leu Gln Arg
1 5 10 15

Phe Met Arg Gln Gly Lys Val Thr Ile Leu Cys Leu Val Leu Thr Val
20 25 30

Ile Val Leu Arg Gly Thr Ile Gly Ala Gly Lys Phe Gly Thr Pro Glu
35 40 45

Lys Asp Ile Glu Glu Ile Arg Glu His Phe Phe Tyr Thr Arg Lys Arg
50 55 60

Gly Glu Pro His Arg Val Leu Val Glu Val Ser Ser Lys Thr Thr Ser
65 70 75 80

Ser Glu Asp Gly Gly Asn Gly Gly Asn Ser Tyr Glu Thr Phe Asp Ile
85 90 95

Asn Lys Leu Phe Val Asp Glu Gly Asp Glu Glu Lys Ser Arg Asp Arg
100 105 110

Thr Asn Lys Pro Tyr Ser Leu Gly Pro Lys Ile Ser Asp Trp Asp Glu
115 120 125

Gln Arg Arg Asp Trp Leu Lys Gln Asn Pro Ser Phe Pro Asn Phe Val
130 135 140

Ala Pro Asn Lys Pro Arg Val Leu Leu Val Thr Gly Ser Ala Pro Lys
145 150 155 160

Pro Cys Glu Asn Pro Val Gly Asp His Tyr Leu Leu Lys Ser Ile Lys
165 170 175

Asn Lys Ile Asp Tyr Cys Arg Ile His Gly Ile Glu Ile Phe Tyr Asn
180 185 190

-continued

```
Met Ala Leu Leu Asp Ala Glu Met Ala Gly Phe Trp Ala Lys Leu Pro
        195                 200                 205

Leu Ile Arg Lys Leu Leu Leu Ser His Pro Glu Ile Glu Phe Leu Trp
    210                 215                 220

Trp Met Asp Ser Asp Ala Met Phe Thr Asp Met Val Phe Glu Leu Pro
225                 230                 235                 240

Trp Glu Arg Tyr Lys Asp Tyr Asn Leu Val Met His Gly Trp Asn Glu
                245                 250                 255

Met Val Tyr Asp Gln Lys Asn Trp Ile Gly Leu Asn Thr Gly Ser Phe
            260                 265                 270

Leu Leu Arg Asn Ser Gln Trp Ser Leu Asp Leu Leu Asp Ala Trp Ala
        275                 280                 285

Pro Met Gly Pro Lys Gly Lys Ile Arg Glu Glu Ala Gly Lys Val Leu
    290                 295                 300

Thr Arg Glu Leu Lys Asp Arg Pro Ala Phe Glu Ala Asp Asp Gln Ser
305                 310                 315                 320

Ala Met Val Tyr Leu Leu Ala Thr Glu Arg Glu Lys Trp Gly Gly Lys
                325                 330                 335

Val Tyr Leu Glu Ser Gly Tyr Tyr Leu His Gly Tyr Trp Gly Ile Leu
            340                 345                 350

Val Asp Arg Tyr Glu Glu Met Ile Glu Asn His Lys Pro Gly Phe Gly
        355                 360                 365

Asp His Arg Trp Pro Leu Val Thr His Phe Val Gly Cys Lys Pro Cys
    370                 375                 380

Gly Lys Phe Gly Asp Tyr Pro Val Glu Arg Cys Leu Arg Gln Met Asp
385                 390                 395                 400

Arg Ala Phe Asn Phe Gly Asp Asn Gln Ile Leu Gln Met Tyr Gly Phe
                405                 410                 415

Thr His Lys Ser Leu Gly Ser Arg Arg Val Lys Pro Thr Arg Asn Gln
            420                 425                 430


Thr Asp Arg Pro Leu Asp Ala Lys Asp Glu Phe Gly Leu Leu His Pro
        435                 440                 445


Pro Phe Lys Ala Ala Lys Leu Ser Thr Thr Thr Thr
    450                 455                 460
```